(12) United States Patent
Xu et al.

(10) Patent No.: US 7,584,087 B2
(45) Date of Patent: Sep. 1, 2009

(54) STRUCTURE OF PROTEIN KINASE C THETA

(75) Inventors: Zhang Bao Xu, Tewksbury, MA (US); Stephane Olland, Arlington, MA (US); Scott Wolfrom, Somerville, MA (US); Karl Malakian, Boxborough, MA (US); Laura Lin, Weston, MA (US); Mark Stahl, Lexington, MA (US); Julie Lee, Somerville, MA (US); Lori Fitz, Somerville, MA (US); Rita Greco, Charlestown, MA (US); Divya Chaudhary, Andover, MA (US); William Stuart Somers, Lexington, MA (US); Lidia Mosyak, Newton, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/099,958

(22) Filed: Apr. 6, 2005

(65) Prior Publication Data
US 2006/0003431 A1     Jan. 5, 2006

Related U.S. Application Data

(60) Provisional application No. 60/560,441, filed on Apr. 7, 2004.

(51) Int. Cl.
| | |
|---|---|
| *G06G 7/58* | (2006.01) |
| *G01N 31/00* | (2006.01) |
| *G01N 33/573* | (2006.01) |
| *G01N 33/53* | (2006.01) |
| *C12Q 1/00* | (2006.01) |
| *C12Q 1/48* | (2006.01) |
| *C12N 9/99* | (2006.01) |
| *C12N 9/12* | (2006.01) |

(52) U.S. Cl. ............................ 703/11; 702/27; 435/4; 435/7.4; 435/7.71; 435/15; 435/184; 435/194

(58) Field of Classification Search ................. 435/194; 702/27
See application file for complete search history.

(56) References Cited

U.S. PATENT DOCUMENTS

| 5,856,116 | A | * | 1/1999 | Wilson et al. ................ 435/23 |
| 6,589,758 | B1 | | 7/2003 | Zhu |
| 2004/0005687 | A1 | | 1/2004 | Barford et al. |
| 2004/0137518 | A1 | * | 7/2004 | Lambert et al. ............. 435/7.1 |

FOREIGN PATENT DOCUMENTS

WO    WO 2004/076654    9/2004

OTHER PUBLICATIONS

U.S. Appl. No. 60/450,780, filed Feb. 2003, Rummel et al.*
Kierzek et al., Biophys Chem 91:1-20.*
Branden et al., "Introduction to Protein Structure Second Edition", Garland Publishing Inc., New York, 1999, pp. 374-375.*
Drenth et al., "Principles of X-ray Crystallography," Springer, New York, 1995, p. 1.*
Flower, Darren R., Drug Design: Cutting Edge Approaches, The Royal Society of Chemistry, 2002, p. 21-27.*
Jones et al., Cellular relocalization of protein kinase C theta caused by staurosporine and some of its analogues, 1997, Biochemical Pharmacology, 53: 1413-1418.*
Alessi et al. "Mechanism of activation of protein kinase B by insulin and IGF-1" *EMBO J.* 15:6541-6551 (1996).
Altman et al. "Protein kinase Cθ: a new essential superstar on the T-cell stage" *Immunol. Today* 21:567-573 (2000).
Arendt et al. "Protein kinase Cθ: signaling from the center of the T-cell synapse" *Curr. Opin. Immunol.* 14:323-330 (2002).
Balendran et al. "PDK1 acquires PDK2 activity in the presence of a synthetic peptide derived from the carboxyl terminus of PRK2" *Curr. Biol.* 9:393-404 (1999).
Biondi et al. "High resolution crystal structure of the human PDK1 catalytic domain defines the regulatory phosphopeptide docking site" *EMBO J.* 21:4219-4228 (2002).
Bossemeyer "The glycine-rich sequence of protein kinases: a multifunctional element" *Trends Biochem. Sci.* 19:201-205 (1994).
Bricogne "Direct Phase Determination by Entropy Maximization and Likelihood Ranking: Status Report and Perspectives" *Acta. Cryst.* D49:37-60 (1993).
Cenni et al. "Regulation of novel protein kinase C ε by phosphorylation" *Biochem. J.* 363:537-545 (2002).
Davies et al. "Specificity and mechanism of action of some commonly used protein kinase inhibitors" *Biochem. J.* 351:95-105 (2000).
De La Fortelle et al. "Maximum-Likelihood Heavy-Atom Parameter Refinement for Multiple Isomorphous Replacement and Multiwavelength Anomalous Diffraction Methods" *Methods Enzymol.* 276:472-494 (1997).
Engh et al. "Structural aspects of protein kinase control-role of conformational flexibility" *Pharmacol. & Therap.* 93:99-111 (2002).
Fabbro et al. "Protein kinases as targets for anticancer agents: from inhibitors to useful drugs" *Pharmacol. & Therap.* 93:79-98 (2002).
Huse et al. "The Conformational Plasticity of Protein Kinases" *Cell* 109:275-282 (2002).
Johnson et al. "Active and Inactive Protein Kinases: Structural Basis for Regulation" *Cell* 85:149-158 (1996).
Liu et al. "Phosphorylation of the protein kinase C-theta activation loop and hydrophobic motif regulates its kinase activity, but only activation loop phosphorylation is critical to in vivo nuclear-factor-κB induction" *Biochem. J.* 361:255-265 (2002).

(Continued)

*Primary Examiner*—Suzanne M. Noakes
*Assistant Examiner*—Jae W Lee
(74) *Attorney, Agent, or Firm*—Lando & Anastasi, LLP

(57) ABSTRACT

A three-dimensional structure of human protein kinase C theta (PKCθ) can be used in methods of designing an agent that interacts with PKCθ. The agent can be an inhibitor of PKCθ activity.

25 Claims, 3 Drawing Sheets

OTHER PUBLICATIONS

Mashhoon et al. "Structure of the Unliganded cAMP-Dependent Protein Kinase Catalytic Subunit from *Saccharomyces cerevisiae*" *Arch. Biochem. Biophys.* 387:11-19 (2001).

Meggio et al. "Different susceptibility of protein kinases to staurosporine inhibition. Kinetic studies and molecular bases for the resistance of protein kinase CK2" *Eur. J. Biochem.* 234:317-322 (1995).

Newton "Regulation of the ABC kinases by phosphorylation: protein kinase C as a paradigm" *Biochem. J.* 370:361-371 (2003).

Nishikawa et al. "Determination of the Specific Substrate Sequence Motifs of Protein Kinase C Isozymes" *J. Biol. Chem.* 272:952-960 (1997).

Taylor et al. "Structural Framework for the Protein Kinase Family" *Annu. Rev. Cell. Biol.* 8:429-462 (1992).

Tronrud "TNT Refinement Package" *Methods Enzymol.* 277:306-319 (1997).

Underwood et al. "Catalytically Active MAP KAP Kinase 2 Structures in Complex with Staurosporine and ADP Reveal Differences with the Autoinhibited Enzyme" *Structure* 11:627-636 (2003).

Villalba et al. "Protein Kinase Cθ (PKCθ), a Potential Drug Target for Therapeutic Intervention with Human T Cell Leukemias" *Current Cancer Drug Targets* 2:125-137 (2002).

Yang et al. "Molecular Mechanism for the Regulation of Protein Kinase B/Akt by Hydrophobic Motif Phosphorylation" *Molecular Cell* 9:1227-1240 (2002).

Yang et al. "Crystal structure of an activated Akt/Protein Kinase B ternary complex with GSK3-peptide and AMP-PNP" *Nature Struct. Biol.* 9:940-944 (2002).

Ochoa W. et al., "Structure of the C2 Domain from Novel Protein Kinase C∈. A Membrane Binding Model for $Ca^{2+}$-independent C2 Domains" Journal of Molecular Biology, vol. 311, Aug. 24, 2001, pp. 837-849.

Pappa H. et al., "Crystal structure of the C2 domain from protein kinase Cδ" Structure (London, England) Jul. 15, 1998, vol. 6, No. 7, pp. 885-894.

International Search Report from International Patent Application No. EP/05763617.7—2406.

Blundell et al., "High-Throughput Crystallography for Lead Discovery in Drug Design" *Nature Reviews* 1(1):45-54 (2002).

Chang et al., "Molecular Cloning and Expression of a cDNA Encoding a Novel Isoenzyme of Protein Kinase C (nPKC)" *J. Biol. Chem.* 268(19):14208-14214 (1993).

Hanks et al., "The eukaryotic protein kinase superfamily: kinase (catalytic domain structure and classification" *FASEB J.* 9:576-596 (1995).

Prade et al., "Staurosporine-induced conformational changes of cAMP-dependent protein kinase catalytic subunit explain inhibitory potential" *Structure* 5(12):1627-1637 (1997).

Xu et al., "Catalytic Domain Crystal Structure of Protein Kinase C-θ (PKCθ)" *J. Biol. Chem.* 279(48):50401-50409 (2004).

\* cited by examiner

```
  1 MSPFLRIGLS NFDCGSCQSC QGEAVNPYCA VLVKEYVESE NGQMYIQKKP TMYPPWDSTF
 61 DAHINKGRVM QIIVKGKNVD LISETTVELY SLAERCRKNN GKTEIWLELK PQGRMLMNAR
121 YFLEMSDTKD MNEFETEGFF ALHQRRGAIK QAKVHHVKCH EFTATFFPQP TFCSVCHEFV
181 WGLNKQGYQC RQCNAAIHKK CIDKVIAKCT GSAINSRETM FHKERFKIDM PHRFKVYNYK
241 SPTFCEHCGT LLWGLARQGL KCDACGMNVH HRCQTKVANL CGINQKLMAE ALAMIESTQQ
301 ARCLRDTEQI FREGPVEIGL PCSIKNEARP PCLPTPGKRE PQGISWESPL DEVDKMCHLP
361 EPELNKERPS LQIKLKIEDF ILHKMLGKGS FGKVFLAEFK KTNQFFAIKA LKKDVVLMDD
421 DVECTMVEKR VLSLAWEHPF LTHMFCTFQT KENLFFVMEY LNGGDLMYHI QSCHKFDLSR
481 ATFYAAEIIL GLQFLHSKGI VYRDLKLDNI LLDKDGHIKI ADFGMCKENM LGDAKTNTFC
541 GTPDYIAPEI LLGQKYNHSV DWWSFGVLLY EMLIGQSPFH GQDEEELFHS IRMDNPFYPR
601 WLEKEAKDLL VKLFVREPEK RLGVRGDIRQ HPLFREINWE ELERKEIDPP FRPKVKSPFD
661 CSNFDKEFLN EKPRLSFADR ALINSMDQNM FRNFSFMNPG MERLIS
       (SEQ ID NO:1)
```

FIG. 3A

```
361 -PELNKERPS LQIKLKIEDF ILHKMLGKGS FGKVFLAEFK KTNQFFAIKA LKKDVVLMDD
421 DVECTMVEKR VLSLAWEHPF LTHMFCTFQT KENLFFVMEY LNGGDLMYHI QSCHKFDLSR
481 ATFYAAEIIL GLQFLHSKGI VYRDLKLDNI LLDKDGHIKI ADFGMCKENM LGDAKTNTFC
541 GTPDYIAPEI LLGQKYNHSV DWWSFGVLLY EMLIGQSPFH GQDEEELFHS IRMDNPFYPR
601 WLEKEAKDLL VKLFVREPEK RLGVRGDIRQ HPLFREINWE ELERKEIDPP FRPKVKSPFD
661 CSNFDKEFLN EKPRLSFADR ALINSMDQNM FRNFSFMNPG MERLISHHHH HH
       (SEQ ID NO:2)
```

FIG. 3B

SEQUENCE LISTING

<160> NUMBER OF SEQ ID NOS: 4

<210> SEQ ID NO 1
<211> LENGTH: 706
<212> TYPE: PRT
<213> ORGANISM: Homo sapiens

<400> SEQUENCE: 1

```
Met Ser Pro Phe Leu Arg Ile Gly Leu Ser Asn Phe Asp Cys Gly Ser
 1               5                  10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
305                 310                 315                 320

Pro Cys Ser Ile Lys Asn Glu Ala Arg Pro Pro Cys Leu Pro Thr Pro
                325                 330                 335

Gly Lys Arg Glu Pro Gln Gly Ile Ser Trp Glu Ser Pro Leu Asp Glu
            340                 345                 350

Val Asp Lys Met Cys His Leu Pro Glu Pro Glu Leu Asn Lys Glu Arg
```

```
                355                 360                 365
Pro Ser Leu Gln Ile Lys Leu Lys Ile Glu Asp Phe Ile Leu His Lys
        370                 375                 380

Met Leu Gly Lys Gly Ser Phe Gly Lys Val Phe Leu Ala Glu Phe Lys
385                 390                 395                 400

Lys Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
    450                 455                 460

Asp Leu Met Tyr His Ile Gln Ser Cys His Lys Phe Asp Leu Ser Arg
465                 470                 475                 480

Ala Thr Phe Tyr Ala Ala Glu Ile Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Lys Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
    530                 535                 540

Tyr Ile Ala Pro Glu Ile Leu Leu Gly Gln Lys Tyr Asn His Ser Val
545                 550                 555                 560

Asp Trp Trp Ser Phe Gly Val Leu Leu Tyr Glu Met Leu Ile Gly Gln
                565                 570                 575

Ser Pro Phe His Gly Gln Asp Glu Glu Leu Phe His Ser Ile Arg
            580                 585                 590

Met Asp Asn Pro Phe Tyr Pro Arg Trp Leu Glu Lys Glu Ala Lys Asp
        595                 600                 605

Leu Leu Val Lys Leu Phe Val Arg Glu Pro Glu Lys Arg Leu Gly Val
    610                 615                 620

Arg Gly Asp Ile Arg Gln His Pro Leu Phe Arg Glu Ile Asn Trp Glu
625                 630                 635                 640

Glu Leu Glu Arg Lys Glu Ile Asp Pro Pro Phe Arg Pro Lys Val Lys
                645                 650                 655

Ser Pro Phe Asp Cys Ser Asn Phe Asp Lys Glu Phe Leu Asn Glu Lys
            660                 665                 670

Pro Arg Leu Ser Phe Ala Asp Arg Ala Leu Ile Asn Ser Met Asp Gln
        675                 680                 685

Asn Met Phe Arg Asn Phe Ser Phe Met Asn Pro Gly Met Glu Arg Leu
    690                 695                 700

Ile Ser
705

<210> SEQ ID NO 2
<211> LENGTH: 351
<212> TYPE: PRT
<213> ORGANISM: Homo sapiens

<400> SEQUENCE: 2

Pro Glu Leu Asn Lys Glu Arg Pro Ser Leu Gln Ile Lys Leu Lys Ile
1               5                   10                  15
```

-continued

```
Glu Asp Phe Ile Leu His Lys Met Leu Gly Lys Gly Ser Phe Gly Lys
             20                  25                  30
Val Phe Leu Ala Glu Phe Lys Lys Thr Asn Gln Phe Phe Ala Ile Lys
         35                  40                  45
Ala Leu Lys Lys Asp Val Val Leu Met Asp Asp Val Glu Cys Thr
 50                  55                  60
Met Val Glu Lys Arg Val Leu Ser Leu Ala Trp Glu His Pro Phe Leu
 65                  70                  75                  80
Thr His Met Phe Cys Thr Phe Gln Thr Lys Glu Asn Leu Phe Phe Val
                 85                  90                  95
Met Glu Tyr Leu Asn Gly Gly Asp Leu Met Tyr His Ile Gln Ser Cys
             100                 105                 110
His Lys Phe Asp Leu Ser Arg Ala Thr Phe Tyr Ala Ala Glu Ile Ile
             115                 120                 125
Leu Gly Leu Gln Phe Leu His Ser Lys Gly Ile Val Tyr Arg Asp Leu
 130                 135                 140
Lys Leu Asp Asn Ile Leu Leu Asp Lys Asp Gly His Ile Lys Ile Ala
145                 150                 155                 160
Asp Phe Gly Met Cys Lys Glu Asn Met Leu Gly Asp Ala Lys Thr Asn
                 165                 170                 175
Thr Phe Cys Gly Thr Pro Asp Tyr Ile Ala Pro Glu Ile Leu Leu Gly
             180                 185                 190
Gln Lys Tyr Asn His Ser Val Asp Trp Trp Ser Phe Gly Val Leu Leu
         195                 200                 205
Tyr Glu Met Leu Ile Gly Gln Ser Pro Phe His Gly Gln Asp Glu Glu
 210                 215                 220
Glu Leu Phe His Ser Ile Arg Met Asp Asn Pro Phe Tyr Pro Arg Trp
225                 230                 235                 240
Leu Glu Lys Glu Ala Lys Asp Leu Leu Val Lys Leu Phe Val Arg Glu
                 245                 250                 255
Pro Glu Lys Arg Leu Gly Val Arg Gly Asp Ile Arg Gln His Pro Leu
             260                 265                 270
Phe Arg Glu Ile Asn Trp Glu Glu Leu Glu Arg Lys Glu Ile Asp Pro
         275                 280                 285
Pro Phe Arg Pro Lys Val Lys Ser Pro Phe Asp Cys Ser Asn Phe Asp
 290                 295                 300
Lys Glu Phe Leu Asn Glu Lys Pro Arg Leu Ser Phe Ala Asp Arg Ala
305                 310                 315                 320
Leu Ile Asn Ser Met Asp Gln Asn Met Phe Arg Asn Phe Ser Phe Met
                 325                 330                 335
Asn Pro Gly Met Glu Arg Leu Ile Ser His His His His His
             340                 345                 350
```

<210> SEQ ID NO 3
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 3

```
Phe Arg Ala Lys Gly Ser Leu Phe Gln
 1               5
```

<210> SEQ ID NO 4
<211> LENGTH: 9

-continued

```
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3, 5, 6, 8
<223> OTHER INFORMATION: X = any amino acid

<400> SEQUENCE: 4

Leu Gly Xaa Gly Xaa Xaa Gly Xaa Val
 1               5
```

STRUCTURE OF PROTEIN KINASE C THETA

RELATED APPLICATIONS

This application claims the benefit of U.S. Provisional Application No. 60/560,441, filed Apr. 7, 2004, which is incorporated herein by reference in its entirety.

TECHNICAL FIELD

This invention relates to a three-dimensional structure of protein kinase C theta.

BACKGROUND

Protein kinases are mediators of signal transduction in eukaryotic cells that play key roles in physiological processes, development, and homeostasis. Deregulated kinases are present in abnormal cellular physiologies and diseases like cancer. As such, protein kinases are attractive targets for modulating disease pathologies. Serine/threonine kinases represent a significant portion of eukaryotic protein kinases and are broadly classified into six major classes called AGC, CAMK, CMGC, TKL, STE, and CK1. The protein kinase C subfamily belongs to the AKT kinase subfamily of the AGC family.

SUMMARY

A three-dimensional model of protein kinase C theta (PKCθ) can aid in the design of an agent that can interact with PKCθ. In particular, the three-dimensional model can include structural coordinates of atoms of PKCθ. A model including structural coordinates can be used in the structure based design or selection of agents, such as inhibitors or substrates, that interact with PKCθ. A comparison of a three-dimensional model of PKCθ with models of other protein kinases can facilitate the design of an agent that interacts selectively with PKCθ.

In one aspect, a composition includes a crystal including a PKCθ polypeptide. The PKCθ polypeptide can include a catalytic domain of PKCθ. The PKCθ polypeptide can include residues 377-696 of SEQ ID NO:1. The composition can include an agent bound to PKCθ. The agent can be a PKCθ substrate or a PKCθ inhibitor. The PKCθ inhibitor can be staurosporine. The crystal can diffract X-rays to a resolution of at least 2.5 Å, or at least 2.2 Å.

In another aspect, a method of designing an agent that interacts with PKCθ includes generating a three-dimensional model of PKCθ. The three-dimensional model can include structural coordinates of atoms of PKCθ. The three-dimensional model of PKCθ can be a three-dimensional model of a catalytic domain of PKCθ. The structural coordinates can be experimentally determined coordinates. The atoms can be atoms of an active site of PKCθ. The structural coordinates can be according to Table 2, ±a root mean square deviation for alpha carbon atoms of not more than 1.5 Å. The three-dimensional model can include structural coordinates of atoms of an agent. The method can include altering the structure of the agent of the model. The method can include altering the structural coordinates of the agent of the model.

The three-dimensional model can include structural coordinates of an atom selected from the group consisting of atoms of residues Leu386, Gly387, Gly389, Val394, Ala407, Lys409, Val422, Met458, Gly459, Tyr460, Leu461, Gly464, Leu466, Asp508, Asn509, Leu511, Ala521, and Asp522. The three-dimensional model can include structural coordinates of an atom selected from the group consisting of atoms of residues Glu428, Arg503, Asp504, Lys527, Thr536, and Thr538. The three-dimensional model can include structural coordinates of an atom selected from the group consisting of atoms of residues Lys413, Val416, Leu417, Val422, Met426, Lys429, Thr447, Gln449, Leu454, Phe456, Phe691, Arg692, Asn693, Phe694, and Ser695.

The method can include determining a fit between PKCθ and an agent. The method can include calculating a distance between atoms of PKCθ and atoms of agent. The method can include docking a three-dimensional model of an agent to the three-dimensional model of PKCθ. The method can include providing a composition including a PKCθ polypeptide. The PKCθ polypeptide can be crystalline. The composition can include an agent that interacts with PKCθ. The method can include determining a catalytic activity of PKCθ, e.g., a kinase activity of PKCθ. The catalytic activity of PKCθ determined in the presence of the agent can be compared to a catalytic activity of PKCθ determined in the absence of the agent.

In another aspect, a method of identifying an agent capable of altering a catalytic activity of PKCθ includes providing a three-dimensional model of PKCθ, and studying the interaction of a candidate agent with the three-dimensional model of PKCθ. In yet another aspect, a method of identifying an agent capable of altering a catalytic activity of PKCθ includes providing a three-dimensional model of PKCθ including structural coordinates of atoms of PKCθ, studying the interaction of a plurality of candidate agents with the three-dimensional model of PKCθ, and selecting from the plurality of candidate agents an agent which is predicted to alter a catalytic activity of PKCθ.

The interaction of a second candidate agent with the three-dimensional model of PKCθ can be studied. The method can include selecting a candidate agent which is predicted to alter a catalytic activity of PKCθ. A catalytic activity of PKCθ can be measured in the presence of the selected agent.

In another aspect, the invention features a method that includes selecting an agent by performing rational drug design with a three-dimensional structure of a crystal that includes PKCθ. The method includes contacting the agent with PKCθ and detecting the ability of the agent to bind PKCθ.

In another aspect, the invention features a method that includes contacting PKCθ with a ligand to form a composition and crystallizing the composition to form a crystalline complex in which the ligand is bound to PKCθ. The crystalline complex diffracts X-rays to a resolution of at least about 3.5 Å.

In yet another aspect, the invention features a software system that includes instructions for causing a computer system to accept information relating to the structure of PKCθ bound to a ligand, accept information relating to a candidate agent, and determine the binding characteristics of the candidate agent to PKCθ. This determination is based on the information relating to the structure of PKCθ bound to the ligand, and the information relating to the candidate agent.

In another aspect, the invention features a computer program on a computer readable medium on which is stored a plurality of instructions. When the instructions are executed by one or more processors, the processor(s) accept information relating to a structure of PKCθ bound to a ligand and a candidate agent, and determine binding characteristics of the agent to the PKCθ polypeptide. The binding characteristics are determined based on the information relating to the structure of PKCθ and the information relating to the candidate agent.

In another aspect the invention features a method that includes accepting information relating to the structure of a complex including PKCθ bound to a ligand and modeling the binding characteristics of PKCθ to a candidate agent. The method is implemented by a software system, for example.

In another aspect, the invention features a computer program on a computer readable medium on which is stored a plurality of instructions. When the instructions are executed by one or more processors, the processor(s) accept information relating to a structure of a complex including PKCθ bound to a ligand and model the binding characteristics of PKCθ to a candidate agent.

In another aspect, the invention features a software system that includes instructions for causing a computer system to accept information relating to a structure of a complex including PKCθ bound to a ligand and model the binding characteristics of PKCθ to a candidate agent.

In another aspect, the invention features a method of modulating PKCθ activity in a subject including using rational drug design to select an agent that is capable of modulating PKCθ activity and administering a therapeutically effective amount of the agent to the subject.

In another aspect, the invention features a method of treating a subject having a condition associated with PKCθ activity including using rational drug design to select an agent that is capable of affecting PKCθ activity and administering a therapeutically effective amount of the agent to a subject in need of the agent.

In another aspect the invention features a method of prophylactically treating a subject susceptible to a condition associated with PKCθ activity including determining that the subject is susceptible to the condition, using rational drug design to select an agent that is capable of effecting PKCθ activity, and administering a therapeutically effective amount of the agent to the subject.

Structure based modeling can allow the identification of an agent capable of interacting with PKCθ, without the need to experimentally test a large variety of compounds in vivo or in vitro with the goal of identifying a chemical structure that can interact with PKCθ. Such screening can be expensive and time-consuming. Modifications to a known agent that interacts with PKCθ can be examined with structure based design to identify an agent with more desirable properties, such as tighter binding or greater selectivity for PKCθ over other protein kinases, without the need to prepare and test each modified agent.

The details of one or more embodiments are set forth in the accompanying drawings and the description below. Other features, objects, and advantages will be apparent from the description and drawings, and from the claims.

DESCRIPTION OF DRAWINGS

FIG. 3A displays the amino acid sequence of full-length human PKCθ (SEQ ID NO:1).

FIG. 3B displays the amino acid sequence of the catalytic domain of human PKCθ with a hexahistidine tag at the C-terminus (SEQ ID NO:2).

DETAILED DESCRIPTION

Figure 1:
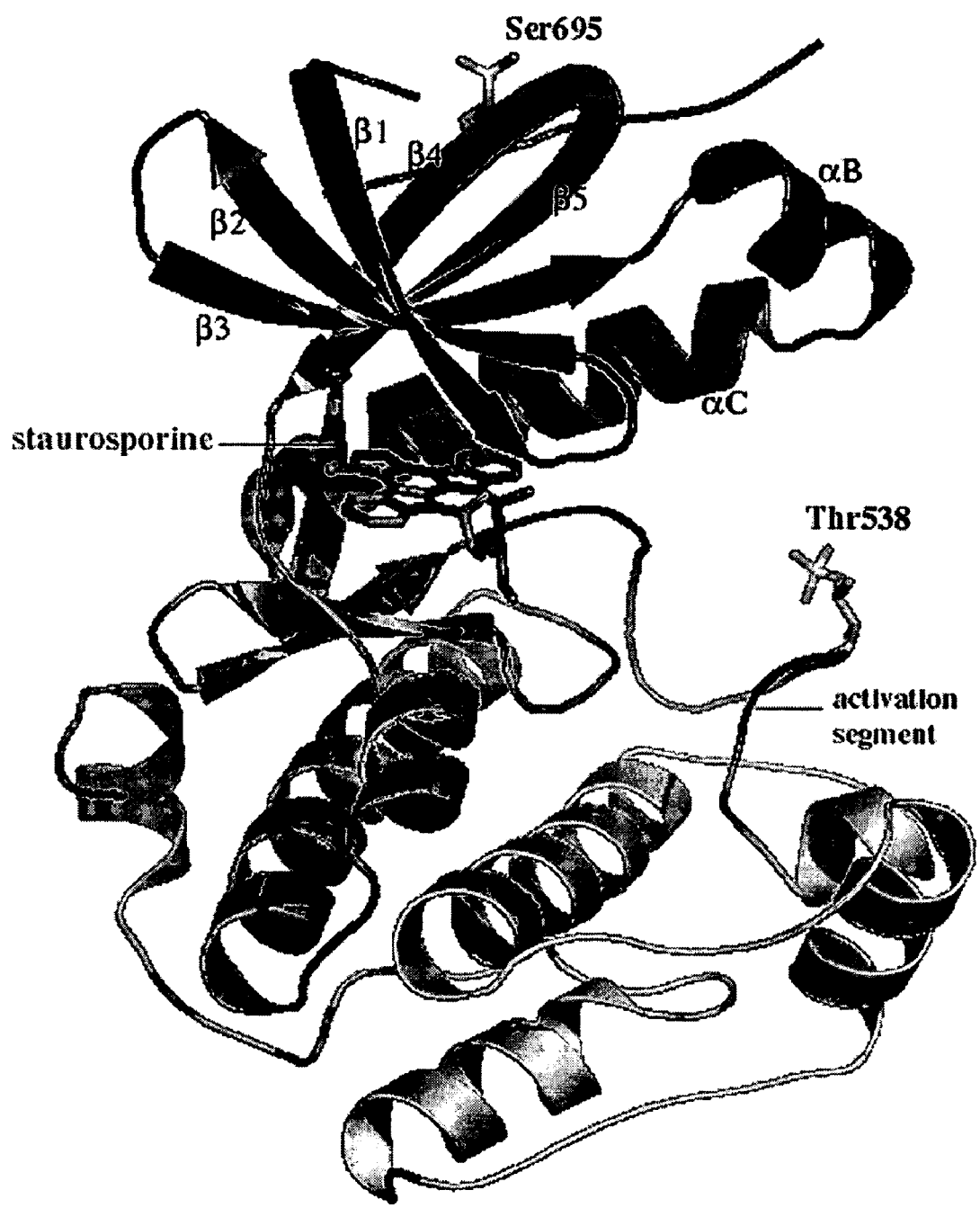
FIG. 1 is a ribbon diagram of human PKCθ complexed with staurosporine.

Protein kinase C theta (PKCθ) and protein kinase B/AKT have been implicated in T cell signaling leading to T cell activation and survival. The expression and role of PKCθ is relatively restricted to T cells, with signaling in response to T cell receptor stimulation contributing to T cell activation and cytokine production. Thus, PKCθ inhibition is desirable in T cell leukemias and T cell mediated autoimmune disorders. See, for example, Fabbro et al., *Pharmacology & Therapeutics* 93:79-98, 2002; and Altman et al., *Immunol. Today* 21:567-573, 2000, each of which is incorporated by reference in its entirety.

Members of the PKC subfamily are regulated by calcium, diacylglycerol (DAG), and phorbol esters and can be divided into three groups based on their cofactor requirements: conventional (PKCα, βI, βII, γ), novel (PKCδ, ε, θ, η), and atypical (PKCζ, ι, λ, μ) isoforms (see Arendt et al., *Curr. Opin. Immunol.* 14:323-330, 2002, which is incorporated by reference in its entirety). These closely related PKC isoenzymes have been shown to have important roles in T cells, B cells, and mast cells contributing to adaptive and innate immunity. They also have diverse roles in cellular functions such as apoptosis, differentiation, motility, insulin resistance, and inflammation. Inhibitors of PKC are currently in clinical trials for various types of cancer.

Three-dimensional structures have been determined for the kinase domain of AKT (PKB) and cAMP dependent PKA, both of which belong to the AGC kinase family (see Huse and Kuriyan, *Cell* 109:257-282, 2002, which is incorporated by reference in its entirety). It can be desirable to have kinase inhibitors that specifically inhibit only one kinase. The structural similarities between the kinase domain ATP binding sites, however, present a challenge in the development of highly specific inhibitors for use as disease therapies (see Davies et al., *Biochem. J.* 351:95-105, 2000, which is incorporated by reference in its entirety). Structural elucidation of kinase active sites and those of closely related family members can increase understanding of inhibitor selectivity and the mechanism of enzyme action. In addition, structural information can aid the rational design and optimization of small molecule inhibitors as therapeutics for T cell mediated allergic and autoimmune diseases.

Structural coordinates are Cartesian coordinates that describe the location of atoms in three-dimensional space in relation to other atoms in a molecule or molecular complex. Structural coordinates may be obtained by using, for example, X-ray crystallography techniques or NMR techniques. Additional structural information can be obtained from spectral techniques (e.g., optical rotary dispersion (ORD), circular dichroism (CD)), homology modeling, and computational methods such as those that include data from molecular mechanics or from dynamics assays.

Various software programs allow for the graphical representation of a set of structural coordinates to obtain a representation of a molecule or molecular complex, such as PKCθ bound to staurosporine. In general, such a representation should accurately reflect (relatively and/or absolutely) structural coordinates, or information derived from structural coordinates, such as distances or angles between features. The representation can be a two-dimensional figure, such as a stereoscopic two-dimensional figure, or an interactive two-dimensional display (e.g., a computer display that can display different faces of the molecule or molecular complex), or an interactive stereoscopic two-dimensional display. The coordinates can be used to direct the creation of a physical three-dimensional representation of the molecule or molecular complex, such as a ball-and-stick model or a model prepared by rapid prototyping. The structural coordinates may be modified by mathematical manipulation, such as by inversion or integer additions or subtractions. As such, the structural coordinates are relative coordinates, and are in no way specifically limited by the actual x, y, z coordinates of Table 2.

A three-dimensional molecular model is a representation of a molecule or molecular complex. A three-dimensional model can be a physical model of a molecular structure (e.g., a ball-and-stick model), or a graphical representation of a molecular structure. A graphical representation can include, for example, a drawing or a figure presented on a computer display. A two-dimensional graphical representation (e.g., a drawing) can be a three-dimensional model when the two-dimensional representation reflects three-dimensional information, for example, through the use of perspective, shading, or the obstruction of features more distant from the viewer by features closer to the viewer. Preferably, the graphical representation accurately reflects structural coordinates, or information derived from structural coordinates, such as distances or angles between features of the model. When the three-dimensional model includes a polypeptide, such as a PKCθ polypeptide, the model can include one or more different levels of structure, such as primary structure (amino acid sequence), secondary structure (e.g., α-helices and β-sheets), tertiary structure (overall fold), and quarternary structure (oligomerization state). A model can include different levels of detail. For example, the model can include the relative locations of secondary structural features of a protein without specifying the positions of atoms. A more detailed model can include the positions of atoms.

The model can include features derived from the structural coordinates and other chemical information. For example, the shape of a solvent accessible surface can be derived from structural coordinates, the van der Waals radii of the atoms of the model, and the van der Waals radius of a solvent (e.g., water). Other features that can be derived from structural coordinates include without limitation, electrostatic potential, the location of voids or pockets within a macromolecular structure, and the location of hydrogen bonds and salt bridges.

The model can include structural coordinates of atoms in the molecular structure. Structural coordinates can be experimentally determined, for example by X-ray crystallography or NMR spectroscopy, or can be generated by, for example, homology modeling. The molecular structure can include a single molecule, a portion of a molecule, a complex of two or more molecules, a group of molecules, or a combination thereof. In a model of a molecular complex, the molecules can be associated by covalent or non-covalent bonds, including, for example, hydrogen bonds, hydrophobic interactions, or electrostatic attraction. A molecular complex can include tightly associated molecules, such as an enzyme/inhibitor complex, and loosely associated molecules, such as a crystalline compound having ordered solvent molecules or ions present in the crystal. A model can include, for example, a complex of a protein bound to an agent, such as, for example, a complex of an enzyme bound to an inhibitor. When the model includes structural coordinates, coordinates of some atoms in a molecule can be omitted.

Conservative substitutions are amino acid substitutions which are functionally or structurally equivalent to the substituted amino acid residue. A conservative substitution can include switching one residue for another with similar polarity, steric arrangement, or belonging to the same class (e.g., hydrophobic, acidic or basic) as the substituted residue. Conservative substitutions include substitutions having an inconsequential effect on the three-dimensional structure of PKCθ with respect to identification and design of agents that interact with PKCθ, as well as for molecular replacement analyses or homology modeling.

An agent includes a protein, polypeptide, peptide, nucleic acid (including DNA or RNA), molecule, compound or drug. An agent can act as a substrate, inhibitor, activator, allosteric effector, or binding partner with an enzyme.

An active site is a region of a molecule or molecular complex that can interact or associate with an agent (including, without limitation, a protein, polypeptide, peptide, nucleic acid, including DNA or RNA, molecule, compound or drug). An active site may include, for example, the site of agent binding, as well as accessory binding sites adjacent or proximal to the actual site of binding that may affect activity upon interaction or association with a particular agent. The active site can include a site of inhibitor binding. The inhibitor can inhibit either by direct interference with the actual site of substrate binding (i.e., by competing for substrate binding) or by indirectly affecting the steric conformation or charge potential, thereby preventing or reducing binding of substrate at the actual site of substrate binding. For example, an active site can be a site of cofactor binding, substrate binding (e.g., the substrate to be phosphorylated) or inhibitor binding. An active site can include a site of allosteric effector binding, or a site of phosphorylation, glycosylation, alkylation, acylation, or other covalent modification.

Root mean square deviation (rms deviation, or rmsd) is the square root of the arithmetic mean of the squares of the deviations from the mean, and is a way of expressing deviation or variation from structural coordinates. Conservative substitutions of amino acid residues can result in a molecular model having structural coordinates within the stated root mean square deviation. In particular, two molecular models of polypeptides that differ from one another by conservative substitutions can have coordinates of backbone atoms within a stated rms deviation, such as less than 1.5 Å, less than 1.0 Å, or less than 0.5 Å. Backbone atoms of a polypeptide include the alpha carbon ($C_\alpha$ or CA) atoms, carbonyl carbon (C) atoms, carbonyl oxygen (O) atoms, and amide nitrogen (N) atoms.

The numbering of the amino acid residues of PKCθ may be different than set forth here, and may contain certain conservative amino acid substitutions, additions or deletions that yield the same three-dimensional structures as those defined by Table 2, ± an rmsd for backbone atoms of less than 1.5 Å. Corresponding amino acids and conservative substitutions in other isoforms or analogs are easily identified by visual inspection of the relevant amino acid sequences or by using commercially available homology software programs (e.g., MODELLAR, MSI Management Simulations, Inc. San Diego, Calif.). An isoform is any of several multiple forms of a protein that differ in their primary structure. An analog is a polypeptide having conservative amino acid substitutions.

"PKCθ" refers to a PKCθ protein or nucleic acid (e.g., a DNA or RNA), or a fragment thereof. In some embodiments, a fragment of PKCθ can include, for example, only the N-terminal domain of the protein, only the C-terminal domain of the protein, or a fragment of either domain of the protein. In another embodiment, a fragment of PKCθ can include both the N-terminal domain and the C-terminal domain. The PKCθ protein or nucleic acid can originate from a nonmammalian or mammalian species. Mammalian PKCθ can originate from a human, for example. Exemplary nonhuman mammals include, a nonhuman primate (such as a monkey or ape), a mouse, rat, goat, cow, bull, pig, horse, sheep, wild boar, sea otter, cat, or dog. Exemplary nonmammalian species include a chicken, turkey, shrimp, alligator, or fish.

PKCθ includes an N-terminal domain and a C-terminal catalytic domain. The N-terminal domain consists of multiple modules and functions as a regulatory domain (see, for example, Newton, A. C., *Biochem. J.* 370, 361-371, 2003, which is incorporated by reference in its entirety). The C-terminal catalytic domain can be expressed from a DNA plasmid as a soluble, active protein, including residues 362-706 of the full-length sequence of human PKCθ. The expression can be driven by a promoter, such as an inducible promoter. FIG. 3A displays the full-length sequence of PKCθ, and FIG. 3B the sequence of residues 362-706 of the catalytic domain with an added C-terminal hexahistidine tag. Other polypeptide sequences than the one shown in FIG. 3B can be used, for example, sequences having additional or fewer residues of the full-length PKCθ sequence at the N-terminus, or sequences having fewer residues at the C-terminus. In some embodiments, PKCθ can be expressed as a fusion protein with a tag other than hexahistidine, such as a glutathione-S-transferase (GST), myc, HA, Strep or FLAG tag. The tag can facilitate isolation of PKCθ from cells, such as from bacterial cells or from a mammalian cell line. For example, PKCθ can be expressed in and isolated from *E. coli* cells. A fusion protein can be cleaved at a protease site engineered into the fusion protein, such as at or near the site of fusion between the polypeptide and the tag. When it is desirable to form a complex between PKCθ and a ligand, such as staurosporine (a natural product kinase inhibitor), PKCθ can be contacted with the ligand following cleavage and purification. For example, PKCθ can be mixed with staurosporine prior to purification (e.g., prior to cleavage of a polypeptide tag), or PKCθ can be mixed with staurosporine after purification. In some embodiments, staurosporine can be mixed with PKCθ prior to purification and again following purification.

PKCθ can be placed in solution for collecting spectral data or NMR data, or for growing a crystal. For example, PKCθ can be crystallized in the presence of a salt (e.g., a sodium salt), a polymer (e.g., polyethylene glycol (PEG)), and/or an organic solvent. Crystals can be grown by various methods, such as, for example, sitting or hanging drop vapor diffusion. In general, crystallization can be performed at a temperature of from about 4° C. to about 60° C. (e.g., from about 4° C. to about 45° C., such as at about 4° C., about 15° C., about 18° C., about 20° C., about 25° C., about 30° C., about 32° C., about 35° C., about 37° C.).

The C-terminal catalytic domain of PKCθ can be crystallized as a complex with an agent. In particular, it can be crystallized as a 1:1 complex with staurosporine (a natural product kinase inhibitor), from a solution including NaCl, $MgCl_2$, dithiothreitol (DTT), and Tris buffer. The solution can include a precipitant, such as ammonium sulfate. A crystal of PKCθ can belong to space group C2, with dimensions a=139.6 Å, b=42.4 Å, c=67.7 Å, and β=116.2°. The space group refers to overall symmetry of the crystal, and includes point symmetry and space symmetry. In certain embodiments, a crystal of PKCθ bound to staurosporine can contain one molecule of PKCθ in the asymmetric unit. The asymmetric unit is the smallest unit from which the crystal structure can be generated by making use of the symmetry operations of the space group. A crystal is generally made up of the motif defined by the space-group symmetry operations on the asymmetric units, and a translation of that motif through the crystal lattice.

In general, a crystal of PKCθ bound to staurosporine can diffract X-rays to a resolution of about 3.5 Å or less (e.g., about 3.2 Å or less, about 3.0 Å or less, about 2.5 Å or less, about 2.4 Å or less, about 2.3 Å or less, about 2.2 Å or less, about 2.1 Å or less, about 2.0 Å or less, about 1.9 Å or less, about 1.8 Å or less, about 1.7 Å or less, about 1.6 Å or less, about 1.5 Å or less, about 1.4 Å or less). In some embodiments, the crystal can diffract X-rays to a resolution of from about 1.6 to about 2.5 Å (e.g., from about 1.8 to about 2.2 Å).

Structural data describing a crystal can be obtained, for example, by X-ray diffraction. X-ray diffraction data for the crystals can be collected by a variety of means in order to obtain structural coordinates. Suitable X-ray sources include rotating anode and synchrotron sources (e.g., Advanced Light Source (ALS), Berkeley, Calif.; or Advanced Photon Source (APS), Argonne, Ill.). In certain embodiments, X-rays for generating diffraction data can have a wavelength of from about 0.5 Å to about 1.6 Å (e.g., about 0.7 Å, about 0.9 Å, about 1.0 Å, about 1.1 Å, about 1.3 Å, about 1.4 Å, about 1.5 Å, about 1.6 Å). Suitable X-ray detectors include area detectors and charge-couple devices (CCDs). X-ray diffraction data of a crystal of a complex of PKCθ bound to staurosporine can be used to obtain the structural coordinates of the atoms in the complex.

In some embodiments, the X-ray diffraction data can be used to construct an electron density map of PKCθ bound to staurosporine, and the electron density map can be used to derive a representation (e.g., a two dimensional representation, a three dimensional representation) of a complex including PKCθ bound to staurosporine, or a fragment of the complex. Creation of an electron density map typically involves using information regarding the phase of the X-ray scatter. Phase information can be extracted, for example, either from the diffraction data or from supplementing diffraction experiments to complete the construction of the electron density map. Methods for calculating phase from X-ray diffraction data, include, without limitation, multiwavelength anomalous dispersion (MAD), multiple isomorphous replacement (MIR), multiple isomorphous replacement with anomalous scattering (MIRAS), reciprocal space solvent flattening, molecular replacement, and single isomorphous replacement with anomalous scattering (SIRAS), or a combination thereof. These methods generate phase information by making isomorphous structural modifications to the native protein, such as by including a heavy atom or changing the scattering strength of a heavy atom already present, and then measuring the diffraction amplitudes for the native protein and each of the modified cases. If the position of the additional heavy atom or the change in its scattering strength is known, then the phase of each diffracted X-ray can be determined by solving a set of simultaneous phase equations. The location of heavy atom sites can be identified using a computer program, such as SHELXS (Sheldrick, Institut Anorg. Chemie, Göttingen, Germany), and diffraction data can be processed using computer programs such as MOSFLM, SCALA, SOLOMON, and SHARP ("The CCP4 Suite: Programs for Protein Crystallography," Acta Crystallogr. Sect. D, 54:905-921, 1997; deLa Fortelle and Brigogne, Meth. Enzym. 276:472-494, 1997). Upon determination of the phase, an electron density map of the complex can be constructed.

The electron density map can be used to derive a representation of a polypeptide, a complex, or a fragment of a polypeptide or complex by aligning a three-dimensional model of a polypeptide or complex (e.g., a complex containing a polypeptide bound to a ligand) with the electron density map. For example, the electron density map corresponding to PKCθ bound to staurosporine can be aligned with a previously determined electron density map corresponding to an unbound TPK1δ polypeptide from *Saccharomyces cerevisiae*. The electron density map can be further aligned by aligning it with an electron density map created from a collection of similar structures (e.g., a collection or 5, 6, or 7 protein kinase structures) overlayed to generate an "average" electron density map.

The alignment process results in a comparative model that shows the degree to which the calculated electron density map varies from the model of the previously known polypeptide or the previously known complex. The comparative model is then refined over one or more cycles (e.g., two cycles, three cycles, four cycles, five cycles, six cycles, seven cycles, eight cycles, nine cycles, 10 cycles) to generate a better fit with the electron density map. A software program such as CNS (Brunger et al., *Acta Crystallogr*. D54:905-921, 1998) can be used to refine the model. The quality of fit in the comparative model can be measured by, for example, an $R_{work}$ or $R_{free}$ value. A smaller value of $R_{work}$ or $R_{free}$ generally indicates a better fit. Misalignments in the comparative model can be adjusted to provide a modified comparative model and a lower $R_{work}$ or $R_{free}$ value. The adjustments can be based on information (e.g., sequence information) relating to other known protein kinase polypeptides (e.g., a TKP1δ polypeptide), a human PKCθ polypeptide, staurosporine, or a human PKCθ polypeptide/staurosporine complex. As an example, in embodiments in which one or more models of previously known protein kinases are used, such as a structural model of a TKP1δ polypeptide, an adjustment can include replacing an amino acid in the previously known protein kinase polypeptide with the amino acid in the corresponding site of a different protein kinase (e.g., the human PKCθ polypeptide). When adjustments to the modified comparative model satisfy a best fit to the electron density map, the resulting model is that which is determined to describe the polypeptide or complex from which the X-ray data was derived. Methods of such processes are disclosed, for example, in Carter and Sweet, eds., "Macromolecular Crystallography" in *Methods in Enzymology*, Vol. 277, Part B, New York: Academic Press, 1997, and articles therein, e.g., Jones and Kjeldgaard, "Electron-Density Map Interpretation," p. 173, and Kleywegt and Jones, "Model Building and Refinement Practice," p. 208.

Discussed above is a method of deriving a representation of a complex by aligning a three-dimensional model of a previously known polypeptide or a previously known complex with a newly calculated electron density map corresponding to a crystal of the polypeptide or the complex. One adjustment that can be used in this modeling process can include replacing the compound in the representation of the previously known complex with staurosporine.

As described above, a three-dimensional model of PKCθ including structural coordinates can be derived from X-ray diffraction data of a PKCθ/staurosporine crystal. The structural coordinates of one such model are shown below in Table 2. A three-dimensional model can include structural coordinates of a portion of PKCθ (for example, a structural core of PKCθ, or an active site of PKCθ) according to Table 2, ± a root mean square deviation from the alpha carbon atoms of amino acids of not more than 1.5 Å, preferably not more than 1.0 Å, and most preferably not more than 0.5 Å. The three-dimensional model of PKCθ is useful for a number of applications, including, but not limited to, the visualization, identification and characterization of various active sites of PKCθ. The active site structures may then be used to design agents that interact with PKCθ.

A machine, such as a computer, can be programmed in memory with the structural coordinates of a PKCθ model, together with a program capable of generating a three-dimensional graphical representation of the structural coordinates on a display connected to the machine. Alternatively or additionally, a software system can be designed and/or utilized to accept and store the structural coordinates. The software system can be capable of generating a graphical representation of the structural coordinates. The software system can also be capable of accessing external databases to identify compounds with similar structural features as staurosporine, and/or to identify one or more candidate agents with characteristics that may render the candidate agent(s) likely to interact with PKCθ.

A machine having a memory containing such data or a software system containing such data can aid in the rational design or selection of inhibitors or activators of PKCθ activity, including the evaluation of the ability of an agent to associate with PKCθ or a PKCθ complex, as well as in the modeling of compounds or proteins related by structural or sequence homology to PKCθ. For example, such a machine or software system can aid in the evaluation of the ability of an agent to associate with PKCθ, or can aid in the modeling of compounds or proteins related by structural or sequence homology to PKCθ. As used herein, an activator, or agonist, refers to a compound that enhances at least one activity of PKCθ, and an inhibitor, or antagonist, refers to a compound that inhibits at least one activity, or has an opposite activity, of a human PKCθ polypeptide. For example, a compound, such as staurosporine can function as an antagonist of a human PKCθ polypeptide by decreasing the rate of PKCθ kinase activity in T cells.

The machine can produce a representation (e.g., a two dimensional representation or a three-dimensional representation) of PKCθ, a portion thereof (such as a portion including an active site or a binding site), a PKCθ/staurosporine complex, or a PKCθ analog. A software system, for example, can cause the machine to produce such information. The machine can include a machine-readable data storage medium comprising a data storage material encoded with machine-readable data. The machine-readable data can include structural coordinates of atoms of PKCθ or PKCθ bound to staurosporine. Machine-readable storage media including data storage material can include conventional computer hard drives, floppy disks, DAT tape, CD-ROM, DVD, and other magnetic, magneto-optical, optical, and other media which may be adapted for use with a computer. The machine can also have a working memory for storing instructions for processing the machine-readable data, as well as a central processing unit (CPU) coupled to the working memory and to the machine-readable data storage medium for the purpose of processing the machine-readable data into the desired three-dimensional representation. Finally, a display can be connected to the CPU so that the three-dimensional representation may be visualized by the user. Accordingly, when used with a machine programmed with instructions for using said data, (e.g., a computer loaded with one or more programs of the sort described herein) the machine is capable of displaying a graphical representation (e.g., a two-dimensional graphical representation, a three-dimensional graphical representation) of any of the molecules or molecular complexes, or portions of molecules of molecular complexes, described herein.

An active site of PKCθ can include an inhibitor binding site, such as a staurosporine binding site. An active site of PKCθ can include one or more of amino acid residues Leu386, Gly387, Gly389, Val394, Ala407, Lys409, Val422, Met458, Glu459, Tyr460, Leu461, Gly464, Leu466, Asp508, Asn509, Leu511, Ala521, and Asp522 (see FIGS. 3A and 3B). An active site can include amino acid residues belonging to the activation segment, residues 522-543, or residues that interact with the activation segment, such as Glu428, Arg503, Asp504, Lys527, Thr536, and Thr538. An active site of PKCθ can include amino acid residues of the hydrophobic motif, or amino acid residues that interact with the hydrophobic motif, such as Lys413, Val416, Leu417, Val422, Met426, Lys429, Thr447, Gln449, Leu454, Phe456, Phe691, Arg692, Asn693, Phe694, and Ser695. An active site of PKCθ can be described by structural coordinates. The structural coordinates can be adjusted±a root mean square deviation for the alpha carbon atoms of amino acids of not more than 1.5 Å, preferably not more than 1.0 Å, and most preferably not more than 0.5 Å. The active site can be described by the structural coordinates in Table 2 (see below).

An agent that interacts with (e.g., binds) PKCθ can be identified or designed by a method that includes using a representation of PKCθ, such as a three-dimensional model of PKCθ bound to staurosporine. The model can be a model of a PKCθ analog having conservative substitutions from the PKCθ amino acid sequence. Preferably the model includes structural coordinates of atoms of PKCθ. The structural coordinates can be, for example, the coordinates in Table 2, optionally adjusted±a root mean square deviation for the alpha carbon atoms of PKCθ of not more than 1.5 Å, not more than 1.0 Å, or not more than 0.5 Å. In the method, a three-dimensional model is generated using structural coordinates of PKCθ bound to staurosporine. The model can include a portion of PKCθ, such as an active site. A candidate agent that interacts with the model can then be designed or identified by performing computer fitting analysis of the candidate agent with the three-dimensional model.

A display (e.g., a computer display) can show a representation of a three-dimensional model of PKCθ, for example, a diagram of an active site of PKCθ, to a user. The model can include an agent bound to PKCθ, or the user can superimpose a three-dimensional model of an agent on the PKCθ model. The agent can be, for example, a substrate or inhibitor of PKCθ, a candidate substrate or candidate inhibitor. The agent in the model can be a known compound, a novel chemical structure, or a fragment of a chemical structure. The user can inspect the resulting three-dimensional model of a PKCθ/agent complex. A three-dimensional model of a PKCθ/agent complex can also be generated, for example, by altering, a previously existing PKCθ/agent complex model, such as a model of a PKCθ/staurosporine complex. It can be desirable for the agent to fit the active site closely. In other words, the agent can have a shape that complements the shape of the active site. There can be a preferred distance, or range of distances, between atoms of the agent and atoms of PKCθ. Distances longer than a preferred distance may be associated with a weak interaction between the agent and PKCθ (e.g., an active site of PKCθ). Distances shorter than a preferred distance may be associated with repulsive forces that can weaken the interaction between the agent and PKCθ. A steric clash can occur when distances between atoms are too short. A steric clash occurs when the locations of two atoms are unreasonably close together, for example, when two atoms are separated by a distance less than the sum of their van der Waals radii. If a steric clash exists, the user can adjust the position of the agent relative to PKCθ (e.g., a rigid body translation or rotation of the agent) until the steric clash is relieved. The user can adjust the conformation of the agent or of PKCθ in the vicinity of the agent in order to relieve a steric clash. Steric clashes can also be removed by altering the structure of the agent, for example, by changing a bulky group, such as an aromatic ring, to a smaller group, such as to a methyl or hydroxyl group, or by changing a-rigid group to a flexible group that can accommodate a conformation that does not produce a steric clash. Electrostatic forces can also influence an interaction between an agent and an active site. For example, electrostatic properties can be associated with repulsive forces that can weaken the interaction between the agent and PKCθ. Electrostatic repulsion can be relieved by altering the charge of the agent, e.g., by replacing a positively charged group with a neutral group.

Forces that influence binding strength between the agent and PKCθ can also be evaluated in the PKCθ/agent model. These can include, but are not limited to, hydrogen bonding, electrostatic forces, hydrophobic interactions, van der Waals interactions, dipole-dipole interactions, π-stacking forces, and cation-π interactions. The user can evaluate these forces visually, for example by noting a hydrogen bond donor/acceptor pair arranged with a distance and angle suitable for a hydrogen bond. Based on the evaluation, the user can alter the model to find a more favorable interaction between PKCθ and the agent. Altering the model can include changing the three-dimensional structure of PKCθ without altering its chemical structure, for example by altering the conformation of amino acid side chains or backbone dihedral angles. Altering the model can include altering the position or conformation of the agent, as described above. Altering the model can also include altering the chemical structure of the agent, for example by substituting, adding or removing groups. For example, if a hydrogen bond donor on PKCθ is located near a hydrogen bond donor on the agent, the user can replace the hydrogen bond donor on the agent with a hydrogen bond acceptor.

The relative locations of the agent and PKCθ, or their conformations, can be adjusted to find an optimized binding geometry for a particular agent to PKCθ. An optimized binding geometry is characterized by, for example, favorable hydrogen bond distances and angles, maximal electrostatic attractions, minimal electrostatic repulsions, the sequestration of hydrophobic moieties away from an aqueous environment, and the absence of steric clashes. The optimized geometry can have the lowest calculated energy of a family of possible geometries for a PKCθ/agent complex. An optimized geometry can be determined, for example, through molecular mechanics or molecular dynamics calculations.

A series of models (e.g., two dimensional models, three-dimensional models) of PKCθ/agent complexes having different bound agents can be generated. A score can be calculated for each model of a PKCθ/agent complex in the series. The score can describe, for example, an expected strength of interaction between PKCθ and the agent. The score can reflect one of the factors described above that influence binding strength described above. The score can be an aggregate score that reflects more than one of the factors. The different agents can be ranked according to their scores.

Steps in the design of the agent can be carried out in an automated fashion by a machine (e.g., a computer). For example, a model of a PKCθ active site can be programmed in the machine, along with models of a series of candidate agents. The machine can find an optimized binding geometry for each of the candidate agents to the PKCθ active site, and calculate a score to determine which of the agents in the series is likely to interact most strongly with PKCθ.

A software system can be designed and/or implemented to facilitate these steps. Software systems (e.g., computer programs) used to generate such three-dimensional models or perform the necessary fitting analyses include, but are not limited to: MCSS, Ludi, QUANTA® (macromolecular X-ray crystallography software), Insight II® (biological compound modeling and simulation software), Cerius$^2$® (modeling and simulation software), CHARMm® (software for simulation of biological macromolecules), and Modeler from Accelrys, Inc. (San Diego, Calif.); SYBYL® (molecular modeling software), Unity, FleXX, and LEAPFROG from TRIPOS, Inc.

(St. Louis, Mo.); AUTODOCK (Scripps Research Institute, La Jolla, Calif.); GRID (Oxford University, Oxford, UK); DOCK (University of California, San Francisco, Calif.); and Flo+ and Flo99 (Thistlesoft, Morris Township, N.J.). Other useful programs include ROCS, ZAP, FRED, Vida, and Szybki from Openeye Scientific Software (Santa Fe, N.Mex.); Maestro, Macromodel, and Glide from Schrodinger, LLC (Portland, Oreg.); MOE (Chemical Computing Group, Montreal, Quebec), Allegrow (Boston De Novo, Boston, Mass.), CNS (Brunger, et al., *Acta Crystall. Sect.* D 54:905- 921, 1997) and GOLD (Jones et al., *J. Mol. Biol.* 245:43-53, 1995). The structural coordinates can also be used to visualize the three-dimensional structure of PKCθ using MOLSCRIPT, RASTER3D, or PYMOL (Kraulis, *J. Appi. Crystallogr.* 24: 946-950, 1991; Bacon and Anderson, *J. Mol. Graph.* 6: 219-220, 1998; DeLano, The PYMOL Molecular Graphics System (2002) DeLano Scientific, San Carlos, Calif.).

The agent, whether an inhibitor or activator, may be selected by screening an appropriate database, may be designed de novo by analyzing the steric configurations and charge potentials of an empty PKCθ active site in conjunction with the appropriate software programs, or may be designed using characteristics of known inhibitors or activators to PKCθ or other protein kinases. The method can be used to design or select PKCθ inhibitors or activators. A software system can be designed and/or implemented to facilitate database searching, and/or agent selection and design.

Once an agent has been designed or identified, it may be obtained or synthesized and further evaluated for its effect on PKCθ activity. For example, the agent may be evaluated by contacting the identified agent with PKCθ and measuring the effect of the agent on PKCθ activity. A method for evaluating the agent can include an activity assay performed in vitro or in vivo. For example, the agent can be evaluated by contacting it with PKCθ and measuring the effect of the agent on kinase activity by the polypeptide. Agents can be assessed by their ability to increase or decrease the ability of PKCθ to phosphorylate a peptide substrate, such as a biotinylated peptide substrate FRAKGSLFQ. Reactions can include labelled ATP (e.g., $^{33}$P-ATP), and kinase activity can be monitored by measuring the resulting levels of labelled peptide substrate.

An activity assay, such as a kinase activity assay, can be performed in vivo. For example, the assay can be a cell-based assay.

Depending upon the action of the agent on PKCθ, the agent may act either as an inhibitor or activator of PKCθ activity. The agent also may be contacted with PKCθ in the presence of staurosporine in order to determine whether or not the agent inhibits binding between PKCθ and staurosporine. A crystal containing PKCθ bound to the identified agent can be grown and the structure determined by X-ray crystallography. A second agent can be designed or identified based on the interaction of the first agent with PKCθ.

Various molecular analysis and rational drug design techniques are further disclosed in, for example, U.S. Pat. Nos. 5,834,228, 5,939,528 and 5,856,116, as well as in PCT Application No. PCT/US98/16879, published WO 99/09148, the contents of which are hereby incorporated by reference.

While certain embodiments have been described, other embodiments are also contemplated. As an example, while embodiments involving PKCθ bound to staurosporine have been described, the description herein is more generally directed to any PKCθ polypeptide and any ligand.

EXAMPLE

The C-terminal catalytic domain of human PKCθ, from residue 362 to residue 706, was cloned into a pET-16b expression vector. This vector introduced a hexa-histidine tag to the C-terminus of the expressed protein (see FIG. 3B). The plasmid was used to transform *E. coli* strain BL21-DE3 for overexpression. A 10-liter cell culture was expanded at 37° C. to an $OD_{600}$ of about 0.4. The temperature was then lowered to 25° C. before addition of IPTG to a final concentration of 0.1 mM to induce expression. The cells were grown for an additional 4 hours before they were harvested.

Harvested cells were resuspended in 25 mM Tris pH 8.0, 25 mM NaCl, 5 mM 2-mercaptoethanol, 5 mM imidazole, 50 μM ATP and protease inhibitors, and lysed using a microfluidizer. The lysate was applied to 20 mL of Nickel-NTA resin for 1 hour at 4° C. The resin was subsequently poured as a chromatography column and washed extensively with the same buffer including 25 mM imidazole. Protein bound to the resin was eluted with 200 mM imidazole buffer. The protein was then immediately loaded onto an anion exchanger HQ (high capacity quaternized polyethyleneimine) and the column was washed with 25 mM Tris pH 8.0, 25 mM NaCl, 5 mM DTT, 50 μM ATP before being resolved by the application of a linear gradient from 25 mM to 500 mM NaCl. Fractions containing PKCθ were selected by SDS-PAGE, pooled, and diluted two-fold with 25 mM Tris pH 8.0, 5 mM DTT and loaded onto a heparin chromatography column. The flow-through was immediately applied to a hydroxy-apatite column and washed extensively with 25 mM Tris pH 8.0, 50 mM NaCl, 5 mM DTT. A linear gradient of sodium phosphate from 0 to 100 mM eluted the target protein. The protein was then sized as a monomer on a Superdex 200 size exclusion chromatography column, dialyzed overnight against 25 mM Tris pH 8.0, 50 mM NaCl, 5 mM DTT and concentrated to 7 mg/mL (determined by Bradford assay) before being used for crystallization experiments. The staurosporine was added at a 1:1.2 molar ratio in excess to PKCθ before the final concentration step.

Bacterial extracts expressing the kinase domain were prepared and analyzed for kinase activity in vitro with 5 μg protein each, with a final concentration of 83 μM biotinylated peptide substrate (FRAKGSLFQ) (SEQ ID NO:3), 166 μM ATP, 0.5 μL of $^{33}$P ATP (specific activity 3000 Ci/mmol, 10 mCi/mL), 84 ng/μL phosphatidylserine, 8.4 ng/μL diacylglycerol in 20 mM MOPS pH 7.2, 2 5mM β-glyceraldehyde, 1 mM sodium orthovanadate, 1 mM DTT, 1 mM $CaCl_2$ in a final volume of 30 μL for 30 minutes at room temperature. Purified kinase was assayed for activity using 4-10 nM kinase domain in similar radioactive kinase assays. Kinase reactions were stopped by addition of buffer containing EDTA and transferred to streptavidin-coated scintiplates for washing and radioactivity detection in a plate reader. Alternatively, 5 to 10 μL of the reaction mixture was spotted on phosphocellulose paper and washed three times in 0.75% phosphoric acid and once in acetone. Scintillation cocktail was added to the phosphocellulose paper and bound radioactivity was detected with a scintillation counter. The radioactivity associated with peptide-only and kinase-only control reactions was subtracted from final counts as background.

The solution of PKCθ with staurosporine was concentrated to 7 mg/mL in 50 mM NaCl, 5 mM MgCl2, 5 mM DTT, 25 mM Tris-HCl buffer, at pH 8.0. Crystals were obtained from hanging drops at 18° C. The drop contained 1 μL of protein solution and 1 μL of precipitating solution. The precipitating solution was 2 M ammonium sulfate, 40 mM DTT and 0.1 M Bis-tris, pH 5.0. Crystals were stabilized in cryo-solution containing the crystallization reagent plus 25% glycerol, mounted in nylon loops and flash-frozen in a 100 K nitrogen stream. The X-ray diffraction data were collected to 2 Å resolution at the Advanced Light Source (Berkeley, Calif.) using a Quantum-4 CCD detector (Area Detector Systems), then reduced using HKL2000 software (see Otwinowski and Minor, *Methods Enzymol.* 276:307-326, 1997, which is incorporated by reference in its entirety). Statistics of data collection are given in Table 1.

A sequence alignment showed that human PKCθ and TPK1δ, a cAMP-dependent protein kinase catalytic subunit from *Saccharomyces cerevisiae*, have a sequence identity of 42% and secondary structure similarity of 63%. Phases were calculated by molecular replacement using AMORE with the structure of TPK1δ (Protein Data Bank code 1FOT) as a search model (see *Acta Cryst.* D50, 1994; and Mashhoon et al., *Arch. Biochem. Biophys.* 387:11-19, 2001, each of which is incorporated by reference in its entirety). The rotation and translation function solutions were found using data from 8 to 3.5 Å. The BUSTER program and TNT were used in generating maximum entropy omit maps to reduce model bias and to produce a more detailed map for the bound inhibitor (see Bricogne, *Acta Cryst.* D49:37-60, 1993; and Tronrud, *Methods in Enzymology* 277B, 1997, each of which is incorporated by reference in its entirety). Some residues in the N-lobe, and all flex loops, fit the map poorly. In order to overcome the model bias and to generate better maps for the PKCθ model, an 'average map' was calculated by overlapping seven protein kinase coordinates including those from the 1FOT.pdb data file. The CNS program was used to calculate the average map (see Brunger et al., *Acta Cryst.* D54:905-921, 1998, which is incorporated by reference in its entirety). The resulting electron density maps were more easily interpreted, especially for loop regions in the N-lobe. The model was further rebuilt and refined, and the quality of the model was judged by the decrease in R-factor, $R_{free}$, as well as how the residues fit the maps. Refinement converged after many rebuilding cycles to an R-factor of 0.201 and $R_{free}$ of 0.216. The refinement statistics are given above in Table 1. The final model included coordinates of residues Ile377-Pro649 and Gln688-Phe696, two phosphate groups (as phosphoserine and phosphothreonine, see below), 115 ordered water molecules and one staurosporine molecule. The first 12 residues at the N-terminus, C-terminal region Pro650-Asp687, and the last 10 residues at the C-terminus were not included in the model due to their electron density disorder.

TABLE 1

Statistics of X-Ray Diffraction Data Collection

Crystal and data collection

| | |
|---|---|
| Crystal system | monoclinic |
| Space group | C2 |
| Unit cell dimensions (Å) | a = 139.6, b = 42.4, c = 67.7, β = 116.2° |
| Data collection temperature | 100 K |
| Number of crystals | 1 |
| Radiation source | ALS, Berkeley, CA |
| X-ray wavelength | 1.0 Å |
| Crystal mosaicity | 0.63° |
| Maximum resolution (Å) | 2.0 |
| $R_{merge}$ | 5.8% |

TABLE 1-continued

Statistics of X-Ray Diffraction Data Collection

Phasing and refinement

| | |
|---|---|
| Model for molecular refinement | 1FOT.pdb (TPK1δ, PKA) |
| Construct (aa) | PKCθ 362-706 |
| Refined model (aa) | 377-649, 688-696 |
| Number atoms (protein) | 2353 |
| Water molecules | 115 |
| Phosphorylation sites | Thr538, Ser695 |
| Compound (inhibitor) | 1 staurosporine |
| PKCθ molecules per asymmetric unit | 1 |
| Resolution range | 20-2.0 Å |
| $R_{cryst}$ | 0.201 (19445 reflections) |
| $R_{free}$ | 0.216 (818 reflections) |
| R.m.s. deviations from ideal bond lengths | 0.005 |
| R.m.s. deviations from ideal bond angles | 1.082° |

The structural coordinates of the refined model are presented below in Table 2. In Table 2, the "#" column assigns an index to each atom for which coordinates are given. The "name" column indicates what type of atom, and the "res" column indicates what type of residue the atom belongs to. The "chain" indicates which polypeptide the atom belongs to. "Res #" gives the residue number for the atom. For example, atom number 1 (the first row in Table 2) is the beta carbon (CB) of Ile377. Its x, y, and z structural coordinates are given in the X, Y, and Z columns, respectively. The column headed "occ" describes the occupancy assigned to the atom (1.00=full occupancy), and the "B" column provides B factors (or temperature factors) in units of Å². Coordinates of bound staurosporine are denoted with the entry "STU" in the res column, and phosphothreonine and phosphoserine are denoted by "TPB" and "SPB," respectively.

The overall fold of the catalytic domain of PKCθ was similar to other protein kinases, including those of the AGC family, PKA and PKB/AKT (see Yang et al., *Nature Struct. Biology* 9:940-944, 2002, which is incorporated by reference in its entirety). A ribbon diagram shown in FIG. 1 illustrates the conserved core of the structure, a small N-terminal lobe (residues 377-461) and a large C-terminal lobe (residues 466-696), connected by a flexible polypeptide linker (residues 462-465, NGGD), which functions as a hinge. The N-terminal lobe included a five-stranded β-sheet (β1-β5) and two alpha helices (αB and αC), and the C-terminal lobe was mostly helical having eight α-helices (αD-αK) and four β-strands (β6-β9).

The ATP-binding pocket was occupied by staurosporine and was located near the hinge segment at the interface of the two lobes. The nucleotide-binding loop between β strands 1 and 2 (residues 386-394), also termed the glycine-rich loop (LGxGxxGxV) (SEQ ID NO:4), shows considerable structural variability in many protein kinases (see Bossemeyer et al., *Trends Biochem. Sci.* 19:201-205, 1994, which is incorporated by reference in its entirety). In the PKCθ structure, the glycine-rich loop adopted a closed, fixed conformation as a result of staurosporine binding. The key catalytic residues that are invariant in all kinases were present in the PKCθ structure. These residues preserved intramolecular interactions observed in other active kinase structures, in accordance with structural criteria used to define catalytically active kinase conformations (see Huse and Kuriyan, *Cell* 109:257-282, 2002, which is incorporated by reference in its entirety).

As in most Ser/Thr kinase structures reflecting active enzymes (Johnson et al., *Cell* 85:149-158, 1996, which is incorporated by reference in its entirety), the activation segment of the C-lobe (residues 526-540) was well ordered, adopted an extended conformation and had a phosphorylated Thr at position 538. The phosphorylation of Thr538 indicated autophosphorylation (as opposed to phosphorylation catalyzed by another enzyme) of the activation segment, as the kinase domain is expressed in *E. coli*. Some of the ionic interactions, in particular between phosphothreonine 538 and positively charged Arg 503 and Lys 527, were similar to the equivalent interactions in PKA and PKB, whereas there were clear differences between those involving helix αC (see below).

The C-terminal hydrophobic motif (HM, sequence: FxxFS*, where * represents phosphorylation of the serine side chain), is a conserved feature across the AGC family. In the PKCθ structure, Ser695 was phosphorylated and was adjacent to the hydrophobic groove of the N-lobe, in a location similar to the FXXF-binding pocket in PKA and PKB. The HM motif is also autophosphorylated by the PKCθ kinase domain. It has been suggested that phosphorylation of the HM serine stabilizes the active conformation of AGC kinases by promoting tight intramolecular association between the HM and the N-lobe (see Yang et al., *Nature Struct. Biology* 9:940-944, 2002). Interactions between the characteristic aromatic residues, phosphoserine 695 and the hydrophobic groove of the N-lobe were preserved, indicating that phosphoserine 695 plays a similar role in PKCθ as in PKA and PKB.

Staurosporine is a natural product protein kinase inhibitor that has low nanomolar potency against PKC isoforms, but only micromolar potency against other protein kinases such as casein kinase 1 (CK1), casein kinase 2 (CK2), mitogen-activated protein kinase (MAPK) and CSK (see Meggio et al., *Eur. J. Biochem.* 234:317-22, 1995, which is incorporated by reference in its entirety). Because of this selectivity, staurosporine has been used as a pharmacophore model for targeting the catalytic site of kinases for rational drug design.

Figure 2:
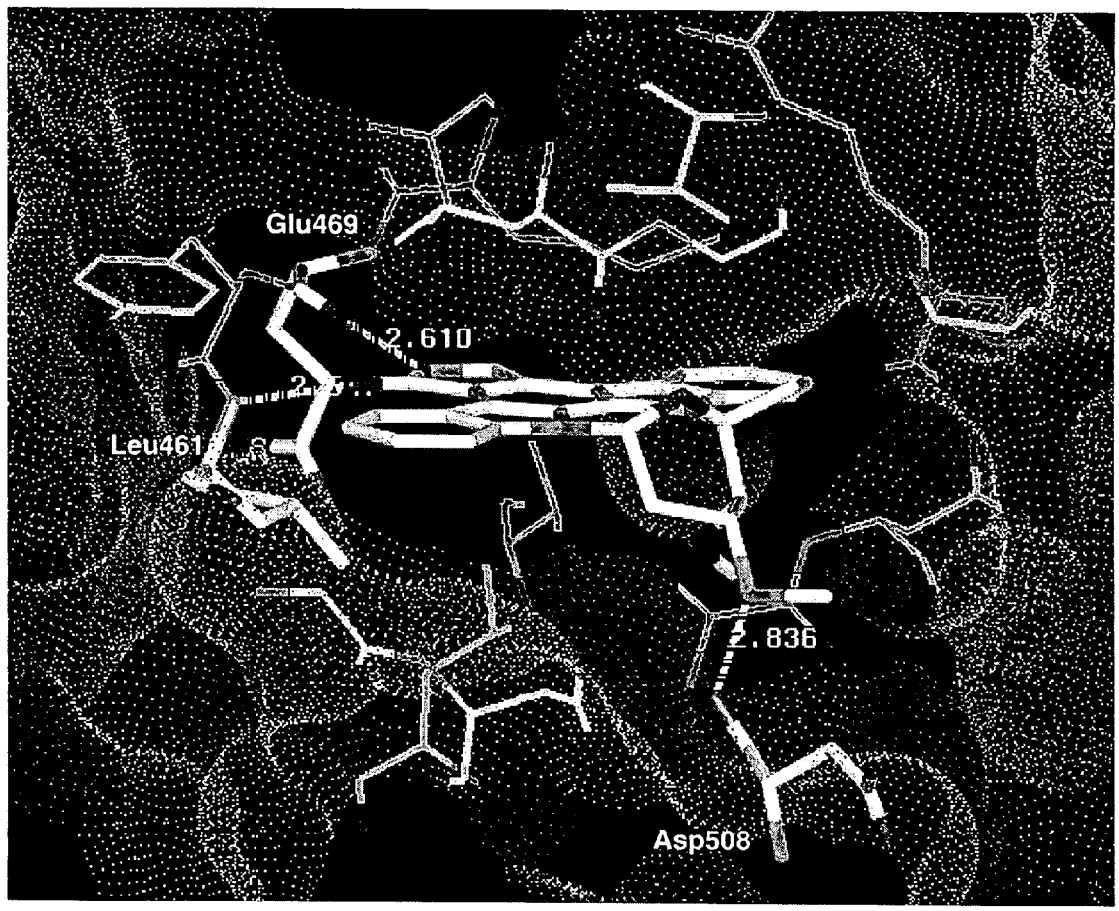
FIG. 2 is a diagram of staurosporine bound to human PKCθ based on experimental structural coordinates.

Staurosporine occupied the adenosine-binding pocket of PKCθ. The inhibitor formed three hydrogen bonds with the backbone of the enzyme and made extensive van der Waals contacts within a deep hydrophobic cleft between the N- and C-lobes. See FIG. 2, which shows van der Waals contacts between staurosporine and PKCθ in the ATP-binding site. The hydrogen-bonding motif involved interactions between the lactam ring of staurosporine and backbone atoms of Glu459 and Leu461, and between the glycosidic ring and carbonyl oxygen of Asp508. The majority of nonpolar interactions came from the glycine-rich loop residues (Leu386, Gly387, Gly389, Val394) and the remaining interactions involved four residues from the N-terminal lobe (Ala407, Lys409, Met458, and Tyr460) and nine residues from the C-terminal lobe (Leu461, Gly464, Leu466, Leu511, Ala521, Val422, Asn509, Ala521, and Asp522).

There were significant differences in staurosporine-PKCθ contacts when compared to structures of the PKA and CDK2 kinases bound to staurosporine. First, staurosporine made only three hydrogen bonds with PKCθ as opposed to the four potential hydrogen bond contacts in both PKA and CDK2. A significant difference lay in the glycine-rich loop. Specifically, in contrast to PKA and CDK2, accommodation of staurosporine in PKCθ led to the full closure of the glycine-rich loop. As a result, the backbone and side-chain residues in this region (residues 388-392) moved deeper into the ATP-binding pocket adopting positions that would clash with ATP, thereby making significantly more non-polar contacts with staurosporine. Similar shifts of the equivalent residues have been observed upon staurosporine binding to MK2 (Underwood et al., *Structure* 11:627-636, 2003, which is incorporated by reference in its entirety).

The activation segment is a highly variable structural element that is critical for regulation and catalytic activity of protein kinases. This region acts as a docking site for activating or inactivating cofactors (see Engh and Bossemeyer, *Pharmrcology & Therapeutics* 93:99-111, 2002, which is incorporated by reference in its entirety) and provides the P+1 pocket for accommodation of peptide substrates. Like in other Ser/Thr protein kinases, the activation segment of PKCθ (residues 522-543) is located between the invariant DFG and TPD motifs and includes a highly conserved phosphorylation site at Thr538. Indeed, clear electron density for the phosphate group attached to this residue was observed, indicating that Thr538 was phosphorylated autocatalytically during expression in *E. coli*. Interestingly, the sequence flanking the phosphorylated Thr538 (KTNT*F, where * represents phosphorylation) contains a positively charged residue at position −3, which is compatible with the preferred substrate sequence recognized by PKC subfamily (RXXT*/S*F) (see Nishikawa et al., *J. Biol. Chem.* 272:952-60, 1997, which is incorporated by reference in its entirety). Unlike the majority of PKC isoforms which lack this basic residue, the presence of Lys535 suggests a possibility for PKCθ to phosphorylate itself on Thr538, and is consistent with the determination the K409W mutant of full-length PKCθ is not phosphorylated at the activation loop and is inactive (see Liu et al., *Biochem. J.* 361:255-265, 2002, which is incorporated by reference in its entirety). Likewise, the K409W mutant of the catalytic domain of PKCθ was not phosphorylated at the activation loop and was inactive.

Structural results have suggested that the key role for the phosphate group in the activation segment is to compensate for a cluster of positively charged residues that point towards the activation segment. In PKCθ, the phosphorylated Thr538 formed two hydrogen bonds with Arg503 and one hydrogen bond with Lys527. This network of interactions is highly conserved in many protein kinases and plays an important role in activation. Specifically, ionic interactions of the Thr538 phosphate through conserved Arg503 can provide a direct link to the catalytic loop helping stabilize the correct orientation of the catalytic base, Asp504. In addition to the electrostatic interaction with basic residues, the phosphorylated Thr538 was also hydrogen bonded to the side chain oxygen of Thr536. In vitro activity studies of full length PKCθ immunoprecipitated from transfected HEK293 cells demonstrated that the Thr538Glu mutant was 3-fold less active than the wild-type enzyme (see Liu et al., *Biochem. J.* 361:255-265, 2002). This is consistent with the finding that all three oxygen atoms of the phosphate group are involved in direct ionic interactions with the protein, indicating that the glutamic acid at this position would provide only a partial mimic of the phosphoamino acid. Overall, these ionic contacts can stabilize the conformation of the phosphorylated activation loop, similar to that observed in active states of PKA and PKB.

Within the PKC subfamily, phosphorylation at the activation segment Thr is distinct between PKCθ, PKCκ, and PKCδ. PKCδ, in contrast to both PKCθ and PKCκ, does not require the activation segment Thr for activity. PKCδ presumably utilizes the nearby Glu500 residue to maintain some of the ionic interactions that described above for the phosphorylated PKCθ kinase domain. Interestingly, Glu500 is unique to PKCδ and not seen on other PKC isoforms. Consistent with this and again in contrast to PKCθ, the Thr to Glu acid substitution on PKCδ serves only to enhance the kinase activity in comparison with wild type (see Liu et al., *Biochem. J.* 361:255-265, 2002), presumably by facilitating the additional ionic interactions with the protein. Unlike PKCθ, the PKCκ activation segment Thr is not capable of autophosphorylation and is reported to be phosphorylated by PDK-1 (see Cenni et al., *Biochem. J.* 363:537-545, 2002, which is incorporated by reference in its entirety). PDK-1 association with PKCθ has been reported also (see Liu et al., *Biochem. J.* 361:255-265, 2002). However, the PKCθ kinase domain can autophosphorylate the activation segment Thr.

In addition to distinctions within the PKC novel subfamily, details of interactions involved in structural coupling between the activation loop and helix αC were quite different in PKCθ compared to other AGC kinases, including PKA or PKB. As in other kinases, the αC helix links together the N-lobe, the C-lobe and the active site. See FIG. 1. Glu428, the invariant glutamate residue at the N-terminus of the helix, formed an ion pair with the invariant lysine residue in the catalytic center, Lys409, and made direct contacts with the conserved DFG motif of the activation segment. A K409R mutation eliminated the catalytic activity of PKCθ (see Villalba and Altman, *Current Cancer Drug Targets* 2:125-137, 2002, which is incorporated by reference in its entirety).

In both PKA and PKB, helix αC provided a basic residue (His87 in PKA and His196 in PKB) to contact the phosphoamino acid. In PKCθ, the structurally equivalent residue is Cys424. Due to this sequence difference, the equivalent ion pair was absent from PKCθ. Instead, a new hydrogen bonding pattern was observed that links the αC helix directly to the activation segment, but did not engage the phosphate group. This pairing scheme involved electrostatic interaction between Glu528 from the N-terminal part of the activation segment and Arg430 from the αC helix. Thus, the structural role of the invariant histidine-phosphothreonine contact to promote the correct lobe orientation in PKA and PKB, can be accomplished in PKCθ by the alternative ion pair involving Glu528 and Arg430.

PKCθ, like other protein kinases, has two additional conserved phosphorylation sites referred to as the turn motif (residues 657-685) and the hydrophobic motif (HM) FxxFS* (residues 691-695). In the PKCθ structure, the region corresponding to the turn motif was completely disordered. There was no clearly defined electron density for residues 650-687. Residues 697-706 were also disordered. Unlike the hydrophobic motif (HM) of PKB, which has a stretch of 17 well-ordered amino acid residues, the HM of PKCθ was considerably shorter (residues 688-696) and showed high B-factor values, indicating disorder in this segment. Together these observations suggested that the turn motif and the HM of PKCθ were inherently flexible, either in this particular crystal form or due to the absence of kinase substrates.

The phosphate group attached at Ser695 of PKCθ had clear electron density and formed two hydrogen bonds with Gln449—one with its side chain atom and another one with its main chain amide nitrogen. The observed hydrogen bonding pattern was consistent with the results of the analysis of PKCθ activity in vitro. Substitution of glutamic acid for serine at this position in full-length PKCθ (i.e., the Ser695Glu mutant) was a satisfactory mimic of the PKCθ HM phosphorylation. Full length PKCθ Ser695Glu had 60% of the catalytic activity of wild type full length PKCθ. (see Liu et al., *Biochem. J.,* 361:255-265, 2002).

There were also extensive hydrophobic contacts between the HM motif and the hydrophobic groove of the N-lobe. These involved the invariant phenylalanine residues (Phe691 and Phe694) and residues from the αB and αC helices and the β5 strand (Lys413, Val416, Leu417, Val422, Met426, Lys429, Thr447, Leu454 and Phe456). Together these interactions can play an important structural role in stabilizing ordered conformations of the αB and αC helices. The equivalent phenylalanine residues in PKA and PKB were shown to be essential for the stability and catalytic activity of these enzymes (see Balendran et al., *Curr. Biol.* 9:393-404, 1999; and Alessi et al., *EMBO J.* 15:6541-6551, 1996, each of which is incorporated by reference in its entirety).

The HM phosphorylation of PKCθ was required for optimal enzyme activity, with 5-fold reduction of kinase activity in the full length PKCθ Ser695Ala mutant immunoprecipitated from transfected HEK293 cells (see Liu et al., *Biochem. J.* 361:255-265, 2002). The PKCθ mutant T538A had completely lost phosphorylation of its hydrophobic motif, indicating that the HM region represents a site of autophosphorylation. See Lang and Cohen, *Sci. STKE* 108:RE17, 2001; and Yang et al., *Molecular Cell* 9:1227-1240, 2002, each of which is incorporated by reference in its entirety. By mutation analysis of the kinase domain expressed in *E. coli*, we have shown that the Ser695Ala catalytic domain mutant has completely lost phosphorylation of the activation segment at Thr538, suggesting that PKCθ autophosphorylation involves both the HM and activation segment phosphorylation as the initial activation mechanism.

The inactive and active conformations of other published AGC kinases, including their phosphorylated and non- or partially-phosphorylated counterparts, displayed different structural features. These differences, in addition to conformational changes seen in the activation segment and in the C-terminal hydrophobic motif, involved the relative disposition of the N- and C-lobes associated with structural disorder or misalignment of the αB and αC helices in the N-lobe. Like PKB and PKA (which were crystallized in their active state), the αB and αC helices, activation segment and HM of PKCθ were well ordered and were aligned with respect to the catalytic site residues. This stands in contrast to the corresponding regions of inactive PKA and PKB, which were characterized by a conformational disorder or structural misalignment.

Moreover, a detailed comparison of PKCθ with two so far reported main conformational states of protein kinases referred to as "open" and "closed" showed that the kinase domain of PKCθ in complex with staurosporine adopted a unique partially closed conformation (see Biondi et al., *EMBO J.* 21:4219-4228, 2002, which is incorporated by reference in its entirety). Two classification criteria were applied to distinguish between open and closed conformation: opening of the glycine-rich loop (based on distance Ser53-Gly186 in the PKA structure) and positioning of the αC-helix (based on the distance between His87 and phosphorylated Thr197). See Taylor et al., *Annu. Rev. Cell. Biol.* 8:429-62, 1992, which is incorporated by reference in its entirety. In order to avoid possible complications related with sequence discrepancy at structurally equivalent positions, and hence make these criteria applicable to PKCθ, the distances between the Cα-atoms of corresponding residues were measured instead. The results of this comparison indicated that, expect for the glycine-rich loop, the relative disposition of the lobes in PKCθ showed most similarity to 'intermediate' kinase structures: PKA in complex with inhibitors staurosporine or balanol and PDK1 in complex with ATP. Thus, the catalytic domain of PCKθ displayed an 'intermediate' conformation along with the full closure of the glycine rich-loop upon staurosporine binding, i.e., a partially closed conformation.

TABLE 2

Structure coordinates for PKCθ
(residues 377-696 of SEQ ID NO: 1)/staurosporine complex

|  | # | name | res | chain | res # | X | Y | Z | occ | B |
|---|---|---|---|---|---|---|---|---|---|---|
| ATOM | 1 | CB | ILE | A | 377 | 61.260 | 10.244 | −14.257 | 1.00 | 43.86 |
| ATOM | 2 | CG2 | ILE | A | 377 | 61.609 | 9.554 | −15.554 | 1.00 | 44.55 |
| ATOM | 3 | CG1 | ILE | A | 377 | 61.570 | 9.315 | −13.080 | 1.00 | 43.99 |
| ATOM | 4 | CD1 | ILE | A | 377 | 60.966 | 9.772 | −11.760 | 1.00 | 43.08 |
| ATOM | 5 | C | ILE | A | 377 | 63.544 | 11.244 | −14.112 | 1.00 | 43.99 |
| ATOM | 6 | O | ILE | A | 377 | 64.112 | 10.883 | −13.080 | 1.00 | 43.10 |
| ATOM | 7 | N | ILE | A | 377 | 61.751 | 12.499 | −15.245 | 1.00 | 43.07 |
| ATOM | 8 | CA | ILE | A | 377 | 62.055 | 11.565 | −14.122 | 1.00 | 43.87 |
| ATOM | 9 | N | GLU | A | 378 | 64.172 | 11.377 | −15.274 | 1.00 | 43.76 |
| ATOM | 10 | CA | GLU | A | 378 | 65.594 | 11.119 | −15.386 | 1.00 | 43.81 |
| ATOM | 11 | CB | GLU | A | 378 | 65.990 | 10.928 | −16.858 | 1.00 | 46.16 |
| ATOM | 12 | CG | GLU | A | 378 | 65.811 | 9.502 | −17.392 | 1.00 | 49.37 |
| ATOM | 13 | CD | GLU | A | 378 | 64.371 | 9.163 | −17.775 | 1.00 | 51.62 |
| ATOM | 14 | OE1 | GLU | A | 378 | 63.490 | 10.047 | −17.676 | 1.00 | 52.31 |
| ATOM | 15 | OE2 | GLU | A | 378 | 64.121 | 8.005 | −18.185 | 1.00 | 53.49 |
| ATOM | 16 | C | GLU | A | 378 | 66.372 | 12.276 | −14.759 | 1.00 | 41.90 |
| ATOM | 17 | O | GLU | A | 378 | 67.591 | 12.205 | −14.607 | 1.00 | 42.24 |
| ATOM | 18 | N | ASP | A | 379 | 65.658 | 13.337 | −14.389 | 1.00 | 39.92 |
| ATOM | 19 | CA | ASP | A | 379 | 66.282 | 14.490 | −13.750 | 1.00 | 38.76 |
| ATOM | 20 | CB | ASP | A | 379 | 65.432 | 15.747 | −13.930 | 1.00 | 39.52 |
| ATOM | 21 | CG | ASP | A | 379 | 65.225 | 16.104 | −15.383 | 1.00 | 40.80 |
| ATOM | 22 | OD1 | ASP | A | 379 | 66.099 | 15.764 | −16.208 | 1.00 | 42.30 |
| ATOM | 23 | OD2 | ASP | A | 379 | 64.195 | 16.736 | −15.698 | 1.00 | 41.13 |
| ATOM | 24 | C | ASP | A | 379 | 66.435 | 14.206 | −12.259 | 1.00 | 36.67 |
| ATOM | 25 | O | ASP | A | 379 | 66.997 | 15.005 | −11.514 | 1.00 | 36.14 |
| ATOM | 26 | N | PHE | A | 380 | 65.927 | 13.054 | −11.838 | 1.00 | 34.33 |
| ATOM | 27 | CA | PHE | A | 380 | 65.990 | 12.649 | −10.443 | 1.00 | 32.84 |
| ATOM | 28 | CB | PHE | A | 380 | 64.579 | 12.429 | −9.885 | 1.00 | 31.32 |
| ATOM | 29 | CG | PHE | A | 380 | 63.740 | 13.675 | −9.801 | 1.00 | 30.09 |
| ATOM | 30 | CD1 | PHE | A | 380 | 63.842 | 14.526 | −8.706 | 1.00 | 29.54 |
| ATOM | 31 | CD2 | PHE | A | 380 | 62.821 | 13.978 | −10.802 | 1.00 | 29.70 |
| ATOM | 32 | CE1 | PHE | A | 380 | 63.039 | 15.660 | −8.605 | 1.00 | 29.54 |
| ATOM | 33 | CE2 | PHE | A | 380 | 62.012 | 15.107 | −10.713 | 1.00 | 29.34 |
| ATOM | 34 | CZ | PHE | A | 380 | 62.120 | 15.952 | −9.610 | 1.00 | 30.14 |
| ATOM | 35 | C | PHE | A | 380 | 66.753 | 11.341 | −10.305 | 1.00 | 32.62 |
| ATOM | 36 | O | PHE | A | 380 | 66.767 | 10.518 | −11.220 | 1.00 | 31.48 |
| ATOM | 37 | N | ILE | A | 381 | 67.392 | 11.165 | −9.155 | 1.00 | 32.46 |
| ATOM | 38 | CA | ILE | A | 381 | 68.098 | 9.932 | −8.855 | 1.00 | 31.18 |
| ATOM | 39 | CB | ILE | A | 381 | 69.502 | 10.179 | −8.239 | 1.00 | 31.14 |
| ATOM | 40 | CG2 | ILE | A | 381 | 70.088 | 8.862 | −7.738 | 1.00 | 29.68 |
| ATOM | 41 | CG1 | ILE | A | 381 | 70.438 | 10.794 | −9.282 | 1.00 | 31.75 |
| ATOM | 42 | CD1 | ILE | A | 381 | 71.799 | 11.184 | −8.733 | 1.00 | 31.78 |
| ATOM | 43 | C | ILE | A | 381 | 67.208 | 9.284 | −7.799 | 1.00 | 31.29 |
| ATOM | 44 | O | ILE | A | 381 | 66.887 | 9.907 | −6.784 | 1.00 | 31.14 |
| ATOM | 45 | N | LEU | A | 382 | 66.787 | 8.051 | −8.047 | 1.00 | 30.65 |
| ATOM | 46 | CA | LEU | A | 382 | 65.940 | 7.347 | −7.098 | 1.00 | 31.26 |
| ATOM | 47 | CB | LEU | A | 382 | 64.956 | 6.435 | −7.837 | 1.00 | 30.86 |
| ATOM | 48 | CG | LEU | A | 382 | 64.040 | 7.140 | −8.842 | 1.00 | 30.89 |
| ATOM | 49 | CD1 | LEU | A | 382 | 62.943 | 6.182 | −9.275 | 1.00 | 31.47 |
| ATOM | 50 | CD2 | LEU | A | 382 | 63.421 | 8.378 | −8.213 | 1.00 | 31.32 |
| ATOM | 51 | C | LEU | A | 382 | 66.830 | 6.535 | −6.172 | 1.00 | 31.58 |
| ATOM | 52 | O | LEU | A | 382 | 67.157 | 5.382 | −6.454 | 1.00 | 31.79 |
| ATOM | 53 | N | HIS | A | 383 | 67.220 | 7.160 | −5.066 | 1.00 | 31.52 |
| ATOM | 54 | CA | HIS | A | 383 | 68.102 | 6.545 | −4.086 | 1.00 | 32.64 |
| ATOM | 55 | CB | HIS | A | 383 | 68.499 | 7.589 | −3.043 | 1.00 | 32.11 |
| ATOM | 56 | CG | HIS | A | 383 | 69.340 | 8.697 | −3.596 | 1.00 | 31.41 |
| ATOM | 57 | CD2 | HIS | A | 383 | 69.024 | 9.963 | −3.956 | 1.00 | 30.95 |
| ATOM | 58 | ND1 | HIS | A | 383 | 70.683 | 8.548 | −3.866 | 1.00 | 32.34 |
| ATOM | 59 | CE1 | HIS | A | 383 | 71.158 | 9.673 | −4.369 | 1.00 | 31.11 |
| ATOM | 60 | NE2 | HIS | A | 383 | 70.171 | 10.547 | −4.434 | 1.00 | 30.71 |
| ATOM | 61 | C | HIS | A | 383 | 67.533 | 5.313 | −3.393 | 1.00 | 34.22 |
| ATOM | 62 | O | HIS | A | 383 | 68.239 | 4.320 | −3.207 | 1.00 | 34.52 |
| ATOM | 63 | N | LYS | A | 384 | 66.266 | 5.373 | −3.001 | 1.00 | 35.09 |
| ATOM | 64 | CA | LYS | A | 384 | 65.653 | 4.235 | −2.329 | 1.00 | 36.72 |
| ATOM | 65 | CB | LYS | A | 384 | 66.178 | 4.120 | −0.897 | 1.00 | 37.82 |
| ATOM | 66 | CG | LYS | A | 384 | 65.945 | 5.359 | −0.043 | 1.00 | 39.26 |
| ATOM | 67 | CD | LYS | A | 384 | 66.465 | 5.158 | 1.375 | 1.00 | 40.56 |
| ATOM | 68 | CE | LYS | A | 384 | 67.963 | 4.875 | 1.390 | 1.00 | 41.12 |
| ATOM | 69 | NZ | LYS | A | 384 | 68.460 | 4.568 | 2.761 | 1.00 | 41.51 |
| ATOM | 70 | C | LYS | A | 384 | 64.139 | 4.302 | −2.296 | 1.00 | 36.60 |
| ATOM | 71 | O | LYS | A | 384 | 63.540 | 5.347 | −2.544 | 1.00 | 36.73 |
| ATOM | 72 | N | MET | A | 385 | 63.525 | 3.170 | −1.988 | 1.00 | 37.13 |
| ATOM | 73 | CA | MET | A | 385 | 62.080 | 3.097 | −1.905 | 1.00 | 38.73 |
| ATOM | 74 | CB | MET | A | 385 | 61.592 | 1.735 | −2.380 | 1.00 | 40.93 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 75 | CG | MET | A | 385 | 60.096 | 1.656 | −2.427 | 1.00 | 44.71 |
| ATOM | 76 | SD | MET | A | 385 | 59.474 | −0.006 | −2.554 | 1.00 | 49.30 |
| ATOM | 77 | CE | MET | A | 385 | 57.783 | 0.362 | −2.870 | 1.00 | 48.67 |
| ATOM | 78 | C | MET | A | 385 | 61.655 | 3.310 | −0.457 | 1.00 | 38.14 |
| ATOM | 79 | O | MET | A | 385 | 62.022 | 2.529 | 0.422 | 1.00 | 38.59 |
| ATOM | 80 | N | LEU | A | 386 | 60.893 | 4.373 | −0.208 | 1.00 | 37.50 |
| ATOM | 81 | CA | LEU | A | 386 | 60.426 | 4.677 | 1.143 | 1.00 | 36.58 |
| ATOM | 82 | CB | LEU | A | 386 | 59.989 | 6.140 | 1.240 | 1.00 | 35.18 |
| ATOM | 83 | CG | LEU | A | 386 | 61.064 | 7.205 | 1.016 | 1.00 | 34.48 |
| ATOM | 84 | CD1 | LEU | A | 386 | 60.429 | 8.595 | 1.020 | 1.00 | 33.98 |
| ATOM | 85 | CD2 | LEU | A | 386 | 62.122 | 7.097 | 2.101 | 1.00 | 34.59 |
| ATOM | 86 | C | LEU | A | 386 | 59.268 | 3.769 | 1.538 | 1.00 | 37.02 |
| ATOM | 87 | O | LEU | A | 386 | 59.131 | 3.396 | 2.703 | 1.00 | 36.40 |
| ATOM | 88 | N | GLY | A | 387 | 58.436 | 3.419 | 0.566 | 1.00 | 37.86 |
| ATOM | 89 | CA | GLY | A | 387 | 57.307 | 2.549 | 0.843 | 1.00 | 40.15 |
| ATOM | 90 | C | GLY | A | 387 | 56.221 | 2.648 | −0.207 | 1.00 | 42.28 |
| ATOM | 91 | O | GLY | A | 387 | 56.404 | 3.282 | −1.246 | 1.00 | 42.47 |
| ATOM | 92 | N | LYS | A | 388 | 55.085 | 2.017 | 0.064 | 1.00 | 44.15 |
| ATOM | 93 | CA | LYS | A | 388 | 53.955 | 2.041 | −0.857 | 1.00 | 46.93 |
| ATOM | 94 | CB | LYS | A | 388 | 53.636 | 0.623 | −1.336 | 1.00 | 48.32 |
| ATOM | 95 | CG | LYS | A | 388 | 53.521 | −0.388 | −0.215 | 1.00 | 50.61 |
| ATOM | 96 | CD | LYS | A | 388 | 53.366 | −1.797 | −0.753 | 1.00 | 52.47 |
| ATOM | 97 | CE | LYS | A | 388 | 53.307 | −2.813 | 0.382 | 1.00 | 53.23 |
| ATOM | 98 | NZ | LYS | A | 388 | 53.228 | −4.212 | −0.129 | 1.00 | 53.72 |
| ATOM | 99 | C | LYS | A | 388 | 52.744 | 2.651 | −0.159 | 1.00 | 48.02 |
| ATOM | 100 | O | LYS | A | 388 | 52.312 | 2.171 | 0.891 | 1.00 | 47.70 |
| ATOM | 101 | N | GLY | A | 389 | 52.210 | 3.723 | −0.733 | 1.00 | 49.03 |
| ATOM | 102 | CA | GLY | A | 389 | 51.059 | 4.372 | −0.130 | 1.00 | 50.80 |
| ATOM | 103 | C | GLY | A | 389 | 49.775 | 4.026 | −0.849 | 1.00 | 52.03 |
| ATOM | 104 | O | GLY | A | 389 | 49.770 | 3.105 | −1.675 | 1.00 | 51.88 |
| ATOM | 105 | N | SER | A | 390 | 48.697 | 4.747 | −0.528 | 1.00 | 53.06 |
| ATOM | 106 | CA | SER | A | 390 | 47.383 | 4.550 | −1.163 | 1.00 | 53.97 |
| ATOM | 107 | CB | SER | A | 390 | 46.682 | 5.903 | −1.340 | 1.00 | 54.09 |
| ATOM | 108 | OG | SER | A | 390 | 47.548 | 6.810 | −1.995 | 1.00 | 55.74 |
| ATOM | 109 | C | SER | A | 390 | 47.577 | 3.868 | −2.491 | 1.00 | 54.31 |
| ATOM | 110 | O | SER | A | 390 | 47.163 | 2.719 | −2.676 | 1.00 | 54.56 |
| ATOM | 111 | N | PHE | A | 391 | 48.192 | 4.586 | −3.425 | 1.00 | 54.43 |
| ATOM | 112 | CA | PHE | A | 391 | 48.541 | 3.992 | −4.720 | 1.00 | 54.69 |
| ATOM | 113 | CB | PHE | A | 391 | 47.506 | 4.274 | −5.842 | 1.00 | 56.06 |
| ATOM | 114 | CG | PHE | A | 391 | 46.793 | 5.613 | −5.742 | 1.00 | 57.62 |
| ATOM | 115 | CD1 | PHE | A | 391 | 47.502 | 6.795 | −5.798 | 1.00 | 58.68 |
| ATOM | 116 | CD2 | PHE | A | 391 | 45.391 | 5.667 | −5.801 | 1.00 | 58.30 |
| ATOM | 117 | CE1 | PHE | A | 391 | 46.874 | 8.022 | −5.926 | 1.00 | 58.76 |
| ATOM | 118 | CE2 | PHE | A | 391 | 44.730 | 6.919 | −5.934 | 1.00 | 59.27 |
| ATOM | 119 | CZ | PHE | A | 391 | 45.484 | 8.096 | −5.998 | 1.00 | 58.75 |
| ATOM | 120 | C | PHE | A | 391 | 49.926 | 4.425 | −5.163 | 1.00 | 53.64 |
| ATOM | 121 | O | PHE | A | 391 | 50.395 | 5.511 | −4.831 | 1.00 | 54.01 |
| ATOM | 122 | N | GLY | A | 392 | 50.598 | 3.542 | −5.888 | 1.00 | 51.85 |
| ATOM | 123 | CA | GLY | A | 392 | 51.936 | 3.838 | −6.377 | 1.00 | 49.32 |
| ATOM | 124 | C | GLY | A | 392 | 52.965 | 3.758 | −5.276 | 1.00 | 47.28 |
| ATOM | 125 | O | GLY | A | 392 | 52.628 | 3.815 | −4.097 | 1.00 | 47.40 |
| ATOM | 126 | N | LYS | A | 393 | 54.222 | 3.624 | −5.671 | 1.00 | 44.62 |
| ATOM | 127 | CA | LYS | A | 393 | 55.312 | 3.526 | −4.724 | 1.00 | 40.96 |
| ATOM | 128 | CB | LYS | A | 393 | 56.394 | 2.601 | −5.284 | 1.00 | 43.12 |
| ATOM | 129 | CG | LYS | A | 393 | 55.882 | 1.238 | −5.751 | 1.00 | 45.23 |
| ATOM | 130 | CD | LYS | A | 393 | 55.351 | 0.417 | −4.584 | 1.00 | 47.97 |
| ATOM | 131 | CE | LYS | A | 393 | 55.013 | −1.016 | −4.985 | 1.00 | 49.61 |
| ATOM | 132 | NZ | LYS | A | 393 | 54.591 | −1.834 | −3.799 | 1.00 | 51.11 |
| ATOM | 133 | C | LYS | A | 393 | 55.902 | 4.906 | −4.447 | 1.00 | 37.45 |
| ATOM | 134 | O | LYS | A | 393 | 55.762 | 5.818 | −5.258 | 1.00 | 35.26 |
| ATOM | 135 | N | VAL | A | 394 | 56.552 | 5.062 | −3.295 | 1.00 | 34.25 |
| ATOM | 136 | CA | VAL | A | 394 | 57.168 | 6.338 | −2.941 | 1.00 | 31.12 |
| ATOM | 137 | CB | VAL | A | 394 | 56.580 | 6.905 | −1.638 | 1.00 | 31.15 |
| ATOM | 138 | CG1 | VAL | A | 394 | 57.249 | 8.238 | −1.304 | 1.00 | 29.93 |
| ATOM | 139 | CG2 | VAL | A | 394 | 55.072 | 7.079 | −1.793 | 1.00 | 28.47 |
| ATOM | 140 | C | VAL | A | 394 | 58.674 | 6.163 | −2.791 | 1.00 | 30.07 |
| ATOM | 141 | O | VAL | A | 394 | 59.137 | 5.286 | −2.061 | 1.00 | 28.52 |
| ATOM | 142 | N | PHE | A | 395 | 59.429 | 7.013 | −3.483 | 1.00 | 28.61 |
| ATOM | 143 | CA | PHE | A | 395 | 60.887 | 6.949 | −3.477 | 1.00 | 28.02 |
| ATOM | 144 | CB | PHE | A | 395 | 61.406 | 6.719 | −4.902 | 1.00 | 28.94 |
| ATOM | 145 | CG | PHE | A | 395 | 60.877 | 5.477 | −5.561 | 1.00 | 30.73 |
| ATOM | 146 | CD1 | PHE | A | 395 | 61.538 | 4.262 | −5.416 | 1.00 | 31.92 |
| ATOM | 147 | CD2 | PHE | A | 395 | 59.718 | 5.520 | −6.329 | 1.00 | 31.34 |
| ATOM | 148 | CE1 | PHE | A | 395 | 61.055 | 3.106 | −6.030 | 1.00 | 32.16 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 149 | CE2 | PHE | A | 395 | 59.224 | 4.368 | −6.947 | 1.00 | 33.06 |
| ATOM | 150 | CZ | PHE | A | 395 | 59.894 | 3.159 | −6.796 | 1.00 | 32.73 |
| ATOM | 151 | C | PHE | A | 395 | 61.557 | 8.213 | −2.956 | 1.00 | 26.85 |
| ATOM | 152 | O | PHE | A | 395 | 61.037 | 9.315 | −3.117 | 1.00 | 27.10 |
| ATOM | 153 | N | LEU | A | 396 | 62.716 | 8.041 | −2.329 | 1.00 | 26.25 |
| ATOM | 154 | CA | LEU | A | 396 | 63.498 | 9.175 | −1.863 | 1.00 | 26.29 |
| ATOM | 155 | CB | LEU | A | 396 | 64.519 | 8.733 | −0.811 | 1.00 | 26.87 |
| ATOM | 156 | CG | LEU | A | 396 | 65.623 | 9.721 | −0.408 | 1.00 | 28.36 |
| ATOM | 157 | CD1 | LEU | A | 396 | 65.023 | 11.005 | 0.163 | 1.00 | 27.25 |
| ATOM | 158 | CD2 | LEU | A | 396 | 66.534 | 9.047 | 0.614 | 1.00 | 27.56 |
| ATOM | 159 | C | LEU | A | 396 | 64.201 | 9.574 | −3.155 | 1.00 | 25.98 |
| ATOM | 160 | O | LEU | A | 396 | 64.960 | 8.784 | −3.718 | 1.00 | 26.49 |
| ATOM | 161 | N | ALA | A | 397 | 63.932 | 10.781 | −3.639 | 1.00 | 25.33 |
| ATOM | 162 | CA | ALA | A | 397 | 64.514 | 11.229 | −4.896 | 1.00 | 24.12 |
| ATOM | 163 | CB | ALA | A | 397 | 63.404 | 11.402 | −5.926 | 1.00 | 24.69 |
| ATOM | 164 | C | ALA | A | 397 | 65.333 | 12.509 | −4.812 | 1.00 | 24.45 |
| ATOM | 165 | O | ALA | A | 397 | 64.947 | 13.475 | −4.155 | 1.00 | 24.98 |
| ATOM | 166 | N | GLU | A | 398 | 66.468 | 12.514 | −5.497 | 1.00 | 24.62 |
| ATOM | 167 | CA | GLU | A | 398 | 67.328 | 13.687 | −5.517 | 1.00 | 24.57 |
| ATOM | 168 | CB | GLU | A | 398 | 68.790 | 13.298 | −5.274 | 1.00 | 23.76 |
| ATOM | 169 | CG | GLU | A | 398 | 69.764 | 14.461 | −5.405 | 1.00 | 21.43 |
| ATOM | 170 | CD | GLU | A | 398 | 71.221 | 14.023 | −5.362 | 1.00 | 21.44 |
| ATOM | 171 | OE1 | GLU | A | 398 | 72.105 | 14.899 | −5.477 | 1.00 | 20.70 |
| ATOM | 172 | OE2 | GLU | A | 398 | 71.482 | 12.810 | −5.216 | 1.00 | 21.19 |
| ATOM | 173 | C | GLU | A | 398 | 67.222 | 14.355 | −6.877 | 1.00 | 25.47 |
| ATOM | 174 | O | GLU | A | 398 | 67.334 | 13.693 | −7.904 | 1.00 | 24.24 |
| ATOM | 175 | N | PHE | A | 399 | 66.987 | 15.663 | −6.879 | 1.00 | 26.98 |
| ATOM | 176 | CA | PHE | A | 399 | 66.924 | 16.411 | −8.126 | 1.00 | 29.36 |
| ATOM | 177 | CB | PHE | A | 399 | 66.165 | 17.722 | −7.924 | 1.00 | 29.46 |
| ATOM | 178 | CG | PHE | A | 399 | 66.030 | 18.544 | −9.173 | 1.00 | 31.11 |
| ATOM | 179 | CD1 | PHE | A | 399 | 65.419 | 18.018 | −10.308 | 1.00 | 32.01 |
| ATOM | 180 | CD2 | PHE | A | 399 | 66.517 | 19.850 | −9.217 | 1.00 | 31.95 |
| ATOM | 181 | CE1 | PHE | A | 399 | 65.293 | 18.783 | −11.472 | 1.00 | 31.30 |
| ATOM | 182 | CE2 | PHE | A | 399 | 66.397 | 20.621 | −10.373 | 1.00 | 31.86 |
| ATOM | 183 | CZ | PHE | A | 399 | 65.783 | 20.084 | −11.501 | 1.00 | 31.32 |
| ATOM | 184 | C | PHE | A | 399 | 68.391 | 16.687 | −8.470 | 1.00 | 30.10 |
| ATOM | 185 | O | PHE | A | 399 | 69.009 | 17.589 | −7.906 | 1.00 | 30.57 |
| ATOM | 186 | N | LYS | A | 400 | 68.931 | 15.891 | −9.389 | 1.00 | 31.06 |
| ATOM | 187 | CA | LYS | A | 400 | 70.331 | 15.975 | −9.821 | 1.00 | 32.56 |
| ATOM | 188 | CB | LYS | A | 400 | 70.492 | 15.305 | −11.185 | 1.00 | 32.12 |
| ATOM | 189 | CG | LYS | A | 400 | 70.230 | 13.817 | −11.161 | 1.00 | 34.00 |
| ATOM | 190 | CD | LYS | A | 400 | 70.351 | 13.218 | −12.547 | 1.00 | 35.11 |
| ATOM | 191 | CE | LYS | A | 400 | 69.953 | 11.757 | −12.533 | 1.00 | 36.02 |
| ATOM | 192 | NZ | LYS | A | 400 | 70.083 | 11.134 | −13.877 | 1.00 | 37.94 |
| ATOM | 193 | C | LYS | A | 400 | 71.026 | 17.332 | −9.865 | 1.00 | 32.31 |
| ATOM | 194 | O | LYS | A | 400 | 72.119 | 17.484 | −9.323 | 1.00 | 32.07 |
| ATOM | 195 | N | LYS | A | 401 | 70.407 | 18.313 | −10.508 | 1.00 | 33.24 |
| ATOM | 196 | CA | LYS | A | 401 | 71.015 | 19.635 | −10.632 | 1.00 | 34.37 |
| ATOM | 197 | CB | LYS | A | 401 | 70.251 | 20.462 | −11.670 | 1.00 | 36.78 |
| ATOM | 198 | CG | LYS | A | 401 | 70.386 | 19.945 | −13.093 | 1.00 | 39.95 |
| ATOM | 199 | CD | LYS | A | 401 | 69.539 | 20.762 | −14.060 | 1.00 | 43.32 |
| ATOM | 200 | CE | LYS | A | 401 | 69.940 | 22.236 | −14.049 | 1.00 | 46.49 |
| ATOM | 201 | NZ | LYS | A | 401 | 69.064 | 23.065 | −14.933 | 1.00 | 48.15 |
| ATOM | 202 | C | LYS | A | 401 | 71.149 | 20.457 | −9.357 | 1.00 | 33.98 |
| ATOM | 203 | O | LYS | A | 401 | 71.881 | 21.441 | −9.338 | 1.00 | 34.73 |
| ATOM | 204 | N | THR | A | 402 | 70.467 | 20.066 | −8.286 | 1.00 | 33.84 |
| ATOM | 205 | CA | THR | A | 402 | 70.538 | 20.852 | −7.059 | 1.00 | 32.57 |
| ATOM | 206 | CB | THR | A | 402 | 69.211 | 21.582 | −6.820 | 1.00 | 33.23 |
| ATOM | 207 | OG1 | THR | A | 402 | 68.154 | 20.619 | −6.741 | 1.00 | 33.77 |
| ATOM | 208 | CG2 | THR | A | 402 | 68.922 | 22.551 | −7.963 | 1.00 | 32.46 |
| ATOM | 209 | C | THR | A | 402 | 70.880 | 20.091 | −5.786 | 1.00 | 31.39 |
| ATOM | 210 | O | THR | A | 402 | 71.137 | 20.705 | −4.750 | 1.00 | 31.77 |
| ATOM | 211 | N | ASN | A | 403 | 70.891 | 18.764 | −5.858 | 1.00 | 30.02 |
| ATOM | 212 | CA | ASN | A | 403 | 71.172 | 17.936 | −4.686 | 1.00 | 29.78 |
| ATOM | 213 | CB | ASN | A | 403 | 72.445 | 18.394 | −3.958 | 1.00 | 30.04 |
| ATOM | 214 | CG | ASN | A | 403 | 73.701 | 18.198 | −4.782 | 1.00 | 27.58 |
| ATOM | 215 | OD1 | ASN | A | 403 | 73.985 | 17.098 | −5.251 | 1.00 | 28.41 |
| ATOM | 216 | ND2 | ASN | A | 403 | 74.465 | 19.268 | −4.952 | 1.00 | 26.62 |
| ATOM | 217 | C | ASN | A | 403 | 70.003 | 17.992 | −3.706 | 1.00 | 30.21 |
| ATOM | 218 | O | ASN | A | 403 | 70.106 | 17.506 | −2.583 | 1.00 | 31.06 |
| ATOM | 219 | N | GLN | A | 404 | 68.894 | 18.592 | −4.126 | 1.00 | 30.39 |
| ATOM | 220 | CA | GLN | A | 404 | 67.718 | 18.676 | −3.264 | 1.00 | 30.79 |
| ATOM | 221 | CB | GLN | A | 404 | 66.780 | 19.787 | −3.731 | 1.00 | 32.65 |
| ATOM | 222 | CG | GLN | A | 404 | 67.366 | 21.179 | −3.633 | 1.00 | 37.04 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 223 | CD | GLN | A | 404 | 66.400 | 22.236 | −4.126 | 1.00 | 40.26 |
| ATOM | 224 | OE1 | GLN | A | 404 | 65.333 | 22.440 | −3.540 | 1.00 | 42.34 |
| ATOM | 225 | NE2 | GLN | A | 404 | 66.761 | 22.907 | −5.215 | 1.00 | 41.47 |
| ATOM | 226 | C | GLN | A | 404 | 66.977 | 17.345 | −3.290 | 1.00 | 28.62 |
| ATOM | 227 | O | GLN | A | 404 | 66.777 | 16.754 | −4.354 | 1.00 | 26.94 |
| ATOM | 228 | N | PHE | A | 405 | 66.576 | 16.871 | −2.115 | 1.00 | 26.69 |
| ATOM | 229 | CA | PHE | A | 405 | 65.869 | 15.604 | −2.028 | 1.00 | 25.08 |
| ATOM | 230 | CB | PHE | A | 405 | 66.432 | 14.756 | −0.880 | 1.00 | 24.63 |
| ATOM | 231 | CG | PHE | A | 405 | 67.770 | 14.140 | −1.190 | 1.00 | 24.41 |
| ATOM | 232 | CD1 | PHE | A | 405 | 68.865 | 14.944 | −1.500 | 1.00 | 23.39 |
| ATOM | 233 | CD2 | PHE | A | 405 | 67.926 | 12.757 | −1.217 | 1.00 | 24.12 |
| ATOM | 234 | CE1 | PHE | A | 405 | 70.095 | 14.379 | −1.837 | 1.00 | 21.96 |
| ATOM | 235 | CE2 | PHE | A | 405 | 69.155 | 12.182 | −1.553 | 1.00 | 24.18 |
| ATOM | 236 | CZ | PHE | A | 405 | 70.241 | 12.997 | −1.865 | 1.00 | 22.68 |
| ATOM | 237 | C | PHE | A | 405 | 64.373 | 15.807 | −1.870 | 1.00 | 24.33 |
| ATOM | 238 | O | PHE | A | 405 | 63.920 | 16.790 | −1.287 | 1.00 | 23.85 |
| ATOM | 239 | N | PHE | A | 406 | 63.614 | 14.860 | −2.409 | 1.00 | 23.00 |
| ATOM | 240 | CA | PHE | A | 406 | 62.163 | 14.904 | −2.376 | 1.00 | 22.04 |
| ATOM | 241 | CB | PHE | A | 406 | 61.625 | 15.456 | −3.702 | 1.00 | 20.90 |
| ATOM | 242 | CG | PHE | A | 406 | 62.029 | 16.872 | −3.986 | 1.00 | 22.14 |
| ATOM | 243 | CD1 | PHE | A | 406 | 61.329 | 17.936 | −3.422 | 1.00 | 22.86 |
| ATOM | 244 | CD2 | PHE | A | 406 | 63.124 | 17.146 | −4.805 | 1.00 | 23.26 |
| ATOM | 245 | CE1 | PHE | A | 406 | 61.713 | 19.256 | −3.667 | 1.00 | 24.28 |
| ATOM | 246 | CE2 | PHE | A | 406 | 63.521 | 18.463 | −5.061 | 1.00 | 23.64 |
| ATOM | 247 | CZ | PHE | A | 406 | 62.818 | 19.518 | −4.491 | 1.00 | 24.60 |
| ATOM | 248 | C | PHE | A | 406 | 61.628 | 13.495 | −2.190 | 1.00 | 22.49 |
| ATOM | 249 | O | PHE | A | 406 | 62.372 | 12.513 | −2.261 | 1.00 | 22.54 |
| ATOM | 250 | N | ALA | A | 407 | 60.330 | 13.402 | −1.945 | 1.00 | 22.28 |
| ATOM | 251 | CA | ALA | A | 407 | 59.688 | 12.108 | −1.811 | 1.00 | 22.69 |
| ATOM | 252 | CB | ALA | A | 407 | 58.898 | 12.032 | −0.531 | 1.00 | 21.54 |
| ATOM | 253 | C | ALA | A | 407 | 58.761 | 12.059 | −3.014 | 1.00 | 23.26 |
| ATOM | 254 | O | ALA | A | 407 | 57.851 | 12.883 | −3.132 | 1.00 | 22.90 |
| ATOM | 255 | N | ILE | A | 408 | 59.006 | 11.115 | −3.918 | 1.00 | 23.59 |
| ATOM | 256 | CA | ILE | A | 408 | 58.180 | 11.002 | −5.112 | 1.00 | 24.60 |
| ATOM | 257 | CB | ILE | A | 408 | 59.047 | 10.971 | −6.400 | 1.00 | 25.27 |
| ATOM | 258 | CG2 | ILE | A | 408 | 58.157 | 10.771 | −7.626 | 1.00 | 25.90 |
| ATOM | 259 | CG1 | ILE | A | 408 | 59.831 | 12.278 | −6.532 | 1.00 | 25.85 |
| ATOM | 260 | CD1 | ILE | A | 408 | 60.663 | 12.382 | −7.789 | 1.00 | 25.12 |
| ATOM | 261 | C | ILE | A | 408 | 57.290 | 9.771 | −5.100 | 1.00 | 25.34 |
| ATOM | 262 | O | ILE | A | 408 | 57.753 | 8.650 | −4.889 | 1.00 | 25.39 |
| ATOM | 263 | N | LYS | A | 409 | 56.001 | 10.003 | −5.313 | 1.00 | 25.71 |
| ATOM | 264 | CA | LYS | A | 409 | 55.021 | 8.935 | −5.377 | 1.00 | 26.54 |
| ATOM | 265 | CB | LYS | A | 409 | 53.689 | 9.415 | −4.802 | 1.00 | 26.41 |
| ATOM | 266 | CG | LYS | A | 409 | 52.586 | 8.363 | −4.757 | 1.00 | 27.51 |
| ATOM | 267 | CD | LYS | A | 409 | 51.415 | 8.892 | −3.945 | 1.00 | 29.29 |
| ATOM | 268 | CE | LYS | A | 409 | 50.377 | 7.827 | −3.668 | 1.00 | 29.58 |
| ATOM | 269 | NZ | LYS | A | 409 | 49.491 | 8.208 | −2.539 | 1.00 | 29.26 |
| ATOM | 270 | C | LYS | A | 409 | 54.872 | 8.637 | −6.864 | 1.00 | 27.38 |
| ATOM | 271 | O | LYS | A | 409 | 54.531 | 9.526 | −7.644 | 1.00 | 27.13 |
| ATOM | 272 | N | ALA | A | 410 | 55.148 | 7.399 | −7.259 | 1.00 | 28.59 |
| ATOM | 273 | CA | ALA | A | 410 | 55.044 | 7.014 | −8.661 | 1.00 | 31.48 |
| ATOM | 274 | CB | ALA | A | 410 | 56.345 | 6.367 | −9.122 | 1.00 | 30.20 |
| ATOM | 275 | C | ALA | A | 410 | 53.878 | 6.058 | −8.869 | 1.00 | 32.81 |
| ATOM | 276 | O | ALA | A | 410 | 53.694 | 5.114 | −8.101 | 1.00 | 32.74 |
| ATOM | 277 | N | LEU | A | 411 | 53.094 | 6.315 | −9.911 | 1.00 | 35.30 |
| ATOM | 278 | CA | LEU | A | 411 | 51.931 | 5.491 | −10.240 | 1.00 | 38.42 |
| ATOM | 279 | CB | LEU | A | 411 | 50.645 | 6.283 | −9.976 | 1.00 | 39.70 |
| ATOM | 280 | CG | LEU | A | 411 | 50.432 | 6.781 | −8.544 | 1.00 | 41.05 |
| ATOM | 281 | CD1 | LEU | A | 411 | 49.441 | 7.921 | −8.485 | 1.00 | 41.56 |
| ATOM | 282 | CD2 | LEU | A | 411 | 49.950 | 5.640 | −7.728 | 1.00 | 41.63 |
| ATOM | 283 | C | LEU | A | 411 | 51.968 | 5.066 | −11.710 | 1.00 | 39.97 |
| ATOM | 284 | O | LEU | A | 411 | 52.261 | 5.877 | −12.590 | 1.00 | 39.82 |
| ATOM | 285 | N | LYS | A | 412 | 51.660 | 3.799 | −11.968 | 1.00 | 41.51 |
| ATOM | 286 | CA | LYS | A | 412 | 51.652 | 3.259 | −13.327 | 1.00 | 42.58 |
| ATOM | 287 | CB | LYS | A | 412 | 51.956 | 1.759 | −13.289 | 1.00 | 43.71 |
| ATOM | 288 | CG | LYS | A | 412 | 53.197 | 1.409 | −12.478 | 1.00 | 45.79 |
| ATOM | 289 | CD | LYS | A | 412 | 53.219 | −0.060 | −12.091 | 1.00 | 48.20 |
| ATOM | 290 | CE | LYS | A | 412 | 53.701 | −0.227 | −10.650 | 1.00 | 49.51 |
| ATOM | 291 | NZ | LYS | A | 412 | 53.861 | −1.657 | −10.241 | 1.00 | 50.84 |
| ATOM | 292 | C | LYS | A | 412 | 50.271 | 3.491 | −13.928 | 1.00 | 42.91 |
| ATOM | 293 | O | LYS | A | 412 | 49.303 | 2.844 | −13.531 | 1.00 | 43.03 |
| ATOM | 294 | N | LYS | A | 413 | 50.183 | 4.419 | −14.875 | 1.00 | 43.31 |
| ATOM | 295 | CA | LYS | A | 413 | 48.913 | 4.738 | −15.518 | 1.00 | 43.75 |
| ATOM | 296 | CB | LYS | A | 413 | 49.159 | 5.491 | −16.825 | 1.00 | 43.54 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 297 | CG | LYS | A | 413 | 49.791 | 6.846 | −16.644 | 1.00 | 42.54 |
| ATOM | 298 | CD | LYS | A | 413 | 50.017 | 7.520 | −17.978 | 1.00 | 42.37 |
| ATOM | 299 | CE | LYS | A | 413 | 50.621 | 8.894 | −17.781 | 1.00 | 41.90 |
| ATOM | 300 | NZ | LYS | A | 413 | 50.949 | 9.566 | −19.064 | 1.00 | 41.51 |
| ATOM | 301 | C | LYS | A | 413 | 48.056 | 3.512 | −15.811 | 1.00 | 45.15 |
| ATOM | 302 | O | LYS | A | 413 | 46.858 | 3.496 | −15.535 | 1.00 | 45.34 |
| ATOM | 303 | N | ASP | A | 414 | 48.684 | 2.482 | −16.365 | 1.00 | 46.13 |
| ATOM | 304 | CA | ASP | A | 414 | 47.997 | 1.257 | −16.738 | 1.00 | 47.18 |
| ATOM | 305 | CB | ASP | A | 414 | 49.008 | 0.352 | −17.463 | 1.00 | 49.16 |
| ATOM | 306 | CG | ASP | A | 414 | 48.491 | −1.051 | −17.728 | 1.00 | 51.39 |
| ATOM | 307 | OD1 | ASP | A | 414 | 47.256 | −1.262 | −17.799 | 1.00 | 52.57 |
| ATOM | 308 | OD2 | ASP | A | 414 | 49.354 | −1.949 | −17.882 | 1.00 | 53.60 |
| ATOM | 309 | C | ASP | A | 414 | 47.265 | 0.535 | −15.599 | 1.00 | 46.66 |
| ATOM | 310 | O | ASP | A | 414 | 46.148 | 0.071 | −15.800 | 1.00 | 46.58 |
| ATOM | 311 | N | VAL | A | 415 | 47.841 | 0.426 | −14.404 | 1.00 | 46.12 |
| ATOM | 312 | CA | VAL | A | 415 | 47.065 | −0.248 | −13.367 | 1.00 | 45.42 |
| ATOM | 313 | CB | VAL | A | 415 | 47.974 | −0.949 | −12.283 | 1.00 | 45.49 |
| ATOM | 314 | CG1 | VAL | A | 415 | 49.222 | −1.503 | −12.951 | 1.00 | 45.84 |
| ATOM | 315 | CG2 | VAL | A | 415 | 48.315 | −0.013 | −11.143 | 1.00 | 45.66 |
| ATOM | 316 | C | VAL | A | 415 | 46.070 | 0.767 | −12.772 | 1.00 | 45.01 |
| ATOM | 317 | O | VAL | A | 415 | 45.032 | 0.383 | −12.229 | 1.00 | 44.28 |
| ATOM | 318 | N | VAL | A | 416 | 46.361 | 2.061 | −12.930 | 1.00 | 44.87 |
| ATOM | 319 | CA | VAL | A | 416 | 45.468 | 3.123 | −12.446 | 1.00 | 45.58 |
| ATOM | 320 | CB | VAL | A | 416 | 46.090 | 4.538 | −12.634 | 1.00 | 45.24 |
| ATOM | 321 | CG1 | VAL | A | 416 | 45.017 | 5.615 | −12.459 | 1.00 | 44.34 |
| ATOM | 322 | CG2 | VAL | A | 416 | 47.212 | 4.757 | −11.627 | 1.00 | 44.33 |
| ATOM | 323 | C | VAL | A | 416 | 44.139 | 3.073 | −13.209 | 1.00 | 46.40 |
| ATOM | 324 | O | VAL | A | 416 | 43.081 | 3.355 | −12.648 | 1.00 | 46.71 |
| ATOM | 325 | N | LEU | A | 417 | 44.200 | 2.708 | −14.487 | 1.00 | 47.08 |
| ATOM | 326 | CA | LEU | A | 417 | 43.005 | 2.618 | −15.322 | 1.00 | 48.24 |
| ATOM | 327 | CB | LEU | A | 417 | 43.392 | 2.711 | −16.798 | 1.00 | 47.71 |
| ATOM | 328 | CG | LEU | A | 417 | 43.745 | 4.126 | −17.252 | 1.00 | 47.40 |
| ATOM | 329 | CD1 | LEU | A | 417 | 44.464 | 4.107 | −18.590 | 1.00 | 47.15 |
| ATOM | 330 | CD2 | LEU | A | 417 | 42.465 | 4.930 | −17.323 | 1.00 | 47.60 |
| ATOM | 331 | C | LEU | A | 417 | 42.244 | 1.326 | −15.062 | 1.00 | 49.31 |
| ATOM | 332 | O | LEU | A | 417 | 41.016 | 1.323 | −14.976 | 1.00 | 49.26 |
| ATOM | 333 | N | MET | A | 418 | 42.983 | 0.230 | −14.934 | 1.00 | 50.92 |
| ATOM | 334 | CA | MET | A | 418 | 42.392 | −1.072 | −14.663 | 1.00 | 52.54 |
| ATOM | 335 | CB | MET | A | 418 | 43.484 | −2.134 | −14.631 | 1.00 | 54.34 |
| ATOM | 336 | CG | MET | A | 418 | 44.252 | −2.259 | −15.928 | 1.00 | 57.38 |
| ATOM | 337 | SD | MET | A | 418 | 43.284 | −3.092 | −17.188 | 1.00 | 61.64 |
| ATOM | 338 | CE | MET | A | 418 | 43.493 | −4.785 | −16.658 | 1.00 | 59.07 |
| ATOM | 339 | C | MET | A | 418 | 41.696 | −1.006 | −13.312 | 1.00 | 52.57 |
| ATOM | 340 | O | MET | A | 418 | 40.559 | −1.448 | −13.163 | 1.00 | 53.07 |
| ATOM | 341 | N | ASP | A | 419 | 42.391 | −0.452 | −12.325 | 1.00 | 52.90 |
| ATOM | 342 | CA | ASP | A | 419 | 41.822 | −0.316 | −10.995 | 1.00 | 52.76 |
| ATOM | 343 | CB | ASP | A | 419 | 42.925 | −0.167 | −9.944 | 1.00 | 53.36 |
| ATOM | 344 | CG | ASP | A | 419 | 43.754 | −1.429 | −9.791 | 1.00 | 53.84 |
| ATOM | 345 | OD1 | ASP | A | 419 | 43.196 | −2.533 | −9.993 | 1.00 | 54.31 |
| ATOM | 346 | OD2 | ASP | A | 419 | 44.953 | −1.318 | −9.455 | 1.00 | 53.61 |
| ATOM | 347 | C | ASP | A | 419 | 40.905 | 0.899 | −10.980 | 1.00 | 52.53 |
| ATOM | 348 | O | ASP | A | 419 | 40.459 | 1.344 | −9.925 | 1.00 | 53.11 |
| ATOM | 349 | N | ASP | A | 420 | 40.635 | 1.424 | −12.172 | 1.00 | 51.98 |
| ATOM | 350 | CA | ASP | A | 420 | 39.754 | 2.572 | −12.361 | 1.00 | 51.41 |
| ATOM | 351 | CB | ASP | A | 420 | 38.320 | 2.086 | −12.526 | 1.00 | 54.26 |
| ATOM | 352 | CG | ASP | A | 420 | 37.841 | 1.287 | −11.328 | 1.00 | 56.90 |
| ATOM | 353 | OD1 | ASP | A | 420 | 38.247 | 0.112 | −11.193 | 1.00 | 58.86 |
| ATOM | 354 | OD2 | ASP | A | 420 | 37.072 | 1.841 | −10.511 | 1.00 | 58.56 |
| ATOM | 355 | C | ASP | A | 420 | 39.788 | 3.606 | −11.238 | 1.00 | 49.91 |
| ATOM | 356 | O | ASP | A | 420 | 38.741 | 4.043 | −10.767 | 1.00 | 49.93 |
| ATOM | 357 | N | ASP | A | 421 | 40.980 | 4.000 | −10.805 | 1.00 | 47.41 |
| ATOM | 358 | CA | ASP | A | 421 | 41.094 | 4.989 | −9.739 | 1.00 | 45.18 |
| ATOM | 359 | CB | ASP | A | 421 | 41.960 | 4.457 | −8.597 | 1.00 | 47.03 |
| ATOM | 360 | CG | ASP | A | 421 | 41.406 | 3.189 | −7.990 | 1.00 | 49.15 |
| ATOM | 361 | OD1 | ASP | A | 421 | 40.170 | 3.002 | −8.033 | 1.00 | 50.60 |
| ATOM | 362 | OD2 | ASP | A | 421 | 42.206 | 2.387 | −7.457 | 1.00 | 50.37 |
| ATOM | 363 | C | ASP | A | 421 | 41.695 | 6.289 | −10.262 | 1.00 | 42.40 |
| ATOM | 364 | O | ASP | A | 421 | 42.558 | 6.890 | −9.619 | 1.00 | 40.21 |
| ATOM | 365 | N | VAL | A | 422 | 41.233 | 6.718 | −11.431 | 1.00 | 39.96 |
| ATOM | 366 | CA | VAL | A | 422 | 41.732 | 7.939 | −12.031 | 1.00 | 38.12 |
| ATOM | 367 | CB | VAL | A | 422 | 41.202 | 8.101 | −13.457 | 1.00 | 37.55 |
| ATOM | 368 | CG1 | VAL | A | 422 | 41.864 | 9.298 | −14.130 | 1.00 | 37.26 |
| ATOM | 369 | CG2 | VAL | A | 422 | 41.496 | 6.835 | −14.242 | 1.00 | 38.40 |
| ATOM | 370 | C | VAL | A | 422 | 41.347 | 9.152 | −11.187 | 1.00 | 37.11 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 371 | O | VAL | A | 422 | 42.165 | 10.048 | −10.999 | 1.00 | 35.39 |
| ATOM | 372 | N | GLU | A | 423 | 40.120 | 9.169 | −10.666 | 1.00 | 36.67 |
| ATOM | 373 | CA | GLU | A | 423 | 39.670 | 10.286 | −9.851 | 1.00 | 37.19 |
| ATOM | 374 | CB | GLU | A | 423 | 38.143 | 10.304 | −9.704 | 1.00 | 38.72 |
| ATOM | 375 | CG | GLU | A | 423 | 37.574 | 11.298 | −8.658 | 1.00 | 41.68 |
| ATOM | 376 | CD | GLU | A | 423 | 37.811 | 12.782 | −8.980 | 1.00 | 43.48 |
| ATOM | 377 | OE1 | GLU | A | 423 | 38.308 | 13.099 | −10.088 | 1.00 | 44.39 |
| ATOM | 378 | OE2 | GLU | A | 423 | 37.484 | 13.635 | −8.117 | 1.00 | 45.44 |
| ATOM | 379 | C | GLU | A | 423 | 40.332 | 10.247 | −8.481 | 1.00 | 36.30 |
| ATOM | 380 | O | GLU | A | 423 | 40.593 | 11.288 | −7.875 | 1.00 | 36.39 |
| ATOM | 381 | N | CYS | A | 424 | 40.616 | 9.040 | −7.984 | 1.00 | 35.01 |
| ATOM | 382 | CA | CYS | A | 424 | 41.300 | 8.930 | −6.693 | 1.00 | 34.82 |
| ATOM | 383 | CB | CYS | A | 424 | 41.450 | 7.479 | −6.278 | 1.00 | 37.40 |
| ATOM | 384 | SG | CYS | A | 424 | 39.877 | 6.714 | −5.865 | 1.00 | 44.91 |
| ATOM | 385 | C | CYS | A | 424 | 42.673 | 9.629 | −6.777 | 1.00 | 32.90 |
| ATOM | 386 | O | CYS | A | 424 | 43.164 | 10.191 | −5.783 | 1.00 | 32.59 |
| ATOM | 387 | N | THR | A | 425 | 43.288 | 9.620 | −7.960 | 1.00 | 30.54 |
| ATOM | 388 | CA | THR | A | 425 | 44.590 | 10.245 | −8.093 | 1.00 | 28.60 |
| ATOM | 389 | CB | THR | A | 425 | 45.380 | 9.784 | −9.353 | 1.00 | 28.67 |
| ATOM | 390 | OG1 | THR | A | 425 | 44.775 | 10.308 | −10.541 | 1.00 | 31.16 |
| ATOM | 391 | CG2 | THR | A | 425 | 45.423 | 8.255 | −9.441 | 1.00 | 27.55 |
| ATOM | 392 | C | THR | A | 425 | 44.418 | 11.754 | −8.134 | 1.00 | 27.85 |
| ATOM | 393 | O | THR | A | 425 | 45.292 | 12.495 | −7.664 | 1.00 | 26.55 |
| ATOM | 394 | N | MET | A | 426 | 43.302 | 12.211 | −8.704 | 1.00 | 25.75 |
| ATOM | 395 | CA | MET | A | 426 | 43.018 | 13.638 | −8.795 | 1.00 | 24.60 |
| ATOM | 396 | CB | MET | A | 426 | 41.820 | 13.897 | −9.713 | 1.00 | 26.29 |
| ATOM | 397 | CG | MET | A | 426 | 42.020 | 13.470 | −11.155 | 1.00 | 28.79 |
| ATOM | 398 | SD | MET | A | 426 | 43.495 | 14.210 | −11.862 | 1.00 | 34.81 |
| ATOM | 399 | CE | MET | A | 426 | 42.926 | 15.904 | −12.146 | 1.00 | 31.22 |
| ATOM | 400 | C | MET | A | 426 | 42.706 | 14.149 | −7.397 | 1.00 | 22.77 |
| ATOM | 401 | O | MET | A | 426 | 43.038 | 15.280 | −7.047 | 1.00 | 21.12 |
| ATOM | 402 | N | VAL | A | 427 | 42.046 | 13.313 | −6.601 | 1.00 | 21.76 |
| ATOM | 403 | CA | VAL | A | 427 | 41.708 | 13.685 | −5.233 | 1.00 | 21.87 |
| ATOM | 404 | CB | VAL | A | 427 | 40.968 | 12.541 | −4.502 | 1.00 | 22.25 |
| ATOM | 405 | CG1 | VAL | A | 427 | 40.756 | 12.905 | −3.033 | 1.00 | 23.11 |
| ATOM | 406 | CG2 | VAL | A | 427 | 39.630 | 12.274 | −5.177 | 1.00 | 23.45 |
| ATOM | 407 | C | VAL | A | 427 | 42.987 | 14.005 | −4.460 | 1.00 | 21.82 |
| ATOM | 408 | O | VAL | A | 427 | 43.105 | 15.071 | −3.853 | 1.00 | 21.18 |
| ATOM | 409 | N | GLU | A | 428 | 43.949 | 13.084 | −4.494 | 1.00 | 21.50 |
| ATOM | 410 | CA | GLU | A | 428 | 45.200 | 13.281 | −3.774 | 1.00 | 22.20 |
| ATOM | 411 | CB | GLU | A | 428 | 46.124 | 12.067 | −3.928 | 1.00 | 23.46 |
| ATOM | 412 | CG | GLU | A | 428 | 47.468 | 12.240 | −3.222 | 1.00 | 27.57 |
| ATOM | 413 | CD | GLU | A | 428 | 48.115 | 10.918 | −2.828 | 1.00 | 30.32 |
| ATOM | 414 | OE1 | GLU | A | 428 | 48.100 | 9.980 | −3.653 | 1.00 | 31.35 |
| ATOM | 415 | OE2 | GLU | A | 428 | 48.646 | 10.826 | −1.692 | 1.00 | 30.95 |
| ATOM | 416 | C | GLU | A | 428 | 45.918 | 14.538 | −4.228 | 1.00 | 20.60 |
| ATOM | 417 | O | GLU | A | 428 | 46.416 | 15.301 | −3.404 | 1.00 | 19.26 |
| ATOM | 418 | N | LYS | A | 429 | 45.969 | 14.749 | −5.538 | 1.00 | 20.00 |
| ATOM | 419 | CA | LYS | A | 429 | 46.615 | 15.930 | −6.088 | 1.00 | 19.74 |
| ATOM | 420 | CB | LYS | A | 429 | 46.485 | 15.956 | −7.615 | 1.00 | 21.81 |
| ATOM | 421 | CG | LYS | A | 429 | 47.074 | 17.217 | −8.231 | 1.00 | 24.06 |
| ATOM | 422 | CD | LYS | A | 429 | 46.877 | 17.277 | −9.729 | 1.00 | 27.54 |
| ATOM | 423 | CE | LYS | A | 429 | 47.223 | 18.668 | −10.246 | 1.00 | 30.32 |
| ATOM | 424 | NZ | LYS | A | 429 | 46.948 | 18.808 | −11.703 | 1.00 | 34.56 |
| ATOM | 425 | C | LYS | A | 429 | 45.957 | 17.182 | −5.522 | 1.00 | 19.15 |
| ATOM | 426 | O | LYS | A | 429 | 46.630 | 18.140 | −5.148 | 1.00 | 17.60 |
| ATOM | 427 | N | ARG | A | 430 | 44.629 | 17.153 | −5.465 | 1.00 | 18.16 |
| ATOM | 428 | CA | ARG | A | 430 | 43.836 | 18.267 | −4.975 | 1.00 | 17.28 |
| ATOM | 429 | CB | ARG | A | 430 | 42.358 | 17.971 | −5.204 | 1.00 | 17.62 |
| ATOM | 430 | CG | ARG | A | 430 | 41.596 | 19.071 | −5.879 | 1.00 | 19.56 |
| ATOM | 431 | CD | ARG | A | 430 | 40.733 | 18.521 | −6.993 | 1.00 | 17.79 |
| ATOM | 432 | NE | ARG | A | 430 | 39.892 | 17.416 | −6.547 | 1.00 | 20.15 |
| ATOM | 433 | CZ | ARG | A | 430 | 39.412 | 16.482 | −7.364 | 1.00 | 20.47 |
| ATOM | 434 | NH1 | ARG | A | 430 | 39.691 | 16.530 | −8.664 | 1.00 | 17.10 |
| ATOM | 435 | NH2 | ARG | A | 430 | 38.672 | 15.491 | −6.882 | 1.00 | 20.20 |
| ATOM | 436 | C | ARG | A | 430 | 44.078 | 18.559 | −3.502 | 1.00 | 17.55 |
| ATOM | 437 | O | ARG | A | 430 | 44.282 | 19.709 | −3.117 | 1.00 | 16.62 |
| ATOM | 438 | N | VAL | A | 431 | 44.048 | 17.523 | −2.674 | 1.00 | 17.10 |
| ATOM | 439 | CA | VAL | A | 431 | 44.260 | 17.708 | −1.246 | 1.00 | 17.74 |
| ATOM | 440 | CB | VAL | A | 431 | 43.914 | 16.419 | −0.460 | 1.00 | 18.52 |
| ATOM | 441 | CG1 | VAL | A | 431 | 44.130 | 16.644 | 1.041 | 1.00 | 17.16 |
| ATOM | 442 | CG2 | VAL | A | 431 | 42.458 | 16.031 | −0.735 | 1.00 | 16.07 |
| ATOM | 443 | C | VAL | A | 431 | 45.705 | 18.133 | −0.975 | 1.00 | 18.19 |
| ATOM | 444 | O | VAL | A | 431 | 45.954 | 18.964 | −0.102 | 1.00 | 18.13 |

TABLE 2-continued

Structure coordinates for PKCθ
(residues 377-696 of SEQ ID NO: 1)/staurosporine complex

|  | # | name | res | chain | res # | X | Y | Z | occ | B |
|---|---|---|---|---|---|---|---|---|---|---|
| ATOM | 445 | N | LEU | A | 432 | 46.654 | 17.591 | −1.731 | 1.00 | 18.42 |
| ATOM | 446 | CA | LEU | A | 432 | 48.044 | 17.988 | −1.541 | 1.00 | 20.18 |
| ATOM | 447 | CB | LEU | A | 432 | 48.989 | 17.147 | −2.411 | 1.00 | 20.15 |
| ATOM | 448 | CG | LEU | A | 432 | 49.309 | 15.711 | −1.987 | 1.00 | 22.09 |
| ATOM | 449 | CD1 | LEU | A | 432 | 50.062 | 15.017 | −3.110 | 1.00 | 20.23 |
| ATOM | 450 | CD2 | LEU | A | 432 | 50.145 | 15.707 | −0.705 | 1.00 | 23.08 |
| ATOM | 451 | C | LEU | A | 432 | 48.204 | 19.475 | −1.889 | 1.00 | 21.02 |
| ATOM | 452 | O | LEU | A | 432 | 48.988 | 20.179 | −1.254 | 1.00 | 20.53 |
| ATOM | 453 | N | SER | A | 433 | 47.468 | 19.953 | −2.894 | 1.00 | 20.67 |
| ATOM | 454 | CA | SER | A | 433 | 47.550 | 21.365 | −3.276 | 1.00 | 22.20 |
| ATOM | 455 | CB | SER | A | 433 | 46.764 | 21.640 | −4.561 | 1.00 | 22.20 |
| ATOM | 456 | OG | SER | A | 433 | 47.364 | 20.970 | −5.654 | 1.00 | 27.08 |
| ATOM | 457 | C | SER | A | 433 | 46.978 | 22.208 | −2.153 | 1.00 | 21.39 |
| ATOM | 458 | O | SER | A | 433 | 47.506 | 23.259 | −1.812 | 1.00 | 21.27 |
| ATOM | 459 | N | LEU | A | 434 | 45.886 | 21.731 | −1.578 | 1.00 | 21.50 |
| ATOM | 460 | CA | LEU | A | 434 | 45.240 | 22.423 | −0.477 | 1.00 | 21.43 |
| ATOM | 461 | CB | LEU | A | 434 | 43.971 | 21.671 | −0.092 | 1.00 | 20.13 |
| ATOM | 462 | CG | LEU | A | 434 | 43.222 | 22.168 | 1.139 | 1.00 | 21.96 |
| ATOM | 463 | CD1 | LEU | A | 434 | 42.574 | 23.518 | 0.855 | 1.00 | 23.04 |
| ATOM | 464 | CD2 | LEU | A | 434 | 42.172 | 21.141 | 1.510 | 1.00 | 22.32 |
| ATOM | 465 | C | LEU | A | 434 | 46.181 | 22.497 | 0.735 | 1.00 | 21.31 |
| ATOM | 466 | O | LEU | A | 434 | 46.363 | 23.560 | 1.327 | 1.00 | 20.57 |
| ATOM | 467 | N | ALA | A | 435 | 46.776 | 21.356 | 1.080 | 1.00 | 22.20 |
| ATOM | 468 | CA | ALA | A | 435 | 47.676 | 21.230 | 2.230 | 1.00 | 22.69 |
| ATOM | 469 | CB | ALA | A | 435 | 48.274 | 19.827 | 2.260 | 1.00 | 21.45 |
| ATOM | 470 | C | ALA | A | 435 | 48.797 | 22.262 | 2.324 | 1.00 | 23.79 |
| ATOM | 471 | O | ALA | A | 435 | 49.353 | 22.475 | 3.401 | 1.00 | 22.59 |
| ATOM | 472 | N | TRP | A | 436 | 49.132 | 22.894 | 1.206 | 1.00 | 25.03 |
| ATOM | 473 | CA | TRP | A | 436 | 50.197 | 23.891 | 1.201 | 1.00 | 27.02 |
| ATOM | 474 | CB | TRP | A | 436 | 50.252 | 24.568 | −0.170 | 1.00 | 29.65 |
| ATOM | 475 | CG | TRP | A | 436 | 51.421 | 25.479 | −0.326 | 1.00 | 31.45 |
| ATOM | 476 | CD2 | TRP | A | 436 | 52.753 | 25.103 | −0.696 | 1.00 | 32.03 |
| ATOM | 477 | CE2 | TRP | A | 436 | 53.538 | 26.276 | −0.677 | 1.00 | 33.34 |
| ATOM | 478 | CE3 | TRP | A | 436 | 53.359 | 23.887 | −1.042 | 1.00 | 32.87 |
| ATOM | 479 | CD1 | TRP | A | 436 | 51.448 | 26.825 | −0.105 | 1.00 | 32.63 |
| ATOM | 480 | NE1 | TRP | A | 436 | 52.717 | 27.312 | −0.313 | 1.00 | 33.25 |
| ATOM | 481 | CZ2 | TRP | A | 436 | 54.906 | 26.270 | −0.990 | 1.00 | 33.88 |
| ATOM | 482 | CZ3 | TRP | A | 436 | 54.718 | 23.880 | −1.353 | 1.00 | 33.29 |
| ATOM | 483 | CH2 | TRP | A | 436 | 55.474 | 25.065 | −1.324 | 1.00 | 33.66 |
| ATOM | 484 | C | TRP | A | 436 | 49.926 | 24.933 | 2.287 | 1.00 | 28.06 |
| ATOM | 485 | O | TRP | A | 436 | 50.838 | 25.464 | 2.914 | 1.00 | 27.33 |
| ATOM | 486 | N | GLU | A | 437 | 48.636 | 25.183 | 2.487 | 1.00 | 28.61 |
| ATOM | 487 | CA | GLU | A | 437 | 48.121 | 26.148 | 3.456 | 1.00 | 28.70 |
| ATOM | 488 | CB | GLU | A | 437 | 46.592 | 26.302 | 3.266 | 1.00 | 31.22 |
| ATOM | 489 | CG | GLU | A | 437 | 45.989 | 27.658 | 3.775 | 1.00 | 35.77 |
| ATOM | 490 | CD | GLU | A | 437 | 44.491 | 27.732 | 3.537 | 1.00 | 37.44 |
| ATOM | 491 | OE1 | GLU | A | 437 | 44.046 | 27.334 | 2.436 | 1.00 | 39.80 |
| ATOM | 492 | OE2 | GLU | A | 437 | 43.763 | 28.248 | 4.417 | 1.00 | 37.82 |
| ATOM | 493 | C | GLU | A | 437 | 48.405 | 25.786 | 4.939 | 1.00 | 28.26 |
| ATOM | 494 | O | GLU | A | 437 | 48.539 | 26.677 | 5.779 | 1.00 | 28.42 |
| ATOM | 495 | N | HIS | A | 438 | 48.513 | 24.491 | 5.241 | 1.00 | 24.97 |
| ATOM | 496 | CA | HIS | A | 438 | 48.705 | 24.035 | 6.620 | 1.00 | 22.59 |
| ATOM | 497 | CB | HIS | A | 438 | 47.622 | 22.997 | 6.936 | 1.00 | 21.19 |
| ATOM | 498 | CG | HIS | A | 438 | 47.344 | 22.830 | 8.396 | 1.00 | 22.04 |
| ATOM | 499 | CD2 | HIS | A | 438 | 47.803 | 21.925 | 9.292 | 1.00 | 21.85 |
| ATOM | 500 | ND1 | HIS | A | 438 | 46.501 | 23.668 | 9.092 | 1.00 | 21.68 |
| ATOM | 501 | CE1 | HIS | A | 438 | 46.452 | 23.288 | 10.356 | 1.00 | 22.37 |
| ATOM | 502 | NE2 | HIS | A | 438 | 47.235 | 22.234 | 10.504 | 1.00 | 22.90 |
| ATOM | 503 | C | HIS | A | 438 | 50.088 | 23.446 | 6.974 | 1.00 | 20.75 |
| ATOM | 504 | O | HIS | A | 438 | 50.654 | 22.673 | 6.211 | 1.00 | 20.81 |
| ATOM | 505 | N | PRO | A | 439 | 50.618 | 23.755 | 8.173 | 1.00 | 19.49 |
| ATOM | 506 | CD | PRO | A | 439 | 50.092 | 24.654 | 9.216 | 1.00 | 18.88 |
| ATOM | 507 | CA | PRO | A | 439 | 51.932 | 23.230 | 8.562 | 1.00 | 18.82 |
| ATOM | 508 | CB | PRO | A | 439 | 52.304 | 24.092 | 9.764 | 1.00 | 18.84 |
| ATOM | 509 | CG | PRO | A | 439 | 50.976 | 24.326 | 10.406 | 1.00 | 18.97 |
| ATOM | 510 | C | PRO | A | 439 | 51.989 | 21.744 | 8.903 | 1.00 | 18.39 |
| ATOM | 511 | O | PRO | A | 439 | 53.053 | 21.132 | 8.817 | 1.00 | 18.26 |
| ATOM | 512 | N | PHE | A | 440 | 50.859 | 21.152 | 9.268 | 1.00 | 18.66 |
| ATOM | 513 | CA | PHE | A | 440 | 50.865 | 19.746 | 9.654 | 1.00 | 19.86 |
| ATOM | 514 | CB | PHE | A | 440 | 50.127 | 19.582 | 10.986 | 1.00 | 18.03 |
| ATOM | 515 | CG | PHE | A | 440 | 50.652 | 20.491 | 12.083 | 1.00 | 20.56 |
| ATOM | 516 | CD1 | PHE | A | 440 | 52.022 | 20.665 | 12.266 | 1.00 | 18.71 |
| ATOM | 517 | CD2 | PHE | A | 440 | 49.773 | 21.192 | 12.911 | 1.00 | 19.36 |
| ATOM | 518 | CE1 | PHE | A | 440 | 52.510 | 21.528 | 13.251 | 1.00 | 20.45 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 519 | CE2 | PHE | A | 440 | 50.249 | 22.055 | 13.897 | 1.00 | 19.82 |
| ATOM | 520 | CZ | PHE | A | 440 | 51.624 | 22.226 | 14.069 | 1.00 | 19.84 |
| ATOM | 521 | C | PHE | A | 440 | 50.349 | 18.758 | 8.607 | 1.00 | 20.28 |
| ATOM | 522 | O | PHE | A | 440 | 49.966 | 17.634 | 8.928 | 1.00 | 20.61 |
| ATOM | 523 | N | LEU | A | 441 | 50.347 | 19.185 | 7.351 | 1.00 | 20.58 |
| ATOM | 524 | CA | LEU | A | 441 | 49.942 | 18.323 | 6.248 | 1.00 | 20.81 |
| ATOM | 525 | CB | LEU | A | 441 | 48.695 | 18.875 | 5.549 | 1.00 | 20.65 |
| ATOM | 526 | CG | LEU | A | 441 | 47.390 | 18.957 | 6.349 | 1.00 | 20.89 |
| ATOM | 527 | CD1 | LEU | A | 441 | 46.274 | 19.442 | 5.436 | 1.00 | 21.21 |
| ATOM | 528 | CD2 | LEU | A | 441 | 47.043 | 17.591 | 6.917 | 1.00 | 20.09 |
| ATOM | 529 | C | LEU | A | 441 | 51.116 | 18.304 | 5.268 | 1.00 | 21.61 |
| ATOM | 530 | O | LEU | A | 441 | 51.814 | 19.306 | 5.110 | 1.00 | 20.26 |
| ATOM | 531 | N | THR | A | 442 | 51.333 | 17.166 | 4.618 | 1.00 | 22.42 |
| ATOM | 532 | CA | THR | A | 442 | 52.424 | 17.037 | 3.658 | 1.00 | 23.21 |
| ATOM | 533 | CB | THR | A | 442 | 52.572 | 15.569 | 3.184 | 1.00 | 23.90 |
| ATOM | 534 | OG1 | THR | A | 442 | 52.751 | 14.715 | 4.322 | 1.00 | 23.44 |
| ATOM | 535 | CG2 | THR | A | 442 | 53.775 | 15.421 | 2.243 | 1.00 | 24.18 |
| ATOM | 536 | C | THR | A | 442 | 52.167 | 17.929 | 2.440 | 1.00 | 24.13 |
| ATOM | 537 | O | THR | A | 442 | 51.056 | 17.950 | 1.904 | 1.00 | 22.62 |
| ATOM | 538 | N | HIS | A | 443 | 53.201 | 18.656 | 2.014 | 1.00 | 24.40 |
| ATOM | 539 | CA | HIS | A | 443 | 53.112 | 19.550 | 0.862 | 1.00 | 25.25 |
| ATOM | 540 | CB | HIS | A | 443 | 53.894 | 20.849 | 1.100 | 1.00 | 24.58 |
| ATOM | 541 | CG | HIS | A | 443 | 53.492 | 21.584 | 2.336 | 1.00 | 23.06 |
| ATOM | 542 | CD2 | HIS | A | 443 | 54.158 | 22.492 | 3.085 | 1.00 | 22.44 |
| ATOM | 543 | ND1 | HIS | A | 443 | 52.254 | 21.436 | 2.924 | 1.00 | 23.95 |
| ATOM | 544 | CE1 | HIS | A | 443 | 52.175 | 22.219 | 3.984 | 1.00 | 19.84 |
| ATOM | 545 | NE2 | HIS | A | 443 | 53.316 | 22.871 | 4.104 | 1.00 | 23.13 |
| ATOM | 546 | C | HIS | A | 443 | 53.665 | 18.905 | −0.403 | 1.00 | 26.11 |
| ATOM | 547 | O | HIS | A | 443 | 54.524 | 18.024 | −0.355 | 1.00 | 26.41 |
| ATOM | 548 | N | MET | A | 444 | 53.173 | 19.381 | −1.537 | 1.00 | 27.13 |
| ATOM | 549 | CA | MET | A | 444 | 53.588 | 18.891 | −2.841 | 1.00 | 28.71 |
| ATOM | 550 | CB | MET | A | 444 | 52.365 | 18.343 | −3.581 | 1.00 | 30.60 |
| ATOM | 551 | CG | MET | A | 444 | 52.556 | 18.113 | −5.061 | 1.00 | 33.85 |
| ATOM | 552 | SD | MET | A | 444 | 51.032 | 17.490 | −5.794 | 1.00 | 40.55 |
| ATOM | 553 | CE | MET | A | 444 | 50.022 | 18.963 | −5.807 | 1.00 | 36.09 |
| ATOM | 554 | C | MET | A | 444 | 54.188 | 20.067 | −3.602 | 1.00 | 28.39 |
| ATOM | 555 | O | MET | A | 444 | 53.653 | 21.171 | −3.553 | 1.00 | 27.44 |
| ATOM | 556 | N | PHE | A | 445 | 55.300 | 19.845 | −4.293 | 1.00 | 29.18 |
| ATOM | 557 | CA | PHE | A | 445 | 55.925 | 20.927 | −5.038 | 1.00 | 30.58 |
| ATOM | 558 | CB | PHE | A | 445 | 57.444 | 20.813 | −4.976 | 1.00 | 30.22 |
| ATOM | 559 | CG | PHE | A | 445 | 58.000 | 21.087 | −3.619 | 1.00 | 30.81 |
| ATOM | 560 | CD1 | PHE | A | 445 | 58.476 | 20.054 | −2.824 | 1.00 | 30.80 |
| ATOM | 561 | CD2 | PHE | A | 445 | 58.001 | 22.381 | −3.112 | 1.00 | 30.89 |
| ATOM | 562 | CE1 | PHE | A | 445 | 58.943 | 20.311 | −1.535 | 1.00 | 31.29 |
| ATOM | 563 | CE2 | PHE | A | 445 | 58.463 | 22.647 | −1.832 | 1.00 | 29.72 |
| ATOM | 564 | CZ | PHE | A | 445 | 58.935 | 21.613 | −1.040 | 1.00 | 30.69 |
| ATOM | 565 | C | PHE | A | 445 | 55.456 | 20.952 | −6.473 | 1.00 | 31.46 |
| ATOM | 566 | O | PHE | A | 445 | 55.149 | 22.008 | −7.022 | 1.00 | 31.13 |
| ATOM | 567 | N | CYS | A | 446 | 55.398 | 19.786 | −7.090 | 1.00 | 32.42 |
| ATOM | 568 | CA | CYS | A | 446 | 54.929 | 19.731 | −8.452 | 1.00 | 34.41 |
| ATOM | 569 | CB | CYS | A | 446 | 56.019 | 20.154 | −9.439 | 1.00 | 35.65 |
| ATOM | 570 | SG | CYS | A | 446 | 57.272 | 18.924 | −9.707 | 1.00 | 41.67 |
| ATOM | 571 | C | CYS | A | 446 | 54.454 | 18.341 | −8.771 | 1.00 | 34.80 |
| ATOM | 572 | O | CYS | A | 446 | 54.503 | 17.428 | −7.947 | 1.00 | 33.47 |
| ATOM | 573 | N | THR | A | 447 | 53.997 | 18.192 | −9.996 | 1.00 | 36.01 |
| ATOM | 574 | CA | THR | A | 447 | 53.470 | 16.941 | −10.453 | 1.00 | 38.05 |
| ATOM | 575 | CB | THR | A | 447 | 51.946 | 16.917 | −10.142 | 1.00 | 39.14 |
| ATOM | 576 | OG1 | THR | A | 447 | 51.537 | 15.592 | −9.798 | 1.00 | 42.34 |
| ATOM | 577 | CG2 | THR | A | 447 | 51.150 | 17.403 | −11.304 | 1.00 | 38.52 |
| ATOM | 578 | C | THR | A | 447 | 53.808 | 16.903 | −11.944 | 1.00 | 38.40 |
| ATOM | 579 | O | THR | A | 447 | 53.855 | 17.942 | −12.607 | 1.00 | 38.77 |
| ATOM | 580 | N | PHE | A | 448 | 54.106 | 15.718 | −12.456 | 1.00 | 38.89 |
| ATOM | 581 | CA | PHE | A | 448 | 54.465 | 15.584 | −13.857 | 1.00 | 40.43 |
| ATOM | 582 | CB | PHE | A | 448 | 55.930 | 15.981 | −14.068 | 1.00 | 40.34 |
| ATOM | 583 | CG | PHE | A | 448 | 56.924 | 14.978 | −13.535 | 1.00 | 40.76 |
| ATOM | 584 | CD1 | PHE | A | 448 | 57.360 | 13.917 | −14.328 | 1.00 | 40.15 |
| ATOM | 585 | CD2 | PHE | A | 448 | 57.441 | 15.105 | −12.247 | 1.00 | 40.30 |
| ATOM | 586 | CE1 | PHE | A | 448 | 58.303 | 13.002 | −13.848 | 1.00 | 41.09 |
| ATOM | 587 | CE2 | PHE | A | 448 | 58.385 | 14.194 | −11.756 | 1.00 | 40.11 |
| ATOM | 588 | CZ | PHE | A | 448 | 58.816 | 13.141 | −12.558 | 1.00 | 40.32 |
| ATOM | 589 | C | PHE | A | 448 | 54.253 | 14.154 | −14.294 | 1.00 | 41.70 |
| ATOM | 590 | O | PHE | A | 448 | 54.101 | 13.260 | −13.460 | 1.00 | 40.26 |
| ATOM | 591 | N | GLN | A | 449 | 54.234 | 13.934 | −15.601 | 1.00 | 43.78 |
| ATOM | 592 | CA | GLN | A | 449 | 54.044 | 12.592 | −16.087 | 1.00 | 46.58 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 593 | CB | GLN | A | 449 | 52.582 | 12.370 | −16.501 | 1.00 | 47.16 |
| ATOM | 594 | CG | GLN | A | 449 | 52.154 | 13.037 | −17.798 | 1.00 | 48.14 |
| ATOM | 595 | CD | GLN | A | 449 | 50.640 | 13.049 | −17.958 | 1.00 | 48.93 |
| ATOM | 596 | OE1 | GLN | A | 449 | 49.989 | 11.999 | −17.922 | 1.00 | 49.32 |
| ATOM | 597 | NE2 | GLN | A | 449 | 50.072 | 14.240 | −18.128 | 1.00 | 48.57 |
| ATOM | 598 | C | GLN | A | 449 | 54.958 | 12.193 | −17.224 | 1.00 | 48.47 |
| ATOM | 599 | O | GLN | A | 449 | 55.549 | 13.022 | −17.928 | 1.00 | 48.22 |
| ATOM | 600 | N | THR | A | 450 | 55.088 | 10.882 | −17.340 | 1.00 | 50.57 |
| ATOM | 601 | CA | THR | A | 450 | 55.850 | 10.233 | −18.381 | 1.00 | 52.90 |
| ATOM | 602 | CB | THR | A | 450 | 56.772 | 9.121 | −17.794 | 1.00 | 53.12 |
| ATOM | 603 | OG1 | THR | A | 450 | 58.074 | 9.666 | −17.552 | 1.00 | 54.78 |
| ATOM | 604 | CG2 | THR | A | 450 | 56.895 | 7.922 | −18.733 | 1.00 | 54.96 |
| ATOM | 605 | C | THR | A | 450 | 54.705 | 9.628 | −19.174 | 1.00 | 53.95 |
| ATOM | 606 | O | THR | A | 450 | 53.539 | 9.886 | −18.877 | 1.00 | 54.26 |
| ATOM | 607 | N | LYS | A | 451 | 55.027 | 8.820 | −20.168 | 1.00 | 55.42 |
| ATOM | 608 | CA | LYS | A | 451 | 54.014 | 8.198 | −20.988 | 1.00 | 55.88 |
| ATOM | 609 | CB | LYS | A | 451 | 54.584 | 7.997 | −22.389 | 1.00 | 56.85 |
| ATOM | 610 | CG | LYS | A | 451 | 53.552 | 7.738 | −23.457 | 1.00 | 58.03 |
| ATOM | 611 | CD | LYS | A | 451 | 54.136 | 7.970 | −24.841 | 1.00 | 59.25 |
| ATOM | 612 | CE | LYS | A | 451 | 54.516 | 9.434 | −25.044 | 1.00 | 59.59 |
| ATOM | 613 | NZ | LYS | A | 451 | 55.019 | 9.688 | −26.424 | 1.00 | 60.34 |
| ATOM | 614 | C | LYS | A | 451 | 53.534 | 6.873 | −20.399 | 1.00 | 55.47 |
| ATOM | 615 | O | LYS | A | 451 | 52.796 | 6.140 | −21.047 | 1.00 | 56.36 |
| ATOM | 616 | N | GLU | A | 452 | 53.937 | 6.567 | −19.167 | 1.00 | 54.71 |
| ATOM | 617 | CA | GLU | A | 452 | 53.526 | 5.314 | −18.535 | 1.00 | 53.39 |
| ATOM | 618 | CB | GLU | A | 452 | 54.588 | 4.240 | −18.786 | 1.00 | 55.47 |
| ATOM | 619 | CG | GLU | A | 452 | 55.039 | 4.142 | −20.235 | 1.00 | 58.58 |
| ATOM | 620 | CD | GLU | A | 452 | 56.351 | 3.397 | −20.391 | 1.00 | 60.72 |
| ATOM | 621 | OE1 | GLU | A | 452 | 56.913 | 3.413 | −21.509 | 1.00 | 62.08 |
| ATOM | 622 | OE2 | GLU | A | 452 | 56.822 | 2.796 | −19.399 | 1.00 | 61.41 |
| ATOM | 623 | C | GLU | A | 452 | 53.302 | 5.460 | −17.029 | 1.00 | 51.25 |
| ATOM | 624 | O | GLU | A | 452 | 52.755 | 4.561 | −16.387 | 1.00 | 50.98 |
| ATOM | 625 | N | ASN | A | 453 | 53.723 | 6.590 | −16.467 | 1.00 | 48.56 |
| ATOM | 626 | CA | ASN | A | 453 | 53.570 | 6.815 | −15.034 | 1.00 | 45.89 |
| ATOM | 627 | CB | ASN | A | 453 | 54.876 | 6.481 | −14.307 | 1.00 | 46.62 |
| ATOM | 628 | CG | ASN | A | 453 | 55.248 | 5.019 | −14.413 | 1.00 | 47.71 |
| ATOM | 629 | OD1 | ASN | A | 453 | 55.677 | 4.548 | −15.466 | 1.00 | 48.67 |
| ATOM | 630 | ND2 | ASN | A | 453 | 55.077 | 4.287 | −13.317 | 1.00 | 48.16 |
| ATOM | 631 | C | ASN | A | 453 | 53.152 | 8.224 | −14.632 | 1.00 | 43.39 |
| ATOM | 632 | O | ASN | A | 453 | 53.283 | 9.179 | −15.401 | 1.00 | 42.73 |
| ATOM | 633 | N | LEU | A | 454 | 52.645 | 8.323 | −13.406 | 1.00 | 40.18 |
| ATOM | 634 | CA | LEU | A | 454 | 52.225 | 9.586 | −12.808 | 1.00 | 37.46 |
| ATOM | 635 | CB | LEU | A | 454 | 50.777 | 9.504 | −12.312 | 1.00 | 38.03 |
| ATOM | 636 | CG | LEU | A | 454 | 49.648 | 9.391 | −13.337 | 1.00 | 39.23 |
| ATOM | 637 | CD1 | LEU | A | 454 | 48.310 | 9.311 | −12.603 | 1.00 | 40.02 |
| ATOM | 638 | CD2 | LEU | A | 454 | 49.671 | 10.588 | −14.270 | 1.00 | 39.29 |
| ATOM | 639 | C | LEU | A | 454 | 53.157 | 9.812 | −11.617 | 1.00 | 34.99 |
| ATOM | 640 | O | LEU | A | 454 | 53.469 | 8.875 | −10.876 | 1.00 | 33.99 |
| ATOM | 641 | N | PHE | A | 455 | 53.595 | 11.049 | −11.424 | 1.00 | 32.51 |
| ATOM | 642 | CA | PHE | A | 455 | 54.508 | 11.347 | −10.331 | 1.00 | 30.22 |
| ATOM | 643 | CB | PHE | A | 455 | 55.914 | 11.600 | −10.884 | 1.00 | 29.47 |
| ATOM | 644 | CG | PHE | A | 455 | 56.529 | 10.411 | −11.572 | 1.00 | 31.00 |
| ATOM | 645 | CD1 | PHE | A | 455 | 57.059 | 9.361 | −10.835 | 1.00 | 30.85 |
| ATOM | 646 | CD2 | PHE | A | 455 | 56.597 | 10.350 | −12.962 | 1.00 | 31.60 |
| ATOM | 647 | CE1 | PHE | A | 455 | 57.650 | 8.269 | −11.471 | 1.00 | 31.16 |
| ATOM | 648 | CE2 | PHE | A | 455 | 57.186 | 9.261 | −13.603 | 1.00 | 31.10 |
| ATOM | 649 | CZ | PHE | A | 455 | 57.713 | 8.221 | −12.852 | 1.00 | 30.97 |
| ATOM | 650 | C | PHE | A | 455 | 54.095 | 12.541 | −9.481 | 1.00 | 28.80 |
| ATOM | 651 | O | PHE | A | 455 | 53.752 | 13.604 | −10.001 | 1.00 | 28.55 |
| ATOM | 652 | N | PHE | A | 456 | 54.125 | 12.352 | −8.166 | 1.00 | 27.87 |
| ATOM | 653 | CA | PHE | A | 456 | 53.817 | 13.426 | −7.225 | 1.00 | 26.89 |
| ATOM | 654 | CB | PHE | A | 456 | 52.835 | 12.977 | −6.132 | 1.00 | 26.92 |
| ATOM | 655 | CG | PHE | A | 456 | 51.474 | 12.567 | −6.636 | 1.00 | 28.68 |
| ATOM | 656 | CD1 | PHE | A | 456 | 51.305 | 11.390 | −7.365 | 1.00 | 29.62 |
| ATOM | 657 | CD2 | PHE | A | 456 | 50.353 | 13.334 | −6.342 | 1.00 | 28.90 |
| ATOM | 658 | CE1 | PHE | A | 456 | 50.039 | 10.986 | −7.787 | 1.00 | 29.67 |
| ATOM | 659 | CE2 | PHE | A | 456 | 49.077 | 12.937 | −6.763 | 1.00 | 29.12 |
| ATOM | 660 | CZ | PHE | A | 456 | 48.920 | 11.764 | −7.484 | 1.00 | 29.10 |
| ATOM | 661 | C | PHE | A | 456 | 55.151 | 13.749 | −6.549 | 1.00 | 26.14 |
| ATOM | 662 | O | PHE | A | 456 | 55.736 | 12.885 | −5.890 | 1.00 | 26.60 |
| ATOM | 663 | N | VAL | A | 457 | 55.646 | 14.968 | −6.716 | 1.00 | 24.61 |
| ATOM | 664 | CA | VAL | A | 457 | 56.897 | 15.347 | −6.069 | 1.00 | 23.87 |
| ATOM | 665 | CB | VAL | A | 457 | 57.771 | 16.240 | −6.982 | 1.00 | 24.28 |
| ATOM | 666 | CG1 | VAL | A | 457 | 59.048 | 16.648 | −6.241 | 1.00 | 24.15 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 667 | CG2 | VAL | A | 457 | 58.127 | 15.487 | −8.262 | 1.00 | 22.51 |
| ATOM | 668 | C | VAL | A | 457 | 56.544 | 16.106 | −4.792 | 1.00 | 23.23 |
| ATOM | 669 | O | VAL | A | 457 | 56.132 | 17.265 | −4.840 | 1.00 | 22.81 |
| ATOM | 670 | N | MET | A | 458 | 56.697 | 15.433 | −3.654 | 1.00 | 21.84 |
| ATOM | 671 | CA | MET | A | 458 | 56.375 | 16.012 | −2.355 | 1.00 | 21.93 |
| ATOM | 672 | CB | MET | A | 458 | 55.502 | 15.039 | −1.563 | 1.00 | 22.15 |
| ATOM | 673 | CG | MET | A | 458 | 54.184 | 14.683 | −2.238 | 1.00 | 22.87 |
| ATOM | 674 | SD | MET | A | 458 | 53.413 | 13.216 | −1.506 | 1.00 | 24.96 |
| ATOM | 675 | CE | MET | A | 458 | 54.231 | 11.926 | −2.446 | 1.00 | 23.53 |
| ATOM | 676 | C | MET | A | 458 | 57.617 | 16.331 | −1.533 | 1.00 | 21.95 |
| ATOM | 677 | O | MET | A | 458 | 58.721 | 15.889 | −1.856 | 1.00 | 20.97 |
| ATOM | 678 | N | GLU | A | 459 | 57.429 | 17.097 | −0.461 | 1.00 | 21.81 |
| ATOM | 679 | CA | GLU | A | 459 | 58.538 | 17.443 | 0.417 | 1.00 | 22.44 |
| ATOM | 680 | CB | GLU | A | 459 | 58.098 | 18.479 | 1.454 | 1.00 | 22.72 |
| ATOM | 681 | CG | GLU | A | 459 | 57.059 | 17.985 | 2.447 | 1.00 | 24.00 |
| ATOM | 682 | CD | GLU | A | 459 | 56.592 | 19.080 | 3.388 | 1.00 | 25.29 |
| ATOM | 683 | OE1 | GLU | A | 459 | 57.454 | 19.798 | 3.930 | 1.00 | 27.08 |
| ATOM | 684 | OE2 | GLU | A | 459 | 55.366 | 19.224 | 3.597 | 1.00 | 25.60 |
| ATOM | 685 | C | GLU | A | 459 | 59.016 | 16.170 | 1.117 | 1.00 | 22.69 |
| ATOM | 686 | O | GLU | A | 459 | 58.225 | 15.263 | 1.395 | 1.00 | 21.45 |
| ATOM | 687 | N | TYR | A | 460 | 60.316 | 16.098 | 1.373 | 1.00 | 22.91 |
| ATOM | 688 | CA | TYR | A | 460 | 60.908 | 14.949 | 2.040 | 1.00 | 23.13 |
| ATOM | 689 | CB | TYR | A | 460 | 62.296 | 14.683 | 1.442 | 1.00 | 24.36 |
| ATOM | 690 | CG | TYR | A | 460 | 63.227 | 13.844 | 2.291 | 1.00 | 24.71 |
| ATOM | 691 | CD1 | TYR | A | 460 | 62.841 | 12.589 | 2.762 | 1.00 | 24.72 |
| ATOM | 692 | CE1 | TYR | A | 460 | 63.706 | 11.810 | 3.529 | 1.00 | 25.19 |
| ATOM | 693 | CD2 | TYR | A | 460 | 64.506 | 14.304 | 2.608 | 1.00 | 25.17 |
| ATOM | 694 | CE2 | TYR | A | 460 | 65.377 | 13.534 | 3.374 | 1.00 | 26.32 |
| ATOM | 695 | CZ | TYR | A | 460 | 64.970 | 12.289 | 3.831 | 1.00 | 25.57 |
| ATOM | 696 | OH | TYR | A | 460 | 65.827 | 11.530 | 4.594 | 1.00 | 27.52 |
| ATOM | 697 | C | TYR | A | 460 | 60.985 | 15.244 | 3.540 | 1.00 | 23.25 |
| ATOM | 698 | O | TYR | A | 460 | 61.509 | 16.274 | 3.960 | 1.00 | 24.64 |
| ATOM | 699 | N | LEU | A | 461 | 60.437 | 14.335 | 4.338 | 1.00 | 22.56 |
| ATOM | 700 | CA | LEU | A | 461 | 60.388 | 14.468 | 5.791 | 1.00 | 22.00 |
| ATOM | 701 | CB | LEU | A | 461 | 58.927 | 14.329 | 6.236 | 1.00 | 21.44 |
| ATOM | 702 | CG | LEU | A | 461 | 57.988 | 15.265 | 5.444 | 1.00 | 22.36 |
| ATOM | 703 | CD1 | LEU | A | 461 | 56.519 | 14.858 | 5.606 | 1.00 | 21.00 |
| ATOM | 704 | CD2 | LEU | A | 461 | 58.206 | 16.699 | 5.912 | 1.00 | 20.61 |
| ATOM | 705 | C | LEU | A | 461 | 61.262 | 13.356 | 6.370 | 1.00 | 22.47 |
| ATOM | 706 | O | LEU | A | 461 | 60.836 | 12.207 | 6.452 | 1.00 | 21.94 |
| ATOM | 707 | N | ASN | A | 462 | 62.481 | 13.708 | 6.774 | 1.00 | 23.06 |
| ATOM | 708 | CA | ASN | A | 462 | 63.441 | 12.721 | 7.268 | 1.00 | 24.58 |
| ATOM | 709 | CB | ASN | A | 462 | 64.869 | 13.287 | 7.219 | 1.00 | 23.70 |
| ATOM | 710 | CG | ASN | A | 462 | 65.091 | 14.430 | 8.196 | 1.00 | 24.22 |
| ATOM | 711 | OD1 | ASN | A | 462 | 64.504 | 14.471 | 9.282 | 1.00 | 24.87 |
| ATOM | 712 | ND2 | ASN | A | 462 | 65.966 | 15.355 | 7.823 | 1.00 | 25.13 |
| ATOM | 713 | C | ASN | A | 462 | 63.228 | 12.083 | 8.631 | 1.00 | 25.66 |
| ATOM | 714 | O | ASN | A | 462 | 64.039 | 11.259 | 9.052 | 1.00 | 26.27 |
| ATOM | 715 | N | GLY | A | 463 | 62.150 | 12.436 | 9.317 | 1.00 | 26.85 |
| ATOM | 716 | CA | GLY | A | 463 | 61.909 | 11.857 | 10.626 | 1.00 | 28.07 |
| ATOM | 717 | C | GLY | A | 463 | 61.325 | 10.459 | 10.597 | 1.00 | 29.05 |
| ATOM | 718 | O | GLY | A | 463 | 61.368 | 9.751 | 11.603 | 1.00 | 31.65 |
| ATOM | 719 | N | GLY | A | 464 | 60.783 | 10.053 | 9.454 | 1.00 | 29.15 |
| ATOM | 720 | CA | GLY | A | 464 | 60.180 | 8.733 | 9.353 | 1.00 | 29.45 |
| ATOM | 721 | C | GLY | A | 464 | 58.743 | 8.751 | 9.865 | 1.00 | 29.34 |
| ATOM | 722 | O | GLY | A | 464 | 58.273 | 9.776 | 10.371 | 1.00 | 29.57 |
| ATOM | 723 | N | ASP | A | 465 | 58.040 | 7.628 | 9.746 | 1.00 | 26.76 |
| ATOM | 724 | CA | ASP | A | 465 | 56.657 | 7.557 | 10.199 | 1.00 | 25.67 |
| ATOM | 725 | CB | ASP | A | 465 | 55.867 | 6.585 | 9.317 | 1.00 | 25.97 |
| ATOM | 726 | CG | ASP | A | 465 | 56.383 | 5.164 | 9.409 | 1.00 | 26.64 |
| ATOM | 727 | OD1 | ASP | A | 465 | 55.795 | 4.368 | 10.172 | 1.00 | 25.67 |
| ATOM | 728 | OD2 | ASP | A | 465 | 57.382 | 4.848 | 8.725 | 1.00 | 27.99 |
| ATOM | 729 | C | ASP | A | 465 | 56.553 | 7.145 | 11.667 | 1.00 | 24.77 |
| ATOM | 730 | O | ASP | A | 465 | 57.456 | 6.505 | 12.210 | 1.00 | 24.43 |
| ATOM | 731 | N | LEU | A | 466 | 55.439 | 7.511 | 12.298 | 1.00 | 23.00 |
| ATOM | 732 | CA | LEU | A | 466 | 55.211 | 7.205 | 13.698 | 1.00 | 22.39 |
| ATOM | 733 | CB | LEU | A | 466 | 53.961 | 7.932 | 14.213 | 1.00 | 21.37 |
| ATOM | 734 | CG | LEU | A | 466 | 54.081 | 9.445 | 14.429 | 1.00 | 20.68 |
| ATOM | 735 | CD1 | LEU | A | 466 | 52.938 | 9.911 | 15.318 | 1.00 | 19.21 |
| ATOM | 736 | CD2 | LEU | A | 466 | 55.410 | 9.780 | 15.093 | 1.00 | 19.57 |
| ATOM | 737 | C | LEU | A | 466 | 55.094 | 5.719 | 13.987 | 1.00 | 23.24 |
| ATOM | 738 | O | LEU | A | 466 | 55.513 | 5.260 | 15.051 | 1.00 | 23.27 |
| ATOM | 739 | N | MET | A | 467 | 54.514 | 4.966 | 13.058 | 1.00 | 23.18 |
| ATOM | 740 | CA | MET | A | 467 | 54.380 | 3.528 | 13.257 | 1.00 | 24.69 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 741 | CB | MET | A | 467 | 53.774 | 2.861 | 12.020 | 1.00 | 26.98 |
| ATOM | 742 | CG | MET | A | 467 | 53.645 | 1.347 | 12.130 | 1.00 | 29.65 |
| ATOM | 743 | SD | MET | A | 467 | 52.639 | 0.815 | 13.534 | 1.00 | 34.87 |
| ATOM | 744 | CE | MET | A | 467 | 51.045 | 0.659 | 12.785 | 1.00 | 33.52 |
| ATOM | 745 | C | MET | A | 467 | 55.762 | 2.942 | 13.535 | 1.00 | 23.90 |
| ATOM | 746 | O | MET | A | 467 | 55.936 | 2.150 | 14.457 | 1.00 | 22.82 |
| ATOM | 747 | N | TYR | A | 468 | 56.742 | 3.342 | 12.734 | 1.00 | 24.06 |
| ATOM | 748 | CA | TYR | A | 468 | 58.109 | 2.867 | 12.896 | 1.00 | 25.72 |
| ATOM | 749 | CB | TYR | A | 468 | 59.022 | 3.502 | 11.844 | 1.00 | 27.04 |
| ATOM | 750 | CG | TYR | A | 468 | 60.472 | 3.148 | 12.045 | 1.00 | 30.91 |
| ATOM | 751 | CD1 | TYR | A | 468 | 60.943 | 1.869 | 11.749 | 1.00 | 33.62 |
| ATOM | 752 | CE1 | TYR | A | 468 | 62.271 | 1.518 | 11.986 | 1.00 | 34.74 |
| ATOM | 753 | CD2 | TYR | A | 468 | 61.368 | 4.073 | 12.582 | 1.00 | 32.99 |
| ATOM | 754 | CE2 | TYR | A | 468 | 62.697 | 3.733 | 12.821 | 1.00 | 34.74 |
| ATOM | 755 | CZ | TYR | A | 468 | 63.138 | 2.454 | 12.520 | 1.00 | 35.55 |
| ATOM | 756 | OH | TYR | A | 468 | 64.451 | 2.116 | 12.755 | 1.00 | 39.66 |
| ATOM | 757 | C | TYR | A | 468 | 58.651 | 3.205 | 14.290 | 1.00 | 25.58 |
| ATOM | 758 | O | TYR | A | 468 | 59.226 | 2.355 | 14.971 | 1.00 | 24.84 |
| ATOM | 759 | N | HIS | A | 469 | 58.464 | 4.454 | 14.705 | 1.00 | 23.87 |
| ATOM | 760 | CA | HIS | A | 469 | 58.937 | 4.898 | 16.007 | 1.00 | 24.51 |
| ATOM | 761 | CB | HIS | A | 469 | 58.727 | 6.404 | 16.147 | 1.00 | 24.84 |
| ATOM | 762 | CG | HIS | A | 469 | 59.557 | 7.208 | 15.196 | 1.00 | 27.55 |
| ATOM | 763 | CD2 | HIS | A | 469 | 59.209 | 8.066 | 14.208 | 1.00 | 28.42 |
| ATOM | 764 | ND1 | HIS | A | 469 | 60.934 | 7.152 | 15.184 | 1.00 | 28.86 |
| ATOM | 765 | CE1 | HIS | A | 469 | 61.399 | 7.940 | 14.231 | 1.00 | 29.62 |
| ATOM | 766 | NE2 | HIS | A | 469 | 60.373 | 8.506 | 13.623 | 1.00 | 28.82 |
| ATOM | 767 | C | HIS | A | 469 | 58.270 | 4.151 | 17.158 | 1.00 | 24.11 |
| ATOM | 768 | O | HIS | A | 469 | 58.929 | 3.812 | 18.138 | 1.00 | 22.55 |
| ATOM | 769 | N | ILE | A | 470 | 56.970 | 3.894 | 17.042 | 1.00 | 23.67 |
| ATOM | 770 | CA | ILE | A | 470 | 56.254 | 3.174 | 18.088 | 1.00 | 25.07 |
| ATOM | 771 | CB | ILE | A | 470 | 54.715 | 3.204 | 17.850 | 1.00 | 25.63 |
| ATOM | 772 | CG2 | ILE | A | 470 | 54.034 | 2.050 | 18.569 | 1.00 | 24.30 |
| ATOM | 773 | CG1 | ILE | A | 470 | 54.143 | 4.546 | 18.332 | 1.00 | 25.19 |
| ATOM | 774 | CD1 | ILE | A | 470 | 54.371 | 4.822 | 19.804 | 1.00 | 27.82 |
| ATOM | 775 | C | ILE | A | 470 | 56.737 | 1.729 | 18.161 | 1.00 | 25.82 |
| ATOM | 776 | O | ILE | A | 470 | 56.762 | 1.137 | 19.234 | 1.00 | 25.55 |
| ATOM | 777 | N | GLN | A | 471 | 57.127 | 1.167 | 17.022 | 1.00 | 26.72 |
| ATOM | 778 | CA | GLN | A | 471 | 57.609 | −0.204 | 16.997 | 1.00 | 28.66 |
| ATOM | 779 | CB | GLN | A | 471 | 57.748 | −0.713 | 15.559 | 1.00 | 30.40 |
| ATOM | 780 | CG | GLN | A | 471 | 56.436 | −0.843 | 14.818 | 1.00 | 33.10 |
| ATOM | 781 | CD | GLN | A | 471 | 56.588 | −1.562 | 13.492 | 1.00 | 36.30 |
| ATOM | 782 | OE1 | GLN | A | 471 | 57.463 | −1.230 | 12.685 | 1.00 | 37.77 |
| ATOM | 783 | NE2 | GLN | A | 471 | 55.731 | −2.549 | 13.254 | 1.00 | 36.53 |
| ATOM | 784 | C | GLN | A | 471 | 58.956 | −0.320 | 17.702 | 1.00 | 29.39 |
| ATOM | 785 | O | GLN | A | 471 | 59.188 | −1.266 | 18.450 | 1.00 | 29.90 |
| ATOM | 786 | N | SER | A | 472 | 59.840 | 0.645 | 17.470 | 1.00 | 28.10 |
| ATOM | 787 | CA | SER | A | 472 | 61.149 | 0.609 | 18.092 | 1.00 | 29.00 |
| ATOM | 788 | CB | SER | A | 472 | 62.157 | 1.394 | 17.250 | 1.00 | 29.93 |
| ATOM | 789 | OG | SER | A | 472 | 61.823 | 2.766 | 17.198 | 1.00 | 33.77 |
| ATOM | 790 | C | SER | A | 472 | 61.150 | 1.133 | 19.527 | 1.00 | 28.13 |
| ATOM | 791 | O | SER | A | 472 | 61.954 | 0.684 | 20.337 | 1.00 | 28.92 |
| ATOM | 792 | N | CYS | A | 473 | 60.252 | 2.068 | 19.841 | 1.00 | 26.87 |
| ATOM | 793 | CA | CYS | A | 473 | 60.164 | 2.653 | 21.185 | 1.00 | 27.39 |
| ATOM | 794 | CB | CYS | A | 473 | 59.800 | 4.139 | 21.092 | 1.00 | 28.88 |
| ATOM | 795 | SG | CYS | A | 473 | 61.012 | 5.194 | 20.268 | 1.00 | 38.25 |
| ATOM | 796 | C | CYS | A | 473 | 59.135 | 1.964 | 22.083 | 1.00 | 26.23 |
| ATOM | 797 | O | CYS | A | 473 | 59.119 | 2.182 | 23.298 | 1.00 | 25.29 |
| ATOM | 798 | N | HIS | A | 474 | 58.284 | 1.149 | 21.462 | 1.00 | 25.07 |
| ATOM | 799 | CA | HIS | A | 474 | 57.202 | 0.408 | 22.109 | 1.00 | 23.85 |
| ATOM | 800 | CB | HIS | A | 474 | 57.670 | −0.285 | 23.393 | 1.00 | 25.37 |
| ATOM | 801 | CG | HIS | A | 474 | 58.661 | −1.384 | 23.167 | 1.00 | 28.20 |
| ATOM | 802 | CD2 | HIS | A | 474 | 59.471 | −1.659 | 22.116 | 1.00 | 29.17 |
| ATOM | 803 | ND1 | HIS | A | 474 | 58.944 | −2.335 | 24.124 | 1.00 | 29.29 |
| ATOM | 804 | CE1 | HIS | A | 474 | 59.886 | −3.145 | 23.676 | 1.00 | 28.53 |
| ATOM | 805 | NE2 | HIS | A | 474 | 60.224 | −2.757 | 22.460 | 1.00 | 30.08 |
| ATOM | 806 | C | HIS | A | 474 | 56.005 | 1.311 | 22.411 | 1.00 | 23.60 |
| ATOM | 807 | O | HIS | A | 474 | 54.859 | 0.920 | 22.193 | 1.00 | 22.42 |
| ATOM | 808 | N | LYS | A | 475 | 56.270 | 2.511 | 22.921 | 1.00 | 22.82 |
| ATOM | 809 | CA | LYS | A | 475 | 55.207 | 3.473 | 23.222 | 1.00 | 22.22 |
| ATOM | 810 | CB | LYS | A | 475 | 54.330 | 2.990 | 24.382 | 1.00 | 24.73 |
| ATOM | 811 | CG | LYS | A | 475 | 55.067 | 2.756 | 25.690 | 1.00 | 26.81 |
| ATOM | 812 | CD | LYS | A | 475 | 54.155 | 2.053 | 26.683 | 1.00 | 29.39 |
| ATOM | 813 | CE | LYS | A | 475 | 54.953 | 1.362 | 27.788 | 1.00 | 31.24 |
| ATOM | 814 | NZ | LYS | A | 475 | 54.107 | 0.400 | 28.559 | 1.00 | 33.84 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 815 | C | LYS | A | 475 | 55.793 | 4.831 | 23.556 | 1.00 | 21.06 |
| ATOM | 816 | O | LYS | A | 475 | 56.987 | 4.946 | 23.839 | 1.00 | 20.31 |
| ATOM | 817 | N | PHE | A | 476 | 54.953 | 5.861 | 23.503 | 1.00 | 19.63 |
| ATOM | 818 | CA | PHE | A | 476 | 55.391 | 7.219 | 23.803 | 1.00 | 19.64 |
| ATOM | 819 | CB | PHE | A | 476 | 54.822 | 8.233 | 22.793 | 1.00 | 19.65 |
| ATOM | 820 | CG | PHE | A | 476 | 55.298 | 8.044 | 21.381 | 1.00 | 19.76 |
| ATOM | 821 | CD1 | PHE | A | 476 | 56.570 | 7.542 | 21.114 | 1.00 | 20.06 |
| ATOM | 822 | CD2 | PHE | A | 476 | 54.481 | 8.414 | 20.313 | 1.00 | 19.20 |
| ATOM | 823 | CE1 | PHE | A | 476 | 57.024 | 7.410 | 19.800 | 1.00 | 19.83 |
| ATOM | 824 | CE2 | PHE | A | 476 | 54.921 | 8.288 | 18.997 | 1.00 | 19.06 |
| ATOM | 825 | CZ | PHE | A | 476 | 56.194 | 7.785 | 18.738 | 1.00 | 19.95 |
| ATOM | 826 | C | PHE | A | 476 | 54.912 | 7.652 | 25.178 | 1.00 | 20.01 |
| ATOM | 827 | O | PHE | A | 476 | 53.826 | 7.269 | 25.620 | 1.00 | 18.73 |
| ATOM | 828 | N | ASP | A | 477 | 55.722 | 8.467 | 25.843 | 1.00 | 20.43 |
| ATOM | 829 | CA | ASP | A | 477 | 55.347 | 9.002 | 27.144 | 1.00 | 21.85 |
| ATOM | 830 | CB | ASP | A | 477 | 56.498 | 9.806 | 27.746 | 1.00 | 24.67 |
| ATOM | 831 | CG | ASP | A | 477 | 56.078 | 10.573 | 28.971 | 1.00 | 29.03 |
| ATOM | 832 | OD1 | ASP | A | 477 | 55.865 | 9.931 | 30.030 | 1.00 | 29.58 |
| ATOM | 833 | OD2 | ASP | A | 477 | 55.943 | 11.817 | 28.872 | 1.00 | 31.01 |
| ATOM | 834 | C | ASP | A | 477 | 54.161 | 9.933 | 26.882 | 1.00 | 21.49 |
| ATOM | 835 | O | ASP | A | 477 | 53.996 | 10.438 | 25.767 | 1.00 | 19.17 |
| ATOM | 836 | N | LEU | A | 478 | 53.355 | 10.183 | 27.908 | 1.00 | 21.46 |
| ATOM | 837 | CA | LEU | A | 478 | 52.173 | 11.024 | 27.745 | 1.00 | 22.04 |
| ATOM | 838 | CB | LEU | A | 478 | 51.420 | 11.149 | 29.073 | 1.00 | 22.92 |
| ATOM | 839 | CG | LEU | A | 478 | 50.177 | 12.045 | 28.987 | 1.00 | 24.53 |
| ATOM | 840 | CD1 | LEU | A | 478 | 49.227 | 11.490 | 27.935 | 1.00 | 26.73 |
| ATOM | 841 | CD2 | LEU | A | 478 | 49.476 | 12.123 | 30.324 | 1.00 | 24.26 |
| ATOM | 842 | C | LEU | A | 478 | 52.413 | 12.415 | 27.159 | 1.00 | 21.48 |
| ATOM | 843 | O | LEU | A | 478 | 51.616 | 12.890 | 26.353 | 1.00 | 20.19 |
| ATOM | 844 | N | SER | A | 479 | 53.493 | 13.074 | 27.560 | 1.00 | 20.76 |
| ATOM | 845 | CA | SER | A | 479 | 53.778 | 14.412 | 27.044 | 1.00 | 22.81 |
| ATOM | 846 | CB | SER | A | 479 | 54.967 | 15.034 | 27.782 | 1.00 | 23.09 |
| ATOM | 847 | OG | SER | A | 479 | 54.631 | 15.275 | 29.138 | 1.00 | 27.61 |
| ATOM | 848 | C | SER | A | 479 | 54.065 | 14.407 | 25.545 | 1.00 | 22.31 |
| ATOM | 849 | O | SER | A | 479 | 53.588 | 15.276 | 24.813 | 1.00 | 22.28 |
| ATOM | 850 | N | ARG | A | 480 | 54.848 | 13.431 | 25.097 | 1.00 | 21.15 |
| ATOM | 851 | CA | ARG | A | 480 | 55.195 | 13.317 | 23.688 | 1.00 | 21.07 |
| ATOM | 852 | CB | ARG | A | 480 | 56.271 | 12.246 | 23.487 | 1.00 | 20.82 |
| ATOM | 853 | CG | ARG | A | 480 | 56.680 | 12.063 | 22.033 | 1.00 | 22.55 |
| ATOM | 854 | CD | ARG | A | 480 | 57.711 | 10.960 | 21.887 | 1.00 | 24.81 |
| ATOM | 855 | NE | ARG | A | 480 | 59.013 | 11.342 | 22.433 | 1.00 | 25.59 |
| ATOM | 856 | CZ | ARG | A | 480 | 59.883 | 12.130 | 21.810 | 1.00 | 27.11 |
| ATOM | 857 | NH1 | ARG | A | 480 | 59.590 | 12.623 | 20.614 | 1.00 | 27.35 |
| ATOM | 858 | NH2 | ARG | A | 480 | 61.049 | 12.421 | 22.380 | 1.00 | 26.65 |
| ATOM | 859 | C | ARG | A | 480 | 53.960 | 12.974 | 22.853 | 1.00 | 20.49 |
| ATOM | 860 | O | ARG | A | 480 | 53.716 | 13.593 | 21.813 | 1.00 | 20.34 |
| ATOM | 861 | N | ALA | A | 481 | 53.186 | 11.993 | 23.316 | 1.00 | 19.22 |
| ATOM | 862 | CA | ALA | A | 481 | 51.969 | 11.563 | 22.626 | 1.00 | 18.63 |
| ATOM | 863 | CB | ALA | A | 481 | 51.355 | 10.365 | 23.336 | 1.00 | 17.26 |
| ATOM | 864 | C | ALA | A | 481 | 50.953 | 12.699 | 22.558 | 1.00 | 18.28 |
| ATOM | 865 | O | ALA | A | 481 | 50.258 | 12.855 | 21.552 | 1.00 | 16.31 |
| ATOM | 866 | N | THR | A | 482 | 50.868 | 13.477 | 23.636 | 1.00 | 17.94 |
| ATOM | 867 | CA | THR | A | 482 | 49.950 | 14.615 | 23.715 | 1.00 | 16.84 |
| ATOM | 868 | CB | THR | A | 482 | 49.979 | 15.269 | 25.113 | 1.00 | 17.81 |
| ATOM | 869 | OG1 | THR | A | 482 | 49.461 | 14.354 | 26.086 | 1.00 | 19.26 |
| ATOM | 870 | CG2 | THR | A | 482 | 49.147 | 16.536 | 25.127 | 1.00 | 18.16 |
| ATOM | 871 | C | THR | A | 482 | 50.323 | 15.672 | 22.682 | 1.00 | 16.38 |
| ATOM | 872 | O | THR | A | 482 | 49.451 | 16.247 | 22.029 | 1.00 | 17.51 |
| ATOM | 873 | N | PHE | A | 483 | 51.620 | 15.929 | 22.538 | 1.00 | 15.89 |
| ATOM | 874 | CA | PHE | A | 483 | 52.103 | 16.913 | 21.573 | 1.00 | 16.51 |
| ATOM | 875 | CB | PHE | A | 483 | 53.628 | 17.068 | 21.685 | 1.00 | 17.27 |
| ATOM | 876 | CG | PHE | A | 483 | 54.207 | 18.094 | 20.748 | 1.00 | 18.29 |
| ATOM | 877 | CD1 | PHE | A | 483 | 54.138 | 19.453 | 21.051 | 1.00 | 19.04 |
| ATOM | 878 | CD2 | PHE | A | 483 | 54.794 | 17.703 | 19.545 | 1.00 | 19.61 |
| ATOM | 879 | CE1 | PHE | A | 483 | 54.643 | 20.410 | 20.170 | 1.00 | 19.59 |
| ATOM | 880 | CE2 | PHE | A | 483 | 55.303 | 18.649 | 18.658 | 1.00 | 20.16 |
| ATOM | 881 | CZ | PHE | A | 483 | 55.226 | 20.011 | 18.972 | 1.00 | 19.94 |
| ATOM | 882 | C | PHE | A | 483 | 51.735 | 16.505 | 20.138 | 1.00 | 16.55 |
| ATOM | 883 | O | PHE | A | 483 | 51.233 | 17.325 | 19.361 | 1.00 | 16.37 |
| ATOM | 884 | N | TYR | A | 484 | 51.983 | 15.244 | 19.785 | 1.00 | 14.77 |
| ATOM | 885 | CA | TYR | A | 484 | 51.667 | 14.768 | 18.439 | 1.00 | 15.27 |
| ATOM | 886 | CB | TYR | A | 484 | 52.197 | 13.349 | 18.198 | 1.00 | 15.72 |
| ATOM | 887 | CG | TYR | A | 484 | 53.707 | 13.215 | 18.235 | 1.00 | 17.82 |
| ATOM | 888 | CD1 | TYR | A | 484 | 54.533 | 14.279 | 17.871 | 1.00 | 17.23 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 889 | CE1 | TYR | A | 484 | 55.917 | 14.146 | 17.857 | 1.00 | 16.78 |
| ATOM | 890 | CD2 | TYR | A | 484 | 54.311 | 12.002 | 18.587 | 1.00 | 17.52 |
| ATOM | 891 | CE2 | TYR | A | 484 | 55.704 | 11.856 | 18.570 | 1.00 | 15.64 |
| ATOM | 892 | CZ | TYR | A | 484 | 56.496 | 12.929 | 18.205 | 1.00 | 16.43 |
| ATOM | 893 | OH | TYR | A | 484 | 57.868 | 12.792 | 18.175 | 1.00 | 16.03 |
| ATOM | 894 | C | TYR | A | 484 | 50.167 | 14.769 | 18.209 | 1.00 | 14.02 |
| ATOM | 895 | O | TYR | A | 484 | 49.704 | 15.118 | 17.130 | 1.00 | 13.93 |
| ATOM | 896 | N | ALA | A | 485 | 49.417 | 14.368 | 19.228 | 1.00 | 13.39 |
| ATOM | 897 | CA | ALA | A | 485 | 47.968 | 14.319 | 19.140 | 1.00 | 14.86 |
| ATOM | 898 | CB | ALA | A | 485 | 47.385 | 13.801 | 20.446 | 1.00 | 12.89 |
| ATOM | 899 | C | ALA | A | 485 | 47.400 | 15.700 | 18.833 | 1.00 | 15.70 |
| ATOM | 900 | O | ALA | A | 485 | 46.507 | 15.843 | 18.000 | 1.00 | 14.51 |
| ATOM | 901 | N | ALA | A | 486 | 47.928 | 16.715 | 19.508 | 1.00 | 16.59 |
| ATOM | 902 | CA | ALA | A | 486 | 47.457 | 18.081 | 19.306 | 1.00 | 16.76 |
| ATOM | 903 | CB | ALA | A | 486 | 48.153 | 19.026 | 20.283 | 1.00 | 17.23 |
| ATOM | 904 | C | ALA | A | 486 | 47.681 | 18.549 | 17.869 | 1.00 | 16.08 |
| ATOM | 905 | O | ALA | A | 486 | 46.789 | 19.136 | 17.272 | 1.00 | 16.59 |
| ATOM | 906 | N | GLU | A | 487 | 48.865 | 18.303 | 17.316 | 1.00 | 14.04 |
| ATOM | 907 | CA | GLU | A | 487 | 49.136 | 18.728 | 15.942 | 1.00 | 16.71 |
| ATOM | 908 | CB | GLU | A | 487 | 50.635 | 18.609 | 15.615 | 1.00 | 16.19 |
| ATOM | 909 | CG | GLU | A | 487 | 51.513 | 19.477 | 16.525 | 1.00 | 18.81 |
| ATOM | 910 | CD | GLU | A | 487 | 52.973 | 19.565 | 16.080 | 1.00 | 20.88 |
| ATOM | 911 | OE1 | GLU | A | 487 | 53.489 | 18.595 | 15.475 | 1.00 | 19.09 |
| ATOM | 912 | OE2 | GLU | A | 487 | 53.615 | 20.608 | 16.359 | 1.00 | 21.07 |
| ATOM | 913 | C | GLU | A | 487 | 48.303 | 17.915 | 14.950 | 1.00 | 15.58 |
| ATOM | 914 | O | GLU | A | 487 | 47.911 | 18.410 | 13.899 | 1.00 | 15.41 |
| ATOM | 915 | N | ILE | A | 488 | 48.026 | 16.664 | 15.291 | 1.00 | 15.26 |
| ATOM | 916 | CA | ILE | A | 488 | 47.208 | 15.841 | 14.424 | 1.00 | 15.55 |
| ATOM | 917 | CB | ILE | A | 488 | 47.203 | 14.379 | 14.891 | 1.00 | 13.11 |
| ATOM | 918 | CG2 | ILE | A | 488 | 46.049 | 13.613 | 14.225 | 1.00 | 15.10 |
| ATOM | 919 | CG1 | ILE | A | 488 | 48.560 | 13.751 | 14.565 | 1.00 | 14.20 |
| ATOM | 920 | CD1 | ILE | A | 488 | 48.755 | 12.349 | 15.125 | 1.00 | 17.27 |
| ATOM | 921 | C | ILE | A | 488 | 45.788 | 16.410 | 14.429 | 1.00 | 15.04 |
| ATOM | 922 | O | ILE | A | 488 | 45.134 | 16.466 | 13.391 | 1.00 | 16.32 |
| ATOM | 923 | N | ILE | A | 489 | 45.324 | 16.843 | 15.597 | 1.00 | 13.00 |
| ATOM | 924 | CA | ILE | A | 489 | 43.995 | 17.427 | 15.721 | 1.00 | 13.70 |
| ATOM | 925 | CB | ILE | A | 489 | 43.711 | 17.892 | 17.173 | 1.00 | 13.58 |
| ATOM | 926 | CG2 | ILE | A | 489 | 42.581 | 18.929 | 17.193 | 1.00 | 13.47 |
| ATOM | 927 | CG1 | ILE | A | 489 | 43.366 | 16.681 | 18.043 | 1.00 | 13.70 |
| ATOM | 928 | CD1 | ILE | A | 489 | 43.269 | 16.992 | 19.535 | 1.00 | 14.08 |
| ATOM | 929 | C | ILE | A | 489 | 43.846 | 18.627 | 14.780 | 1.00 | 15.43 |
| ATOM | 930 | O | ILE | A | 489 | 42.853 | 18.718 | 14.049 | 1.00 | 14.03 |
| ATOM | 931 | N | LEU | A | 490 | 44.827 | 19.535 | 14.792 | 1.00 | 13.69 |
| ATOM | 932 | CA | LEU | A | 490 | 44.767 | 20.718 | 13.937 | 1.00 | 16.37 |
| ATOM | 933 | CB | LEU | A | 490 | 45.920 | 21.683 | 14.258 | 1.00 | 17.37 |
| ATOM | 934 | CG | LEU | A | 490 | 45.834 | 22.352 | 15.637 | 1.00 | 17.35 |
| ATOM | 935 | CD1 | LEU | A | 490 | 47.078 | 23.223 | 15.895 | 1.00 | 18.38 |
| ATOM | 936 | CD2 | LEU | A | 490 | 44.572 | 23.197 | 15.702 | 1.00 | 17.12 |
| ATOM | 937 | C | LEU | A | 490 | 44.789 | 20.335 | 12.460 | 1.00 | 16.50 |
| ATOM | 938 | O | LEU | A | 490 | 44.086 | 20.925 | 11.652 | 1.00 | 16.06 |
| ATOM | 939 | N | GLY | A | 491 | 45.593 | 19.336 | 12.115 | 1.00 | 18.00 |
| ATOM | 940 | CA | GLY | A | 491 | 45.649 | 18.888 | 10.737 | 1.00 | 17.83 |
| ATOM | 941 | C | GLY | A | 491 | 44.290 | 18.366 | 10.288 | 1.00 | 17.31 |
| ATOM | 942 | O | GLY | A | 491 | 43.831 | 18.695 | 9.190 | 1.00 | 16.63 |
| ATOM | 943 | N | LEU | A | 492 | 43.650 | 17.557 | 11.134 | 1.00 | 16.73 |
| ATOM | 944 | CA | LEU | A | 492 | 42.336 | 16.991 | 10.832 | 1.00 | 18.49 |
| ATOM | 945 | CB | LEU | A | 492 | 41.895 | 15.981 | 11.900 | 1.00 | 19.00 |
| ATOM | 946 | CG | LEU | A | 492 | 42.388 | 14.532 | 11.900 | 1.00 | 23.20 |
| ATOM | 947 | CD1 | LEU | A | 492 | 41.595 | 13.767 | 12.971 | 1.00 | 23.49 |
| ATOM | 948 | CD2 | LEU | A | 492 | 42.171 | 13.877 | 10.530 | 1.00 | 23.88 |
| ATOM | 949 | C | LEU | A | 492 | 41.266 | 18.048 | 10.742 | 1.00 | 17.70 |
| ATOM | 950 | O | LEU | A | 492 | 40.418 | 18.034 | 9.821 | 1.00 | 16.53 |
| ATOM | 951 | N | GLN | A | 493 | 41.265 | 18.965 | 11.706 | 1.00 | 16.20 |
| ATOM | 952 | CA | GLN | A | 493 | 40.261 | 20.017 | 11.721 | 1.00 | 16.22 |
| ATOM | 953 | CB | GLN | A | 493 | 40.341 | 20.884 | 12.996 | 1.00 | 14.50 |
| ATOM | 954 | CG | GLN | A | 493 | 39.909 | 20.077 | 14.252 | 1.00 | 16.12 |
| ATOM | 955 | CD | GLN | A | 493 | 39.912 | 20.900 | 15.495 | 1.00 | 15.87 |
| ATOM | 956 | OE1 | GLN | A | 493 | 40.673 | 21.816 | 15.648 | 1.00 | 18.33 |
| ATOM | 957 | NE2 | GLN | A | 493 | 39.033 | 20.544 | 16.442 | 1.00 | 15.27 |
| ATOM | 958 | C | GLN | A | 493 | 40.361 | 20.936 | 10.523 | 1.00 | 15.70 |
| ATOM | 959 | O | GLN | A | 493 | 39.363 | 21.445 | 10.019 | 1.00 | 15.96 |
| ATOM | 960 | N | PHE | A | 494 | 41.597 | 21.132 | 10.022 | 1.00 | 15.39 |
| ATOM | 961 | CA | PHE | A | 494 | 41.794 | 21.954 | 8.855 | 1.00 | 16.44 |
| ATOM | 962 | CB | PHE | A | 494 | 43.302 | 22.146 | 8.556 | 1.00 | 15.32 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 963 | CG | PHE | A | 494 | 43.541 | 22.832 | 7.252 | 1.00 | 17.38 |
| ATOM | 964 | CD1 | PHE | A | 494 | 43.305 | 24.203 | 7.116 | 1.00 | 17.01 |
| ATOM | 965 | CD2 | PHE | A | 494 | 43.981 | 22.110 | 6.152 | 1.00 | 15.36 |
| ATOM | 966 | CE1 | PHE | A | 494 | 43.517 | 24.840 | 5.902 | 1.00 | 17.03 |
| ATOM | 967 | CE2 | PHE | A | 494 | 44.197 | 22.736 | 4.930 | 1.00 | 17.93 |
| ATOM | 968 | CZ | PHE | A | 494 | 43.968 | 24.106 | 4.804 | 1.00 | 17.43 |
| ATOM | 969 | C | PHE | A | 494 | 41.124 | 21.245 | 7.694 | 1.00 | 16.04 |
| ATOM | 970 | O | PHE | A | 494 | 40.313 | 21.844 | 6.981 | 1.00 | 16.17 |
| ATOM | 971 | N | LEU | A | 495 | 41.433 | 19.961 | 7.531 | 1.00 | 14.64 |
| ATOM | 972 | CA | LEU | A | 495 | 40.841 | 19.165 | 6.459 | 1.00 | 15.79 |
| ATOM | 973 | CB | LEU | A | 495 | 41.341 | 17.711 | 6.515 | 1.00 | 15.11 |
| ATOM | 974 | CG | LEU | A | 495 | 42.802 | 17.470 | 6.129 | 1.00 | 16.37 |
| ATOM | 975 | CD1 | LEU | A | 495 | 43.151 | 15.991 | 6.298 | 1.00 | 15.22 |
| ATOM | 976 | CD2 | LEU | A | 495 | 43.028 | 17.925 | 4.695 | 1.00 | 15.83 |
| ATOM | 977 | C | LEU | A | 495 | 39.322 | 19.173 | 6.519 | 1.00 | 14.97 |
| ATOM | 978 | O | LEU | A | 495 | 38.652 | 19.327 | 5.500 | 1.00 | 14.55 |
| ATOM | 979 | N | HIS | A | 496 | 38.780 | 18.997 | 7.718 | 1.00 | 15.73 |
| ATOM | 980 | CA | HIS | A | 496 | 37.332 | 19.002 | 7.903 | 1.00 | 16.47 |
| ATOM | 981 | CB | HIS | A | 496 | 36.983 | 18.639 | 9.347 | 1.00 | 16.06 |
| ATOM | 982 | CG | HIS | A | 496 | 37.336 | 17.232 | 9.717 | 1.00 | 17.23 |
| ATOM | 983 | CD2 | HIS | A | 496 | 37.791 | 16.199 | 8.969 | 1.00 | 17.32 |
| ATOM | 984 | ND1 | HIS | A | 496 | 37.232 | 16.754 | 11.004 | 1.00 | 16.18 |
| ATOM | 985 | CE1 | HIS | A | 496 | 37.609 | 15.488 | 11.034 | 1.00 | 16.71 |
| ATOM | 986 | NE2 | HIS | A | 496 | 37.954 | 15.127 | 9.813 | 1.00 | 15.84 |
| ATOM | 987 | C | HIS | A | 496 | 36.722 | 20.360 | 7.572 | 1.00 | 16.31 |
| ATOM | 988 | O | HIS | A | 496 | 35.634 | 20.433 | 7.004 | 1.00 | 16.29 |
| ATOM | 989 | N | SER | A | 497 | 37.423 | 21.438 | 7.920 | 1.00 | 17.23 |
| ATOM | 990 | CA | SER | A | 497 | 36.898 | 22.779 | 7.662 | 1.00 | 16.89 |
| ATOM | 991 | CB | SER | A | 497 | 37.748 | 23.854 | 8.361 | 1.00 | 16.11 |
| ATOM | 992 | OG | SER | A | 497 | 38.983 | 24.063 | 7.696 | 1.00 | 15.31 |
| ATOM | 993 | C | SER | A | 497 | 36.867 | 23.034 | 6.166 | 1.00 | 16.85 |
| ATOM | 994 | O | SER | A | 497 | 36.124 | 23.884 | 5.699 | 1.00 | 18.00 |
| ATOM | 995 | N | LYS | A | 498 | 37.672 | 22.285 | 5.419 | 1.00 | 15.86 |
| ATOM | 996 | CA | LYS | A | 498 | 37.718 | 22.424 | 3.972 | 1.00 | 16.00 |
| ATOM | 997 | CB | LYS | A | 498 | 39.162 | 22.272 | 3.474 | 1.00 | 15.59 |
| ATOM | 998 | CG | LYS | A | 498 | 40.095 | 23.416 | 3.892 | 1.00 | 16.30 |
| ATOM | 999 | CD | LYS | A | 498 | 39.712 | 24.745 | 3.238 | 1.00 | 16.10 |
| ATOM | 1000 | CE | LYS | A | 498 | 40.597 | 25.893 | 3.744 | 1.00 | 18.48 |
| ATOM | 1001 | NZ | LYS | A | 498 | 40.415 | 27.173 | 2.962 | 1.00 | 16.93 |
| ATOM | 1002 | C | LYS | A | 498 | 36.804 | 21.412 | 3.261 | 1.00 | 16.12 |
| ATOM | 1003 | O | LYS | A | 498 | 36.950 | 21.170 | 2.062 | 1.00 | 16.06 |
| ATOM | 1004 | N | GLY | A | 499 | 35.870 | 20.828 | 4.007 | 1.00 | 16.27 |
| ATOM | 1005 | CA | GLY | A | 499 | 34.936 | 19.862 | 3.438 | 1.00 | 18.36 |
| ATOM | 1006 | C | GLY | A | 499 | 35.532 | 18.508 | 3.086 | 1.00 | 19.34 |
| ATOM | 1007 | O | GLY | A | 499 | 35.057 | 17.823 | 2.172 | 1.00 | 19.30 |
| ATOM | 1008 | N | ILE | A | 500 | 36.565 | 18.112 | 3.818 | 1.00 | 19.00 |
| ATOM | 1009 | CA | ILE | A | 500 | 37.236 | 16.848 | 3.559 | 1.00 | 18.78 |
| ATOM | 1010 | CB | ILE | A | 500 | 38.721 | 17.095 | 3.182 | 1.00 | 19.08 |
| ATOM | 1011 | CG2 | ILE | A | 500 | 39.463 | 15.769 | 3.009 | 1.00 | 18.70 |
| ATOM | 1012 | CG1 | ILE | A | 500 | 38.796 | 17.921 | 1.897 | 1.00 | 20.51 |
| ATOM | 1013 | CD1 | ILE | A | 500 | 40.157 | 18.517 | 1.637 | 1.00 | 19.85 |
| ATOM | 1014 | C | ILE | A | 500 | 37.192 | 15.891 | 4.748 | 1.00 | 19.58 |
| ATOM | 1015 | O | ILE | A | 500 | 37.392 | 16.291 | 5.896 | 1.00 | 19.29 |
| ATOM | 1016 | N | VAL | A | 501 | 36.901 | 14.628 | 4.455 | 1.00 | 19.79 |
| ATOM | 1017 | CA | VAL | A | 501 | 36.886 | 13.574 | 5.457 | 1.00 | 19.06 |
| ATOM | 1018 | CB | VAL | A | 501 | 35.579 | 12.752 | 5.410 | 1.00 | 19.05 |
| ATOM | 1019 | CG1 | VAL | A | 501 | 35.662 | 11.582 | 6.397 | 1.00 | 19.68 |
| ATOM | 1020 | CG2 | VAL | A | 501 | 34.387 | 13.645 | 5.773 | 1.00 | 18.08 |
| ATOM | 1021 | C | VAL | A | 501 | 38.085 | 12.733 | 5.017 | 1.00 | 19.05 |
| ATOM | 1022 | O | VAL | A | 501 | 38.126 | 12.250 | 3.883 | 1.00 | 17.88 |
| ATOM | 1023 | N | TYR | A | 502 | 39.066 | 12.597 | 5.907 | 1.00 | 19.22 |
| ATOM | 1024 | CA | TYR | A | 502 | 40.315 | 11.887 | 5.620 | 1.00 | 20.24 |
| ATOM | 1025 | CB | TYR | A | 502 | 41.325 | 12.184 | 6.734 | 1.00 | 20.54 |
| ATOM | 1026 | CG | TYR | A | 502 | 42.708 | 11.634 | 6.490 | 1.00 | 22.30 |
| ATOM | 1027 | CD1 | TYR | A | 502 | 43.403 | 11.921 | 5.313 | 1.00 | 22.57 |
| ATOM | 1028 | CE1 | TYR | A | 502 | 44.701 | 11.428 | 5.103 | 1.00 | 22.84 |
| ATOM | 1029 | CD2 | TYR | A | 502 | 43.338 | 10.844 | 7.447 | 1.00 | 22.27 |
| ATOM | 1030 | CE2 | TYR | A | 502 | 44.630 | 10.351 | 7.243 | 1.00 | 22.73 |
| ATOM | 1031 | CZ | TYR | A | 502 | 45.302 | 10.647 | 6.074 | 1.00 | 21.57 |
| ATOM | 1032 | OH | TYR | A | 502 | 46.573 | 10.152 | 5.885 | 1.00 | 21.68 |
| ATOM | 1033 | C | TYR | A | 502 | 40.161 | 10.382 | 5.411 | 1.00 | 21.47 |
| ATOM | 1034 | O | TYR | A | 502 | 40.691 | 9.829 | 4.448 | 1.00 | 22.30 |
| ATOM | 1035 | N | ARG | A | 503 | 39.450 | 9.732 | 6.326 | 1.00 | 22.06 |
| ATOM | 1036 | CA | ARG | A | 503 | 39.161 | 8.305 | 6.251 | 1.00 | 23.80 |

TABLE 2-continued

Structure coordinates for PKCθ
(residues 377-696 of SEQ ID NO: 1)/staurosporine complex

|  | # | name | res | chain | res # | X | Y | Z | occ | B |
|---|---|---|---|---|---|---|---|---|---|---|
| ATOM | 1037 | CB | ARG | A | 503 | 38.349 | 8.005 | 4.991 | 1.00 | 23.28 |
| ATOM | 1038 | CG | ARG | A | 503 | 37.008 | 8.703 | 4.975 | 1.00 | 22.23 |
| ATOM | 1039 | CD | ARG | A | 503 | 36.081 | 8.075 | 3.975 | 1.00 | 17.63 |
| ATOM | 1040 | NE | ARG | A | 503 | 36.523 | 8.241 | 2.591 | 1.00 | 15.18 |
| ATOM | 1041 | CZ | ARG | A | 503 | 35.739 | 7.973 | 1.550 | 1.00 | 15.46 |
| ATOM | 1042 | NH1 | ARG | A | 503 | 34.502 | 7.538 | 1.765 | 1.00 | 14.35 |
| ATOM | 1043 | NH2 | ARG | A | 503 | 36.175 | 8.148 | 0.307 | 1.00 | 12.82 |
| ATOM | 1044 | C | ARG | A | 503 | 40.310 | 7.311 | 6.336 | 1.00 | 24.61 |
| ATOM | 1045 | O | ARG | A | 503 | 40.080 | 6.097 | 6.296 | 1.00 | 25.89 |
| ATOM | 1046 | N | ASP | A | 504 | 41.540 | 7.790 | 6.441 | 1.00 | 24.36 |
| ATOM | 1047 | CA | ASP | A | 504 | 42.643 | 6.851 | 6.548 | 1.00 | 24.64 |
| ATOM | 1048 | CB | ASP | A | 504 | 43.305 | 6.645 | 5.182 | 1.00 | 26.23 |
| ATOM | 1049 | CG | ASP | A | 504 | 44.133 | 5.372 | 5.130 | 1.00 | 28.98 |
| ATOM | 1050 | OD1 | ASP | A | 504 | 43.706 | 4.359 | 5.735 | 1.00 | 30.02 |
| ATOM | 1051 | OD2 | ASP | A | 504 | 45.198 | 5.379 | 4.479 | 1.00 | 29.70 |
| ATOM | 1052 | C | ASP | A | 504 | 43.678 | 7.267 | 7.587 | 1.00 | 23.66 |
| ATOM | 1053 | O | ASP | A | 504 | 44.880 | 7.080 | 7.388 | 1.00 | 23.47 |
| ATOM | 1054 | N | LEU | A | 505 | 43.205 | 7.816 | 8.703 | 1.00 | 22.88 |
| ATOM | 1055 | CA | LEU | A | 505 | 44.102 | 8.242 | 9.768 | 1.00 | 22.30 |
| ATOM | 1056 | CB | LEU | A | 505 | 43.376 | 9.177 | 10.743 | 1.00 | 22.34 |
| ATOM | 1057 | CG | LEU | A | 505 | 44.238 | 9.787 | 11.856 | 1.00 | 23.32 |
| ATOM | 1058 | CD1 | LEU | A | 505 | 45.359 | 10.602 | 11.232 | 1.00 | 23.36 |
| ATOM | 1059 | CD2 | LEU | A | 505 | 43.379 | 10.667 | 12.763 | 1.00 | 24.16 |
| ATOM | 1060 | C | LEU | A | 505 | 44.653 | 7.038 | 10.521 | 1.00 | 21.25 |
| ATOM | 1061 | O | LEU | A | 505 | 43.911 | 6.283 | 11.139 | 1.00 | 22.74 |
| ATOM | 1062 | N | LYS | A | 506 | 45.964 | 6.858 | 10.449 | 1.00 | 20.30 |
| ATOM | 1063 | CA | LYS | A | 506 | 46.626 | 5.756 | 11.129 | 1.00 | 20.81 |
| ATOM | 1064 | CB | LYS | A | 506 | 46.515 | 4.480 | 10.286 | 1.00 | 20.22 |
| ATOM | 1065 | CG | LYS | A | 506 | 47.103 | 4.593 | 8.900 | 1.00 | 21.40 |
| ATOM | 1066 | CD | LYS | A | 506 | 46.811 | 3.341 | 8.079 | 1.00 | 23.11 |
| ATOM | 1067 | CE | LYS | A | 506 | 47.477 | 3.423 | 6.722 | 1.00 | 21.39 |
| ATOM | 1068 | NZ | LYS | A | 506 | 47.106 | 2.286 | 5.856 | 1.00 | 26.55 |
| ATOM | 1069 | C | LYS | A | 506 | 48.089 | 6.139 | 11.356 | 1.00 | 20.61 |
| ATOM | 1070 | O | LYS | A | 506 | 48.603 | 7.038 | 10.688 | 1.00 | 20.40 |
| ATOM | 1071 | N | LEU | A | 507 | 48.748 | 5.476 | 12.303 | 1.00 | 20.46 |
| ATOM | 1072 | CA | LEU | A | 507 | 50.152 | 5.769 | 12.622 | 1.00 | 21.72 |
| ATOM | 1073 | CB | LEU | A | 507 | 50.694 | 4.765 | 13.637 | 1.00 | 21.51 |
| ATOM | 1074 | CG | LEU | A | 507 | 50.214 | 4.857 | 15.083 | 1.00 | 20.98 |
| ATOM | 1075 | CD1 | LEU | A | 507 | 50.845 | 3.730 | 15.870 | 1.00 | 23.11 |
| ATOM | 1076 | CD2 | LEU | A | 507 | 50.589 | 6.204 | 15.671 | 1.00 | 21.75 |
| ATOM | 1077 | C | LEU | A | 507 | 51.062 | 5.758 | 11.405 | 1.00 | 21.54 |
| ATOM | 1078 | O | LEU | A | 507 | 51.983 | 6.565 | 11.294 | 1.00 | 20.97 |
| ATOM | 1079 | N | ASP | A | 508 | 50.799 | 4.816 | 10.507 | 1.00 | 22.57 |
| ATOM | 1080 | CA | ASP | A | 508 | 51.564 | 4.650 | 9.277 | 1.00 | 22.87 |
| ATOM | 1081 | CB | ASP | A | 508 | 50.966 | 3.518 | 8.440 | 1.00 | 25.88 |
| ATOM | 1082 | CG | ASP | A | 508 | 50.753 | 2.250 | 9.239 | 1.00 | 31.04 |
| ATOM | 1083 | OD1 | ASP | A | 508 | 49.997 | 2.274 | 10.248 | 1.00 | 33.35 |
| ATOM | 1084 | OD2 | ASP | A | 508 | 51.339 | 1.223 | 8.848 | 1.00 | 32.58 |
| ATOM | 1085 | C | ASP | A | 508 | 51.558 | 5.921 | 8.436 | 1.00 | 21.45 |
| ATOM | 1086 | O | ASP | A | 508 | 52.495 | 6.170 | 7.666 | 1.00 | 20.81 |
| ATOM | 1087 | N | ASN | A | 509 | 50.501 | 6.719 | 8.576 | 1.00 | 19.00 |
| ATOM | 1088 | CA | ASN | A | 509 | 50.380 | 7.943 | 7.798 | 1.00 | 19.78 |
| ATOM | 1089 | CB | ASN | A | 509 | 48.950 | 8.091 | 7.266 | 1.00 | 19.10 |
| ATOM | 1090 | CG | ASN | A | 509 | 48.630 | 7.069 | 6.197 | 1.00 | 20.16 |
| ATOM | 1091 | OD1 | ASN | A | 509 | 49.535 | 6.518 | 5.573 | 1.00 | 22.44 |
| ATOM | 1092 | ND2 | ASN | A | 509 | 47.348 | 6.818 | 5.968 | 1.00 | 20.65 |
| ATOM | 1093 | C | ASN | A | 509 | 50.807 | 9.225 | 8.490 | 1.00 | 19.25 |
| ATOM | 1094 | O | ASN | A | 509 | 50.560 | 10.313 | 7.974 | 1.00 | 19.05 |
| ATOM | 1095 | N | ILE | A | 510 | 51.441 | 9.105 | 9.652 | 1.00 | 18.04 |
| ATOM | 1096 | CA | ILE | A | 510 | 51.917 | 10.289 | 10.358 | 1.00 | 18.42 |
| ATOM | 1097 | CB | ILE | A | 510 | 51.516 | 10.297 | 11.851 | 1.00 | 16.95 |
| ATOM | 1098 | CG2 | ILE | A | 510 | 52.019 | 11.575 | 12.505 | 1.00 | 17.62 |
| ATOM | 1099 | CG1 | ILE | A | 510 | 49.989 | 10.212 | 12.002 | 1.00 | 16.30 |
| ATOM | 1100 | CD1 | ILE | A | 510 | 49.236 | 11.393 | 11.424 | 1.00 | 17.39 |
| ATOM | 1101 | C | ILE | A | 510 | 53.433 | 10.298 | 10.275 | 1.00 | 18.57 |
| ATOM | 1102 | O | ILE | A | 510 | 54.100 | 9.418 | 10.816 | 1.00 | 18.85 |
| ATOM | 1103 | N | LEU | A | 511 | 53.976 | 11.298 | 9.588 | 1.00 | 19.12 |
| ATOM | 1104 | CA | LEU | A | 511 | 55.418 | 11.410 | 9.433 | 1.00 | 18.91 |
| ATOM | 1105 | CB | LEU | A | 511 | 55.769 | 11.695 | 7.972 | 1.00 | 17.90 |
| ATOM | 1106 | CG | LEU | A | 511 | 55.364 | 10.653 | 6.928 | 1.00 | 19.17 |
| ATOM | 1107 | CD1 | LEU | A | 511 | 55.419 | 11.289 | 5.549 | 1.00 | 18.27 |
| ATOM | 1108 | CD2 | LEU | A | 511 | 56.279 | 9.429 | 7.014 | 1.00 | 16.37 |
| ATOM | 1109 | C | LEU | A | 511 | 55.967 | 12.526 | 10.304 | 1.00 | 19.34 |
| ATOM | 1110 | O | LEU | A | 511 | 55.246 | 13.453 | 10.676 | 1.00 | 19.91 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1111 | N | LEU | A | 512 | 57.251 | 12.429 | 10.622 | 1.00 | 20.38 |
| ATOM | 1112 | CA | LEU | A | 512 | 57.928 | 13.434 | 11.429 | 1.00 | 22.06 |
| ATOM | 1113 | CB | LEU | A | 512 | 58.739 | 12.768 | 12.545 | 1.00 | 24.58 |
| ATOM | 1114 | CG | LEU | A | 512 | 58.000 | 12.360 | 13.812 | 1.00 | 26.71 |
| ATOM | 1115 | CD1 | LEU | A | 512 | 58.905 | 11.544 | 14.724 | 1.00 | 27.64 |
| ATOM | 1116 | CD2 | LEU | A | 512 | 57.537 | 13.619 | 14.514 | 1.00 | 29.31 |
| ATOM | 1117 | C | LEU | A | 512 | 58.866 | 14.244 | 10.551 | 1.00 | 21.66 |
| ATOM | 1118 | O | LEU | A | 512 | 59.627 | 13.677 | 9.761 | 1.00 | 20.77 |
| ATOM | 1119 | N | ASP | A | 513 | 58.808 | 15.566 | 10.686 | 1.00 | 22.75 |
| ATOM | 1120 | CA | ASP | A | 513 | 59.675 | 16.449 | 9.911 | 1.00 | 24.28 |
| ATOM | 1121 | CB | ASP | A | 513 | 59.031 | 17.826 | 9.743 | 1.00 | 25.47 |
| ATOM | 1122 | CG | ASP | A | 513 | 59.607 | 18.602 | 8.567 | 1.00 | 27.30 |
| ATOM | 1123 | OD1 | ASP | A | 513 | 60.754 | 18.315 | 8.146 | 1.00 | 27.20 |
| ATOM | 1124 | OD2 | ASP | A | 513 | 58.913 | 19.512 | 8.067 | 1.00 | 28.69 |
| ATOM | 1125 | C | ASP | A | 513 | 60.996 | 16.578 | 10.673 | 1.00 | 24.55 |
| ATOM | 1126 | O | ASP | A | 513 | 61.116 | 16.087 | 11.793 | 1.00 | 24.45 |
| ATOM | 1127 | N | LYS | A | 514 | 61.976 | 17.248 | 10.075 | 1.00 | 24.50 |
| ATOM | 1128 | CA | LYS | A | 514 | 63.289 | 17.405 | 10.694 | 1.00 | 25.34 |
| ATOM | 1129 | CB | LYS | A | 514 | 64.286 | 17.922 | 9.660 | 1.00 | 26.21 |
| ATOM | 1130 | CG | LYS | A | 514 | 63.951 | 19.297 | 9.124 | 1.00 | 28.18 |
| ATOM | 1131 | CD | LYS | A | 514 | 64.978 | 19.740 | 8.102 | 1.00 | 30.84 |
| ATOM | 1132 | CE | LYS | A | 514 | 64.762 | 21.187 | 7.709 | 1.00 | 31.77 |
| ATOM | 1133 | NZ | LYS | A | 514 | 63.452 | 21.388 | 7.045 | 1.00 | 33.28 |
| ATOM | 1134 | C | LYS | A | 514 | 63.299 | 18.320 | 11.915 | 1.00 | 25.71 |
| ATOM | 1135 | O | LYS | A | 514 | 64.280 | 18.357 | 12.658 | 1.00 | 25.54 |
| ATOM | 1136 | N | ASP | A | 515 | 62.209 | 19.053 | 12.116 | 1.00 | 25.46 |
| ATOM | 1137 | CA | ASP | A | 515 | 62.087 | 19.962 | 13.246 | 1.00 | 24.68 |
| ATOM | 1138 | CB | ASP | A | 515 | 61.316 | 21.222 | 12.830 | 1.00 | 26.41 |
| ATOM | 1139 | CG | ASP | A | 515 | 60.014 | 20.904 | 12.097 | 1.00 | 28.98 |
| ATOM | 1140 | OD1 | ASP | A | 515 | 59.613 | 19.714 | 12.063 | 1.00 | 28.81 |
| ATOM | 1141 | OD2 | ASP | A | 515 | 59.389 | 21.850 | 11.555 | 1.00 | 28.10 |
| ATOM | 1142 | C | ASP | A | 515 | 61.385 | 19.290 | 14.421 | 1.00 | 23.39 |
| ATOM | 1143 | O | ASP | A | 515 | 61.292 | 19.856 | 15.509 | 1.00 | 22.94 |
| ATOM | 1144 | N | GLY | A | 516 | 60.886 | 18.079 | 14.203 | 1.00 | 21.31 |
| ATOM | 1145 | CA | GLY | A | 516 | 60.207 | 17.375 | 15.274 | 1.00 | 20.30 |
| ATOM | 1146 | C | GLY | A | 516 | 58.695 | 17.476 | 15.227 | 1.00 | 19.36 |
| ATOM | 1147 | O | GLY | A | 516 | 58.000 | 16.860 | 16.033 | 1.00 | 20.02 |
| ATOM | 1148 | N | HIS | A | 517 | 58.175 | 18.262 | 14.293 | 1.00 | 19.59 |
| ATOM | 1149 | CA | HIS | A | 517 | 56.732 | 18.410 | 14.155 | 1.00 | 20.79 |
| ATOM | 1150 | CB | HIS | A | 517 | 56.394 | 19.796 | 13.618 | 1.00 | 21.14 |
| ATOM | 1151 | CG | HIS | A | 517 | 56.776 | 20.902 | 14.550 | 1.00 | 22.26 |
| ATOM | 1152 | CD2 | HIS | A | 517 | 57.803 | 21.783 | 14.515 | 1.00 | 22.56 |
| ATOM | 1153 | ND1 | HIS | A | 517 | 56.079 | 21.169 | 15.709 | 1.00 | 22.64 |
| ATOM | 1154 | CE1 | HIS | A | 517 | 56.661 | 22.169 | 16.348 | 1.00 | 23.15 |
| ATOM | 1155 | NE2 | HIS | A | 517 | 57.709 | 22.559 | 15.644 | 1.00 | 23.02 |
| ATOM | 1156 | C | HIS | A | 517 | 56.223 | 17.334 | 13.203 | 1.00 | 21.25 |
| ATOM | 1157 | O | HIS | A | 517 | 56.987 | 16.817 | 12.390 | 1.00 | 21.56 |
| ATOM | 1158 | N | ILE | A | 518 | 54.945 | 16.986 | 13.303 | 1.00 | 20.88 |
| ATOM | 1159 | CA | ILE | A | 518 | 54.409 | 15.953 | 12.432 | 1.00 | 22.70 |
| ATOM | 1160 | CB | ILE | A | 518 | 53.478 | 14.970 | 13.215 | 1.00 | 22.97 |
| ATOM | 1161 | CG2 | ILE | A | 518 | 54.286 | 14.225 | 14.271 | 1.00 | 24.54 |
| ATOM | 1162 | CG1 | ILE | A | 518 | 52.318 | 15.714 | 13.879 | 1.00 | 23.64 |
| ATOM | 1163 | CD1 | ILE | A | 518 | 51.147 | 16.010 | 12.951 | 1.00 | 23.04 |
| ATOM | 1164 | C | ILE | A | 518 | 53.676 | 16.483 | 11.204 | 1.00 | 22.23 |
| ATOM | 1165 | O | ILE | A | 518 | 53.343 | 17.666 | 11.107 | 1.00 | 21.28 |
| ATOM | 1166 | N | LYS | A | 519 | 53.454 | 15.584 | 10.256 | 1.00 | 21.56 |
| ATOM | 1167 | CA | LYS | A | 519 | 52.748 | 15.907 | 9.033 | 1.00 | 20.61 |
| ATOM | 1168 | CB | LYS | A | 519 | 53.731 | 16.327 | 7.935 | 1.00 | 21.67 |
| ATOM | 1169 | CG | LYS | A | 519 | 53.957 | 17.838 | 7.872 | 1.00 | 21.69 |
| ATOM | 1170 | CD | LYS | A | 519 | 55.005 | 18.201 | 6.853 | 1.00 | 22.59 |
| ATOM | 1171 | CE | LYS | A | 519 | 55.246 | 19.704 | 6.800 | 1.00 | 22.86 |
| ATOM | 1172 | NZ | LYS | A | 519 | 54.122 | 20.434 | 6.147 | 1.00 | 23.05 |
| ATOM | 1173 | C | LYS | A | 519 | 51.939 | 14.706 | 8.583 | 1.00 | 20.45 |
| ATOM | 1174 | O | LYS | A | 519 | 52.455 | 13.591 | 8.510 | 1.00 | 19.68 |
| ATOM | 1175 | N | ILE | A | 520 | 50.659 | 14.935 | 8.308 | 1.00 | 19.04 |
| ATOM | 1176 | CA | ILE | A | 520 | 49.784 | 13.877 | 7.837 | 1.00 | 18.49 |
| ATOM | 1177 | CB | ILE | A | 520 | 48.309 | 14.288 | 7.978 | 1.00 | 19.91 |
| ATOM | 1178 | CG2 | ILE | A | 520 | 47.412 | 13.244 | 7.334 | 1.00 | 19.22 |
| ATOM | 1179 | CG1 | ILE | A | 520 | 47.969 | 14.480 | 9.464 | 1.00 | 19.20 |
| ATOM | 1180 | CD1 | ILE | A | 520 | 46.572 | 15.018 | 9.729 | 1.00 | 20.35 |
| ATOM | 1181 | C | ILE | A | 520 | 50.115 | 13.645 | 6.360 | 1.00 | 19.25 |
| ATOM | 1182 | O | ILE | A | 520 | 50.351 | 14.601 | 5.613 | 1.00 | 18.82 |
| ATOM | 1183 | N | ALA | A | 521 | 50.147 | 12.380 | 5.949 | 1.00 | 18.64 |
| ATOM | 1184 | CA | ALA | A | 521 | 50.464 | 12.034 | 4.568 | 1.00 | 19.29 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1185 | CB | ALA | A | 521 | 51.893 | 11.486 | 4.483 | 1.00 | 20.21 |
| ATOM | 1186 | C | ALA | A | 521 | 49.491 | 11.022 | 3.968 | 1.00 | 19.71 |
| ATOM | 1187 | O | ALA | A | 521 | 48.763 | 10.343 | 4.692 | 1.00 | 18.05 |
| ATOM | 1188 | N | ASP | A | 522 | 49.501 | 10.935 | 2.639 | 1.00 | 18.55 |
| ATOM | 1189 | CA | ASP | A | 522 | 48.653 | 10.024 | 1.878 | 1.00 | 20.06 |
| ATOM | 1190 | CB | ASP | A | 522 | 48.794 | 8.580 | 2.373 | 1.00 | 20.92 |
| ATOM | 1191 | CG | ASP | A | 522 | 48.319 | 7.571 | 1.339 | 1.00 | 24.08 |
| ATOM | 1192 | OD1 | ASP | A | 522 | 47.547 | 7.969 | 0.441 | 1.00 | 24.83 |
| ATOM | 1193 | OD2 | ASP | A | 522 | 48.704 | 6.382 | 1.417 | 1.00 | 25.31 |
| ATOM | 1194 | C | ASP | A | 522 | 47.192 | 10.428 | 1.940 | 1.00 | 20.15 |
| ATOM | 1195 | O | ASP | A | 522 | 46.472 | 10.049 | 2.863 | 1.00 | 20.16 |
| ATOM | 1196 | N | PHE | A | 523 | 46.749 | 11.174 | 0.934 | 1.00 | 20.43 |
| ATOM | 1197 | CA | PHE | A | 523 | 45.373 | 11.649 | 0.899 | 1.00 | 21.18 |
| ATOM | 1198 | CB | PHE | A | 523 | 45.360 | 13.167 | 0.695 | 1.00 | 20.08 |
| ATOM | 1199 | CG | PHE | A | 523 | 46.182 | 13.920 | 1.707 | 1.00 | 19.62 |
| ATOM | 1200 | CD1 | PHE | A | 523 | 47.416 | 14.455 | 1.358 | 1.00 | 19.23 |
| ATOM | 1201 | CD2 | PHE | A | 523 | 45.733 | 14.070 | 3.019 | 1.00 | 19.33 |
| ATOM | 1202 | CE1 | PHE | A | 523 | 48.196 | 15.133 | 2.300 | 1.00 | 20.66 |
| ATOM | 1203 | CE2 | PHE | A | 523 | 46.502 | 14.742 | 3.969 | 1.00 | 18.29 |
| ATOM | 1204 | CZ | PHE | A | 523 | 47.738 | 15.278 | 3.610 | 1.00 | 17.84 |
| ATOM | 1205 | C | PHE | A | 523 | 44.539 | 10.975 | −0.173 | 1.00 | 21.50 |
| ATOM | 1206 | O | PHE | A | 523 | 43.498 | 11.491 | −0.575 | 1.00 | 22.40 |
| ATOM | 1207 | N | GLY | A | 524 | 44.982 | 9.805 | −0.615 | 1.00 | 22.46 |
| ATOM | 1208 | CA | GLY | A | 524 | 44.261 | 9.091 | −1.651 | 1.00 | 24.81 |
| ATOM | 1209 | C | GLY | A | 524 | 42.866 | 8.605 | −1.296 | 1.00 | 25.97 |
| ATOM | 1210 | O | GLY | A | 524 | 42.076 | 8.307 | −2.188 | 1.00 | 27.99 |
| ATOM | 1211 | N | MET | A | 525 | 42.542 | 8.534 | −0.010 | 1.00 | 24.70 |
| ATOM | 1212 | CA | MET | A | 525 | 41.236 | 8.045 | 0.404 | 1.00 | 24.83 |
| ATOM | 1213 | CB | MET | A | 525 | 41.413 | 6.973 | 1.483 | 1.00 | 26.53 |
| ATOM | 1214 | CG | MET | A | 525 | 42.290 | 5.812 | 1.017 | 1.00 | 33.82 |
| ATOM | 1215 | SD | MET | A | 525 | 42.556 | 4.523 | 2.254 | 1.00 | 40.11 |
| ATOM | 1216 | CE | MET | A | 525 | 40.911 | 3.792 | 2.275 | 1.00 | 38.02 |
| ATOM | 1217 | C | MET | A | 525 | 40.278 | 9.131 | 0.888 | 1.00 | 23.45 |
| ATOM | 1218 | O | MET | A | 525 | 39.189 | 8.833 | 1.375 | 1.00 | 23.04 |
| ATOM | 1219 | N | CYS | A | 526 | 40.676 | 10.390 | 0.745 | 1.00 | 21.76 |
| ATOM | 1220 | CA | CYS | A | 526 | 39.827 | 11.494 | 1.173 | 1.00 | 21.47 |
| ATOM | 1221 | CB | CYS | A | 526 | 40.571 | 12.825 | 1.068 | 1.00 | 21.15 |
| ATOM | 1222 | SG | CYS | A | 526 | 41.970 | 12.999 | 2.168 | 1.00 | 22.41 |
| ATOM | 1223 | C | CYS | A | 526 | 38.551 | 11.608 | 0.352 | 1.00 | 21.18 |
| ATOM | 1224 | O | CYS | A | 526 | 38.493 | 11.195 | −0.807 | 1.00 | 21.68 |
| ATOM | 1225 | N | LYS | A | 527 | 37.530 | 12.177 | 0.976 | 1.00 | 21.26 |
| ATOM | 1226 | CA | LYS | A | 527 | 36.244 | 12.422 | 0.337 | 1.00 | 20.63 |
| ATOM | 1227 | CB | LYS | A | 527 | 35.124 | 11.711 | 1.101 | 1.00 | 21.60 |
| ATOM | 1228 | CG | LYS | A | 527 | 33.745 | 11.808 | 0.443 | 1.00 | 24.61 |
| ATOM | 1229 | CD | LYS | A | 527 | 33.673 | 10.958 | −0.815 | 1.00 | 25.95 |
| ATOM | 1230 | CE | LYS | A | 527 | 32.294 | 11.031 | −1.459 | 1.00 | 28.67 |
| ATOM | 1231 | NZ | LYS | A | 527 | 32.222 | 10.153 | −2.671 | 1.00 | 30.33 |
| ATOM | 1232 | C | LYS | A | 527 | 36.071 | 13.936 | 0.457 | 1.00 | 19.86 |
| ATOM | 1233 | O | LYS | A | 527 | 36.138 | 14.482 | 1.556 | 1.00 | 20.20 |
| ATOM | 1234 | N | GLU | A | 528 | 35.876 | 14.615 | −0.666 | 1.00 | 19.60 |
| ATOM | 1235 | CA | GLU | A | 528 | 35.704 | 16.067 | −0.664 | 1.00 | 19.76 |
| ATOM | 1236 | CB | GLU | A | 528 | 36.455 | 16.682 | −1.838 | 1.00 | 21.13 |
| ATOM | 1237 | CG | GLU | A | 528 | 37.935 | 16.434 | −1.810 | 1.00 | 22.94 |
| ATOM | 1238 | CD | GLU | A | 528 | 38.526 | 16.446 | −3.193 | 1.00 | 24.78 |
| ATOM | 1239 | OE1 | GLU | A | 528 | 38.133 | 15.575 | −3.998 | 1.00 | 25.30 |
| ATOM | 1240 | OE2 | GLU | A | 528 | 39.375 | 17.319 | −3.478 | 1.00 | 26.54 |
| ATOM | 1241 | C | GLU | A | 528 | 34.240 | 16.467 | −0.757 | 1.00 | 19.00 |
| ATOM | 1242 | O | GLU | A | 528 | 33.358 | 15.615 | −0.798 | 1.00 | 17.13 |
| ATOM | 1243 | N | ASN | A | 529 | 34.001 | 17.775 | −0.796 | 1.00 | 20.30 |
| ATOM | 1244 | CA | ASN | A | 529 | 32.655 | 18.342 | −0.879 | 1.00 | 21.66 |
| ATOM | 1245 | CB | ASN | A | 529 | 31.993 | 17.982 | −2.215 | 1.00 | 22.30 |
| ATOM | 1246 | CG | ASN | A | 529 | 31.283 | 19.174 | −2.859 | 1.00 | 25.51 |
| ATOM | 1247 | OD1 | ASN | A | 529 | 30.672 | 19.053 | −3.924 | 1.00 | 25.61 |
| ATOM | 1248 | ND2 | ASN | A | 529 | 31.368 | 20.332 | −2.214 | 1.00 | 24.70 |
| ATOM | 1249 | C | ASN | A | 529 | 31.790 | 17.854 | 0.273 | 1.00 | 22.28 |
| ATOM | 1250 | O | ASN | A | 529 | 30.571 | 17.804 | 0.173 | 1.00 | 23.01 |
| ATOM | 1251 | N | MET | A | 530 | 32.433 | 17.485 | 1.372 | 1.00 | 23.55 |
| ATOM | 1252 | CA | MET | A | 530 | 31.720 | 17.032 | 2.548 | 1.00 | 24.81 |
| ATOM | 1253 | CB | MET | A | 530 | 32.573 | 16.021 | 3.305 | 1.00 | 25.43 |
| ATOM | 1254 | CG | MET | A | 530 | 32.747 | 14.702 | 2.561 | 1.00 | 23.70 |
| ATOM | 1255 | SD | MET | A | 530 | 31.167 | 13.851 | 2.400 | 1.00 | 24.80 |
| ATOM | 1256 | CE | MET | A | 530 | 31.074 | 13.081 | 3.935 | 1.00 | 24.48 |
| ATOM | 1257 | C | MET | A | 530 | 31.460 | 18.280 | 3.377 | 1.00 | 26.65 |
| ATOM | 1258 | O | MET | A | 530 | 32.145 | 18.562 | 4.356 | 1.00 | 27.54 |

TABLE 2-continued

Structure coordinates for PKCθ
(residues 377-696 of SEQ ID NO: 1)/staurosporine complex

|  | # | name | res | chain | res # | X | Y | Z | occ | B |
|---|---|---|---|---|---|---|---|---|---|---|
| ATOM | 1259 | N | LEU | A | 531 | 30.457 | 19.030 | 2.959 | 1.00 | 27.74 |
| ATOM | 1260 | CA | LEU | A | 531 | 30.066 | 20.265 | 3.612 | 1.00 | 28.65 |
| ATOM | 1261 | CB | LEU | A | 531 | 30.125 | 21.383 | 2.543 | 1.00 | 30.08 |
| ATOM | 1262 | CG | LEU | A | 531 | 31.569 | 21.373 | 2.004 | 1.00 | 31.31 |
| ATOM | 1263 | CD1 | LEU | A | 531 | 31.756 | 22.247 | 0.787 | 1.00 | 32.06 |
| ATOM | 1264 | CD2 | LEU | A | 531 | 32.496 | 21.745 | 3.120 | 1.00 | 32.22 |
| ATOM | 1265 | C | LEU | A | 531 | 28.674 | 20.223 | 4.220 | 1.00 | 28.40 |
| ATOM | 1266 | O | LEU | A | 531 | 27.791 | 19.556 | 3.691 | 1.00 | 27.67 |
| ATOM | 1267 | N | GLY | A | 532 | 28.494 | 20.989 | 5.291 | 1.00 | 28.00 |
| ATOM | 1268 | CA | GLY | A | 532 | 27.211 | 21.027 | 5.954 | 1.00 | 28.28 |
| ATOM | 1269 | C | GLY | A | 532 | 26.782 | 19.666 | 6.486 | 1.00 | 27.84 |
| ATOM | 1270 | O | GLY | A | 532 | 27.524 | 19.017 | 7.225 | 1.00 | 27.59 |
| ATOM | 1271 | N | ASP | A | 533 | 25.588 | 19.230 | 6.093 | 1.00 | 27.81 |
| ATOM | 1272 | CA | ASP | A | 533 | 25.069 | 17.944 | 6.534 | 1.00 | 28.45 |
| ATOM | 1273 | CB | ASP | A | 533 | 23.546 | 18.014 | 6.716 | 1.00 | 30.53 |
| ATOM | 1274 | CG | ASP | A | 533 | 22.805 | 18.320 | 5.417 | 1.00 | 33.51 |
| ATOM | 1275 | OD1 | ASP | A | 533 | 23.327 | 18.004 | 4.326 | 1.00 | 34.72 |
| ATOM | 1276 | OD2 | ASP | A | 533 | 21.680 | 18.864 | 5.485 | 1.00 | 36.06 |
| ATOM | 1277 | C | ASP | A | 533 | 25.407 | 16.812 | 5.565 | 1.00 | 27.34 |
| ATOM | 1278 | O | ASP | A | 533 | 24.810 | 15.746 | 5.613 | 1.00 | 27.74 |
| ATOM | 1279 | N | ALA | A | 534 | 26.369 | 17.039 | 4.683 | 1.00 | 25.29 |
| ATOM | 1280 | CA | ALA | A | 534 | 26.740 | 16.018 | 3.721 | 1.00 | 23.54 |
| ATOM | 1281 | CB | ALA | A | 534 | 27.753 | 16.582 | 2.728 | 1.00 | 20.51 |
| ATOM | 1282 | C | ALA | A | 534 | 27.299 | 14.767 | 4.393 | 1.00 | 23.05 |
| ATOM | 1283 | O | ALA | A | 534 | 28.096 | 14.849 | 5.325 | 1.00 | 23.22 |
| ATOM | 1284 | N | LYS | A | 535 | 26.867 | 13.603 | 3.919 | 1.00 | 22.84 |
| ATOM | 1285 | CA | LYS | A | 535 | 27.365 | 12.331 | 4.442 | 1.00 | 23.86 |
| ATOM | 1286 | CB | LYS | A | 535 | 26.342 | 11.696 | 5.357 | 1.00 | 24.88 |
| ATOM | 1287 | CG | LYS | A | 535 | 26.270 | 12.449 | 6.653 | 1.00 | 27.41 |
| ATOM | 1288 | CD | LYS | A | 535 | 25.282 | 11.871 | 7.646 | 1.00 | 29.64 |
| ATOM | 1289 | CE | LYS | A | 535 | 25.147 | 12.824 | 8.869 | 1.00 | 32.50 |
| ATOM | 1290 | NZ | LYS | A | 535 | 24.325 | 12.249 | 10.014 | 1.00 | 36.38 |
| ATOM | 1291 | C | LYS | A | 535 | 27.692 | 11.445 | 3.252 | 1.00 | 23.49 |
| ATOM | 1292 | O | LYS | A | 535 | 27.214 | 11.692 | 2.144 | 1.00 | 23.82 |
| ATOM | 1293 | N | THR | A | 536 | 28.556 | 10.455 | 3.451 | 1.00 | 22.12 |
| ATOM | 1294 | CA | THR | A | 536 | 28.924 | 9.545 | 2.374 | 1.00 | 20.15 |
| ATOM | 1295 | CB | THR | A | 536 | 30.354 | 9.807 | 1.869 | 1.00 | 19.00 |
| ATOM | 1296 | OG1 | THR | A | 536 | 30.545 | 9.092 | 0.650 | 1.00 | 18.73 |
| ATOM | 1297 | CG2 | THR | A | 536 | 31.398 | 9.355 | 2.884 | 1.00 | 18.42 |
| ATOM | 1298 | C | THR | A | 536 | 28.757 | 8.107 | 2.860 | 1.00 | 19.94 |
| ATOM | 1299 | O | THR | A | 536 | 28.426 | 7.884 | 4.024 | 1.00 | 19.89 |
| ATOM | 1300 | N | ASN | A | 537 | 28.997 | 7.131 | 1.989 | 1.00 | 19.53 |
| ATOM | 1301 | CA | ASN | A | 537 | 28.763 | 5.745 | 2.382 | 1.00 | 18.63 |
| ATOM | 1302 | CB | ASN | A | 537 | 27.359 | 5.349 | 1.937 | 1.00 | 18.00 |
| ATOM | 1303 | CG | ASN | A | 537 | 27.148 | 5.571 | 0.452 | 1.00 | 18.88 |
| ATOM | 1304 | OD1 | ASN | A | 537 | 28.109 | 5.756 | −0.302 | 1.00 | 17.85 |
| ATOM | 1305 | ND2 | ASN | A | 537 | 25.892 | 5.549 | 0.020 | 1.00 | 19.43 |
| ATOM | 1306 | C | ASN | A | 537 | 29.728 | 4.658 | 1.911 | 1.00 | 18.16 |
| ATOM | 1307 | O | ASN | A | 537 | 29.398 | 3.471 | 1.991 | 1.00 | 17.90 |
| ATOM | 1308 | N | THR | A | 538 | 30.902 | 5.021 | 1.418 | 1.00 | 17.96 |
| ATOM | 1309 | CA | THR | A | 538 | 31.816 | 3.980 | 0.963 | 1.00 | 18.05 |
| ATOM | 1310 | CG2 | THR | A | 538 | 33.680 | 3.407 | −0.628 | 1.00 | 15.91 |
| ATOM | 1311 | C | THR | A | 538 | 32.488 | 3.279 | 2.151 | 1.00 | 19.24 |
| ATOM | 1312 | O | THR | A | 538 | 33.025 | 3.933 | 3.049 | 1.00 | 19.51 |
| ATOM | 1313 | OG1 | THR | A | 538 | 32.329 | 5.358 | −1.001 | 1.00 | 20.05 |
| ATOM | 1314 | CB | THR | A | 538 | 32.919 | 4.549 | 0.031 | 1.00 | 17.40 |
| ATOM | 1315 | N | PHE | A | 539 | 32.441 | 1.948 | 2.172 | 1.00 | 19.27 |
| ATOM | 1316 | CA | PHE | A | 539 | 33.095 | 1.186 | 3.239 | 1.00 | 19.63 |
| ATOM | 1317 | CB | PHE | A | 539 | 32.643 | −0.283 | 3.222 | 1.00 | 19.06 |
| ATOM | 1318 | CG | PHE | A | 539 | 33.265 | −1.131 | 4.308 | 1.00 | 18.84 |
| ATOM | 1319 | CD1 | PHE | A | 539 | 32.556 | −1.435 | 5.468 | 1.00 | 17.91 |
| ATOM | 1320 | CD2 | PHE | A | 539 | 34.561 | −1.623 | 4.173 | 1.00 | 18.45 |
| ATOM | 1321 | CE1 | PHE | A | 539 | 33.131 | −2.222 | 6.475 | 1.00 | 19.16 |
| ATOM | 1322 | CE2 | PHE | A | 539 | 35.145 | −2.411 | 5.179 | 1.00 | 17.02 |
| ATOM | 1323 | CZ | PHE | A | 539 | 34.431 | −2.710 | 6.325 | 1.00 | 16.34 |
| ATOM | 1324 | C | PHE | A | 539 | 34.593 | 1.243 | 2.943 | 1.00 | 20.41 |
| ATOM | 1325 | O | PHE | A | 539 | 35.040 | 0.757 | 1.907 | 1.00 | 19.47 |
| ATOM | 1326 | N | CYS | A | 540 | 35.373 | 1.848 | 3.831 | 1.00 | 22.16 |
| ATOM | 1327 | CA | CYS | A | 540 | 36.814 | 1.916 | 3.597 | 1.00 | 23.85 |
| ATOM | 1328 | CB | CYS | A | 540 | 37.123 | 2.913 | 2.478 | 1.00 | 24.97 |
| ATOM | 1329 | SG | CYS | A | 540 | 36.649 | 4.612 | 2.834 | 1.00 | 28.24 |
| ATOM | 1330 | C | CYS | A | 540 | 37.621 | 2.272 | 4.839 | 1.00 | 22.97 |
| ATOM | 1331 | O | CYS | A | 540 | 37.072 | 2.699 | 5.847 | 1.00 | 23.35 |
| ATOM | 1332 | N | GLY | A | 541 | 38.933 | 2.079 | 4.745 | 1.00 | 23.63 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1333 | CA | GLY | A | 541 | 39.827 | 2.365 | 5.851 | 1.00 | 23.21 |
| ATOM | 1334 | C | GLY | A | 541 | 40.575 | 1.112 | 6.270 | 1.00 | 23.07 |
| ATOM | 1335 | O | GLY | A | 541 | 40.190 | 0.004 | 5.898 | 1.00 | 23.87 |
| ATOM | 1336 | N | THR | A | 542 | 41.651 | 1.285 | 7.031 | 1.00 | 22.53 |
| ATOM | 1337 | CA | THR | A | 542 | 42.447 | 0.169 | 7.523 | 1.00 | 21.10 |
| ATOM | 1338 | CB | THR | A | 542 | 43.800 | 0.665 | 8.059 | 1.00 | 21.37 |
| ATOM | 1339 | OG1 | THR | A | 542 | 44.521 | 1.295 | 6.992 | 1.00 | 23.21 |
| ATOM | 1340 | CG2 | THR | A | 542 | 44.627 | −0.488 | 8.618 | 1.00 | 20.71 |
| ATOM | 1341 | C | THR | A | 542 | 41.623 | −0.425 | 8.656 | 1.00 | 21.55 |
| ATOM | 1342 | O | THR | A | 542 | 41.233 | 0.289 | 9.579 | 1.00 | 20.88 |
| ATOM | 1343 | N | PRO | A | 543 | 41.345 | −1.738 | 8.599 | 1.00 | 20.55 |
| ATOM | 1344 | CD | PRO | A | 543 | 41.784 | −2.675 | 7.553 | 1.00 | 21.83 |
| ATOM | 1345 | CA | PRO | A | 543 | 40.548 | −2.431 | 9.619 | 1.00 | 20.72 |
| ATOM | 1346 | CB | PRO | A | 543 | 40.818 | −3.921 | 9.343 | 1.00 | 20.34 |
| ATOM | 1347 | CG | PRO | A | 543 | 41.951 | −3.942 | 8.325 | 1.00 | 22.49 |
| ATOM | 1348 | C | PRO | A | 543 | 40.721 | −2.053 | 11.090 | 1.00 | 20.46 |
| ATOM | 1349 | O | PRO | A | 543 | 39.727 | −1.836 | 11.789 | 1.00 | 20.10 |
| ATOM | 1350 | N | ASP | A | 544 | 41.957 | −1.973 | 11.570 | 1.00 | 19.91 |
| ATOM | 1351 | CA | ASP | A | 544 | 42.190 | −1.614 | 12.970 | 1.00 | 20.86 |
| ATOM | 1352 | CB | ASP | A | 544 | 43.688 | −1.532 | 13.275 | 1.00 | 23.86 |
| ATOM | 1353 | CG | ASP | A | 544 | 44.310 | −2.879 | 13.543 | 1.00 | 25.82 |
| ATOM | 1354 | OD1 | ASP | A | 544 | 43.808 | −3.607 | 14.418 | 1.00 | 29.20 |
| ATOM | 1355 | OD2 | ASP | A | 544 | 45.314 | −3.202 | 12.888 | 1.00 | 29.50 |
| ATOM | 1356 | C | ASP | A | 544 | 41.574 | −0.271 | 13.344 | 1.00 | 19.45 |
| ATOM | 1357 | O | ASP | A | 544 | 41.189 | −0.064 | 14.495 | 1.00 | 18.17 |
| ATOM | 1358 | N | TYR | A | 545 | 41.488 | 0.630 | 12.366 | 1.00 | 18.20 |
| ATOM | 1359 | CA | TYR | A | 545 | 40.979 | 1.982 | 12.575 | 1.00 | 17.69 |
| ATOM | 1360 | CB | TYR | A | 545 | 41.909 | 2.987 | 11.893 | 1.00 | 16.32 |
| ATOM | 1361 | CG | TYR | A | 545 | 43.359 | 2.893 | 12.309 | 1.00 | 18.41 |
| ATOM | 1362 | CD1 | TYR | A | 545 | 44.213 | 1.935 | 11.748 | 1.00 | 17.28 |
| ATOM | 1363 | CE1 | TYR | A | 545 | 45.559 | 1.867 | 12.122 | 1.00 | 17.83 |
| ATOM | 1364 | CD2 | TYR | A | 545 | 43.885 | 3.771 | 13.258 | 1.00 | 18.29 |
| ATOM | 1365 | CE2 | TYR | A | 545 | 45.221 | 3.707 | 13.641 | 1.00 | 16.95 |
| ATOM | 1366 | CZ | TYR | A | 545 | 46.051 | 2.761 | 13.069 | 1.00 | 17.88 |
| ATOM | 1367 | OH | TYR | A | 545 | 47.382 | 2.746 | 13.419 | 1.00 | 19.97 |
| ATOM | 1368 | C | TYR | A | 545 | 39.553 | 2.283 | 12.115 | 1.00 | 17.84 |
| ATOM | 1369 | O | TYR | A | 545 | 39.072 | 3.401 | 12.298 | 1.00 | 16.52 |
| ATOM | 1370 | N | ILE | A | 546 | 38.875 | 1.309 | 11.517 | 1.00 | 17.86 |
| ATOM | 1371 | CA | ILE | A | 546 | 37.518 | 1.540 | 11.032 | 1.00 | 17.94 |
| ATOM | 1372 | CB | ILE | A | 546 | 37.026 | 0.344 | 10.201 | 1.00 | 18.45 |
| ATOM | 1373 | CG2 | ILE | A | 546 | 35.580 | 0.552 | 9.783 | 1.00 | 18.31 |
| ATOM | 1374 | CG1 | ILE | A | 546 | 37.913 | 0.192 | 8.964 | 1.00 | 20.01 |
| ATOM | 1375 | CD1 | ILE | A | 546 | 37.523 | −0.974 | 8.067 | 1.00 | 20.46 |
| ATOM | 1376 | C | ILE | A | 546 | 36.500 | 1.845 | 12.129 | 1.00 | 17.48 |
| ATOM | 1377 | O | ILE | A | 546 | 36.361 | 1.090 | 13.091 | 1.00 | 17.82 |
| ATOM | 1378 | N | ALA | A | 547 | 35.785 | 2.957 | 11.973 | 1.00 | 17.10 |
| ATOM | 1379 | CA | ALA | A | 547 | 34.778 | 3.373 | 12.948 | 1.00 | 16.70 |
| ATOM | 1380 | CB | ALA | A | 547 | 34.341 | 4.806 | 12.671 | 1.00 | 16.80 |
| ATOM | 1381 | C | ALA | A | 547 | 33.557 | 2.454 | 12.961 | 1.00 | 17.48 |
| ATOM | 1382 | O | ALA | A | 547 | 33.155 | 1.905 | 11.934 | 1.00 | 18.59 |
| ATOM | 1383 | N | PRO | A | 548 | 32.943 | 2.281 | 14.136 | 1.00 | 16.72 |
| ATOM | 1384 | CD | PRO | A | 548 | 33.309 | 2.870 | 15.435 | 1.00 | 15.05 |
| ATOM | 1385 | CA | PRO | A | 548 | 31.767 | 1.425 | 14.259 | 1.00 | 17.04 |
| ATOM | 1386 | CB | PRO | A | 548 | 31.451 | 1.481 | 15.757 | 1.00 | 17.00 |
| ATOM | 1387 | CG | PRO | A | 548 | 32.002 | 2.814 | 16.180 | 1.00 | 16.79 |
| ATOM | 1388 | C | PRO | A | 548 | 30.580 | 1.834 | 13.391 | 1.00 | 18.54 |
| ATOM | 1389 | O | PRO | A | 548 | 29.833 | 0.968 | 12.935 | 1.00 | 19.16 |
| ATOM | 1390 | N | GLU | A | 549 | 30.395 | 3.135 | 13.153 | 1.00 | 17.85 |
| ATOM | 1391 | CA | GLU | A | 549 | 29.262 | 3.547 | 12.340 | 1.00 | 17.87 |
| ATOM | 1392 | CB | GLU | A | 549 | 29.072 | 5.079 | 12.337 | 1.00 | 17.17 |
| ATOM | 1393 | CG | GLU | A | 549 | 30.270 | 5.928 | 11.945 | 1.00 | 15.50 |
| ATOM | 1394 | CD | GLU | A | 549 | 31.084 | 6.387 | 13.142 | 1.00 | 17.51 |
| ATOM | 1395 | OE1 | GLU | A | 549 | 31.651 | 7.504 | 13.084 | 1.00 | 17.84 |
| ATOM | 1396 | OE2 | GLU | A | 549 | 31.163 | 5.634 | 14.140 | 1.00 | 15.71 |
| ATOM | 1397 | C | GLU | A | 549 | 29.378 | 3.007 | 10.919 | 1.00 | 18.90 |
| ATOM | 1398 | O | GLU | A | 549 | 28.358 | 2.755 | 10.268 | 1.00 | 18.05 |
| ATOM | 1399 | N | ILE | A | 550 | 30.611 | 2.819 | 10.447 | 1.00 | 17.17 |
| ATOM | 1400 | CA | ILE | A | 550 | 30.841 | 2.274 | 9.115 | 1.00 | 17.57 |
| ATOM | 1401 | CB | ILE | A | 550 | 32.313 | 2.469 | 8.652 | 1.00 | 15.79 |
| ATOM | 1402 | CG2 | ILE | A | 550 | 32.618 | 1.589 | 7.453 | 1.00 | 14.30 |
| ATOM | 1403 | CG1 | ILE | A | 550 | 32.553 | 3.927 | 8.264 | 1.00 | 16.11 |
| ATOM | 1404 | CD1 | ILE | A | 550 | 34.010 | 4.251 | 8.007 | 1.00 | 15.68 |
| ATOM | 1405 | C | ILE | A | 550 | 30.524 | 0.779 | 9.163 | 1.00 | 18.67 |
| ATOM | 1406 | O | ILE | A | 550 | 29.876 | 0.248 | 8.264 | 1.00 | 18.69 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1407 | N | LEU | A | 551 | 30.973 | 0.110 | 10.221 | 1.00 | 18.36 |
| ATOM | 1408 | CA | LEU | A | 551 | 30.716 | −1.320 | 10.375 | 1.00 | 20.69 |
| ATOM | 1409 | CB | LEU | A | 551 | 31.422 | −1.860 | 11.622 | 1.00 | 19.36 |
| ATOM | 1410 | CG | LEU | A | 551 | 32.950 | −1.777 | 11.604 | 1.00 | 19.90 |
| ATOM | 1411 | CD1 | LEU | A | 551 | 33.495 | −2.356 | 12.895 | 1.00 | 17.81 |
| ATOM | 1412 | CD2 | LEU | A | 551 | 33.502 | −2.534 | 10.389 | 1.00 | 17.70 |
| ATOM | 1413 | C | LEU | A | 551 | 29.221 | −1.618 | 10.475 | 1.00 | 21.63 |
| ATOM | 1414 | O | LEU | A | 551 | 28.772 | −2.680 | 10.048 | 1.00 | 21.95 |
| ATOM | 1415 | N | LEU | A | 552 | 28.457 | −0.683 | 11.040 | 1.00 | 22.00 |
| ATOM | 1416 | CA | LEU | A | 552 | 27.017 | −0.856 | 11.192 | 1.00 | 23.63 |
| ATOM | 1417 | CB | LEU | A | 552 | 26.507 | −0.081 | 12.409 | 1.00 | 25.79 |
| ATOM | 1418 | CG | LEU | A | 552 | 26.980 | −0.550 | 13.792 | 1.00 | 28.51 |
| ATOM | 1419 | CD1 | LEU | A | 552 | 26.501 | 0.419 | 14.866 | 1.00 | 29.25 |
| ATOM | 1420 | CD2 | LEU | A | 552 | 26.443 | −1.949 | 14.062 | 1.00 | 30.34 |
| ATOM | 1421 | C | LEU | A | 552 | 26.264 | −0.399 | 9.946 | 1.00 | 23.90 |
| ATOM | 1422 | O | LEU | A | 552 | 25.034 | −0.424 | 9.911 | 1.00 | 24.62 |
| ATOM | 1423 | N | GLY | A | 553 | 27.009 | 0.031 | 8.936 | 1.00 | 23.62 |
| ATOM | 1424 | CA | GLY | A | 553 | 26.407 | 0.450 | 7.684 | 1.00 | 23.80 |
| ATOM | 1425 | C | GLY | A | 553 | 25.667 | 1.778 | 7.635 | 1.00 | 23.76 |
| ATOM | 1426 | O | GLY | A | 553 | 24.747 | 1.937 | 6.833 | 1.00 | 23.17 |
| ATOM | 1427 | N | GLN | A | 554 | 26.063 | 2.746 | 8.463 | 1.00 | 22.25 |
| ATOM | 1428 | CA | GLN | A | 554 | 25.383 | 4.049 | 8.458 | 1.00 | 22.80 |
| ATOM | 1429 | CB | GLN | A | 554 | 25.355 | 4.691 | 9.848 | 1.00 | 25.52 |
| ATOM | 1430 | CG | GLN | A | 554 | 24.839 | 3.820 | 10.969 | 1.00 | 30.22 |
| ATOM | 1431 | CD | GLN | A | 554 | 25.167 | 4.358 | 12.362 | 1.00 | 34.81 |
| ATOM | 1432 | OE1 | GLN | A | 554 | 25.229 | 3.649 | 13.350 | 1.00 | 37.99 |
| ATOM | 1433 | NE2 | GLN | A | 554 | 25.418 | 5.684 | 12.416 | 1.00 | 35.48 |
| ATOM | 1434 | C | GLN | A | 554 | 26.099 | 5.044 | 7.550 | 1.00 | 21.79 |
| ATOM | 1435 | O | GLN | A | 554 | 27.319 | 4.996 | 7.419 | 1.00 | 22.01 |
| ATOM | 1436 | N | LYS | A | 555 | 25.348 | 5.959 | 6.938 | 1.00 | 21.37 |
| ATOM | 1437 | CA | LYS | A | 555 | 25.941 | 7.027 | 6.107 | 1.00 | 22.83 |
| ATOM | 1438 | CB | LYS | A | 555 | 24.832 | 7.920 | 5.511 | 1.00 | 23.48 |
| ATOM | 1439 | CG | LYS | A | 555 | 24.206 | 7.374 | 4.230 | 1.00 | 28.36 |
| ATOM | 1440 | CD | LYS | A | 555 | 23.078 | 8.260 | 3.663 | 1.00 | 31.39 |
| ATOM | 1441 | CE | LYS | A | 555 | 21.670 | 7.676 | 3.931 | 1.00 | 35.16 |
| ATOM | 1442 | NZ | LYS | A | 555 | 21.143 | 7.934 | 5.313 | 1.00 | 38.46 |
| ATOM | 1443 | C | LYS | A | 555 | 26.773 | 7.813 | 7.147 | 1.00 | 21.05 |
| ATOM | 1444 | O | LYS | A | 555 | 26.330 | 7.969 | 8.288 | 1.00 | 20.47 |
| ATOM | 1445 | N | TYR | A | 556 | 27.955 | 8.308 | 6.784 | 1.00 | 19.68 |
| ATOM | 1446 | CA | TYR | A | 556 | 28.788 | 9.006 | 7.777 | 1.00 | 18.52 |
| ATOM | 1447 | CB | TYR | A | 556 | 29.838 | 8.034 | 8.322 | 1.00 | 15.77 |
| ATOM | 1448 | CG | TYR | A | 556 | 30.772 | 7.535 | 7.242 | 1.00 | 14.96 |
| ATOM | 1449 | CD1 | TYR | A | 556 | 31.900 | 8.273 | 6.872 | 1.00 | 13.59 |
| ATOM | 1450 | CE1 | TYR | A | 556 | 32.712 | 7.869 | 5.814 | 1.00 | 13.56 |
| ATOM | 1451 | CD2 | TYR | A | 556 | 30.479 | 6.369 | 6.527 | 1.00 | 14.85 |
| ATOM | 1452 | CE2 | TYR | A | 556 | 31.277 | 5.954 | 5.463 | 1.00 | 14.04 |
| ATOM | 1453 | CZ | TYR | A | 556 | 32.393 | 6.710 | 5.108 | 1.00 | 14.22 |
| ATOM | 1454 | OH | TYR | A | 556 | 33.178 | 6.326 | 4.046 | 1.00 | 12.73 |
| ATOM | 1455 | C | TYR | A | 556 | 29.495 | 10.265 | 7.298 | 1.00 | 18.90 |
| ATOM | 1456 | O | TYR | A | 556 | 29.526 | 10.566 | 6.107 | 1.00 | 18.27 |
| ATOM | 1457 | N | ASN | A | 557 | 30.072 | 10.991 | 8.254 | 1.00 | 20.62 |
| ATOM | 1458 | CA | ASN | A | 557 | 30.811 | 12.215 | 7.968 | 1.00 | 21.51 |
| ATOM | 1459 | CB | ASN | A | 557 | 30.007 | 13.448 | 8.397 | 1.00 | 22.20 |
| ATOM | 1460 | CG | ASN | A | 557 | 29.695 | 13.457 | 9.873 | 1.00 | 23.40 |
| ATOM | 1461 | OD1 | ASN | A | 557 | 30.404 | 12.850 | 10.677 | 1.00 | 25.63 |
| ATOM | 1462 | ND2 | ASN | A | 557 | 28.640 | 14.169 | 10.247 | 1.00 | 25.64 |
| ATOM | 1463 | C | ASN | A | 557 | 32.169 | 12.192 | 8.682 | 1.00 | 21.51 |
| ATOM | 1464 | O | ASN | A | 557 | 32.709 | 11.119 | 8.942 | 1.00 | 21.91 |
| ATOM | 1465 | N | HIS | A | 558 | 32.706 | 13.366 | 9.014 | 1.00 | 20.63 |
| ATOM | 1466 | CA | HIS | A | 558 | 34.017 | 13.466 | 9.664 | 1.00 | 20.92 |
| ATOM | 1467 | CB | HIS | A | 558 | 34.383 | 14.934 | 9.913 | 1.00 | 23.43 |
| ATOM | 1468 | CG | HIS | A | 558 | 33.599 | 15.578 | 11.013 | 1.00 | 26.42 |
| ATOM | 1469 | CD2 | HIS | A | 558 | 33.975 | 16.006 | 12.242 | 1.00 | 27.12 |
| ATOM | 1470 | ND1 | HIS | A | 558 | 32.249 | 15.845 | 10.912 | 1.00 | 28.39 |
| ATOM | 1471 | CE1 | HIS | A | 558 | 31.828 | 16.409 | 12.031 | 1.00 | 27.49 |
| ATOM | 1472 | NE2 | HIS | A | 558 | 32.856 | 16.518 | 12.854 | 1.00 | 27.42 |
| ATOM | 1473 | C | HIS | A | 558 | 34.145 | 12.697 | 10.979 | 1.00 | 19.52 |
| ATOM | 1474 | O | HIS | A | 558 | 35.248 | 12.489 | 11.469 | 1.00 | 15.91 |
| ATOM | 1475 | N | SER | A | 559 | 33.018 | 12.286 | 11.550 | 1.00 | 18.52 |
| ATOM | 1476 | CA | SER | A | 559 | 33.037 | 11.538 | 12.803 | 1.00 | 18.47 |
| ATOM | 1477 | CB | SER | A | 559 | 31.623 | 11.075 | 13.173 | 1.00 | 18.34 |
| ATOM | 1478 | OG | SER | A | 559 | 31.176 | 10.056 | 12.302 | 1.00 | 19.25 |
| ATOM | 1479 | C | SER | A | 559 | 33.947 | 10.315 | 12.751 | 1.00 | 17.88 |
| ATOM | 1480 | O | SER | A | 559 | 34.505 | 9.914 | 13.776 | 1.00 | 17.73 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1481 | N | VAL | A | 560 | 34.084 | 9.710 | 11.569 | 1.00 | 16.09 |
| ATOM | 1482 | CA | VAL | A | 560 | 34.917 | 8.526 | 11.443 | 1.00 | 15.29 |
| ATOM | 1483 | CB | VAL | A | 560 | 34.743 | 7.832 | 10.055 | 1.00 | 15.81 |
| ATOM | 1484 | CG1 | VAL | A | 560 | 33.267 | 7.487 | 9.838 | 1.00 | 13.22 |
| ATOM | 1485 | CG2 | VAL | A | 560 | 35.261 | 8.729 | 8.929 | 1.00 | 15.40 |
| ATOM | 1486 | C | VAL | A | 560 | 36.384 | 8.846 | 11.681 | 1.00 | 15.76 |
| ATOM | 1487 | O | VAL | A | 560 | 37.136 | 7.995 | 12.152 | 1.00 | 15.26 |
| ATOM | 1488 | N | ASP | A | 561 | 36.801 | 10.072 | 11.375 | 1.00 | 15.18 |
| ATOM | 1489 | CA | ASP | A | 561 | 38.196 | 10.424 | 11.600 | 1.00 | 14.98 |
| ATOM | 1490 | CB | ASP | A | 561 | 38.574 | 11.743 | 10.922 | 1.00 | 14.46 |
| ATOM | 1491 | CG | ASP | A | 561 | 38.593 | 11.642 | 9.407 | 1.00 | 15.59 |
| ATOM | 1492 | OD1 | ASP | A | 561 | 38.836 | 10.537 | 8.871 | 1.00 | 15.64 |
| ATOM | 1493 | OD2 | ASP | A | 561 | 38.379 | 12.683 | 8.748 | 1.00 | 16.11 |
| ATOM | 1494 | C | ASP | A | 561 | 38.481 | 10.542 | 13.088 | 1.00 | 14.85 |
| ATOM | 1495 | O | ASP | A | 561 | 39.591 | 10.251 | 13.529 | 1.00 | 12.08 |
| ATOM | 1496 | N | TRP | A | 562 | 37.484 | 10.969 | 13.860 | 1.00 | 14.47 |
| ATOM | 1497 | CA | TRP | A | 562 | 37.681 | 11.124 | 15.299 | 1.00 | 16.86 |
| ATOM | 1498 | CB | TRP | A | 562 | 36.569 | 11.992 | 15.900 | 1.00 | 15.19 |
| ATOM | 1499 | CG | TRP | A | 562 | 36.704 | 13.416 | 15.419 | 1.00 | 17.27 |
| ATOM | 1500 | CD2 | TRP | A | 562 | 37.832 | 14.281 | 15.622 | 1.00 | 17.57 |
| ATOM | 1501 | CE2 | TRP | A | 562 | 37.581 | 15.471 | 14.905 | 1.00 | 17.29 |
| ATOM | 1502 | CE3 | TRP | A | 562 | 39.035 | 14.161 | 16.339 | 1.00 | 16.59 |
| ATOM | 1503 | CD1 | TRP | A | 562 | 35.837 | 14.102 | 14.616 | 1.00 | 17.03 |
| ATOM | 1504 | NE1 | TRP | A | 562 | 36.359 | 15.336 | 14.300 | 1.00 | 17.38 |
| ATOM | 1505 | CZ2 | TRP | A | 562 | 38.487 | 16.539 | 14.880 | 1.00 | 17.77 |
| ATOM | 1506 | CZ3 | TRP | A | 562 | 39.940 | 15.221 | 16.314 | 1.00 | 18.82 |
| ATOM | 1507 | CH2 | TRP | A | 562 | 39.660 | 16.397 | 15.589 | 1.00 | 18.40 |
| ATOM | 1508 | C | TRP | A | 562 | 37.803 | 9.786 | 16.006 | 1.00 | 16.65 |
| ATOM | 1509 | O | TRP | A | 562 | 38.416 | 9.697 | 17.063 | 1.00 | 16.32 |
| ATOM | 1510 | N | TRP | A | 563 | 37.232 | 8.742 | 15.412 | 1.00 | 17.84 |
| ATOM | 1511 | CA | TRP | A | 563 | 37.343 | 7.407 | 15.983 | 1.00 | 16.49 |
| ATOM | 1512 | CB | TRP | A | 563 | 36.315 | 6.466 | 15.364 | 1.00 | 16.30 |
| ATOM | 1513 | CG | TRP | A | 563 | 36.466 | 5.049 | 15.826 | 1.00 | 15.78 |
| ATOM | 1514 | CD2 | TRP | A | 563 | 35.790 | 4.435 | 16.927 | 1.00 | 16.38 |
| ATOM | 1515 | CE2 | TRP | A | 563 | 36.280 | 3.114 | 17.033 | 1.00 | 16.34 |
| ATOM | 1516 | CE3 | TRP | A | 563 | 34.816 | 4.872 | 17.836 | 1.00 | 16.67 |
| ATOM | 1517 | CD1 | TRP | A | 563 | 37.312 | 4.106 | 15.322 | 1.00 | 13.61 |
| ATOM | 1518 | NE1 | TRP | A | 563 | 37.209 | 2.942 | 16.040 | 1.00 | 16.49 |
| ATOM | 1519 | CZ2 | TRP | A | 563 | 35.831 | 2.225 | 18.009 | 1.00 | 15.68 |
| ATOM | 1520 | CZ3 | TRP | A | 563 | 34.366 | 3.984 | 18.813 | 1.00 | 16.70 |
| ATOM | 1521 | CH2 | TRP | A | 563 | 34.876 | 2.674 | 18.889 | 1.00 | 17.15 |
| ATOM | 1522 | C | TRP | A | 563 | 38.756 | 6.908 | 15.684 | 1.00 | 17.23 |
| ATOM | 1523 | O | TRP | A | 563 | 39.465 | 6.426 | 16.574 | 1.00 | 16.67 |
| ATOM | 1524 | N | SER | A | 564 | 39.172 | 7.036 | 14.428 | 1.00 | 17.73 |
| ATOM | 1525 | CA | SER | A | 564 | 40.510 | 6.609 | 14.034 | 1.00 | 17.56 |
| ATOM | 1526 | CB | SER | A | 564 | 40.743 | 6.896 | 12.553 | 1.00 | 18.31 |
| ATOM | 1527 | OG | SER | A | 564 | 39.776 | 6.222 | 11.771 | 1.00 | 24.56 |
| ATOM | 1528 | C | SER | A | 564 | 41.568 | 7.328 | 14.867 | 1.00 | 17.10 |
| ATOM | 1529 | O | SER | A | 564 | 42.596 | 6.744 | 15.213 | 1.00 | 15.95 |
| ATOM | 1530 | N | PHE | A | 565 | 41.315 | 8.602 | 15.172 | 1.00 | 16.47 |
| ATOM | 1531 | CA | PHE | A | 565 | 42.232 | 9.399 | 15.981 | 1.00 | 15.31 |
| ATOM | 1532 | CB | PHE | A | 565 | 41.700 | 10.838 | 16.121 | 1.00 | 15.68 |
| ATOM | 1533 | CG | PHE | A | 565 | 42.493 | 11.701 | 17.069 | 1.00 | 15.08 |
| ATOM | 1534 | CD1 | PHE | A | 565 | 43.754 | 12.184 | 16.725 | 1.00 | 14.90 |
| ATOM | 1535 | CD2 | PHE | A | 565 | 41.966 | 12.039 | 18.309 | 1.00 | 16.71 |
| ATOM | 1536 | CE1 | PHE | A | 565 | 44.476 | 12.996 | 17.608 | 1.00 | 16.17 |
| ATOM | 1537 | CE2 | PHE | A | 565 | 42.680 | 12.853 | 19.202 | 1.00 | 15.19 |
| ATOM | 1538 | CZ | PHE | A | 565 | 43.934 | 13.331 | 18.848 | 1.00 | 14.70 |
| ATOM | 1539 | C | PHE | A | 565 | 42.354 | 8.745 | 17.353 | 1.00 | 14.00 |
| ATOM | 1540 | O | PHE | A | 565 | 43.453 | 8.607 | 17.889 | 1.00 | 15.28 |
| ATOM | 1541 | N | GLY | A | 566 | 41.221 | 8.346 | 17.922 | 1.00 | 12.97 |
| ATOM | 1542 | CA | GLY | A | 566 | 41.242 | 7.685 | 19.214 | 1.00 | 14.08 |
| ATOM | 1543 | C | GLY | A | 566 | 42.097 | 6.423 | 19.184 | 1.00 | 15.08 |
| ATOM | 1544 | O | GLY | A | 566 | 42.873 | 6.156 | 20.108 | 1.00 | 13.47 |
| ATOM | 1545 | N | VAL | A | 567 | 41.961 | 5.643 | 18.114 | 1.00 | 15.37 |
| ATOM | 1546 | CA | VAL | A | 567 | 42.729 | 4.414 | 17.977 | 1.00 | 15.73 |
| ATOM | 1547 | CB | VAL | A | 567 | 42.344 | 3.644 | 16.698 | 1.00 | 15.71 |
| ATOM | 1548 | CG1 | VAL | A | 567 | 43.162 | 2.361 | 16.596 | 1.00 | 15.31 |
| ATOM | 1549 | CG2 | VAL | A | 567 | 40.853 | 3.318 | 16.714 | 1.00 | 16.84 |
| ATOM | 1550 | C | VAL | A | 567 | 44.205 | 4.762 | 17.914 | 1.00 | 15.83 |
| ATOM | 1551 | O | VAL | A | 567 | 45.028 | 4.147 | 18.597 | 1.00 | 16.87 |
| ATOM | 1552 | N | LEU | A | 568 | 44.525 | 5.761 | 17.101 | 1.00 | 15.86 |
| ATOM | 1553 | CA | LEU | A | 568 | 45.895 | 6.228 | 16.924 | 1.00 | 16.67 |
| ATOM | 1554 | CB | LEU | A | 568 | 45.918 | 7.345 | 15.876 | 1.00 | 16.39 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1555 | CG | LEU | A | 568 | 47.275 | 7.815 | 15.347 | 1.00 | 18.99 |
| ATOM | 1556 | CD1 | LEU | A | 568 | 47.061 | 8.561 | 14.034 | 1.00 | 16.82 |
| ATOM | 1557 | CD2 | LEU | A | 568 | 47.978 | 8.712 | 16.375 | 1.00 | 17.66 |
| ATOM | 1558 | C | LEU | A | 568 | 46.501 | 6.729 | 18.242 | 1.00 | 16.60 |
| ATOM | 1559 | O | LEU | A | 568 | 47.652 | 6.419 | 18.569 | 1.00 | 15.53 |
| ATOM | 1560 | N | LEU | A | 569 | 45.730 | 7.509 | 18.995 | 1.00 | 15.33 |
| ATOM | 1561 | CA | LEU | A | 569 | 46.218 | 8.030 | 20.269 | 1.00 | 15.32 |
| ATOM | 1562 | CB | LEU | A | 569 | 45.227 | 9.038 | 20.851 | 1.00 | 13.60 |
| ATOM | 1563 | CG | LEU | A | 569 | 45.501 | 9.573 | 22.264 | 1.00 | 13.58 |
| ATOM | 1564 | CD1 | LEU | A | 569 | 46.914 | 10.130 | 22.364 | 1.00 | 12.08 |
| ATOM | 1565 | CD2 | LEU | A | 569 | 44.470 | 10.648 | 22.586 | 1.00 | 12.30 |
| ATOM | 1566 | C | LEU | A | 569 | 46.425 | 6.879 | 21.248 | 1.00 | 15.28 |
| ATOM | 1567 | O | LEU | A | 569 | 47.431 | 6.829 | 21.946 | 1.00 | 15.83 |
| ATOM | 1568 | N | TYR | A | 570 | 45.467 | 5.958 | 21.297 | 1.00 | 14.84 |
| ATOM | 1569 | CA | TYR | A | 570 | 45.567 | 4.799 | 22.173 | 1.00 | 15.24 |
| ATOM | 1570 | CB | TYR | A | 570 | 44.343 | 3.891 | 21.980 | 1.00 | 15.81 |
| ATOM | 1571 | CG | TYR | A | 570 | 44.328 | 2.641 | 22.838 | 1.00 | 16.40 |
| ATOM | 1572 | CD1 | TYR | A | 570 | 45.140 | 1.549 | 22.530 | 1.00 | 16.48 |
| ATOM | 1573 | CE1 | TYR | A | 570 | 45.137 | 0.402 | 23.321 | 1.00 | 15.88 |
| ATOM | 1574 | CD2 | TYR | A | 570 | 43.508 | 2.556 | 23.965 | 1.00 | 15.81 |
| ATOM | 1575 | CE2 | TYR | A | 570 | 43.498 | 1.417 | 24.762 | 1.00 | 14.45 |
| ATOM | 1576 | CZ | TYR | A | 570 | 44.314 | 0.341 | 24.434 | 1.00 | 16.92 |
| ATOM | 1577 | OH | TYR | A | 570 | 44.293 | −0.803 | 25.204 | 1.00 | 15.75 |
| ATOM | 1578 | C | TYR | A | 570 | 46.860 | 4.053 | 21.846 | 1.00 | 15.87 |
| ATOM | 1579 | O | TYR | A | 570 | 47.621 | 3.695 | 22.743 | 1.00 | 14.37 |
| ATOM | 1580 | N | GLU | A | 571 | 47.126 | 3.845 | 20.560 | 1.00 | 16.10 |
| ATOM | 1581 | CA | GLU | A | 571 | 48.339 | 3.145 | 20.151 | 1.00 | 17.33 |
| ATOM | 1582 | CB | GLU | A | 571 | 48.355 | 2.918 | 18.640 | 1.00 | 18.05 |
| ATOM | 1583 | CG | GLU | A | 571 | 47.252 | 2.011 | 18.118 | 1.00 | 20.46 |
| ATOM | 1584 | CD | GLU | A | 571 | 47.329 | 1.830 | 16.610 | 1.00 | 23.05 |
| ATOM | 1585 | OE1 | GLU | A | 571 | 47.545 | 2.837 | 15.902 | 1.00 | 23.73 |
| ATOM | 1586 | OE2 | GLU | A | 571 | 47.165 | 0.689 | 16.126 | 1.00 | 24.78 |
| ATOM | 1587 | C | GLU | A | 571 | 49.629 | 3.860 | 20.561 | 1.00 | 17.33 |
| ATOM | 1588 | O | GLU | A | 571 | 50.577 | 3.216 | 20.980 | 1.00 | 17.42 |
| ATOM | 1589 | N | MET | A | 572 | 49.677 | 5.183 | 20.434 | 1.00 | 17.45 |
| ATOM | 1590 | CA | MET | A | 572 | 50.883 | 5.917 | 20.805 | 1.00 | 17.86 |
| ATOM | 1591 | CB | MET | A | 572 | 50.745 | 7.411 | 20.491 | 1.00 | 15.64 |
| ATOM | 1592 | CG | MET | A | 572 | 50.800 | 7.768 | 19.015 | 1.00 | 15.50 |
| ATOM | 1593 | SD | MET | A | 572 | 51.162 | 9.527 | 18.803 | 1.00 | 15.78 |
| ATOM | 1594 | CE | MET | A | 572 | 49.593 | 10.292 | 19.306 | 1.00 | 11.33 |
| ATOM | 1595 | C | MET | A | 572 | 51.209 | 5.770 | 22.288 | 1.00 | 17.96 |
| ATOM | 1596 | O | MET | A | 572 | 52.379 | 5.709 | 22.679 | 1.00 | 17.73 |
| ATOM | 1597 | N | LEU | A | 573 | 50.163 | 5.715 | 23.106 | 1.00 | 18.08 |
| ATOM | 1598 | CA | LEU | A | 573 | 50.313 | 5.621 | 24.559 | 1.00 | 20.18 |
| ATOM | 1599 | CB | LEU | A | 573 | 49.114 | 6.259 | 25.252 | 1.00 | 19.31 |
| ATOM | 1600 | CG | LEU | A | 573 | 48.880 | 7.763 | 25.185 | 1.00 | 20.70 |
| ATOM | 1601 | CD1 | LEU | A | 573 | 47.441 | 8.038 | 25.613 | 1.00 | 17.92 |
| ATOM | 1602 | CD2 | LEU | A | 573 | 49.874 | 8.485 | 26.113 | 1.00 | 19.54 |
| ATOM | 1603 | C | LEU | A | 573 | 50.462 | 4.222 | 25.122 | 1.00 | 20.83 |
| ATOM | 1604 | O | LEU | A | 573 | 51.148 | 4.018 | 26.127 | 1.00 | 20.62 |
| ATOM | 1605 | N | ILE | A | 574 | 49.807 | 3.264 | 24.477 | 1.00 | 20.98 |
| ATOM | 1606 | CA | ILE | A | 574 | 49.807 | 1.893 | 24.957 | 1.00 | 22.95 |
| ATOM | 1607 | CB | ILE | A | 574 | 48.365 | 1.340 | 24.966 | 1.00 | 23.26 |
| ATOM | 1608 | CG2 | ILE | A | 574 | 48.345 | −0.051 | 25.555 | 1.00 | 23.31 |
| ATOM | 1609 | CG1 | ILE | A | 574 | 47.449 | 2.275 | 25.768 | 1.00 | 22.98 |
| ATOM | 1610 | CD1 | ILE | A | 574 | 47.864 | 2.457 | 27.215 | 1.00 | 25.32 |
| ATOM | 1611 | C | ILE | A | 574 | 50.706 | 0.954 | 24.167 | 1.00 | 23.41 |
| ATOM | 1612 | O | ILE | A | 574 | 51.141 | −0.073 | 24.683 | 1.00 | 23.85 |
| ATOM | 1613 | N | GLY | A | 575 | 50.977 | 1.302 | 22.914 | 1.00 | 23.52 |
| ATOM | 1614 | CA | GLY | A | 575 | 51.836 | 0.468 | 22.100 | 1.00 | 24.90 |
| ATOM | 1615 | C | GLY | A | 575 | 51.135 | −0.756 | 21.542 | 1.00 | 25.99 |
| ATOM | 1616 | O | GLY | A | 575 | 51.775 | −1.630 | 20.959 | 1.00 | 25.65 |
| ATOM | 1617 | N | GLN | A | 576 | 49.821 | −0.809 | 21.729 | 1.00 | 25.92 |
| ATOM | 1618 | CA | GLN | A | 576 | 48.982 | −1.899 | 21.240 | 1.00 | 26.08 |
| ATOM | 1619 | CB | GLN | A | 576 | 48.544 | −2.817 | 22.384 | 1.00 | 29.36 |
| ATOM | 1620 | CG | GLN | A | 576 | 49.638 | −3.531 | 23.145 | 1.00 | 36.00 |
| ATOM | 1621 | CD | GLN | A | 576 | 49.063 | −4.335 | 24.296 | 1.00 | 39.14 |
| ATOM | 1622 | OE1 | GLN | A | 576 | 48.967 | −3.853 | 25.427 | 1.00 | 42.47 |
| ATOM | 1623 | NE2 | GLN | A | 576 | 48.648 | −5.560 | 24.006 | 1.00 | 41.45 |
| ATOM | 1624 | C | GLN | A | 576 | 47.719 | −1.259 | 20.678 | 1.00 | 24.01 |
| ATOM | 1625 | O | GLN | A | 576 | 47.381 | −0.130 | 21.040 | 1.00 | 23.45 |
| ATOM | 1626 | N | SER | A | 577 | 47.012 | −1.983 | 19.818 | 1.00 | 21.78 |
| ATOM | 1627 | CA | SER | A | 577 | 45.759 | −1.487 | 19.254 | 1.00 | 20.53 |
| ATOM | 1628 | CB | SER | A | 577 | 45.414 | −2.221 | 17.957 | 1.00 | 20.28 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1629 | OG | SER | A | 577 | 46.319 | −1.864 | 16.924 | 1.00 | 21.59 |
| ATOM | 1630 | C | SER | A | 577 | 44.676 | −1.744 | 20.292 | 1.00 | 20.48 |
| ATOM | 1631 | O | SER | A | 577 | 44.709 | −2.750 | 20.994 | 1.00 | 20.26 |
| ATOM | 1632 | N | PRO | A | 578 | 43.703 | −0.833 | 20.408 | 1.00 | 20.02 |
| ATOM | 1633 | CD | PRO | A | 578 | 43.571 | 0.447 | 19.689 | 1.00 | 20.14 |
| ATOM | 1634 | CA | PRO | A | 578 | 42.627 | −1.002 | 21.387 | 1.00 | 20.99 |
| ATOM | 1635 | CB | PRO | A | 578 | 41.949 | 0.369 | 21.391 | 1.00 | 19.33 |
| ATOM | 1636 | CG | PRO | A | 578 | 42.136 | 0.839 | 19.982 | 1.00 | 18.62 |
| ATOM | 1637 | C | PRO | A | 578 | 41.652 | −2.147 | 21.108 | 1.00 | 22.22 |
| ATOM | 1638 | O | PRO | A | 578 | 41.073 | −2.713 | 22.035 | 1.00 | 23.94 |
| ATOM | 1639 | N | PHE | A | 579 | 41.460 | −2.490 | 19.841 | 1.00 | 23.82 |
| ATOM | 1640 | CA | PHE | A | 579 | 40.548 | −3.575 | 19.482 | 1.00 | 23.84 |
| ATOM | 1641 | CB | PHE | A | 579 | 39.417 | −3.028 | 18.605 | 1.00 | 22.19 |
| ATOM | 1642 | CG | PHE | A | 579 | 38.696 | −1.868 | 19.227 | 1.00 | 20.44 |
| ATOM | 1643 | CD1 | PHE | A | 579 | 38.963 | −0.564 | 18.821 | 1.00 | 19.24 |
| ATOM | 1644 | CD2 | PHE | A | 579 | 37.823 | −2.072 | 20.292 | 1.00 | 20.80 |
| ATOM | 1645 | CE1 | PHE | A | 579 | 38.378 | 0.520 | 19.471 | 1.00 | 19.55 |
| ATOM | 1646 | CE2 | PHE | A | 579 | 37.234 | −0.997 | 20.952 | 1.00 | 20.02 |
| ATOM | 1647 | CZ | PHE | A | 579 | 37.513 | 0.302 | 20.543 | 1.00 | 20.44 |
| ATOM | 1648 | C | PHE | A | 579 | 41.326 | −4.685 | 18.779 | 1.00 | 25.48 |
| ATOM | 1649 | O | PHE | A | 579 | 42.094 | −4.417 | 17.858 | 1.00 | 26.10 |
| ATOM | 1650 | N | HIS | A | 580 | 41.135 | −5.921 | 19.241 | 1.00 | 27.92 |
| ATOM | 1651 | CA | HIS | A | 580 | 41.846 | −7.087 | 18.706 | 1.00 | 30.44 |
| ATOM | 1652 | CB | HIS | A | 580 | 42.578 | −7.857 | 19.817 | 1.00 | 32.29 |
| ATOM | 1653 | CG | HIS | A | 580 | 43.521 | −7.032 | 20.626 | 1.00 | 35.99 |
| ATOM | 1654 | CD2 | HIS | A | 580 | 44.836 | −6.756 | 20.457 | 1.00 | 38.57 |
| ATOM | 1655 | ND1 | HIS | A | 580 | 43.144 | −6.407 | 21.795 | 1.00 | 38.02 |
| ATOM | 1656 | CE1 | HIS | A | 580 | 44.188 | −5.783 | 22.313 | 1.00 | 39.52 |
| ATOM | 1657 | NE2 | HIS | A | 580 | 45.228 | −5.979 | 21.521 | 1.00 | 40.35 |
| ATOM | 1658 | C | HIS | A | 580 | 40.956 | −8.099 | 18.012 | 1.00 | 29.39 |
| ATOM | 1659 | O | HIS | A | 580 | 39.734 | −8.046 | 18.105 | 1.00 | 30.42 |
| ATOM | 1660 | N | GLY | A | 581 | 41.606 | −9.048 | 17.348 | 1.00 | 29.70 |
| ATOM | 1661 | CA | GLY | A | 581 | 40.906 | −10.106 | 16.649 | 1.00 | 29.49 |
| ATOM | 1662 | C | GLY | A | 581 | 41.906 | −10.980 | 15.923 | 1.00 | 29.16 |
| ATOM | 1663 | O | GLY | A | 581 | 42.903 | −10.473 | 15.404 | 1.00 | 28.80 |
| ATOM | 1664 | N | GLN | A | 582 | 41.656 | −12.287 | 15.888 | 1.00 | 29.65 |
| ATOM | 1665 | CA | GLN | A | 582 | 42.564 | −13.201 | 15.204 | 1.00 | 28.88 |
| ATOM | 1666 | CB | GLN | A | 582 | 42.185 | −14.656 | 15.476 | 1.00 | 29.32 |
| ATOM | 1667 | CG | GLN | A | 582 | 43.336 | −15.615 | 15.225 | 1.00 | 28.13 |
| ATOM | 1668 | CD | GLN | A | 582 | 44.455 | −15.441 | 16.242 | 1.00 | 28.61 |
| ATOM | 1669 | OE1 | GLN | A | 582 | 45.635 | −15.573 | 15.918 | 1.00 | 28.38 |
| ATOM | 1670 | NE2 | GLN | A | 582 | 44.083 | −15.157 | 17.484 | 1.00 | 27.38 |
| ATOM | 1671 | C | GLN | A | 582 | 42.480 | −12.914 | 13.714 | 1.00 | 29.02 |
| ATOM | 1672 | O | GLN | A | 582 | 43.436 | −13.126 | 12.972 | 1.00 | 29.72 |
| ATOM | 1673 | N | ASP | A | 583 | 41.316 | −12.438 | 13.286 | 1.00 | 30.16 |
| ATOM | 1674 | CA | ASP | A | 583 | 41.082 | −12.076 | 11.890 | 1.00 | 31.10 |
| ATOM | 1675 | CB | ASP | A | 583 | 40.417 | −13.226 | 11.126 | 1.00 | 33.62 |
| ATOM | 1676 | CG | ASP | A | 583 | 39.171 | −13.747 | 11.817 | 1.00 | 36.31 |
| ATOM | 1677 | OD1 | ASP | A | 583 | 38.443 | −12.944 | 12.442 | 1.00 | 37.13 |
| ATOM | 1678 | OD2 | ASP | A | 583 | 38.912 | −14.966 | 11.721 | 1.00 | 38.41 |
| ATOM | 1679 | C | ASP | A | 583 | 40.189 | −10.838 | 11.852 | 1.00 | 30.92 |
| ATOM | 1680 | O | ASP | A | 583 | 39.749 | −10.351 | 12.897 | 1.00 | 30.04 |
| ATOM | 1681 | N | GLU | A | 584 | 39.912 | −10.332 | 10.656 | 1.00 | 31.45 |
| ATOM | 1682 | CA | GLU | A | 584 | 39.081 | −9.139 | 10.516 | 1.00 | 31.84 |
| ATOM | 1683 | CB | GLU | A | 584 | 38.998 | −8.728 | 9.046 | 1.00 | 33.47 |
| ATOM | 1684 | CG | GLU | A | 584 | 40.307 | −8.168 | 8.514 | 1.00 | 38.25 |
| ATOM | 1685 | CD | GLU | A | 584 | 40.212 | −7.736 | 7.068 | 1.00 | 41.02 |
| ATOM | 1686 | OE1 | GLU | A | 584 | 39.265 | −6.992 | 6.735 | 1.00 | 42.48 |
| ATOM | 1687 | OE2 | GLU | A | 584 | 41.088 | −8.130 | 6.267 | 1.00 | 42.67 |
| ATOM | 1688 | C | GLU | A | 584 | 37.679 | −9.257 | 11.099 | 1.00 | 31.35 |
| ATOM | 1689 | O | GLU | A | 584 | 37.173 | −8.309 | 11.701 | 1.00 | 30.38 |
| ATOM | 1690 | N | GLU | A | 585 | 37.046 | −10.414 | 10.933 | 1.00 | 31.03 |
| ATOM | 1691 | CA | GLU | A | 585 | 35.703 | −10.593 | 11.461 | 1.00 | 31.13 |
| ATOM | 1692 | CB | GLU | A | 585 | 35.152 | −11.975 | 11.095 | 1.00 | 34.50 |
| ATOM | 1693 | CG | GLU | A | 585 | 35.192 | −12.301 | 9.608 | 1.00 | 39.82 |
| ATOM | 1694 | CD | GLU | A | 585 | 34.189 | −13.378 | 9.227 | 1.00 | 43.33 |
| ATOM | 1695 | OE1 | GLU | A | 585 | 33.925 | −14.278 | 10.059 | 1.00 | 44.73 |
| ATOM | 1696 | OE2 | GLU | A | 585 | 33.670 | −13.329 | 8.090 | 1.00 | 45.88 |
| ATOM | 1697 | C | GLU | A | 585 | 35.691 | −10.431 | 12.976 | 1.00 | 29.88 |
| ATOM | 1698 | O | GLU | A | 585 | 34.793 | −9.795 | 13.532 | 1.00 | 29.57 |
| ATOM | 1699 | N | GLU | A | 586 | 36.686 | −11.005 | 13.646 | 1.00 | 28.10 |
| ATOM | 1700 | CA | GLU | A | 586 | 36.755 | −10.907 | 15.098 | 1.00 | 27.35 |
| ATOM | 1701 | CB | GLU | A | 586 | 37.824 | −11.856 | 15.641 | 1.00 | 30.54 |
| ATOM | 1702 | CG | GLU | A | 586 | 37.761 | −12.054 | 17.149 | 1.00 | 34.93 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1703 | CD | GLU | A | 586 | 38.813 | −13.029 | 17.644 | 1.00 | 37.75 |
| ATOM | 1704 | OE1 | GLU | A | 586 | 38.971 | −14.103 | 17.019 | 1.00 | 39.44 |
| ATOM | 1705 | OE2 | GLU | A | 586 | 39.480 | −12.722 | 18.655 | 1.00 | 39.69 |
| ATOM | 1706 | C | GLU | A | 586 | 37.083 | −9.469 | 15.484 | 1.00 | 24.29 |
| ATOM | 1707 | O | GLU | A | 586 | 36.561 | −8.936 | 16.465 | 1.00 | 22.10 |
| ATOM | 1708 | N | LEU | A | 587 | 37.955 | −8.846 | 14.701 | 1.00 | 22.26 |
| ATOM | 1709 | CA | LEU | A | 587 | 38.333 | −7.465 | 14.957 | 1.00 | 21.64 |
| ATOM | 1710 | CB | LEU | A | 587 | 39.364 | −6.998 | 13.929 | 1.00 | 19.76 |
| ATOM | 1711 | CG | LEU | A | 587 | 39.666 | −5.495 | 13.899 | 1.00 | 19.53 |
| ATOM | 1712 | CD1 | LEU | A | 587 | 40.252 | −5.050 | 15.231 | 1.00 | 18.49 |
| ATOM | 1713 | CD2 | LEU | A | 587 | 40.636 | −5.197 | 12.777 | 1.00 | 18.54 |
| ATOM | 1714 | C | LEU | A | 587 | 37.081 | −6.592 | 14.872 | 1.00 | 22.22 |
| ATOM | 1715 | O | LEU | A | 587 | 36.829 | −5.773 | 15.753 | 1.00 | 22.02 |
| ATOM | 1716 | N | PHE | A | 588 | 36.282 | −6.785 | 13.825 | 1.00 | 22.51 |
| ATOM | 1717 | CA | PHE | A | 588 | 35.074 | −5.979 | 13.658 | 1.00 | 23.33 |
| ATOM | 1718 | CB | PHE | A | 588 | 34.388 | −6.282 | 12.321 | 1.00 | 22.37 |
| ATOM | 1719 | CG | PHE | A | 588 | 35.178 | −5.828 | 11.115 | 1.00 | 23.33 |
| ATOM | 1720 | CD1 | PHE | A | 588 | 36.218 | −4.911 | 11.248 | 1.00 | 22.14 |
| ATOM | 1721 | CD2 | PHE | A | 588 | 34.870 | −6.309 | 9.841 | 1.00 | 25.16 |
| ATOM | 1722 | CE1 | PHE | A | 588 | 36.946 | −4.476 | 10.135 | 1.00 | 23.11 |
| ATOM | 1723 | CE2 | PHE | A | 588 | 35.590 | −5.881 | 8.715 | 1.00 | 24.51 |
| ATOM | 1724 | CZ | PHE | A | 588 | 36.631 | −4.962 | 8.864 | 1.00 | 24.93 |
| ATOM | 1725 | C | PHE | A | 588 | 34.106 | −6.164 | 14.803 | 1.00 | 23.40 |
| ATOM | 1726 | O | PHE | A | 588 | 33.482 | −5.207 | 15.258 | 1.00 | 23.18 |
| ATOM | 1727 | N | HIS | A | 589 | 33.976 | −7.396 | 15.277 | 1.00 | 25.00 |
| ATOM | 1728 | CA | HIS | A | 589 | 33.087 | −7.654 | 16.399 | 1.00 | 26.65 |
| ATOM | 1729 | CB | HIS | A | 589 | 33.030 | −9.154 | 16.700 | 1.00 | 29.36 |
| ATOM | 1730 | CG | HIS | A | 589 | 32.383 | −9.478 | 18.011 | 1.00 | 33.33 |
| ATOM | 1731 | CD2 | HIS | A | 589 | 31.135 | −9.914 | 18.307 | 1.00 | 34.26 |
| ATOM | 1732 | ND1 | HIS | A | 589 | 33.025 | −9.306 | 19.220 | 1.00 | 33.60 |
| ATOM | 1733 | CE1 | HIS | A | 589 | 32.200 | −9.620 | 20.203 | 1.00 | 34.51 |
| ATOM | 1734 | NE2 | HIS | A | 589 | 31.046 | −9.991 | 19.676 | 1.00 | 34.62 |
| ATOM | 1735 | C | HIS | A | 589 | 33.608 | −6.891 | 17.618 | 1.00 | 25.74 |
| ATOM | 1736 | O | HIS | A | 589 | 32.839 | −6.302 | 18.377 | 1.00 | 25.34 |
| ATOM | 1737 | N | SER | A | 590 | 34.925 | −6.895 | 17.789 | 1.00 | 26.30 |
| ATOM | 1738 | CA | SER | A | 590 | 35.557 | −6.213 | 18.917 | 1.00 | 26.09 |
| ATOM | 1739 | CB | SER | A | 590 | 37.057 | −6.513 | 18.927 | 1.00 | 26.34 |
| ATOM | 1740 | OG | SER | A | 590 | 37.707 | −5.806 | 19.961 | 1.00 | 28.64 |
| ATOM | 1741 | C | SER | A | 590 | 35.325 | −4.703 | 18.851 | 1.00 | 25.75 |
| ATOM | 1742 | O | SER | A | 590 | 35.034 | −4.068 | 19.861 | 1.00 | 25.33 |
| ATOM | 1743 | N | ILE | A | 591 | 35.459 | −4.134 | 17.657 | 1.00 | 25.04 |
| ATOM | 1744 | CA | ILE | A | 591 | 35.251 | −2.704 | 17.461 | 1.00 | 25.15 |
| ATOM | 1745 | CB | ILE | A | 591 | 35.577 | −2.299 | 15.997 | 1.00 | 23.60 |
| ATOM | 1746 | CG2 | ILE | A | 591 | 35.082 | −0.877 | 15.703 | 1.00 | 22.21 |
| ATOM | 1747 | CG1 | ILE | A | 591 | 37.087 | −2.411 | 15.764 | 1.00 | 22.39 |
| ATOM | 1748 | CD1 | ILE | A | 591 | 37.506 | −2.243 | 14.312 | 1.00 | 21.00 |
| ATOM | 1749 | C | ILE | A | 591 | 33.800 | −2.342 | 17.785 | 1.00 | 27.12 |
| ATOM | 1750 | O | ILE | A | 591 | 33.523 | −1.273 | 18.330 | 1.00 | 26.48 |
| ATOM | 1751 | N | ARG | A | 592 | 32.880 | −3.246 | 17.465 | 1.00 | 29.01 |
| ATOM | 1752 | CA | ARG | A | 592 | 31.464 | −3.006 | 17.719 | 1.00 | 32.00 |
| ATOM | 1753 | CB | ARG | A | 592 | 30.598 | −3.892 | 16.809 | 1.00 | 32.52 |
| ATOM | 1754 | CG | ARG | A | 592 | 30.678 | −3.588 | 15.318 | 1.00 | 33.53 |
| ATOM | 1755 | CD | ARG | A | 592 | 29.561 | −4.307 | 14.566 | 1.00 | 35.57 |
| ATOM | 1756 | NE | ARG | A | 592 | 29.655 | −5.767 | 14.656 | 1.00 | 36.97 |
| ATOM | 1757 | CZ | ARG | A | 592 | 30.300 | −6.536 | 13.780 | 1.00 | 38.65 |
| ATOM | 1758 | NH1 | ARG | A | 592 | 30.910 | −5.990 | 12.735 | 1.00 | 38.86 |
| ATOM | 1759 | NH2 | ARG | A | 592 | 30.336 | −7.855 | 13.945 | 1.00 | 39.69 |
| ATOM | 1760 | C | ARG | A | 592 | 31.009 | −3.231 | 19.165 | 1.00 | 33.46 |
| ATOM | 1761 | O | ARG | A | 592 | 30.113 | −2.542 | 19.647 | 1.00 | 34.26 |
| ATOM | 1762 | N | MET | A | 593 | 31.628 | −4.175 | 19.862 | 1.00 | 35.85 |
| ATOM | 1763 | CA | MET | A | 593 | 31.186 | −4.503 | 21.217 | 1.00 | 38.64 |
| ATOM | 1764 | CB | MET | A | 593 | 30.766 | −5.976 | 21.260 | 1.00 | 41.97 |
| ATOM | 1765 | CG | MET | A | 593 | 29.685 | −6.360 | 20.272 | 1.00 | 46.33 |
| ATOM | 1766 | SD | MET | A | 593 | 28.092 | −5.700 | 20.752 | 1.00 | 54.48 |
| ATOM | 1767 | CE | MET | A | 593 | 27.587 | −6.935 | 21.934 | 1.00 | 52.43 |
| ATOM | 1768 | C | MET | A | 593 | 32.119 | −4.258 | 22.398 | 1.00 | 38.21 |
| ATOM | 1769 | O | MET | A | 593 | 31.676 | −3.839 | 23.465 | 1.00 | 38.65 |
| ATOM | 1770 | N | ASP | A | 594 | 33.405 | −4.522 | 22.221 | 1.00 | 37.44 |
| ATOM | 1771 | CA | ASP | A | 594 | 34.343 | −4.388 | 23.325 | 1.00 | 36.80 |
| ATOM | 1772 | CB | ASP | A | 594 | 35.613 | −5.187 | 23.020 | 1.00 | 37.02 |
| ATOM | 1773 | CG | ASP | A | 594 | 35.321 | −6.644 | 22.737 | 1.00 | 37.70 |
| ATOM | 1774 | OD1 | ASP | A | 594 | 34.353 | −7.175 | 23.326 | 1.00 | 38.82 |
| ATOM | 1775 | OD2 | ASP | A | 594 | 36.064 | −7.257 | 21.941 | 1.00 | 38.55 |
| ATOM | 1776 | C | ASP | A | 594 | 34.751 | −3.014 | 23.834 | 1.00 | 35.81 |

TABLE 2-continued

Structure coordinates for PKCθ
(residues 377-696 of SEQ ID NO: 1)/staurosporine complex

|  | # | name | res | chain | res # | X | Y | Z | occ | B |
|---|---|---|---|---|---|---|---|---|---|---|
| ATOM | 1777 | O | ASP | A | 594 | 34.643 | −1.993 | 23.153 | 1.00 | 34.95 |
| ATOM | 1778 | N | ASN | A | 595 | 35.218 | −3.023 | 25.074 | 1.00 | 34.85 |
| ATOM | 1779 | CA | ASN | A | 595 | 35.714 | −1.834 | 25.731 | 1.00 | 33.81 |
| ATOM | 1780 | CB | ASN | A | 595 | 35.162 | −1.740 | 27.151 | 1.00 | 36.16 |
| ATOM | 1781 | CG | ASN | A | 595 | 33.818 | −1.049 | 27.203 | 1.00 | 38.48 |
| ATOM | 1782 | OD1 | ASN | A | 595 | 33.106 | −1.134 | 28.204 | 1.00 | 41.34 |
| ATOM | 1783 | ND2 | ASN | A | 595 | 33.468 | −0.346 | 26.129 | 1.00 | 39.15 |
| ATOM | 1784 | C | ASN | A | 595 | 37.213 | −2.033 | 25.766 | 1.00 | 31.92 |
| ATOM | 1785 | O | ASN | A | 595 | 37.692 | −3.071 | 26.216 | 1.00 | 31.53 |
| ATOM | 1786 | N | PRO | A | 596 | 37.978 | −1.056 | 25.260 | 1.00 | 30.60 |
| ATOM | 1787 | CD | PRO | A | 596 | 37.546 | 0.176 | 24.583 | 1.00 | 29.67 |
| ATOM | 1788 | CA | PRO | A | 596 | 39.440 | −1.169 | 25.256 | 1.00 | 29.64 |
| ATOM | 1789 | CB | PRO | A | 596 | 39.883 | 0.132 | 24.595 | 1.00 | 29.35 |
| ATOM | 1790 | CG | PRO | A | 596 | 38.723 | 0.471 | 23.707 | 1.00 | 30.33 |
| ATOM | 1791 | C | PRO | A | 596 | 39.994 | −1.308 | 26.670 | 1.00 | 28.01 |
| ATOM | 1792 | O | PRO | A | 596 | 39.380 | −0.863 | 27.636 | 1.00 | 28.24 |
| ATOM | 1793 | N | PHE | A | 597 | 41.157 | −1.935 | 26.788 | 1.00 | 27.78 |
| ATOM | 1794 | CA | PHE | A | 597 | 41.792 | −2.106 | 28.088 | 1.00 | 26.60 |
| ATOM | 1795 | CB | PHE | A | 597 | 42.682 | −3.351 | 28.086 | 1.00 | 27.31 |
| ATOM | 1796 | CG | PHE | A | 597 | 43.592 | −3.446 | 29.280 | 1.00 | 30.04 |
| ATOM | 1797 | CD1 | PHE | A | 597 | 43.094 | −3.809 | 30.525 | 1.00 | 29.77 |
| ATOM | 1798 | CD2 | PHE | A | 597 | 44.953 | −3.160 | 29.159 | 1.00 | 29.89 |
| ATOM | 1799 | CE1 | PHE | A | 597 | 43.935 | −3.887 | 31.636 | 1.00 | 30.89 |
| ATOM | 1800 | CE2 | PHE | A | 597 | 45.801 | −3.235 | 30.265 | 1.00 | 31.09 |
| ATOM | 1801 | CZ | PHE | A | 597 | 45.291 | −3.599 | 31.503 | 1.00 | 30.00 |
| ATOM | 1802 | C | PHE | A | 597 | 42.652 | −0.886 | 28.392 | 1.00 | 25.52 |
| ATOM | 1803 | O | PHE | A | 597 | 43.442 | −0.455 | 27.554 | 1.00 | 25.53 |
| ATOM | 1804 | N | TYR | A | 598 | 42.494 | −0.327 | 29.585 | 1.00 | 24.22 |
| ATOM | 1805 | CA | TYR | A | 598 | 43.291 | 0.817 | 29.991 | 1.00 | 23.67 |
| ATOM | 1806 | CB | TYR | A | 598 | 42.394 | 1.995 | 30.378 | 1.00 | 22.81 |
| ATOM | 1807 | CG | TYR | A | 598 | 41.446 | 2.445 | 29.287 | 1.00 | 22.42 |
| ATOM | 1808 | CD1 | TYR | A | 598 | 40.103 | 2.078 | 29.312 | 1.00 | 22.51 |
| ATOM | 1809 | CE1 | TYR | A | 598 | 39.216 | 2.507 | 28.322 | 1.00 | 23.12 |
| ATOM | 1810 | CD2 | TYR | A | 598 | 41.889 | 3.254 | 28.236 | 1.00 | 22.09 |
| ATOM | 1811 | CE2 | TYR | A | 598 | 41.011 | 3.690 | 27.237 | 1.00 | 22.62 |
| ATOM | 1812 | CZ | TYR | A | 598 | 39.675 | 3.312 | 27.290 | 1.00 | 22.97 |
| ATOM | 1813 | OH | TYR | A | 598 | 38.797 | 3.745 | 26.328 | 1.00 | 22.74 |
| ATOM | 1814 | C | TYR | A | 598 | 44.157 | 0.412 | 31.189 | 1.00 | 24.15 |
| ATOM | 1815 | O | TYR | A | 598 | 43.636 | 0.028 | 32.234 | 1.00 | 23.99 |
| ATOM | 1816 | N | PRO | A | 599 | 45.491 | 0.474 | 31.040 | 1.00 | 23.70 |
| ATOM | 1817 | CD | PRO | A | 599 | 46.192 | 0.727 | 29.769 | 1.00 | 23.44 |
| ATOM | 1818 | CA | PRO | A | 599 | 46.445 | 0.122 | 32.102 | 1.00 | 24.35 |
| ATOM | 1819 | CB | PRO | A | 599 | 47.805 | 0.292 | 31.426 | 1.00 | 23.90 |
| ATOM | 1820 | CG | PRO | A | 599 | 47.504 | 0.014 | 29.983 | 1.00 | 25.50 |
| ATOM | 1821 | C | PRO | A | 599 | 46.311 | 1.039 | 33.315 | 1.00 | 24.95 |
| ATOM | 1822 | O | PRO | A | 599 | 45.901 | 2.195 | 33.187 | 1.00 | 24.15 |
| ATOM | 1823 | N | ARG | A | 600 | 46.672 | 0.527 | 34.490 | 1.00 | 26.05 |
| ATOM | 1824 | CA | ARG | A | 600 | 46.588 | 1.318 | 35.713 | 1.00 | 25.85 |
| ATOM | 1825 | CB | ARG | A | 600 | 46.892 | 0.455 | 36.942 | 1.00 | 29.45 |
| ATOM | 1826 | CG | ARG | A | 600 | 45.769 | −0.484 | 37.347 | 1.00 | 34.03 |
| ATOM | 1827 | CD | ARG | A | 600 | 45.998 | −1.898 | 36.832 | 1.00 | 39.90 |
| ATOM | 1828 | NE | ARG | A | 600 | 46.299 | −2.836 | 37.917 | 1.00 | 44.39 |
| ATOM | 1829 | CZ | ARG | A | 600 | 46.470 | −4.146 | 37.751 | 1.00 | 46.14 |
| ATOM | 1830 | NH1 | ARG | A | 600 | 46.372 | −4.682 | 36.538 | 1.00 | 45.41 |
| ATOM | 1831 | NH2 | ARG | A | 600 | 46.743 | −4.923 | 38.797 | 1.00 | 46.69 |
| ATOM | 1832 | C | ARG | A | 600 | 47.513 | 2.529 | 35.708 | 1.00 | 23.47 |
| ATOM | 1833 | O | ARG | A | 600 | 47.302 | 3.470 | 36.463 | 1.00 | 23.50 |
| ATOM | 1834 | N | TRP | A | 601 | 48.537 | 2.512 | 34.862 | 1.00 | 21.86 |
| ATOM | 1835 | CA | TRP | A | 601 | 49.460 | 3.638 | 34.809 | 1.00 | 22.35 |
| ATOM | 1836 | CB | TRP | A | 601 | 50.870 | 3.169 | 34.445 | 1.00 | 20.25 |
| ATOM | 1837 | CG | TRP | A | 601 | 50.933 | 2.223 | 33.283 | 1.00 | 22.07 |
| ATOM | 1838 | CD2 | TRP | A | 601 | 50.945 | 2.569 | 31.890 | 1.00 | 20.12 |
| ATOM | 1839 | CE2 | TRP | A | 601 | 51.049 | 1.362 | 31.159 | 1.00 | 20.17 |
| ATOM | 1840 | CE3 | TRP | A | 601 | 50.880 | 3.782 | 31.189 | 1.00 | 20.56 |
| ATOM | 1841 | CD1 | TRP | A | 601 | 51.019 | 0.857 | 33.339 | 1.00 | 21.89 |
| ATOM | 1842 | NE1 | TRP | A | 601 | 51.091 | 0.335 | 32.065 | 1.00 | 21.32 |
| ATOM | 1843 | CZ2 | TRP | A | 601 | 51.091 | 1.333 | 29.758 | 1.00 | 20.08 |
| ATOM | 1844 | CZ3 | TRP | A | 601 | 50.922 | 3.754 | 29.788 | 1.00 | 19.61 |
| ATOM | 1845 | CH2 | TRP | A | 601 | 51.027 | 2.535 | 29.093 | 1.00 | 17.82 |
| ATOM | 1846 | C | TRP | A | 601 | 49.035 | 4.739 | 33.846 | 1.00 | 23.13 |
| ATOM | 1847 | O | TRP | A | 601 | 49.686 | 5.778 | 33.770 | 1.00 | 24.05 |
| ATOM | 1848 | N | LEU | A | 602 | 47.956 | 4.516 | 33.102 | 1.00 | 22.98 |
| ATOM | 1849 | CA | LEU | A | 602 | 47.487 | 5.526 | 32.162 | 1.00 | 22.13 |
| ATOM | 1850 | CB | LEU | A | 602 | 46.467 | 4.934 | 31.188 | 1.00 | 22.04 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1851 | CG | LEU | A | 602 | 45.941 | 5.879 | 30.097 | 1.00 | 21.71 |
| ATOM | 1852 | CD1 | LEU | A | 602 | 47.102 | 6.406 | 29.268 | 1.00 | 20.07 |
| ATOM | 1853 | CD2 | LEU | A | 602 | 44.955 | 5.138 | 29.201 | 1.00 | 20.91 |
| ATOM | 1854 | C | LEU | A | 602 | 46.850 | 6.671 | 32.931 | 1.00 | 21.89 |
| ATOM | 1855 | O | LEU | A | 602 | 45.929 | 6.464 | 33.716 | 1.00 | 21.33 |
| ATOM | 1856 | N | GLU | A | 603 | 47.350 | 7.879 | 32.704 | 1.00 | 22.45 |
| ATOM | 1857 | CA | GLU | A | 603 | 46.832 | 9.062 | 33.378 | 1.00 | 25.25 |
| ATOM | 1858 | CB | GLU | A | 603 | 47.572 | 10.302 | 32.870 | 1.00 | 27.46 |
| ATOM | 1859 | CG | GLU | A | 603 | 47.469 | 11.519 | 33.775 | 1.00 | 32.35 |
| ATOM | 1860 | CD | GLU | A | 603 | 48.100 | 11.301 | 35.152 | 1.00 | 34.52 |
| ATOM | 1861 | OE1 | GLU | A | 603 | 49.335 | 11.121 | 35.240 | 1.00 | 34.96 |
| ATOM | 1862 | OE2 | GLU | A | 603 | 47.352 | 11.309 | 36.151 | 1.00 | 37.44 |
| ATOM | 1863 | C | GLU | A | 603 | 45.318 | 9.215 | 33.168 | 1.00 | 25.68 |
| ATOM | 1864 | O | GLU | A | 603 | 44.787 | 8.914 | 32.092 | 1.00 | 23.45 |
| ATOM | 1865 | N | LYS | A | 604 | 44.636 | 9.684 | 34.207 | 1.00 | 26.33 |
| ATOM | 1866 | CA | LYS | A | 604 | 43.192 | 9.870 | 34.178 | 1.00 | 28.53 |
| ATOM | 1867 | CB | LYS | A | 604 | 42.709 | 10.438 | 35.515 | 1.00 | 30.83 |
| ATOM | 1868 | CG | LYS | A | 604 | 41.958 | 9.436 | 36.370 | 1.00 | 34.84 |
| ATOM | 1869 | CD | LYS | A | 604 | 42.820 | 8.216 | 36.660 | 1.00 | 38.17 |
| ATOM | 1870 | CE | LYS | A | 604 | 42.058 | 7.169 | 37.450 | 1.00 | 39.22 |
| ATOM | 1871 | NZ | LYS | A | 604 | 42.011 | 5.874 | 36.709 | 1.00 | 42.12 |
| ATOM | 1872 | C | LYS | A | 604 | 42.645 | 10.742 | 33.055 | 1.00 | 27.71 |
| ATOM | 1873 | O | LYS | A | 604 | 41.671 | 10.373 | 32.405 | 1.00 | 27.04 |
| ATOM | 1874 | N | GLU | A | 605 | 43.246 | 11.902 | 32.817 | 1.00 | 27.80 |
| ATOM | 1875 | CA | GLU | A | 605 | 42.713 | 12.752 | 31.766 | 1.00 | 28.43 |
| ATOM | 1876 | CB | GLU | A | 605 | 43.309 | 14.174 | 31.858 | 1.00 | 31.54 |
| ATOM | 1877 | CG | GLU | A | 605 | 43.354 | 14.810 | 33.294 | 1.00 | 38.39 |
| ATOM | 1878 | CD | GLU | A | 605 | 41.989 | 14.959 | 34.018 | 1.00 | 43.04 |
| ATOM | 1879 | OE1 | GLU | A | 605 | 40.929 | 14.566 | 33.460 | 1.00 | 45.70 |
| ATOM | 1880 | OE2 | GLU | A | 605 | 41.989 | 15.476 | 35.168 | 1.00 | 45.62 |
| ATOM | 1881 | C | GLU | A | 605 | 42.937 | 12.113 | 30.372 | 1.00 | 26.18 |
| ATOM | 1882 | O | GLU | A | 605 | 42.181 | 12.412 | 29.427 | 1.00 | 24.76 |
| ATOM | 1883 | N | ALA | A | 606 | 43.935 | 11.239 | 30.229 | 1.00 | 23.82 |
| ATOM | 1884 | CA | ALA | A | 606 | 44.161 | 10.570 | 28.933 | 1.00 | 22.57 |
| ATOM | 1885 | CB | ALA | A | 606 | 45.578 | 9.939 | 28.874 | 1.00 | 21.71 |
| ATOM | 1886 | C | ALA | A | 606 | 43.106 | 9.484 | 28.740 | 1.00 | 22.43 |
| ATOM | 1887 | O | ALA | A | 606 | 42.544 | 9.350 | 27.655 | 1.00 | 20.21 |
| ATOM | 1888 | N | LYS | A | 607 | 42.824 | 8.734 | 29.807 | 1.00 | 21.01 |
| ATOM | 1889 | CA | LYS | A | 607 | 41.809 | 7.692 | 29.741 | 1.00 | 21.08 |
| ATOM | 1890 | CB | LYS | A | 607 | 41.675 | 6.964 | 31.083 | 1.00 | 21.77 |
| ATOM | 1891 | CG | LYS | A | 607 | 40.450 | 6.049 | 31.133 | 1.00 | 24.04 |
| ATOM | 1892 | CD | LYS | A | 607 | 40.400 | 5.159 | 32.366 | 1.00 | 26.01 |
| ATOM | 1893 | CE | LYS | A | 607 | 39.151 | 4.277 | 32.318 | 1.00 | 28.75 |
| ATOM | 1894 | NZ | LYS | A | 607 | 39.036 | 3.355 | 33.483 | 1.00 | 30.88 |
| ATOM | 1895 | C | LYS | A | 607 | 40.472 | 8.333 | 29.403 | 1.00 | 20.56 |
| ATOM | 1896 | O | LYS | A | 607 | 39.698 | 7.802 | 28.597 | 1.00 | 18.86 |
| ATOM | 1897 | N | ASP | A | 608 | 40.213 | 9.476 | 30.031 | 1.00 | 18.92 |
| ATOM | 1898 | CA | ASP | A | 608 | 38.963 | 10.190 | 29.822 | 1.00 | 19.51 |
| ATOM | 1899 | CB | ASP | A | 608 | 38.865 | 11.381 | 30.784 | 1.00 | 20.44 |
| ATOM | 1900 | CG | ASP | A | 608 | 37.577 | 12.168 | 30.611 | 1.00 | 23.54 |
| ATOM | 1901 | OD1 | ASP | A | 608 | 37.527 | 13.064 | 29.740 | 1.00 | 26.83 |
| ATOM | 1902 | OD2 | ASP | A | 608 | 36.603 | 11.884 | 31.341 | 1.00 | 24.81 |
| ATOM | 1903 | C | ASP | A | 608 | 38.803 | 10.664 | 28.381 | 1.00 | 18.24 |
| ATOM | 1904 | O | ASP | A | 608 | 37.700 | 10.629 | 27.831 | 1.00 | 17.10 |
| ATOM | 1905 | N | LEU | A | 609 | 39.893 | 11.114 | 27.771 | 1.00 | 16.92 |
| ATOM | 1906 | CA | LEU | A | 609 | 39.828 | 11.581 | 26.392 | 1.00 | 17.82 |
| ATOM | 1907 | CB | LEU | A | 609 | 41.163 | 12.192 | 25.963 | 1.00 | 17.75 |
| ATOM | 1908 | CG | LEU | A | 609 | 41.279 | 12.576 | 24.481 | 1.00 | 18.80 |
| ATOM | 1909 | CD1 | LEU | A | 609 | 40.140 | 13.512 | 24.080 | 1.00 | 16.89 |
| ATOM | 1910 | CD2 | LEU | A | 609 | 42.633 | 13.233 | 24.240 | 1.00 | 17.44 |
| ATOM | 1911 | C | LEU | A | 609 | 39.483 | 10.402 | 25.490 | 1.00 | 17.65 |
| ATOM | 1912 | O | LEU | A | 609 | 38.585 | 10.491 | 24.650 | 1.00 | 16.34 |
| ATOM | 1913 | N | LEU | A | 610 | 40.190 | 9.291 | 25.684 | 1.00 | 17.49 |
| ATOM | 1914 | CA | LEU | A | 610 | 39.964 | 8.088 | 24.887 | 1.00 | 17.58 |
| ATOM | 1915 | CB | LEU | A | 610 | 40.971 | 7.000 | 25.282 | 1.00 | 16.75 |
| ATOM | 1916 | CG | LEU | A | 610 | 42.401 | 7.321 | 24.844 | 1.00 | 18.71 |
| ATOM | 1917 | CD1 | LEU | A | 610 | 43.379 | 6.313 | 25.414 | 1.00 | 19.41 |
| ATOM | 1918 | CD2 | LEU | A | 610 | 42.458 | 7.333 | 23.315 | 1.00 | 16.53 |
| ATOM | 1919 | C | LEU | A | 610 | 38.538 | 7.557 | 25.018 | 1.00 | 17.89 |
| ATOM | 1920 | O | LEU | A | 610 | 37.920 | 7.158 | 24.024 | 1.00 | 18.16 |
| ATOM | 1921 | N | VAL | A | 611 | 38.015 | 7.561 | 26.241 | 1.00 | 18.35 |
| ATOM | 1922 | CA | VAL | A | 611 | 36.663 | 7.078 | 26.503 | 1.00 | 18.91 |
| ATOM | 1923 | CB | VAL | A | 611 | 36.338 | 7.109 | 28.022 | 1.00 | 19.47 |
| ATOM | 1924 | CG1 | VAL | A | 611 | 34.865 | 6.801 | 28.255 | 1.00 | 20.48 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1925 | CG2 | VAL | A | 611 | 37.193 | 6.089 | 28.762 | 1.00 | 18.53 |
| ATOM | 1926 | C | VAL | A | 611 | 35.648 | 7.937 | 25.751 | 1.00 | 19.87 |
| ATOM | 1927 | O | VAL | A | 611 | 34.666 | 7.428 | 25.195 | 1.00 | 20.48 |
| ATOM | 1928 | N | LYS | A | 612 | 35.887 | 9.242 | 25.725 | 1.00 | 20.16 |
| ATOM | 1929 | CA | LYS | A | 612 | 34.991 | 10.153 | 25.024 | 1.00 | 20.51 |
| ATOM | 1930 | CB | LYS | A | 612 | 35.268 | 11.599 | 25.439 | 1.00 | 22.37 |
| ATOM | 1931 | CG | LYS | A | 612 | 34.768 | 11.960 | 26.831 | 1.00 | 23.80 |
| ATOM | 1932 | CD | LYS | A | 612 | 35.319 | 13.315 | 27.235 | 1.00 | 25.64 |
| ATOM | 1933 | CE | LYS | A | 612 | 34.726 | 13.822 | 28.552 | 1.00 | 27.36 |
| ATOM | 1934 | NZ | LYS | A | 612 | 34.451 | 12.718 | 29.518 | 1.00 | 29.33 |
| ATOM | 1935 | C | LYS | A | 612 | 35.143 | 10.017 | 23.506 | 1.00 | 19.09 |
| ATOM | 1936 | O | LYS | A | 612 | 34.246 | 10.373 | 22.751 | 1.00 | 18.65 |
| ATOM | 1937 | N | LEU | A | 613 | 36.287 | 9.517 | 23.060 | 1.00 | 18.34 |
| ATOM | 1938 | CA | LEU | A | 613 | 36.505 | 9.332 | 21.635 | 1.00 | 18.28 |
| ATOM | 1939 | CB | LEU | A | 613 | 37.996 | 9.380 | 21.303 | 1.00 | 16.91 |
| ATOM | 1940 | CG | LEU | A | 613 | 38.628 | 10.773 | 21.333 | 1.00 | 18.21 |
| ATOM | 1941 | CD1 | LEU | A | 613 | 40.147 | 10.653 | 21.287 | 1.00 | 17.29 |
| ATOM | 1942 | CD2 | LEU | A | 613 | 38.089 | 11.593 | 20.155 | 1.00 | 16.95 |
| ATOM | 1943 | C | LEU | A | 613 | 35.929 | 7.996 | 21.189 | 1.00 | 19.04 |
| ATOM | 1944 | O | LEU | A | 613 | 35.481 | 7.863 | 20.052 | 1.00 | 18.79 |
| ATOM | 1945 | N | PHE | A | 614 | 35.931 | 7.009 | 22.083 | 1.00 | 18.64 |
| ATOM | 1946 | CA | PHE | A | 614 | 35.421 | 5.686 | 21.727 | 1.00 | 20.32 |
| ATOM | 1947 | CB | PHE | A | 614 | 36.187 | 4.588 | 22.478 | 1.00 | 18.01 |
| ATOM | 1948 | CG | PHE | A | 614 | 37.619 | 4.431 | 22.029 | 1.00 | 18.67 |
| ATOM | 1949 | CD1 | PHE | A | 614 | 37.937 | 4.415 | 20.671 | 1.00 | 15.87 |
| ATOM | 1950 | CD2 | PHE | A | 614 | 38.648 | 4.286 | 22.962 | 1.00 | 18.49 |
| ATOM | 1951 | CE1 | PHE | A | 614 | 39.253 | 4.255 | 20.246 | 1.00 | 15.71 |
| ATOM | 1952 | CE2 | PHE | A | 614 | 39.976 | 4.123 | 22.549 | 1.00 | 17.66 |
| ATOM | 1953 | CZ | PHE | A | 614 | 40.279 | 4.107 | 21.189 | 1.00 | 15.59 |
| ATOM | 1954 | C | PHE | A | 614 | 33.921 | 5.498 | 21.927 | 1.00 | 21.76 |
| ATOM | 1955 | O | PHE | A | 614 | 33.443 | 4.384 | 22.132 | 1.00 | 23.60 |
| ATOM | 1956 | N | VAL | A | 615 | 33.177 | 6.591 | 21.870 | 1.00 | 23.03 |
| ATOM | 1957 | CA | VAL | A | 615 | 31.732 | 6.517 | 21.998 | 1.00 | 24.19 |
| ATOM | 1958 | CB | VAL | A | 615 | 31.138 | 7.908 | 22.325 | 1.00 | 23.89 |
| ATOM | 1959 | CG1 | VAL | A | 615 | 29.638 | 7.920 | 22.070 | 1.00 | 23.25 |
| ATOM | 1960 | CG2 | VAL | A | 615 | 31.424 | 8.253 | 23.789 | 1.00 | 25.32 |
| ATOM | 1961 | C | VAL | A | 615 | 31.220 | 6.017 | 20.643 | 1.00 | 24.80 |
| ATOM | 1962 | O | VAL | A | 615 | 31.557 | 6.582 | 19.602 | 1.00 | 23.38 |
| ATOM | 1963 | N | ARG | A | 616 | 30.436 | 4.942 | 20.666 | 1.00 | 26.89 |
| ATOM | 1964 | CA | ARG | A | 616 | 29.880 | 4.344 | 19.449 | 1.00 | 29.04 |
| ATOM | 1965 | CB | ARG | A | 616 | 29.056 | 3.103 | 19.793 | 1.00 | 31.64 |
| ATOM | 1966 | CG | ARG | A | 616 | 29.785 | 1.778 | 19.607 | 1.00 | 34.39 |
| ATOM | 1967 | CD | ARG | A | 616 | 30.963 | 1.656 | 20.540 | 1.00 | 36.74 |
| ATOM | 1968 | NE | ARG | A | 616 | 31.607 | 0.346 | 20.450 | 1.00 | 39.00 |
| ATOM | 1969 | CZ | ARG | A | 616 | 32.574 | −0.060 | 21.272 | 1.00 | 39.50 |
| ATOM | 1970 | NH1 | ARG | A | 616 | 33.001 | 0.742 | 22.241 | 1.00 | 40.12 |
| ATOM | 1971 | NH2 | ARG | A | 616 | 33.123 | −1.258 | 21.124 | 1.00 | 39.14 |
| ATOM | 1972 | C | ARG | A | 616 | 29.012 | 5.304 | 18.642 | 1.00 | 28.72 |
| ATOM | 1973 | O | ARG | A | 616 | 29.221 | 5.472 | 17.443 | 1.00 | 30.06 |
| ATOM | 1974 | N | GLU | A | 617 | 28.024 | 5.910 | 19.294 | 1.00 | 28.29 |
| ATOM | 1975 | CA | GLU | A | 617 | 27.141 | 6.860 | 18.628 | 1.00 | 27.91 |
| ATOM | 1976 | CB | GLU | A | 617 | 26.036 | 7.314 | 19.586 | 1.00 | 29.77 |
| ATOM | 1977 | CG | GLU | A | 617 | 25.340 | 8.598 | 19.163 | 1.00 | 34.82 |
| ATOM | 1978 | CD | GLU | A | 617 | 24.729 | 8.501 | 17.776 | 1.00 | 38.01 |
| ATOM | 1979 | OE1 | GLU | A | 617 | 24.977 | 9.408 | 16.944 | 1.00 | 38.60 |
| ATOM | 1980 | OE2 | GLU | A | 617 | 23.999 | 7.518 | 17.520 | 1.00 | 39.63 |
| ATOM | 1981 | C | GLU | A | 617 | 27.973 | 8.058 | 18.177 | 1.00 | 25.97 |
| ATOM | 1982 | O | GLU | A | 617 | 28.435 | 8.848 | 18.994 | 1.00 | 24.63 |
| ATOM | 1983 | N | PRO | A | 618 | 28.178 | 8.204 | 16.858 | 1.00 | 25.94 |
| ATOM | 1984 | CD | PRO | A | 618 | 27.663 | 7.357 | 15.769 | 1.00 | 24.89 |
| ATOM | 1985 | CA | PRO | A | 618 | 28.970 | 9.317 | 16.324 | 1.00 | 25.61 |
| ATOM | 1986 | CB | PRO | A | 618 | 28.913 | 9.089 | 14.810 | 1.00 | 24.66 |
| ATOM | 1987 | CG | PRO | A | 618 | 27.646 | 8.316 | 14.614 | 1.00 | 24.37 |
| ATOM | 1988 | C | PRO | A | 618 | 28.534 | 10.728 | 16.726 | 1.00 | 26.29 |
| ATOM | 1989 | O | PRO | A | 618 | 29.377 | 11.608 | 16.895 | 1.00 | 25.62 |
| ATOM | 1990 | N | GLU | A | 619 | 27.235 | 10.948 | 16.893 | 1.00 | 26.10 |
| ATOM | 1991 | CA | GLU | A | 619 | 26.761 | 12.276 | 17.259 | 1.00 | 26.97 |
| ATOM | 1992 | CB | GLU | A | 619 | 25.254 | 12.401 | 16.990 | 1.00 | 29.74 |
| ATOM | 1993 | CG | GLU | A | 619 | 24.859 | 11.991 | 15.572 | 1.00 | 35.15 |
| ATOM | 1994 | CD | GLU | A | 619 | 23.476 | 12.472 | 15.170 | 1.00 | 39.06 |
| ATOM | 1995 | OE1 | GLU | A | 619 | 22.501 | 12.210 | 15.915 | 1.00 | 40.39 |
| ATOM | 1996 | OE2 | GLU | A | 619 | 23.365 | 13.109 | 14.097 | 1.00 | 40.52 |
| ATOM | 1997 | C | GLU | A | 619 | 27.075 | 12.652 | 18.704 | 1.00 | 25.65 |
| ATOM | 1998 | O | GLU | A | 619 | 26.899 | 13.798 | 19.097 | 1.00 | 25.78 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 1999 | N | LYS | A | 620 | 27.542 | 11.696 | 19.498 | 1.00 | 24.88 |
| ATOM | 2000 | CA | LYS | A | 620 | 27.881 | 11.980 | 20.895 | 1.00 | 24.66 |
| ATOM | 2001 | CB | LYS | A | 620 | 27.165 | 11.007 | 21.835 | 1.00 | 25.75 |
| ATOM | 2002 | CG | LYS | A | 620 | 25.642 | 11.143 | 21.881 | 1.00 | 29.43 |
| ATOM | 2003 | CD | LYS | A | 620 | 25.042 | 10.075 | 22.802 | 1.00 | 32.34 |
| ATOM | 2004 | CE | LYS | A | 620 | 23.525 | 10.167 | 22.864 | 1.00 | 36.50 |
| ATOM | 2005 | NZ | LYS | A | 620 | 22.929 | 9.083 | 23.703 | 1.00 | 39.45 |
| ATOM | 2006 | C | LYS | A | 620 | 29.388 | 11.867 | 21.123 | 1.00 | 22.83 |
| ATOM | 2007 | O | LYS | A | 620 | 29.856 | 11.904 | 22.259 | 1.00 | 21.86 |
| ATOM | 2008 | N | ARG | A | 621 | 30.138 | 11.723 | 20.034 | 1.00 | 21.02 |
| ATOM | 2009 | CA | ARG | A | 621 | 31.584 | 11.570 | 20.105 | 1.00 | 18.14 |
| ATOM | 2010 | CB | ARG | A | 621 | 32.073 | 10.749 | 18.911 | 1.00 | 16.86 |
| ATOM | 2011 | CG | ARG | A | 621 | 33.562 | 10.398 | 18.932 | 1.00 | 17.14 |
| ATOM | 2012 | CD | ARG | A | 621 | 33.927 | 9.530 | 17.723 | 1.00 | 16.79 |
| ATOM | 2013 | NE | ARG | A | 621 | 33.102 | 8.324 | 17.686 | 1.00 | 16.88 |
| ATOM | 2014 | CZ | ARG | A | 621 | 32.660 | 7.748 | 16.569 | 1.00 | 16.19 |
| ATOM | 2015 | NH1 | ARG | A | 621 | 32.972 | 8.259 | 15.379 | 1.00 | 14.37 |
| ATOM | 2016 | NH2 | ARG | A | 621 | 31.870 | 6.685 | 16.644 | 1.00 | 12.08 |
| ATOM | 2017 | C | ARG | A | 621 | 32.317 | 12.903 | 20.139 | 1.00 | 18.18 |
| ATOM | 2018 | O | ARG | A | 621 | 32.048 | 13.792 | 19.326 | 1.00 | 17.33 |
| ATOM | 2019 | N | LEU | A | 622 | 33.243 | 13.036 | 21.087 | 1.00 | 17.53 |
| ATOM | 2020 | CA | LEU | A | 622 | 34.033 | 14.254 | 21.209 | 1.00 | 18.54 |
| ATOM | 2021 | CB | LEU | A | 622 | 35.085 | 14.099 | 22.321 | 1.00 | 19.59 |
| ATOM | 2022 | CG | LEU | A | 622 | 35.931 | 15.323 | 22.711 | 1.00 | 20.18 |
| ATOM | 2023 | CD1 | LEU | A | 622 | 35.034 | 16.518 | 23.061 | 1.00 | 20.18 |
| ATOM | 2024 | CD2 | LEU | A | 622 | 36.807 | 14.962 | 23.903 | 1.00 | 20.55 |
| ATOM | 2025 | C | LEU | A | 622 | 34.694 | 14.443 | 19.847 | 1.00 | 17.81 |
| ATOM | 2026 | O | LEU | A | 622 | 35.144 | 13.478 | 19.228 | 1.00 | 17.38 |
| ATOM | 2027 | N | GLY | A | 623 | 34.743 | 15.680 | 19.377 | 1.00 | 17.75 |
| ATOM | 2028 | CA | GLY | A | 623 | 35.309 | 15.948 | 18.066 | 1.00 | 18.80 |
| ATOM | 2029 | C | GLY | A | 623 | 34.144 | 16.258 | 17.139 | 1.00 | 20.02 |
| ATOM | 2030 | O | GLY | A | 623 | 34.220 | 17.140 | 16.286 | 1.00 | 20.81 |
| ATOM | 2031 | N | VAL | A | 624 | 33.058 | 15.512 | 17.309 | 1.00 | 21.39 |
| ATOM | 2032 | CA | VAL | A | 624 | 31.837 | 15.714 | 16.536 | 1.00 | 22.85 |
| ATOM | 2033 | CB | VAL | A | 624 | 31.053 | 14.392 | 16.373 | 1.00 | 22.84 |
| ATOM | 2034 | CG1 | VAL | A | 624 | 29.697 | 14.662 | 15.726 | 1.00 | 22.60 |
| ATOM | 2035 | CG2 | VAL | A | 624 | 31.866 | 13.402 | 15.545 | 1.00 | 21.63 |
| ATOM | 2036 | C | VAL | A | 624 | 31.014 | 16.673 | 17.391 | 1.00 | 25.48 |
| ATOM | 2037 | O | VAL | A | 624 | 30.473 | 17.668 | 16.911 | 1.00 | 27.26 |
| ATOM | 2038 | N | ARG | A | 625 | 30.947 | 16.348 | 18.677 | 1.00 | 27.42 |
| ATOM | 2039 | CA | ARG | A | 625 | 30.232 | 17.133 | 19.663 | 1.00 | 30.03 |
| ATOM | 2040 | CB | ARG | A | 625 | 29.289 | 16.241 | 20.467 | 1.00 | 33.23 |
| ATOM | 2041 | CG | ARG | A | 625 | 28.593 | 17.086 | 21.482 | 1.00 | 39.62 |
| ATOM | 2042 | CD | ARG | A | 625 | 27.798 | 16.404 | 22.568 | 1.00 | 43.58 |
| ATOM | 2043 | NE | ARG | A | 625 | 26.835 | 17.422 | 22.942 | 1.00 | 47.75 |
| ATOM | 2044 | CZ | ARG | A | 625 | 27.128 | 18.510 | 23.641 | 1.00 | 49.41 |
| ATOM | 2045 | NH1 | ARG | A | 625 | 28.356 | 18.723 | 24.085 | 1.00 | 50.35 |
| ATOM | 2046 | NH2 | ARG | A | 625 | 26.201 | 19.440 | 23.826 | 1.00 | 50.78 |
| ATOM | 2047 | C | ARG | A | 625 | 31.248 | 17.760 | 20.633 | 1.00 | 30.21 |
| ATOM | 2048 | O | ARG | A | 625 | 32.221 | 17.108 | 21.012 | 1.00 | 30.87 |
| ATOM | 2049 | N | GLY | A | 626 | 31.022 | 19.007 | 21.044 | 1.00 | 29.54 |
| ATOM | 2050 | CA | GLY | A | 626 | 31.937 | 19.653 | 21.972 | 1.00 | 27.47 |
| ATOM | 2051 | C | GLY | A | 626 | 33.178 | 20.236 | 21.319 | 1.00 | 26.92 |
| ATOM | 2052 | O | GLY | A | 626 | 33.237 | 20.367 | 20.094 | 1.00 | 26.89 |
| ATOM | 2053 | N | ASP | A | 627 | 34.172 | 20.580 | 22.135 | 1.00 | 25.86 |
| ATOM | 2054 | CA | ASP | A | 627 | 35.424 | 21.161 | 21.646 | 1.00 | 24.96 |
| ATOM | 2055 | CB | ASP | A | 627 | 35.552 | 22.605 | 22.138 | 1.00 | 26.17 |
| ATOM | 2056 | CG | ASP | A | 627 | 36.691 | 23.350 | 21.472 | 1.00 | 27.16 |
| ATOM | 2057 | OD1 | ASP | A | 627 | 37.589 | 22.693 | 20.902 | 1.00 | 28.82 |
| ATOM | 2058 | OD2 | ASP | A | 627 | 36.695 | 24.597 | 21.527 | 1.00 | 28.40 |
| ATOM | 2059 | C | ASP | A | 627 | 36.593 | 20.339 | 22.179 | 1.00 | 23.74 |
| ATOM | 2060 | O | ASP | A | 627 | 37.027 | 20.531 | 23.317 | 1.00 | 24.37 |
| ATOM | 2061 | N | ILE | A | 628 | 37.113 | 19.431 | 21.355 | 1.00 | 22.06 |
| ATOM | 2062 | CA | ILE | A | 628 | 38.211 | 18.570 | 21.773 | 1.00 | 19.76 |
| ATOM | 2063 | CB | ILE | A | 628 | 38.633 | 17.593 | 20.646 | 1.00 | 19.34 |
| ATOM | 2064 | CG2 | ILE | A | 628 | 39.300 | 18.358 | 19.500 | 1.00 | 16.53 |
| ATOM | 2065 | CG1 | ILE | A | 628 | 39.591 | 16.538 | 21.212 | 1.00 | 18.57 |
| ATOM | 2066 | CD1 | ILE | A | 628 | 39.876 | 15.380 | 20.255 | 1.00 | 20.57 |
| ATOM | 2067 | C | ILE | A | 628 | 39.442 | 19.335 | 22.247 | 1.00 | 20.24 |
| ATOM | 2068 | O | ILE | A | 628 | 40.214 | 18.821 | 23.056 | 1.00 | 19.32 |
| ATOM | 2069 | N | ARG | A | 629 | 39.623 | 20.558 | 21.754 | 1.00 | 20.13 |
| ATOM | 2070 | CA | ARG | A | 629 | 40.776 | 21.364 | 22.149 | 1.00 | 21.20 |
| ATOM | 2071 | CB | ARG | A | 629 | 40.873 | 22.625 | 21.302 | 1.00 | 23.00 |
| ATOM | 2072 | CG | ARG | A | 629 | 41.103 | 22.422 | 19.813 | 1.00 | 26.51 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 2073 | CD | ARG | A | 629 | 41.067 | 23.790 | 19.146 | 1.00 | 28.34 |
| ATOM | 2074 | NE | ARG | A | 629 | 40.993 | 23.709 | 17.695 | 1.00 | 32.08 |
| ATOM | 2075 | CZ | ARG | A | 629 | 40.515 | 24.679 | 16.924 | 1.00 | 31.10 |
| ATOM | 2076 | NH1 | ARG | A | 629 | 40.067 | 25.802 | 17.472 | 1.00 | 32.62 |
| ATOM | 2077 | NH2 | ARG | A | 629 | 40.475 | 24.520 | 15.609 | 1.00 | 31.06 |
| ATOM | 2078 | C | ARG | A | 629 | 40.715 | 21.780 | 23.615 | 1.00 | 21.03 |
| ATOM | 2079 | O | ARG | A | 629 | 41.749 | 22.024 | 24.235 | 1.00 | 20.90 |
| ATOM | 2080 | N | GLN | A | 630 | 39.500 | 21.876 | 24.153 | 1.00 | 21.32 |
| ATOM | 2081 | CA | GLN | A | 630 | 39.297 | 22.269 | 25.542 | 1.00 | 21.75 |
| ATOM | 2082 | CB | GLN | A | 630 | 37.947 | 22.995 | 25.695 | 1.00 | 24.51 |
| ATOM | 2083 | CG | GLN | A | 630 | 37.898 | 24.386 | 25.041 | 1.00 | 28.07 |
| ATOM | 2084 | CD | GLN | A | 630 | 36.482 | 24.948 | 24.936 | 1.00 | 32.22 |
| ATOM | 2085 | OE1 | GLN | A | 630 | 36.075 | 25.432 | 23.875 | 1.00 | 35.05 |
| ATOM | 2086 | NE2 | GLN | A | 630 | 35.728 | 24.892 | 26.033 | 1.00 | 34.16 |
| ATOM | 2087 | C | GLN | A | 630 | 39.364 | 21.092 | 26.518 | 1.00 | 21.79 |
| ATOM | 2088 | O | GLN | A | 630 | 39.085 | 21.256 | 27.708 | 1.00 | 20.81 |
| ATOM | 2089 | N | HIS | A | 631 | 39.732 | 19.905 | 26.038 | 1.00 | 20.56 |
| ATOM | 2090 | CA | HIS | A | 631 | 39.820 | 18.770 | 26.949 | 1.00 | 20.96 |
| ATOM | 2091 | CB | HIS | A | 631 | 39.964 | 17.443 | 26.186 | 1.00 | 20.32 |
| ATOM | 2092 | CG | HIS | A | 631 | 39.883 | 16.235 | 27.071 | 1.00 | 19.91 |
| ATOM | 2093 | CD2 | HIS | A | 631 | 38.844 | 15.419 | 27.373 | 1.00 | 19.57 |
| ATOM | 2094 | ND1 | HIS | A | 631 | 40.940 | 15.805 | 27.843 | 1.00 | 18.48 |
| ATOM | 2095 | CE1 | HIS | A | 631 | 40.557 | 14.781 | 28.585 | 1.00 | 18.06 |
| ATOM | 2096 | NE2 | HIS | A | 631 | 39.288 | 14.527 | 28.319 | 1.00 | 18.09 |
| ATOM | 2097 | C | HIS | A | 631 | 41.019 | 18.985 | 27.873 | 1.00 | 21.47 |
| ATOM | 2098 | O | HIS | A | 631 | 42.080 | 19.429 | 27.433 | 1.00 | 20.95 |
| ATOM | 2099 | N | PRO | A | 632 | 40.859 | 18.682 | 29.172 | 1.00 | 21.77 |
| ATOM | 2100 | CD | PRO | A | 632 | 39.638 | 18.111 | 29.774 | 1.00 | 22.35 |
| ATOM | 2101 | CA | PRO | A | 632 | 41.908 | 18.835 | 30.187 | 1.00 | 22.53 |
| ATOM | 2102 | CB | PRO | A | 632 | 41.333 | 18.083 | 31.387 | 1.00 | 22.88 |
| ATOM | 2103 | CG | PRO | A | 632 | 39.876 | 18.334 | 31.258 | 1.00 | 22.65 |
| ATOM | 2104 | C | PRO | A | 632 | 43.290 | 18.312 | 29.788 | 1.00 | 22.97 |
| ATOM | 2105 | O | PRO | A | 632 | 44.312 | 18.880 | 30.181 | 1.00 | 22.81 |
| ATOM | 2106 | N | LEU | A | 633 | 43.322 | 17.231 | 29.014 | 1.00 | 22.42 |
| ATOM | 2107 | CA | LEU | A | 633 | 44.591 | 16.654 | 28.580 | 1.00 | 22.24 |
| ATOM | 2108 | CB | LEU | A | 633 | 44.351 | 15.454 | 27.657 | 1.00 | 22.84 |
| ATOM | 2109 | CG | LEU | A | 633 | 45.628 | 14.711 | 27.245 | 1.00 | 24.28 |
| ATOM | 2110 | CD1 | LEU | A | 633 | 46.275 | 14.108 | 28.488 | 1.00 | 23.65 |
| ATOM | 2111 | CD2 | LEU | A | 633 | 45.308 | 13.618 | 26.233 | 1.00 | 24.13 |
| ATOM | 2112 | C | LEU | A | 633 | 45.464 | 17.665 | 27.846 | 1.00 | 22.12 |
| ATOM | 2113 | O | LEU | A | 633 | 46.691 | 17.586 | 27.898 | 1.00 | 21.96 |
| ATOM | 2114 | N | PHE | A | 634 | 44.828 | 18.612 | 27.164 | 1.00 | 21.41 |
| ATOM | 2115 | CA | PHE | A | 634 | 45.546 | 19.627 | 26.393 | 1.00 | 22.24 |
| ATOM | 2116 | CB | PHE | A | 634 | 44.846 | 19.827 | 25.040 | 1.00 | 19.99 |
| ATOM | 2117 | CG | PHE | A | 634 | 44.737 | 18.568 | 24.216 | 1.00 | 19.23 |
| ATOM | 2118 | CD1 | PHE | A | 634 | 45.879 | 17.954 | 23.711 | 1.00 | 17.11 |
| ATOM | 2119 | CD2 | PHE | A | 634 | 43.497 | 17.998 | 23.945 | 1.00 | 17.62 |
| ATOM | 2120 | CE1 | PHE | A | 634 | 45.794 | 16.788 | 22.944 | 1.00 | 17.67 |
| ATOM | 2121 | CE2 | PHE | A | 634 | 43.397 | 16.828 | 23.179 | 1.00 | 18.20 |
| ATOM | 2122 | CZ | PHE | A | 634 | 44.553 | 16.223 | 22.678 | 1.00 | 15.92 |
| ATOM | 2123 | C | PHE | A | 634 | 45.627 | 20.979 | 27.109 | 1.00 | 24.10 |
| ATOM | 2124 | O | PHE | A | 634 | 45.938 | 21.999 | 26.488 | 1.00 | 22.28 |
| ATOM | 2125 | N | ARG | A | 635 | 45.374 | 20.986 | 28.413 | 1.00 | 25.98 |
| ATOM | 2126 | CA | ARG | A | 635 | 45.362 | 22.238 | 29.156 | 1.00 | 29.34 |
| ATOM | 2127 | CB | ARG | A | 635 | 45.081 | 21.963 | 30.639 | 1.00 | 32.29 |
| ATOM | 2128 | CG | ARG | A | 635 | 46.271 | 21.515 | 31.461 | 1.00 | 37.47 |
| ATOM | 2129 | CD | ARG | A | 635 | 45.774 | 21.019 | 32.786 | 1.00 | 42.18 |
| ATOM | 2130 | NE | ARG | A | 635 | 45.403 | 19.616 | 32.675 | 1.00 | 47.46 |
| ATOM | 2131 | CZ | ARG | A | 635 | 45.616 | 18.713 | 33.627 | 1.00 | 49.68 |
| ATOM | 2132 | NH1 | ARG | A | 635 | 46.208 | 19.074 | 34.752 | 1.00 | 51.44 |
| ATOM | 2133 | NH2 | ARG | A | 635 | 45.200 | 17.449 | 33.486 | 1.00 | 51.05 |
| ATOM | 2134 | C | ARG | A | 635 | 46.574 | 23.154 | 28.996 | 1.00 | 29.35 |
| ATOM | 2135 | O | ARG | A | 635 | 46.422 | 24.370 | 28.968 | 1.00 | 29.93 |
| ATOM | 2136 | N | GLU | A | 636 | 47.767 | 22.590 | 28.872 | 1.00 | 29.88 |
| ATOM | 2137 | CA | GLU | A | 636 | 48.954 | 23.416 | 28.720 | 1.00 | 31.27 |
| ATOM | 2138 | CB | GLU | A | 636 | 50.173 | 22.690 | 29.285 | 1.00 | 34.01 |
| ATOM | 2139 | CG | GLU | A | 636 | 50.127 | 22.511 | 30.785 | 1.00 | 38.90 |
| ATOM | 2140 | CD | GLU | A | 636 | 51.453 | 22.058 | 31.342 | 1.00 | 43.00 |
| ATOM | 2141 | OE1 | GLU | A | 636 | 51.890 | 20.938 | 31.001 | 1.00 | 45.28 |
| ATOM | 2142 | OE2 | GLU | A | 636 | 52.067 | 22.824 | 32.117 | 1.00 | 44.88 |
| ATOM | 2143 | C | GLU | A | 636 | 49.256 | 23.859 | 27.289 | 1.00 | 30.50 |
| ATOM | 2144 | O | GLU | A | 636 | 50.222 | 24.581 | 27.051 | 1.00 | 30.25 |
| ATOM | 2145 | N | ILE | A | 637 | 48.434 | 23.446 | 26.333 | 1.00 | 28.70 |
| ATOM | 2146 | CA | ILE | A | 637 | 48.689 | 23.828 | 24.954 | 1.00 | 26.92 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 2147 | CB | ILE | A | 637 | 48.282 | 22.695 | 23.977 | 1.00 | 27.47 |
| ATOM | 2148 | CG2 | ILE | A | 637 | 48.187 | 23.232 | 22.550 | 1.00 | 26.79 |
| ATOM | 2149 | CG1 | ILE | A | 637 | 49.301 | 21.553 | 24.075 | 1.00 | 28.20 |
| ATOM | 2150 | CD1 | ILE | A | 637 | 49.044 | 20.425 | 23.133 | 1.00 | 30.14 |
| ATOM | 2151 | C | ILE | A | 637 | 48.031 | 25.119 | 24.482 | 1.00 | 25.43 |
| ATOM | 2152 | O | ILE | A | 637 | 46.837 | 25.338 | 24.670 | 1.00 | 24.21 |
| ATOM | 2153 | N | ASN | A | 638 | 48.838 | 25.981 | 23.876 | 1.00 | 24.21 |
| ATOM | 2154 | CA | ASN | A | 638 | 48.337 | 27.217 | 23.301 | 1.00 | 23.39 |
| ATOM | 2155 | CB | ASN | A | 638 | 49.351 | 28.352 | 23.455 | 1.00 | 24.07 |
| ATOM | 2156 | CG | ASN | A | 638 | 48.853 | 29.653 | 22.853 | 1.00 | 26.79 |
| ATOM | 2157 | OD1 | ASN | A | 638 | 48.461 | 29.698 | 21.684 | 1.00 | 25.82 |
| ATOM | 2158 | ND2 | ASN | A | 638 | 48.861 | 30.719 | 23.647 | 1.00 | 27.55 |
| ATOM | 2159 | C | ASN | A | 638 | 48.215 | 26.811 | 21.829 | 1.00 | 21.26 |
| ATOM | 2160 | O | ASN | A | 638 | 49.211 | 26.754 | 21.108 | 1.00 | 20.39 |
| ATOM | 2161 | N | TRP | A | 639 | 46.996 | 26.509 | 21.398 | 1.00 | 21.08 |
| ATOM | 2162 | CA | TRP | A | 639 | 46.752 | 26.050 | 20.031 | 1.00 | 21.27 |
| ATOM | 2163 | CB | TRP | A | 639 | 45.269 | 25.727 | 19.848 | 1.00 | 19.17 |
| ATOM | 2164 | CG | TRP | A | 639 | 44.831 | 24.646 | 20.779 | 1.00 | 19.03 |
| ATOM | 2165 | CD2 | TRP | A | 639 | 44.866 | 23.236 | 20.530 | 1.00 | 17.97 |
| ATOM | 2166 | CE2 | TRP | A | 639 | 44.434 | 22.594 | 21.709 | 1.00 | 17.66 |
| ATOM | 2167 | CE3 | TRP | A | 639 | 45.223 | 22.452 | 19.423 | 1.00 | 16.87 |
| ATOM | 2168 | CD1 | TRP | A | 639 | 44.391 | 24.797 | 22.058 | 1.00 | 18.23 |
| ATOM | 2169 | NE1 | TRP | A | 639 | 44.150 | 23.572 | 22.626 | 1.00 | 18.28 |
| ATOM | 2170 | CZ2 | TRP | A | 639 | 44.345 | 21.202 | 21.818 | 1.00 | 17.89 |
| ATOM | 2171 | CZ3 | TRP | A | 639 | 45.135 | 21.065 | 19.528 | 1.00 | 15.97 |
| ATOM | 2172 | CH2 | TRP | A | 639 | 44.698 | 20.454 | 20.720 | 1.00 | 18.31 |
| ATOM | 2173 | C | TRP | A | 639 | 47.228 | 26.958 | 18.916 | 1.00 | 21.59 |
| ATOM | 2174 | O | TRP | A | 639 | 47.739 | 26.483 | 17.898 | 1.00 | 22.22 |
| ATOM | 2175 | N | GLU | A | 640 | 47.074 | 28.261 | 19.090 | 1.00 | 21.76 |
| ATOM | 2176 | CA | GLU | A | 640 | 47.528 | 29.174 | 18.057 | 1.00 | 23.40 |
| ATOM | 2177 | CB | GLU | A | 640 | 47.065 | 30.584 | 18.362 | 1.00 | 26.20 |
| ATOM | 2178 | CG | GLU | A | 640 | 45.569 | 30.708 | 18.357 | 1.00 | 30.88 |
| ATOM | 2179 | CD | GLU | A | 640 | 45.135 | 32.134 | 18.488 | 1.00 | 32.97 |
| ATOM | 2180 | OE1 | GLU | A | 640 | 45.463 | 32.935 | 17.586 | 1.00 | 35.29 |
| ATOM | 2181 | OE2 | GLU | A | 640 | 44.476 | 32.447 | 19.497 | 1.00 | 36.31 |
| ATOM | 2182 | C | GLU | A | 640 | 49.037 | 29.147 | 17.933 | 1.00 | 22.82 |
| ATOM | 2183 | O | GLU | A | 640 | 49.571 | 29.147 | 16.828 | 1.00 | 22.84 |
| ATOM | 2184 | N | GLU | A | 641 | 49.729 | 29.136 | 19.065 | 1.00 | 22.39 |
| ATOM | 2185 | CA | GLU | A | 641 | 51.186 | 29.094 | 19.031 | 1.00 | 23.98 |
| ATOM | 2186 | CB | GLU | A | 641 | 51.776 | 29.251 | 20.434 | 1.00 | 26.01 |
| ATOM | 2187 | CG | GLU | A | 641 | 51.439 | 30.561 | 21.124 | 1.00 | 31.35 |
| ATOM | 2188 | CD | GLU | A | 641 | 52.274 | 30.783 | 22.372 | 1.00 | 34.23 |
| ATOM | 2189 | OE1 | GLU | A | 641 | 52.348 | 29.872 | 23.225 | 1.00 | 36.36 |
| ATOM | 2190 | OE2 | GLU | A | 641 | 52.858 | 31.875 | 22.502 | 1.00 | 38.31 |
| ATOM | 2191 | C | GLU | A | 641 | 51.640 | 27.756 | 18.454 | 1.00 | 23.36 |
| ATOM | 2192 | O | GLU | A | 641 | 52.658 | 27.680 | 17.761 | 1.00 | 22.24 |
| ATOM | 2193 | N | LEU | A | 642 | 50.879 | 26.703 | 18.744 | 1.00 | 22.32 |
| ATOM | 2194 | CA | LEU | A | 642 | 51.219 | 25.371 | 18.250 | 1.00 | 23.34 |
| ATOM | 2195 | CB | LEU | A | 642 | 50.221 | 24.323 | 18.764 | 1.00 | 21.57 |
| ATOM | 2196 | CG | LEU | A | 642 | 50.513 | 22.875 | 18.338 | 1.00 | 21.78 |
| ATOM | 2197 | CD1 | LEU | A | 642 | 51.791 | 22.400 | 19.001 | 1.00 | 21.06 |
| ATOM | 2198 | CD2 | LEU | A | 642 | 49.355 | 21.956 | 18.719 | 1.00 | 19.88 |
| ATOM | 2199 | C | LEU | A | 642 | 51.218 | 25.375 | 16.728 | 1.00 | 23.43 |
| ATOM | 2200 | O | LEU | A | 642 | 52.178 | 24.925 | 16.101 | 1.00 | 23.67 |
| ATOM | 2201 | N | GLU | A | 643 | 50.148 | 25.900 | 16.138 | 1.00 | 23.70 |
| ATOM | 2202 | CA | GLU | A | 643 | 50.043 | 25.948 | 14.688 | 1.00 | 24.81 |
| ATOM | 2203 | CB | GLU | A | 643 | 48.658 | 26.452 | 14.257 | 1.00 | 24.68 |
| ATOM | 2204 | CG | GLU | A | 643 | 48.483 | 26.454 | 12.745 | 1.00 | 26.60 |
| ATOM | 2205 | CD | GLU | A | 643 | 47.038 | 26.569 | 12.298 | 1.00 | 27.36 |
| ATOM | 2206 | OE1 | GLU | A | 643 | 46.821 | 26.936 | 11.121 | 1.00 | 28.53 |
| ATOM | 2207 | OE2 | GLU | A | 643 | 46.125 | 26.287 | 13.101 | 1.00 | 26.79 |
| ATOM | 2208 | C | GLU | A | 643 | 51.136 | 26.820 | 14.079 | 1.00 | 25.41 |
| ATOM | 2209 | O | GLU | A | 643 | 51.582 | 26.572 | 12.959 | 1.00 | 24.61 |
| ATOM | 2210 | N | ARG | A | 644 | 51.563 | 27.843 | 14.813 | 1.00 | 26.83 |
| ATOM | 2211 | CA | ARG | A | 644 | 52.626 | 28.719 | 14.331 | 1.00 | 28.50 |
| ATOM | 2212 | CB | ARG | A | 644 | 52.551 | 30.095 | 15.005 | 1.00 | 29.97 |
| ATOM | 2213 | CG | ARG | A | 644 | 51.364 | 30.947 | 14.557 | 1.00 | 31.25 |
| ATOM | 2214 | CD | ARG | A | 644 | 51.617 | 32.428 | 14.813 | 1.00 | 33.14 |
| ATOM | 2215 | NE | ARG | A | 644 | 51.705 | 32.749 | 16.234 | 1.00 | 34.76 |
| ATOM | 2216 | CZ | ARG | A | 644 | 50.656 | 32.828 | 17.044 | 1.00 | 36.97 |
| ATOM | 2217 | NH1 | ARG | A | 644 | 49.437 | 32.613 | 16.568 | 1.00 | 37.67 |
| ATOM | 2218 | NH2 | ARG | A | 644 | 50.825 | 33.120 | 18.329 | 1.00 | 37.98 |
| ATOM | 2219 | C | ARG | A | 644 | 53.969 | 28.071 | 14.626 | 1.00 | 29.00 |
| ATOM | 2220 | O | ARG | A | 644 | 55.023 | 28.635 | 14.339 | 1.00 | 28.66 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 2221 | N | LYS | A | 645 | 53.916 | 26.875 | 15.203 | 1.00 | 30.31 |
| ATOM | 2222 | CA | LYS | A | 645 | 55.114 | 26.120 | 15.553 | 1.00 | 32.34 |
| ATOM | 2223 | CB | LYS | A | 645 | 55.872 | 25.715 | 14.283 | 1.00 | 32.10 |
| ATOM | 2224 | CG | LYS | A | 645 | 55.185 | 24.595 | 13.509 | 1.00 | 33.62 |
| ATOM | 2225 | CD | LYS | A | 645 | 55.978 | 24.184 | 12.282 | 1.00 | 35.74 |
| ATOM | 2226 | CE | LYS | A | 645 | 56.003 | 25.306 | 11.264 | 1.00 | 37.15 |
| ATOM | 2227 | NZ | LYS | A | 645 | 56.787 | 24.936 | 10.063 | 1.00 | 40.47 |
| ATOM | 2228 | C | LYS | A | 645 | 56.042 | 26.866 | 16.503 | 1.00 | 33.09 |
| ATOM | 2229 | O | LYS | A | 645 | 57.263 | 26.846 | 16.346 | 1.00 | 33.06 |
| ATOM | 2230 | N | GLU | A | 646 | 55.453 | 27.511 | 17.502 | 1.00 | 33.86 |
| ATOM | 2231 | CA | GLU | A | 646 | 56.225 | 28.254 | 18.483 | 1.00 | 35.00 |
| ATOM | 2232 | CB | GLU | A | 646 | 55.568 | 29.613 | 18.725 | 1.00 | 35.84 |
| ATOM | 2233 | CG | GLU | A | 646 | 55.268 | 30.319 | 17.412 | 1.00 | 37.58 |
| ATOM | 2234 | CD | GLU | A | 646 | 54.806 | 31.749 | 17.574 | 1.00 | 38.66 |
| ATOM | 2235 | OE1 | GLU | A | 646 | 54.026 | 32.034 | 18.508 | 1.00 | 39.13 |
| ATOM | 2236 | OE2 | GLU | A | 646 | 55.214 | 32.589 | 16.745 | 1.00 | 40.48 |
| ATOM | 2237 | C | GLU | A | 646 | 56.339 | 27.447 | 19.770 | 1.00 | 35.47 |
| ATOM | 2238 | O | GLU | A | 646 | 56.824 | 27.933 | 20.791 | 1.00 | 36.41 |
| ATOM | 2239 | N | ILE | A | 647 | 55.878 | 26.204 | 19.707 | 1.00 | 35.36 |
| ATOM | 2240 | CA | ILE | A | 647 | 55.955 | 25.290 | 20.834 | 1.00 | 35.47 |
| ATOM | 2241 | CB | ILE | A | 647 | 54.571 | 24.703 | 21.190 | 1.00 | 35.20 |
| ATOM | 2242 | CG2 | ILE | A | 647 | 54.713 | 23.671 | 22.302 | 1.00 | 33.81 |
| ATOM | 2243 | CG1 | ILE | A | 647 | 53.622 | 25.828 | 21.618 | 1.00 | 35.13 |
| ATOM | 2244 | CD1 | ILE | A | 647 | 52.235 | 25.355 | 22.030 | 1.00 | 33.56 |
| ATOM | 2245 | C | ILE | A | 647 | 56.873 | 24.164 | 20.377 | 1.00 | 37.06 |
| ATOM | 2246 | O | ILE | A | 647 | 56.533 | 23.416 | 19.461 | 1.00 | 37.68 |
| ATOM | 2247 | N | ASP | A | 648 | 58.045 | 24.059 | 20.997 | 1.00 | 38.56 |
| ATOM | 2248 | CA | ASP | A | 648 | 59.013 | 23.025 | 20.639 | 1.00 | 40.29 |
| ATOM | 2249 | CB | ASP | A | 648 | 60.322 | 23.232 | 21.405 | 1.00 | 42.67 |
| ATOM | 2250 | CG | ASP | A | 648 | 61.016 | 24.528 | 21.040 | 1.00 | 45.84 |
| ATOM | 2251 | OD1 | ASP | A | 648 | 60.430 | 25.607 | 21.275 | 1.00 | 47.54 |
| ATOM | 2252 | OD2 | ASP | A | 648 | 62.153 | 24.467 | 20.521 | 1.00 | 48.45 |
| ATOM | 2253 | C | ASP | A | 648 | 58.486 | 21.622 | 20.930 | 1.00 | 40.04 |
| ATOM | 2254 | O | ASP | A | 648 | 57.721 | 21.419 | 21.872 | 1.00 | 38.73 |
| ATOM | 2255 | N | PRO | A | 649 | 58.891 | 20.635 | 20.113 | 1.00 | 40.99 |
| ATOM | 2256 | CD | PRO | A | 649 | 59.642 | 20.810 | 18.858 | 1.00 | 41.23 |
| ATOM | 2257 | CA | PRO | A | 649 | 58.474 | 19.237 | 20.271 | 1.00 | 41.88 |
| ATOM | 2258 | CB | PRO | A | 649 | 59.185 | 18.538 | 19.118 | 1.00 | 41.36 |
| ATOM | 2259 | CG | PRO | A | 649 | 59.227 | 19.596 | 18.065 | 1.00 | 40.72 |
| ATOM | 2260 | C | PRO | A | 649 | 58.887 | 18.668 | 21.627 | 1.00 | 43.01 |
| ATOM | 2261 | O | PRO | A | 649 | 58.087 | 18.025 | 22.310 | 1.00 | 45.59 |
| ATOM | 2262 | N | GLN | A | 688 | 41.314 | 7.240 | −24.146 | 1.00 | 83.82 |
| ATOM | 2263 | CA | GLN | A | 688 | 42.769 | 7.135 | −24.124 | 1.00 | 83.73 |
| ATOM | 2264 | CB | GLN | A | 688 | 43.215 | 7.098 | −25.580 | 1.00 | 83.75 |
| ATOM | 2265 | CG | GLN | A | 688 | 44.097 | 8.259 | −25.932 | 1.00 | 83.71 |
| ATOM | 2266 | CD | GLN | A | 688 | 45.193 | 7.784 | −26.854 | 1.00 | 83.92 |
| ATOM | 2267 | OE1 | GLN | A | 688 | 45.538 | 8.351 | −27.892 | 1.00 | 83.95 |
| ATOM | 2268 | NE2 | GLN | A | 688 | 45.763 | 6.636 | −26.451 | 1.00 | 83.84 |
| ATOM | 2269 | C | GLN | A | 688 | 43.451 | 8.249 | −23.348 | 1.00 | 83.82 |
| ATOM | 2270 | O | GLN | A | 688 | 44.406 | 8.040 | −22.612 | 1.00 | 83.80 |
| ATOM | 2271 | N | ASN | A | 689 | 42.906 | 9.466 | −23.474 | 1.00 | 83.51 |
| ATOM | 2272 | CA | ASN | A | 689 | 43.489 | 10.638 | −22.833 | 1.00 | 83.17 |
| ATOM | 2273 | CB | ASN | A | 689 | 43.071 | 11.853 | −23.685 | 1.00 | 83.43 |
| ATOM | 2274 | CG | ASN | A | 689 | 43.546 | 11.712 | −25.110 | 1.00 | 83.69 |
| ATOM | 2275 | OD1 | ASN | A | 689 | 44.764 | 11.714 | −25.356 | 1.00 | 84.06 |
| ATOM | 2276 | ND2 | ASN | A | 689 | 42.626 | 11.582 | −26.042 | 1.00 | 83.71 |
| ATOM | 2277 | C | ASN | A | 689 | 43.248 | 10.870 | −21.349 | 1.00 | 82.77 |
| ATOM | 2278 | O | ASN | A | 689 | 43.497 | 11.952 | −20.833 | 1.00 | 82.58 |
| ATOM | 2279 | N | MET | A | 690 | 42.815 | 9.811 | −20.670 | 1.00 | 82.42 |
| ATOM | 2280 | CA | MET | A | 690 | 42.543 | 9.813 | −19.231 | 1.00 | 82.16 |
| ATOM | 2281 | CB | MET | A | 690 | 42.735 | 8.400 | −18.667 | 1.00 | 82.70 |
| ATOM | 2282 | CG | MET | A | 690 | 41.516 | 7.537 | −18.874 | 1.00 | 83.62 |
| ATOM | 2283 | SD | MET | A | 690 | 39.999 | 8.450 | −18.468 | 1.00 | 84.51 |
| ATOM | 2284 | CE | MET | A | 690 | 39.003 | 7.203 | −17.691 | 1.00 | 84.56 |
| ATOM | 2285 | C | MET | A | 690 | 43.228 | 10.790 | −18.283 | 1.00 | 81.66 |
| ATOM | 2286 | O | MET | A | 690 | 42.568 | 11.362 | −17.429 | 1.00 | 81.44 |
| ATOM | 2287 | N | PHE | A | 691 | 44.530 | 11.007 | −18.415 | 1.00 | 81.19 |
| ATOM | 2288 | CA | PHE | A | 691 | 45.202 | 11.917 | −17.479 | 1.00 | 80.70 |
| ATOM | 2289 | CB | PHE | A | 691 | 46.234 | 11.132 | −16.670 | 1.00 | 80.81 |
| ATOM | 2290 | CG | PHE | A | 691 | 45.918 | 9.669 | −16.538 | 1.00 | 80.86 |
| ATOM | 2291 | CD1 | PHE | A | 691 | 46.505 | 8.737 | −17.388 | 1.00 | 80.98 |
| ATOM | 2292 | CD2 | PHE | A | 691 | 45.024 | 9.222 | −15.568 | 1.00 | 81.28 |
| ATOM | 2293 | CE1 | PHE | A | 691 | 46.211 | 7.385 | −17.276 | 1.00 | 81.55 |
| ATOM | 2294 | CE2 | PHE | A | 691 | 44.724 | 7.868 | −15.448 | 1.00 | 81.78 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 2295 | CZ | PHE | A | 691 | 45.319 | 6.949 | −16.304 | 1.00 | 81.86 |
| ATOM | 2296 | C | PHE | A | 691 | 45.890 | 13.136 | −18.086 | 1.00 | 80.23 |
| ATOM | 2297 | O | PHE | A | 691 | 47.095 | 13.334 | −17.909 | 1.00 | 79.78 |
| ATOM | 2298 | N | ARG | A | 692 | 45.127 | 13.948 | −18.804 | 1.00 | 80.06 |
| ATOM | 2299 | CA | ARG | A | 692 | 45.686 | 15.140 | −19.434 | 1.00 | 80.00 |
| ATOM | 2300 | CB | ARG | A | 692 | 44.936 | 15.437 | −20.728 | 1.00 | 80.57 |
| ATOM | 2301 | CG | ARG | A | 692 | 45.745 | 16.213 | −21.722 | 1.00 | 81.51 |
| ATOM | 2302 | CD | ARG | A | 692 | 45.071 | 17.518 | −22.074 | 1.00 | 82.17 |
| ATOM | 2303 | NE | ARG | A | 692 | 44.443 | 17.467 | −23.388 | 1.00 | 82.75 |
| ATOM | 2304 | CZ | ARG | A | 692 | 44.169 | 18.547 | −24.109 | 1.00 | 82.92 |
| ATOM | 2305 | NH1 | ARG | A | 692 | 44.470 | 19.745 | −23.630 | 1.00 | 82.73 |
| ATOM | 2306 | NH2 | ARG | A | 692 | 43.608 | 18.433 | −25.306 | 1.00 | 83.03 |
| ATOM | 2307 | C | ARG | A | 692 | 45.623 | 16.347 | −18.495 | 1.00 | 79.58 |
| ATOM | 2308 | O | ARG | A | 692 | 44.663 | 16.508 | −17.744 | 1.00 | 79.25 |
| ATOM | 2309 | N | ASN | A | 693 | 46.653 | 17.191 | −18.544 | 1.00 | 79.24 |
| ATOM | 2310 | CA | ASN | A | 693 | 46.735 | 18.379 | −17.691 | 1.00 | 78.70 |
| ATOM | 2311 | CB | ASN | A | 693 | 45.475 | 19.234 | −17.831 | 1.00 | 78.66 |
| ATOM | 2312 | CG | ASN | A | 693 | 45.669 | 20.401 | −18.771 | 1.00 | 78.73 |
| ATOM | 2313 | OD1 | ASN | A | 693 | 44.724 | 21.123 | −19.084 | 1.00 | 79.24 |
| ATOM | 2314 | ND2 | ASN | A | 693 | 46.902 | 20.600 | −19.220 | 1.00 | 78.29 |
| ATOM | 2315 | C | ASN | A | 693 | 46.929 | 17.985 | −16.238 | 1.00 | 78.26 |
| ATOM | 2316 | O | ASN | A | 693 | 46.594 | 18.736 | −15.315 | 1.00 | 77.68 |
| ATOM | 2317 | N | PHE | A | 694 | 47.481 | 16.794 | −16.042 | 1.00 | 78.23 |
| ATOM | 2318 | CA | PHE | A | 694 | 47.731 | 16.269 | −14.707 | 1.00 | 78.24 |
| ATOM | 2319 | CB | PHE | A | 694 | 47.923 | 14.757 | −14.773 | 1.00 | 78.00 |
| ATOM | 2320 | CG | PHE | A | 694 | 48.428 | 14.166 | −13.491 | 1.00 | 78.00 |
| ATOM | 2321 | CD1 | PHE | A | 694 | 47.583 | 14.024 | −12.393 | 1.00 | 77.64 |
| ATOM | 2322 | CD2 | PHE | A | 694 | 49.760 | 13.789 | −13.364 | 1.00 | 77.71 |
| ATOM | 2323 | CE1 | PHE | A | 694 | 48.061 | 13.509 | −11.188 | 1.00 | 77.25 |
| ATOM | 2324 | CE2 | PHE | A | 694 | 50.248 | 13.273 | −12.165 | 1.00 | 77.28 |
| ATOM | 2325 | CZ | PHE | A | 694 | 49.396 | 13.132 | −11.075 | 1.00 | 77.21 |
| ATOM | 2326 | C | PHE | A | 694 | 48.963 | 16.902 | −14.080 | 1.00 | 78.53 |
| ATOM | 2327 | O | PHE | A | 694 | 49.072 | 16.982 | −12.857 | 1.00 | 78.24 |
| ATOM | 2328 | N | SER | A | 695 | 49.877 | 17.345 | −14.941 | 1.00 | 79.31 |
| ATOM | 2329 | CA | SER | A | 695 | 51.127 | 17.966 | −14.492 | 1.00 | 80.01 |
| ATOM | 2330 | C | SER | A | 695 | 50.844 | 19.279 | −13.788 | 1.00 | 79.90 |
| ATOM | 2331 | O | SER | A | 695 | 49.834 | 19.926 | −14.055 | 1.00 | 79.91 |
| ATOM | 2332 | OG | SER | A | 695 | 51.914 | 17.184 | −16.614 | 1.00 | 82.44 |
| ATOM | 2333 | CB | SER | A | 695 | 52.033 | 18.234 | −15.681 | 1.00 | 80.87 |
| ATOM | 2334 | N | PHE | A | 696 | 51.769 | 19.663 | −12.917 | 1.00 | 79.79 |
| ATOM | 2335 | CA | PHE | A | 696 | 51.592 | 20.863 | −12.165 | 1.00 | 79.91 |
| ATOM | 2336 | CB | PHE | A | 696 | 50.313 | 20.684 | −11.292 | 1.00 | 79.86 |
| ATOM | 2337 | CG | PHE | A | 696 | 50.348 | 21.362 | −9.959 | 1.00 | 79.95 |
| ATOM | 2338 | CD1 | PHE | A | 696 | 51.375 | 21.095 | −9.055 | 1.00 | 80.04 |
| ATOM | 2339 | CD2 | PHE | A | 696 | 49.290 | 22.184 | −9.579 | 1.00 | 80.04 |
| ATOM | 2340 | CE1 | PHE | A | 696 | 51.367 | 21.633 | −7.797 | 1.00 | 80.18 |
| ATOM | 2341 | CE2 | PHE | A | 696 | 49.274 | 22.737 | −8.293 | 1.00 | 80.17 |
| ATOM | 2342 | CZ | PHE | A | 696 | 50.317 | 22.454 | −7.405 | 1.00 | 80.32 |
| ATOM | 2343 | C | PHE | A | 696 | 52.806 | 21.120 | −11.337 | 1.00 | 79.99 |
| ATOM | 2344 | O | PHE | A | 696 | 53.315 | 20.153 | −10.786 | 1.00 | 80.34 |
| ATOM | 2345 | OXT | PHE | A | 696 | 53.291 | 22.241 | −11.239 | 1.00 | 80.10 |
| ATOM | 2346 | O | HOH | W | 1 | 44.405 | −5.257 | 16.067 | 1.00 | 27.81 |
| ATOM | 2347 | O | HOH | W | 2 | 43.908 | −7.626 | 15.396 | 1.00 | 31.97 |
| ATOM | 2348 | O | HOH | W | 3 | 38.566 | 0.748 | 15.081 | 1.00 | 17.03 |
| ATOM | 2349 | O | HOH | W | 4 | 51.061 | 33.563 | 21.928 | 1.00 | 46.43 |
| ATOM | 2350 | O | HOH | W | 5 | 37.775 | 5.803 | −2.008 | 1.00 | 43.14 |
| ATOM | 2351 | O | HOH | W | 6 | 40.381 | 8.066 | 9.339 | 1.00 | 10.44 |
| ATOM | 2352 | O | HOH | W | 7 | 61.824 | 18.216 | 0.279 | 1.00 | 20.16 |
| ATOM | 2353 | O | HOH | W | 8 | 43.782 | 24.225 | 12.173 | 1.00 | 18.02 |
| ATOM | 2354 | O | HOH | W | 9 | 31.125 | 0.199 | 0.285 | 1.00 | 19.97 |
| ATOM | 2355 | O | HOH | W | 10 | 42.051 | −3.360 | 24.518 | 1.00 | 21.43 |
| ATOM | 2356 | O | HOH | W | 11 | 55.788 | 23.461 | 6.982 | 1.00 | 27.61 |
| ATOM | 2357 | O | HOH | W | 12 | 52.691 | 6.016 | 27.604 | 1.00 | 16.16 |
| ATOM | 2358 | O | HOH | W | 13 | 29.699 | −1.807 | 1.877 | 1.00 | 23.21 |
| ATOM | 2359 | O | HOH | W | 14 | 42.543 | 21.972 | 26.847 | 1.00 | 20.54 |
| ATOM | 2360 | O | HOH | W | 15 | 54.858 | 19.831 | 10.485 | 1.00 | 28.97 |
| ATOM | 2361 | O | HOH | W | 16 | 27.082 | 7.849 | 11.073 | 1.00 | 20.41 |
| ATOM | 2362 | O | HOH | W | 17 | 59.280 | 15.191 | 17.943 | 1.00 | 16.31 |
| ATOM | 2363 | O | HOH | W | 18 | 36.410 | 18.910 | 15.687 | 1.00 | 22.10 |
| ATOM | 2364 | O | HOH | W | 19 | 35.848 | 19.335 | 18.774 | 1.00 | 30.89 |
| ATOM | 2365 | O | HOH | W | 20 | 50.064 | 12.660 | 0.176 | 1.00 | 32.24 |
| ATOM | 2366 | O | HOH | W | 21 | 28.589 | 10.090 | 11.006 | 1.00 | 17.76 |
| ATOM | 2367 | O | HOH | W | 22 | 60.540 | 19.603 | −7.946 | 1.00 | 51.97 |
| ATOM | 2368 | O | HOH | W | 23 | 35.553 | 17.240 | 27.309 | 1.00 | 33.05 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 2369 | O | HOH | W | 24 | 27.328 | 15.237 | 13.103 | 1.00 | 43.62 |
| ATOM | 2370 | O | HOH | W | 25 | 36.165 | 23.947 | 17.186 | 1.00 | 50.30 |
| ATOM | 2371 | O | HOH | W | 26 | 35.357 | 20.052 | −0.144 | 1.00 | 15.44 |
| ATOM | 2372 | O | HOH | W | 27 | 36.806 | 22.336 | 11.783 | 1.00 | 43.54 |
| ATOM | 2373 | O | HOH | W | 28 | 38.060 | 4.589 | 0.128 | 1.00 | 49.83 |
| ATOM | 2374 | O | HOH | W | 29 | 43.220 | −9.174 | 10.881 | 1.00 | 44.22 |
| ATOM | 2375 | O | HOH | W | 30 | 41.490 | 25.041 | 11.497 | 1.00 | 35.34 |
| ATOM | 2376 | O | HOH | W | 31 | 67.616 | 18.210 | 0.377 | 1.00 | 30.10 |
| ATOM | 2377 | O | HOH | W | 32 | 24.046 | 14.749 | 11.303 | 1.00 | 45.32 |
| ATOM | 2378 | O | HOH | W | 33 | 36.391 | 18.472 | 13.067 | 1.00 | 26.28 |
| ATOM | 2379 | O | HOH | W | 34 | 54.306 | 24.084 | 17.765 | 1.00 | 29.86 |
| ATOM | 2380 | O | HOH | W | 35 | 44.689 | 24.321 | 25.503 | 1.00 | 28.37 |
| ATOM | 2381 | O | HOH | W | 36 | 42.290 | −1.232 | 16.750 | 1.00 | 16.71 |
| ATOM | 2382 | O | HOH | W | 37 | 36.342 | 3.064 | 26.596 | 1.00 | 33.46 |
| ATOM | 2383 | O | HOH | W | 38 | 48.333 | 19.882 | 28.225 | 1.00 | 30.75 |
| ATOM | 2384 | O | HOH | W | 39 | 57.496 | 7.469 | 30.873 | 1.00 | 34.58 |
| ATOM | 2385 | O | HOH | W | 40 | 50.553 | 5.293 | 3.188 | 1.00 | 36.61 |
| ATOM | 2386 | O | HOH | W | 41 | 70.620 | 20.787 | −1.977 | 1.00 | 54.10 |
| ATOM | 2387 | O | HOH | W | 42 | 47.632 | −2.376 | 34.252 | 1.00 | 32.36 |
| ATOM | 2388 | O | HOH | W | 43 | 37.180 | 5.176 | 10.395 | 1.00 | 28.30 |
| ATOM | 2389 | O | HOH | W | 44 | 65.382 | 14.396 | 11.655 | 1.00 | 31.23 |
| ATOM | 2390 | O | HOH | W | 45 | 57.263 | 1.539 | 4.750 | 1.00 | 49.90 |
| ATOM | 2391 | O | HOH | W | 46 | 44.607 | 28.285 | 22.864 | 1.00 | 26.64 |
| ATOM | 2392 | O | HOH | W | 47 | 34.058 | 4.713 | 25.333 | 1.00 | 42.08 |
| ATOM | 2393 | O | HOH | W | 48 | 49.651 | 16.194 | 28.767 | 1.00 | 37.23 |
| ATOM | 2394 | O | HOH | W | 49 | 50.072 | 7.974 | 31.762 | 1.00 | 23.99 |
| ATOM | 2395 | O | HOH | W | 50 | 49.465 | 19.105 | 33.214 | 1.00 | 53.04 |
| ATOM | 2396 | O | HOH | W | 51 | 24.188 | 7.651 | 14.892 | 1.00 | 43.42 |
| ATOM | 2397 | O | HOH | W | 52 | 65.318 | 2.953 | −5.733 | 1.00 | 53.32 |
| ATOM | 2398 | O | HOH | W | 53 | 34.951 | 9.039 | −3.115 | 1.00 | 31.77 |
| ATOM | 2399 | O | HOH | W | 54 | 62.788 | 16.520 | 6.541 | 1.00 | 27.93 |
| ATOM | 2400 | O | HOH | W | 55 | 65.317 | 0.908 | −1.037 | 1.00 | 39.92 |
| ATOM | 2401 | O | HOH | W | 56 | 22.736 | 6.224 | 7.854 | 1.00 | 37.18 |
| ATOM | 2402 | O | HOH | W | 57 | 22.354 | −0.345 | 8.024 | 1.00 | 45.57 |
| ATOM | 2403 | O | HOH | W | 58 | 39.754 | −10.441 | 4.356 | 1.00 | 41.90 |
| ATOM | 2404 | O | HOH | W | 59 | 28.903 | 2.816 | 5.921 | 1.00 | 36.89 |
| ATOM | 2405 | O | HOH | W | 60 | 51.831 | 3.389 | 5.105 | 1.00 | 41.56 |
| ATOM | 2406 | O | HOH | W | 61 | 68.191 | 17.402 | −12.335 | 1.00 | 28.50 |
| ATOM | 2407 | O | HOH | W | 62 | 38.575 | −5.049 | 5.076 | 1.00 | 32.80 |
| ATOM | 2408 | O | HOH | W | 63 | 67.628 | 6.871 | −10.290 | 1.00 | 32.96 |
| ATOM | 2409 | O | HOH | W | 64 | 61.069 | 15.027 | −16.486 | 1.00 | 44.39 |
| ATOM | 2410 | O | HOH | W | 65 | 51.197 | 21.314 | −1.255 | 1.00 | 33.50 |
| ATOM | 2411 | O | HOH | W | 66 | 43.407 | −8.262 | 13.149 | 1.00 | 43.24 |
| ATOM | 2412 | O | HOH | W | 67 | 28.328 | 20.172 | 21.424 | 1.00 | 55.05 |
| ATOM | 2413 | O | HOH | W | 68 | 24.787 | 13.752 | 1.867 | 1.00 | 33.58 |
| ATOM | 2414 | O | HOH | W | 69 | 56.831 | 16.690 | 24.349 | 1.00 | 42.38 |
| ATOM | 2415 | O | HOH | W | 70 | 49.409 | 8.548 | −21.438 | 1.00 | 44.91 |
| ATOM | 2416 | O | HOH | W | 71 | 52.613 | 18.410 | 25.629 | 1.00 | 40.22 |
| ATOM | 2417 | O | HOH | W | 72 | 40.592 | 26.447 | 8.059 | 1.00 | 35.07 |
| ATOM | 2418 | O | HOH | W | 73 | 37.597 | 5.018 | 7.744 | 1.00 | 32.52 |
| ATOM | 2419 | O | HOH | W | 74 | 41.658 | 29.146 | 4.538 | 1.00 | 34.36 |
| ATOM | 2420 | O | HOH | W | 75 | 29.114 | 3.872 | 23.333 | 1.00 | 37.14 |
| ATOM | 2421 | O | HOH | W | 76 | 47.138 | 27.828 | 26.613 | 1.00 | 45.54 |
| ATOM | 2422 | O | HOH | W | 77 | 48.429 | 14.683 | 34.149 | 1.00 | 45.72 |
| ATOM | 2423 | O | HOH | W | 78 | 44.818 | 26.959 | 9.627 | 1.00 | 36.07 |
| ATOM | 2424 | O | HOH | W | 79 | 32.245 | 16.035 | 7.600 | 1.00 | 29.86 |
| ATOM | 2425 | O | HOH | W | 80 | 34.287 | 18.006 | 20.219 | 1.00 | 49.58 |
| ATOM | 2426 | O | HOH | W | 81 | 46.140 | 8.973 | 36.904 | 1.00 | 41.01 |
| ATOM | 2427 | O | HOH | W | 82 | 36.178 | 13.580 | −3.440 | 1.00 | 35.51 |
| ATOM | 2428 | O | HOH | W | 83 | 43.909 | 13.668 | 37.111 | 1.00 | 58.57 |
| ATOM | 2429 | O | HOH | W | 84 | 28.754 | 0.872 | 3.464 | 1.00 | 53.40 |
| ATOM | 2430 | O | HOH | W | 85 | 58.227 | −2.893 | 27.346 | 1.00 | 35.17 |
| ATOM | 2431 | O | HOH | W | 86 | 51.679 | −1.044 | 27.253 | 1.00 | 32.70 |
| ATOM | 2432 | O | HOH | W | 87 | 54.344 | −1.547 | 20.337 | 1.00 | 40.72 |
| ATOM | 2433 | O | HOH | W | 88 | 55.722 | 20.496 | −13.650 | 1.00 | 57.49 |
| ATOM | 2434 | O | HOH | W | 89 | 28.429 | 13.038 | −1.037 | 1.00 | 46.69 |
| ATOM | 2435 | O | HOH | W | 90 | 29.231 | 9.216 | −1.912 | 1.00 | 46.23 |
| ATOM | 2436 | O | HOH | W | 91 | 54.865 | 1.093 | 3.517 | 1.00 | 43.59 |
| ATOM | 2437 | O | HOH | W | 92 | 58.721 | 1.874 | 6.787 | 1.00 | 50.25 |
| ATOM | 2438 | O | HOH | W | 93 | 64.156 | 3.084 | 3.700 | 1.00 | 51.88 |
| ATOM | 2439 | O | HOH | W | 94 | 65.008 | 6.626 | 5.313 | 1.00 | 46.57 |
| ATOM | 2440 | O | HOH | W | 95 | 64.832 | 4.948 | 10.246 | 1.00 | 61.80 |
| ATOM | 2441 | O | HOH | W | 96 | 74.347 | 21.947 | −3.124 | 1.00 | 52.18 |
| ATOM | 2442 | O | HOH | W | 97 | 76.689 | 18.777 | −2.619 | 1.00 | 61.15 |

TABLE 2-continued

Structure coordinates for PKCθ
(residues 377-696 of SEQ ID NO: 1)/staurosporine complex

| | # | name | res | chain | res # | X | Y | Z | occ | B |
|---|---|---|---|---|---|---|---|---|---|---|
| ATOM | 2443 | O | HOH | W | 98 | 38.819 | −15.466 | 14.853 | 1.00 | 41.26 |
| ATOM | 2444 | O | HOH | W | 99 | 37.941 | 10.962 | −12.972 | 1.00 | 48.80 |
| ATOM | 2445 | O | HOH | W | 100 | 32.483 | 6.619 | −4.835 | 1.00 | 39.40 |
| ATOM | 2446 | O | HOH | W | 101 | 48.304 | 28.153 | 9.505 | 1.00 | 34.82 |
| ATOM | 2447 | O | HOH | W | 102 | 51.901 | −2.777 | 16.129 | 1.00 | 48.45 |
| ATOM | 2448 | O | HOH | W | 103 | 45.328 | 12.905 | 34.608 | 1.00 | 38.67 |
| ATOM | 2449 | O | HOH | W | 104 | 32.098 | 11.673 | 24.028 | 1.00 | 31.67 |
| ATOM | 2450 | O | HOH | W | 105 | 48.096 | 7.776 | 37.247 | 1.00 | 61.92 |
| ATOM | 2451 | O | HOH | W | 106 | 60.343 | 17.220 | −15.584 | 1.00 | 47.08 |
| ATOM | 2452 | O | HOH | W | 107 | 41.259 | 28.308 | 6.780 | 1.00 | 48.27 |
| ATOM | 2453 | O | HOH | W | 108 | 51.326 | 8.898 | 36.188 | 1.00 | 41.59 |
| ATOM | 2454 | O | HOH | W | 109 | 30.252 | 22.907 | 5.497 | 1.00 | 52.21 |
| ATOM | 2455 | O | HOH | W | 110 | 57.413 | 20.830 | 9.293 | 1.00 | 46.14 |
| ATOM | 2456 | O | HOH | W | 111 | 46.088 | 14.217 | 41.579 | 1.00 | 42.28 |
| ATOM | 2457 | O | HOH | W | 112 | 40.128 | 1.136 | 2.224 | 1.00 | 32.09 |
| ATOM | 2458 | O | HOH | W | 113 | 33.992 | 17.400 | 6.607 | 1.00 | 41.25 |
| ATOM | 2459 | O | HOH | W | 114 | 54.842 | 22.676 | 31.236 | 1.00 | 62.02 |
| ATOM | 2460 | O | HOH | W | 115 | 48.235 | −0.372 | 10.526 | 1.00 | 51.22 |
| ATOM | 2461 | O5 | STU | A | 1 | 59.277 | 12.216 | 3.424 | 1.00 | 21.44 |
| ATOM | 2462 | C8 | STU | A | 1 | 58.213 | 11.942 | 2.911 | 1.00 | 19.74 |
| ATOM | 2463 | N1 | STU | A | 1 | 57.427 | 12.742 | 2.229 | 1.00 | 18.27 |
| ATOM | 2464 | C7 | STU | A | 1 | 57.488 | 10.647 | 2.887 | 1.00 | 19.44 |
| ATOM | 2465 | C6 | STU | A | 1 | 57.931 | 9.292 | 3.545 | 1.00 | 19.72 |
| ATOM | 2466 | C5 | STU | A | 1 | 58.992 | 8.833 | 4.330 | 1.00 | 21.14 |
| ATOM | 2467 | C20 | STU | A | 1 | 58.755 | 7.365 | 4.590 | 1.00 | 22.15 |
| ATOM | 2468 | C1 | STU | A | 1 | 59.705 | 6.568 | 5.431 | 1.00 | 22.07 |
| ATOM | 2469 | C2 | STU | A | 1 | 60.918 | 7.223 | 5.917 | 1.00 | 22.36 |
| ATOM | 2470 | C3 | STU | A | 1 | 61.177 | 8.665 | 5.634 | 1.00 | 21.99 |
| ATOM | 2471 | C4 | STU | A | 1 | 60.241 | 9.426 | 4.840 | 1.00 | 21.85 |
| ATOM | 2472 | N3 | STU | A | 1 | 57.542 | 6.993 | 4.044 | 1.00 | 21.06 |
| ATOM | 2473 | C19 | STU | A | 1 | 56.975 | 8.152 | 3.343 | 1.00 | 20.78 |
| ATOM | 2474 | C25 | STU | A | 1 | 57.043 | 5.523 | 3.938 | 1.00 | 21.48 |
| ATOM | 2475 | O4 | STU | A | 1 | 56.126 | 5.390 | 2.811 | 1.00 | 21.40 |
| ATOM | 2476 | C10 | STU | A | 1 | 56.331 | 10.786 | 2.200 | 1.00 | 19.21 |
| ATOM | 2477 | C9 | STU | A | 1 | 56.206 | 12.205 | 1.700 | 1.00 | 18.62 |
| ATOM | 2478 | C11 | STU | A | 1 | 55.387 | 9.642 | 1.986 | 1.00 | 19.47 |
| ATOM | 2479 | C12 | STU | A | 1 | 54.129 | 9.482 | 1.354 | 1.00 | 19.14 |
| ATOM | 2480 | C13 | STU | A | 1 | 53.280 | 10.398 | 0.573 | 1.00 | 17.85 |
| ATOM | 2481 | C14 | STU | A | 1 | 52.012 | 9.993 | −0.013 | 1.00 | 17.84 |
| ATOM | 2482 | C15 | STU | A | 1 | 51.571 | 8.563 | 0.145 | 1.00 | 18.71 |
| ATOM | 2483 | C17 | STU | A | 1 | 53.682 | 8.044 | 1.472 | 1.00 | 19.90 |
| ATOM | 2484 | C16 | STU | A | 1 | 52.377 | 7.645 | 0.890 | 1.00 | 20.47 |
| ATOM | 2485 | C18 | STU | A | 1 | 55.759 | 8.309 | 2.603 | 1.00 | 19.80 |
| ATOM | 2486 | N2 | STU | A | 1 | 54.678 | 7.380 | 2.283 | 1.00 | 20.08 |
| ATOM | 2487 | C21 | STU | A | 1 | 54.759 | 5.875 | 2.756 | 1.00 | 20.72 |
| ATOM | 2488 | C26 | STU | A | 1 | 54.119 | 4.791 | 1.859 | 1.00 | 21.87 |
| ATOM | 2489 | C22 | STU | A | 1 | 53.967 | 5.789 | 4.219 | 1.00 | 21.57 |
| ATOM | 2490 | O6 | STU | A | 1 | 54.005 | 7.111 | 4.939 | 1.00 | 22.98 |
| ATOM | 2491 | C27 | STU | A | 1 | 52.783 | 7.836 | 4.894 | 1.00 | 21.48 |
| ATOM | 2492 | C23 | STU | A | 1 | 54.712 | 4.695 | 5.051 | 1.00 | 22.41 |
| ATOM | 2493 | C24 | STU | A | 1 | 56.254 | 5.136 | 5.300 | 1.00 | 22.58 |
| ATOM | 2494 | N4 | STU | A | 1 | 54.087 | 4.411 | 6.485 | 1.00 | 25.14 |
| ATOM | 2495 | C28 | STU | A | 1 | 54.826 | 3.300 | 7.233 | 1.00 | 24.32 |
| ATOM | 2496 | O1P | TPB | A | 2 | 34.001 | 6.990 | −1.433 | 1.00 | 18.24 |
| ATOM | 2497 | O2P | TPB | A | 2 | 32.139 | 7.348 | 0.244 | 1.00 | 20.04 |
| ATOM | 2498 | O3P | TPB | A | 2 | 31.766 | 7.269 | −2.303 | 1.00 | 18.89 |
| ATOM | 2499 | P | TPB | A | 2 | 32.585 | 6.763 | −1.066 | 1.00 | 21.60 |
| ATOM | 2500 | O1P | SPB | A | 3 | 53.748 | 18.218 | −17.683 | 1.00 | 83.37 |
| ATOM | 2501 | O2P | SPB | A | 3 | 51.814 | 16.872 | −18.638 | 1.00 | 83.11 |
| ATOM | 2502 | O3P | SPB | A | 3 | 53.921 | 15.822 | −17.583 | 1.00 | 83.40 |
| ATOM | 2503 | P | SPB | A | 3 | 52.898 | 17.012 | −17.594 | 1.00 | 83.90 |

Other embodiments are within the scope of the claims.

What is claimed is:

1. A method of designing a candidate agent that interacts with protein kinase C theta (PKCθ), comprising:
   (a) generating a three-dimensional model of the catalytic domain of PKCθ defined by the three-dimensional structural coordinates of the complex of the catalytic domain of PKCθ and staurosporine according to Table 2, ± a root mean square deviation for alpha carbon atoms of not more than 0.5 Å, wherein the catalytic domain of PKCθ of the complex according to Table 2 consists of amino acids Ile377 to Pro649 and Gln688 to Phe696 of SEQ ID NO: 1;
   (b) identifying the amino acid residues forming the ATP-binding pocket of the catalytic domain of PKCθ from the three-dimensional model in step (a) in order to generate a three-dimensional representation of the ATP-binding pocket which comprises the structural coordinates of residues Leu386, Gly387, Gly389, Val394, Ala407, Lys409, Val422, Glu428, Met458, Glu459, Tyr460, Leu461, Gly464, Leu466, Arg503, Asp504, Asp508, Asn509, Leu511, Ala521, Asp522, Lys527, Thr536, and Thr538 according to Table 2± a root mean square deviation for alpha carbon atoms of not more than 0.5 Å;
   (c) employing said three-dimensional representation from step (b) to design said candidate agent;
   (d) synthesizing said candidate agent;
   (e) contacting said candidate agent with said catalytic domain of PKCθ polypeptide; and
   (f) detecting the ability of the candidate agent to bind to the catalytic domain of the PKCθ polypeptide,
   whereby the detection of the ability of said candidate agent to interact or bind said catalytic domain of PKCθ polypeptide thereby identifies said candidate agent as an agent that interacts with PKCθ.

2. The method of claim 1, wherein the complex of the catalytic domain of PKCθ and staurosporine is a crystalline complex and has a space group symmetry C2, with dimensions a=139.6 Å, b=42.4 Å, c=67.7 Å and β=116.2°.

3. The method of claim 1, wherein the contacting of said candidate agent with said catalytic domain of PKCθ polypeptide occurs in vitro or in a cell-based assay.

4. The method of claim 1, wherein the three-dimensional model comprises structural coordinates of atoms of the candidate agent.

5. The method of claim 4, further comprising altering the structural coordinates of the candidate agent of the model.

6. The method of claim 1, wherein the three-dimensional representation further comprises structural coordinates of residues Lys413, Val416, Leu417, Met426, Lys429, Thr447, Gln449, Leu454, Phe456, Phe691, Arg692, Asn693, Phe694, and Ser695 according to Table 2± a root mean square deviation for alpha carbon atoms of not more than 0.5 Å.

7. The method of claim 1, wherein designing of the candidate agent comprises calculating a distance between an atom of the PKCθ and an atom of the candidate agent.

8. The method of claim 4, further comprising calculating a distance between atoms of the PKCθ and atoms of the candidate agent.

9. The method of claim 1, wherein designing of the candidate agent comprises docking a three-dimensional model of the candidate agent to the three-dimensional model of the catalytic domain of PKCθ.

10. The method of claim 1, wherein the PKCθ polypeptide used in steps (e) and (f) comprises a catalytic domain from amino acids 362 to 706 of SEQ ID NO: 1.

11. The method of claim 1, further comprising determining a catalytic activity of the PKCθ polypeptide.

12. The method of claim 1, further comprising comparing the catalytic activity of a PKCθ polypeptide determined in the presence of the candidate agent to a catalytic activity of the PKCθ polypeptide determined in the absence of the candidate agent.

13. The method of claim 12, wherein the catalytic activity of PKCθ is evaluated in vitro.

14. The method of claim 12, wherein the catalytic activity of PKCθ is evaluated in a cell-based assay.

15. A method of identifying a candidate agent capable of altering a catalytic activity of PKCθ comprising:
   (a) generating a three-dimensional model of the catalytic domain of PKCθ defined by the three-dimensional structural coordinates of the complex of the catalytic domain of PKCθ and staurosporine according to Table 2, ± a root mean square deviation for alpha carbon atoms of not more than 0.5 Å, wherein the catalytic domain of PKCθ in the complex according to Table 2 consists of amino acids Ile377 to Pro649 and Gln688 to Phe696 of SEQ ID NO: 1;
   (b) identifying the amino acid residues forming the ATP-binding pocket of the catalytic domain of PKCθ from the three-dimensional model in step (a) in order to generate a three-dimensional representation of the ATP-binding pocket which comprises the structural coordinates of residues Leu386, Gly387, Gly389, Val394, Ala407, Lys409, Val422, Met458, Glu459, Tyr460, Leu461, Gly464, Leu466, Arg503, Asp504, Asp508, Asn509, Leu511, Ala521, Asp522, Lys527, Thr536, and Thr538 according to Table 2± a root mean square deviation for alpha carbon atoms of not more than 0.5 Å;
   (c) studying the interaction of a plurality of candidate agents with the three-dimensional representation of the ATP-binding pocket from step (b);

(d) selecting from the plurality of candidate agents an agent which is predicted to alter a catalytic activity of the catalytic domain of PKCθ; and (e) determining a catalytic activity of the catalytic domain of a PKCθ polypeptide in the presence or the absence of the candidate agent.

16. The method of claim 15, wherein the catalytic domain of the PKCθ polypeptide according to step (e) comprises a catalytic domain from amino acids 362 to 706 of SEQ ID NO: 1.

17. A method of designing an agent that binds to a PKCθ polypeptide, comprising:
(a) generating a three-dimensional model of the catalytic domain of PKCθ defined by the three-dimensional structural coordinates of the crystalline complex of the catalytic domain of PKCθ and staurosporine according to Table 2, ± a root mean square deviation for alpha carbon atoms of not more than 0.5 Å, wherein the catalytic domain of PKCθ in the complex according to Table 2 consists of amino acids Ile377 to Pro649 and Gln688 to Phe696 of SEQ ID NO: 1;
(b) identifying the amino acid residues forming the ATP-binding pocket of the catalytic domain of PKCθ from the three-dimensional model in step (a) in order to generate a three-dimensional representation of the ATP-binding pocket which comprises the structural coordinates of residues Leu386, Gly387, Gly389, Val394, Ala407, Lys409, Lys413, Val416, Leu417, Val422, Met426, Glu428, Lys429, Thr447, Gln449, Leu454, Phe456, Met458, Glu459, Tyr460, Leu461, Gly464, Leu466, Arg503, Asp504, Asp508, Asn509, Leu511, Ala521, Asp522, Lys527, Thr536, Thr538, Phe691, Arg692, Asn693, Phe694, and Ser695 according to Table 2± a root mean square deviation for alpha carbon atoms of not more than 0.5 Å;
(c) selecting a candidate agent by performing rational drug design with the three-dimensional representation of the ATP-binding pocket from step (b);
(d) altering the structure of the candidate agent in the three-dimensional representation from step (b);
(e) contacting the candidate agent with the catalytic domain of a PKCθ polypeptide; and
(f) detecting the ability of the candidate agent to bind to the catalytic domain of the PKCθ polypeptide.

18. The method of claim 17, wherein the catalytic domain of the PKCθ polypeptide according to step (e) or (f) comprises a catalytic domain from amino acids 362 to 706 of SEQ ID NO: 1.

19. The method of claim 17, further comprising determining a catalytic activity of the PKCθ polypeptide.

20. The method of claim 17, wherein the crystalline complex has a space group symmetry C2, with dimensions a=139.6 Å, b=42.4 Å, c=67.7 Å and β=116.2°.

21. A method of designing a candidate agent that interacts with protein kinase C theta (PKCθ), comprising:
generating a three-dimensional model of a crystalline complex comprising the structural coordinates of a crystalline complex of a catalytic domain of a PKCθ and staurosporine defined by Table 2, ± a root mean square deviation for alpha carbon atoms of not more than 0.5 Å, wherein the PKCθ in the complex according to Table 2 consists of the amino acid sequence of SEQ ID NO: 2, said structural coordinates of the crystalline complex being obtained by subjecting a co-crystal comprising the catalytic domain of PKCθ and staurosporine to X-ray diffraction and collecting data sufficient to determine the three-dimensional structure of said crystalline complex, wherein the crystalline complex has a space group symmetry C2, with dimensions a=139.6 Å, b=42.4 Å, c=67.7 Å and β=116.2°;
determining a fit between the structural coordinates of atoms of the three-dimensional model of the catalytic domain of PKCθ and a candidate;
altering the structure of the candidate agent in the three-dimensional model,
obtaining the candidate agent; and
detecting the ability of the candidate agent to bind to the catalytic domain of a PKCθ polypeptide.

22. The method of claim 21, wherein the PKCθ polypeptide of step (e) comprises a catalytic domain from amino acids 362 to 706 of SEQ ID NO: 1.

23. A method of designing a candidate agent that interacts with protein kinase C theta (PKCθ), comprising:
(a) generating a three-dimensional model of the catalytic domain of PKCθ defined by the three-dimensional structural coordinates of the crystalline complex of the catalytic domain of PKCθ and staurosporine according to Table 2± a root mean square deviation for alpha carbon atoms of not more than 0.5 Å, wherein the catalytic domain of PKCθ in the complex according to Table 2 consists of amino acids Ile377 to Pro649 and Gln688 to Phe696 of SEQ ID NO: 1;
(b) identifying the amino acid residues forming the ATP-binding pocket of the catalytic domain of PKCθ from the three-dimensional model in step (a) in order to generate a three-dimensional representation of the ATP-binding pocket which comprises the structural coordinates of residues Leu386, Gly387, Gly389, Val394, Ala407, Lys409, Lys413, Val416, Leu417, Val422, Met426, Glu428, Lys429, Thr447, Gln449, Leu454, Phe456, Met458, Glu459, Tyr460, Leu461, Gly464, Leu466, Arg503, Asp504, Asp508, Asn509, Leu511, Ala521, Asp522, Lys527, Thr536, Thr538, Phe691, Arg692, Asn693, Phe694, and Ser695 according to Table 2± a root mean square deviation for alpha carbon atoms of not more than 0.5 Å, wherein the ATP-binding pocket of the catalytic domain of PKCθ has a closed conformation;
(c) determining a fit between said three-dimensional model and a candidate agent;
(d) altering the structure of the candidate agent in the three-dimensional model,
(e) synthesizing the candidate agent; and
(f) detecting the ability of the candidate agent to bind to the catalytic domain of a PKCθ polypeptide.

24. The method of claim 23, wherein the PKCθ polypeptide of steps (e) and (f) comprises a catalytic domain from amino acids 362 to 706 of SEQ ID NO: 1.

25. A method of designing a candidate agent that interacts with protein kinase C theta (PKCθ), comprising:
(a) generating a three-dimensional model of the catalytic domain of PKCθ defined by the three-dimensional structural coordinates of the complex of the catalytic domain of PKCθ and staurosporine according to Table 2, ± a root mean square deviation for alpha carbon atoms of not more than 0.5 Å, wherein the catalytic domain of PKCθ of the complex according to Table 2 consists of amino acids Ile377 to Pro649 and Gln688 to Phe696 of SEQ ID NO: 1;
(b) identifying the amino acid residues forming the ATP-binding pocket of the catalytic domain of PKCθ from the three-dimensional model in step (a) in order to generate a three-dimensional representation of the ATP-binding pocket which comprises the structural coordinates of residues Leu386, Gly387, Gly389, Val394, Ala407, Lys409, Val422, Glu428, Met458, Glu459, Tyr460, Leu461, Gly464, Leu466, Arg503, Asp504, Asp508, Asn509, Leu511, Ala521, Asp522, Lys527, Thr536, and Thr538 according to Table 2± a root mean square deviation for alpha carbon atoms of not more than 0.5 Å;

(c) employing said three-dimensional representation from step (b) to design said candidate agent;
(d) obtaining said candidate agent; and
(e) contacting said candidate agent with said catalytic domain of PKCθ to determine the ability of said candidate agent to interact or bind with said three-dimensional model of the catalytic domain of PKCθ, whereby the detection of the ability of said candidate agent to interact or bind said catalytic domain of PKCθ thereby identifies said candidate agent as an agent that interacts with PKCθ.

* * * * *